US009323153B2

(12) United States Patent
Hirano et al.

(10) Patent No.: US 9,323,153 B2
(45) Date of Patent: Apr. 26, 2016

(54) ACTINIC RAY-SENSITIVE OR RADIATION-SENSITIVE RESIN COMPOSITION, AND, ACTINIC RAY-SENSITIVE OR RADIATION-SENSITIVE FILM AND PATTERN FORMING METHOD, EACH USING THE SAME

(71) Applicant: FUJIFILM Corporation, Minato-Ku, Tokyo (JP)

(72) Inventors: Shuji Hirano, Haibara-gun (JP); Hiroo Takizawa, Haibara-gun (JP); Hideaki Tsubaki, Haibara-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/478,135

(22) Filed: Sep. 5, 2014

(65) Prior Publication Data

US 2015/0004533 A1 Jan. 1, 2015

Related U.S. Application Data

(63) Continuation of application No. PCT/JP2013/059791, filed on Mar. 25, 2013.

(30) Foreign Application Priority Data

Mar. 29, 2012 (JP) ................................ 2012-077761
Feb. 22, 2013 (JP) ................................ 2013-033638

(51) Int. Cl.

| | |
|---|---|
| ***G03F 7/039*** | (2006.01) |
| ***G03F 7/004*** | (2006.01) |
| ***G03F 7/20*** | (2006.01) |
| ***G03F 7/30*** | (2006.01) |
| ***G03F 7/09*** | (2006.01) |
| ***C07D 235/12*** | (2006.01) |
| ***C07D 235/16*** | (2006.01) |
| ***C07D 235/22*** | (2006.01) |
| ***C07D 235/26*** | (2006.01) |
| ***C07D 235/28*** | (2006.01) |
| ***G03F 7/11*** | (2006.01) |
| ***G03F 7/32*** | (2006.01) |
| ***G03F 7/027*** | (2006.01) |
| ***G03F 7/038*** | (2006.01) |

(52) U.S. Cl.

CPC ............ *G03F 7/0397* (2013.01); *C07D 235/12* (2013.01); *C07D 235/16* (2013.01); *C07D 235/22* (2013.01); *C07D 235/26* (2013.01); *C07D 235/28* (2013.01); *G03F 7/0045* (2013.01); *G03F 7/0046* (2013.01); *G03F 7/027* (2013.01); *G03F 7/038* (2013.01); *G03F 7/0392* (2013.01); *G03F 7/09* (2013.01); *G03F 7/11* (2013.01); *G03F 7/2002* (2013.01); *G03F 7/2041* (2013.01); *G03F 7/30* (2013.01); *G03F 7/322* (2013.01); *G03F 7/325* (2013.01)

(58) Field of Classification Search

None

See application file for complete search history.

(56) References Cited

U.S. PATENT DOCUMENTS

| | | | | |
|---|---|---|---|---|
| 4,835,085 | A * | 5/1989 | Bauer | C07D 235/20 430/165 |
| 2005/0008968 | A1 * | 1/2005 | Watanabe et al. | 430/270.1 |
| 2007/0292802 | A1 | 12/2007 | Sato | |
| 2008/0102407 | A1 * | 5/2008 | Ohsawa et al. | 430/286.1 |
| 2011/0159670 | A1 * | 6/2011 | Wang et al. | 438/514 |
| 2013/0078426 | A1 * | 3/2013 | Koshijima et al. | 428/156 |

FOREIGN PATENT DOCUMENTS

| | | | |
|---|---|---|---|
| JP | 62-290702 | * | 12/1987 |
| JP | 2004-347738 | A | 12/2004 |
| JP | 2006-065071 | A | 3/2006 |

(Continued)

OTHER PUBLICATIONS

Derwent English abstract for JP62-290702 (1987).*

(Continued)

*Primary Examiner* — Sin Lee
(74) *Attorney, Agent, or Firm* — Sughrue Mion, PLLC

(57) ABSTRACT

An actinic ray-sensitive or radiation-sensitive resin composition in the present invention contains a nitrogen-containing compound (N) which is represented by the following general formula (N1):

[Chem. 1]

(N1)

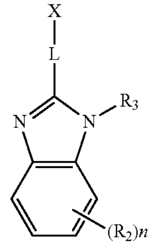

wherein, in the general formula (N1),

X represents a group including a hetero atom;

L represents a single bond or an alkylene group;

$R_2$ represents a substituent, in the case where a plurality of $R_2$'s are present, they may be the same as or different from each other and a plurality of $R_2$'s may be bonded to each other to form a ring;

$R_3$ represents a hydrogen atom or a substituent; and n represents an integer of 0 to 4.

17 Claims, No Drawings

(56) References Cited

FOREIGN PATENT DOCUMENTS

| | | | | |
|---|---|---|---|---|
| JP | 3790649 | B2 | | 6/2006 |
| JP | 2007-320306 | A | | 12/2007 |
| JP | 2010-61087 | | * | 3/2010 |
| JP | 4425405 | B2 | | 3/2010 |
| JP | 2010-231107 | A | | 10/2010 |
| JP | 4710193 | B2 | | 6/2011 |
| JP | 2012-008526 | A | | 1/2012 |
| KR | 10-2008-0038049 | A | | 5/2008 |

OTHER PUBLICATIONS

Derwent English abstract for JP2010-231107 (2010).*

Machine-assisted English translation for JP2010-231107 (2010) provided by JPO.*

Derwent English abstract for JP2010-61087 (2010).*

Machine-assisted English translation for JP2010-61087 (2010) provided by JPO.*

Notice of Reasons for Rejection, mailed Aug. 5, 2014, issued in corresponding JP Application No. 2013-033638, 8 pages in English and Japanese.

International Search Report for PCT/JP2013/059791 dated Jun. 11, 2013, 2 pages.

Written Opinion for PCT/JP2013/059791 dated Jun. 11, 2013, 5 pages.

Notice of Reasons for Rejection, dispatched Mar. 10, 2015, issued in corresponding JP Application No. 2013-033638, 10 pages in English and Japanese.

Office Action dated May 8, 2015, issued by the Korean Intellectual Property Office in counterpart Korean Application No. 10-2014-7023305.

Notice Requesting Submission of Opinion, mailed Jan. 12, 2015, issued in corresponding KR Application No. 10-2014-7023305, 10 pages in English and Korean.

Notice of Rejection for Amendment dated Aug. 4, 2015 from the Korean Intellectual Property Office in counterpart Korean Application No. 10-2014-7023305.

Notice of Final Reasons dated Aug. 4, 2015 from the Korean Intellectual Property Office in counterpart Korean Application No. 10-2014-7023305.

* cited by examiner

ACTINIC RAY-SENSITIVE OR RADIATION-SENSITIVE RESIN COMPOSITION, AND, ACTINIC RAY-SENSITIVE OR RADIATION-SENSITIVE FILM AND PATTERN FORMING METHOD, EACH USING THE SAME

CROSS-REFERENCE TO RELATED APPLICATIONS

This application is a Continuation of PCT International Application No. PCT/JP2013/059791, filed on Mar. 25, 2013, which claims priority under 35 U.S.C. §119(a) to Japanese Patent Application No. 2012-077761, filed on Mar. 29, 2012 and Japanese Patent Application No. 2013-033638, filed on Feb. 22, 2013. Each of the above application(s) is hereby expressly incorporated by reference, in its entirety, into the present application.

BACKGROUND OF THE INVENTION

1. Field of the Invention

The present invention relates to an actinic ray-sensitive or radiation-sensitive resin composition, and, an actinic ray-sensitive or radiation-sensitive film and a pattern forming method, each using the same. More specifically, the present invention relates to an actinic ray-sensitive or radiation-sensitive resin composition which is suitable for use in an ultra-microlithography process applicable to a process for manufacturing a super-LSI or a high-capacity microchip, a process for fabricating a nanoimprint mold, a process for producing a high-density information recording medium, and the like, and other photofabrication processes, and an actinic ray-sensitive or radiation-sensitive film and a pattern forming method, each using the same.

2. Description of the Related Art

In the production process for semiconductor devices such as ICs and LSIs, it is a practice in the related art to perform microfabrication by lithography using a photoresist composition. Recently, the formation of an ultrafine pattern in the submicron region or quarter-micron region has been demanded in accordance with the realization of high integration for integrated circuits. In accompaniment with this, a trend of wavelength shortening in the exposure wavelength from g-rays to i-rays, further to a KrF excimer laser light can be seen, and in recent years, an exposure device has been developed with an ArF excimer laser light with a 193 nm wavelength as a light source. In addition, as a technique for further increasing resolving power, a method in which a liquid with a high refractive index is filled in between a projection lens and a sample (hereinafter also referred to as an "immersion liquid"), the so-called immersion method has been developed. Furthermore, in recent years, developments in lithography using an electron beam, X-rays, EUV light or the like other than an excimer laser light is progressing. In particular, electron beam lithography is positioned as pattern forming technology of the next generation or a more advanced generation.

In lithography, a resist composition with high sensitivity and high resolution is desired. As a resist composition in which the sensitivity and/or resolution are improved, various kinds of resist compositions have so far been proposed (for example, refer to JP4710193B, JP3790649B, JP4425405B and JP2004-347738A). However, in these resist compositions, there is scope for further improvement in a pattern shape and defocus latitude (Depth of Focus; DOF)

SUMMARY OF THE INVENTION

An object of the present invention is to provide an actinic ray-sensitive or radiation-sensitive resin composition that can form a pattern with high sensitivity, resolution and defocus latitude (DOF), and with an excellent shape, and, an actinic ray-sensitive or radiation-sensitive film and a pattern forming method, each using the same.

The inventors have reached the completion of the present invention which is shown below as a result of extensive studies in order to solve the issues described above.

[1] An actinic ray-sensitive or radiation-sensitive resin composition containing a nitrogen-containing compound (N) which is represented by the following general formula (N1):

[Chem. 1]

(N1)

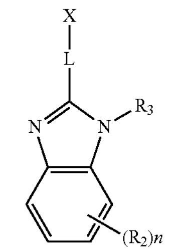

wherein, in the general formula (N1),

X represents a group including a heteroatom;

L represents a single bond or an alkylene group;

$R_2$ represents a substituent, in the case where a plurality of $R_2$'s are present, they may be the same as or different from each other and a plurality of $R_2$'s may be bonded to each other to form a ring;

$R_3$ represents a hydrogen atom or a substituent; and n represents an integer of 0 to 4.

[2] The actinic ray-sensitive or radiation-sensitive resin composition according to [1], wherein $R_3$ is a hydrogen atom, $-COOR_4$ or $-SO_2R_5$ and $R_4$ and $R_5$ are an alkyl group, an aryl group, an aralkyl group, an alkenyl group or a cycloalkyl group.

[3] The actinic ray-sensitive or radiation-sensitive resin composition according to [1] or [2], wherein $R_3$ is a hydrogen atom or $-COOR_4$ and a carbon atom in $R_4$ which is bonded to $-COO$ group in $-COOR_4$ above is a tertiary carbon atom.

[4] The actinic ray-sensitive or radiation-sensitive resin composition according to any one of [1] to [3], wherein $R_3$ is a hydrogen atom or $-COOR_4$ and $R_4$ is a tertiary alkyl group having 5 or more carbon atoms.

[5] The actinic ray-sensitive or radiation-sensitive resin composition according to any one of [1] to [4], wherein X is a hydroxyl group and a cyano group.

[6] The actinic ray-sensitive or radiation-sensitive resin composition according to any one of [1] to [5], wherein a nitrogen-containing compound (N) which is represented by the general formula (N1) is represented by any of the following general formulae.

[Chem. 2]

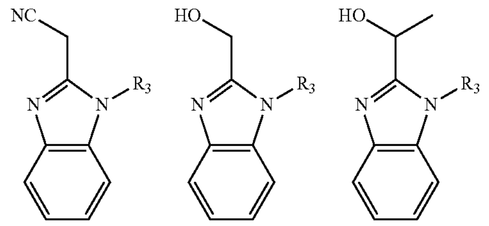

-continued

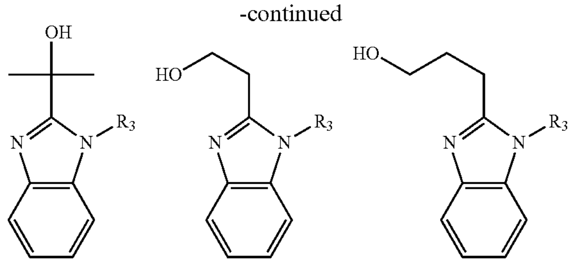

wherein, in the general formulae, $R_3$ represents a hydrogen atom or —$COOR_4$ and $R_4$ represents an alkyl group, an aryl group, an aralkyl group, an alkenyl group or a cycloalkyl group.

[7] The actinic ray-sensitive or radiation-sensitive resin composition according to [6], wherein $R_3$ is —$COOR_4$ and $R_4$ is t-amyl.

[8] The actinic ray-sensitive or radiation-sensitive resin composition according to any one of [1] to [7] further containing; a resin (Ab) of which the polarity changes by the action of an acid.

[9] The actinic ray-sensitive or radiation-sensitive resin composition according to [8], wherein the resin (Ab) contains a repeating unit (B) having a structural site which generates an acid by irradiation with actinic rays or radiation.

[10] The actinic ray-sensitive or radiation-sensitive resin composition according to [8] or [9], wherein the resin (Ab) contains at least one kind of repeating units (A) which is represented by the following general formula (A):

[Chem. 3]

(A)

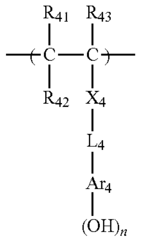

wherein, in the general formula (A), $R_{41}$, $R_{42}$ and $R_{43}$ each independently represent an hydrogen atom, an alkyl group, a cycloalkyl group, a halogen atom, a cyano group or an alkoxycarbonyl group (However, $R_{42}$ may be bonded to $Ar_4$ to form a ring and in this case, $R_{42}$ represents a single bond or an alkylene group.);

$X_4$ represents a single bond, —COO— or —$CONR_{64}$ (Here, $R_{64}$ represents a hydrogen atom or an alkyl group.);

$L_4$ represents a single bond or an alkylene group;

$Ar_4$ represents a (n+1)-valent aromatic ring group and in a case of being bonded to $R_{42}$ to form a ring, represents a (n+2)-valent aromatic ring group; and n represents an integer of 1 to 4.

[11] The actinic ray-sensitive or radiation-sensitive resin composition according to any one of [1] to [10] further containing; a compound which generates an acid by irradiation with actinic rays or radiation.

[12] An actinic ray-sensitive or radiation-sensitive film containing; the actinic ray-sensitive or radiation-sensitive resin composition according to any one of [1] to [11].

[13] A pattern forming method containing; forming a film including a composition according to any one of Claims 1 to 11, irradiating the film with actinic rays or radiation, and developing the irradiated film with actinic rays or radiation.

[14] The pattern forming method according to [13], wherein the actinic rays or radiation is EUV light.

[15] A semiconductor device which is manufactured according to steps including the pattern forming method according to [13] or [14].

According to the present invention, an actinic ray-sensitive or radiation-sensitive resin composition that can form a pattern with high sensitivity, resolution and defocus latitude (DOF), and with an excellent shape, and, an actinic ray-sensitive or radiation-sensitive film and a pattern forming method each using the same, can be provided.

DESCRIPTION OF THE PREFERRED EMBODIMENTS

Hereinafter, embodiments of the present invention will be described in detail.

In denotation of a group and an atomic group in the specification, in a case where substituted or unsubstituted is not specified, both a group and an atomic group which do not have a substituent and a group and an atomic group which have a substituent are included. For example, "an alkyl group" in which substituted or unsubstituted is not specified includes not only an alkyl group which does not have a substituent (unsubstituted alkyl group) but also an alkyl group which has a substituent (substituted alkyl group).

In the present invention, "actinic rays" or "radiation" refers to, for example, a bright line spectrum of a mercury lamp, far ultraviolet rays typified by an excimer laser, extreme ultraviolet rays (EUV light), an X-ray, a particle beam such as an electron beam and an ion beam, and the like. In addition, "light" in the present invention refers to the actinic rays or the radiation.

In addition, unless otherwise specified, "exposure" in this specification includes not only the exposure performed using a mercury lamp, far ultraviolet rays which are typified an excimer laser, an X-ray, extreme ultraviolet rays (EUV light) or the like, but also drawing performed using a particle beam such as an electron beam or an ion beam.

The actinic ray-sensitive or radiation-sensitive resin composition (hereinafter also simply referred to as a "composition of the present invention") according to the present invention contains [1] a nitrogen-containing compound (N) which is represented by the following general formula (N1) described later. The composition of the present invention may include [2] a resin (Ab) of which the polarity changes by the action of an acid. The composition according to the present invention may further include [3] a compound which generates an acid by irradiation with actinic rays or radiation. Examples of the other component which can be included in the composition according to the present invention include [4] a resin (Aa) including at least any of a fluorine atom and a silicon atom, [5] a basic compound, [6] a surfactant, [7] a dye, [8] a photo-base generator, [9] an antioxidant, [10] a solvent or the like. The composition of the present invention, for example, can be used for a pattern formation according to a method described later as a "pattern forming method"

The actinic ray-sensitive or radiation-sensitive resin composition according to the present invention may be used for a negative-tone development (a development in which the exposed portion remains as a pattern while the non-exposed portion is removed) and may be used in a positive-tone development (a development in which the exposed portion is removed while a non-exposed portion remains as a pattern). That is, the actinic ray-sensitive or radiation-sensitive resin composition according to the present invention may be an actinic ray-sensitive or radiation-sensitive resin composition for an organic solvent development, which is used for a development preformed using a developer that contains an organic solvent and may be an actinic ray-sensitive or radiation-sensitive resin composition for an alkali development which is used in a development using an alkali developer. Herein, "for an organic solvent development" means an application at least provided to the developing using a developer that contains an organic solvent and "for an alkali development" means an application at least provided to the developing using an alkali developer.

The actinic ray-sensitive or radiation-sensitive resin composition according to the present invention becomes a composition which can form a pattern with high sensitivity, resolution and defocus latitude (DOF), and with an excellent shape due to including a nitrogen-containing compound (N).

Hereinafter, each component described above will be described in order.

[1] Nitrogen-Containing Compound (N)

A nitrogen-containing compound (N) included in a composition of the present invention is represented by the following general formula (N1).

[Chem. 4]

(N1)

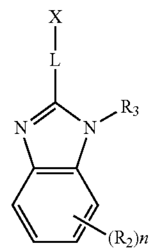

In the general formula (N1),

X represents a group including a heteroatom;

L represents a single bond or an alkylene group;

$R_2$ represents a substituent, in the case where a plurality of $R_2$'s are present, they may be the same as or different from each other and a plurality of $R_2$'s may be bonded to each other to form a ring;

$R_3$ represents a hydrogen atom or a substituent; and n represents an integer of 0 to 4.

Examples of the heteroatom in X include O, N, S, a halogen atom or the like and O or N is preferable. Examples of the group which is represented by X and includes a heteroatom, include a hydroxyl group, a cyano group, a thiol group, an ether group, a thioether group, an amino group and an amide group, a hydroxyl group or a cyano group is preferable and a hydroxyl group is particularly preferable.

An alkylene group which is represented by L may be either linear or branched, the number of carbon atoms is preferably 1 to 10, more preferably 1 to 5 and particularly preferably 1 to 3. An alkylene group which is represented by L may have a substituent. Examples of the substituent include an aryl group, a hydroxyl group, a halogen atom or the like.

Examples of the substituent which is represented by $R_2$ include an alkyl group, an aryl group, an alkoxy group, a hydroxyl group, a halogen atom, a nitro group, an alkylcarbonyl group, an arylcarbonyl group, a group formed by a combination of these groups and an ester group or an ether group or the like. Among these, an alkyl group, a group formed by a combination of an alkyl group and an ether group or an ester group and a hydroxyl group are preferable.

As an alkyl group, for example, an alkyl group having 1 to 20 carbon atoms is preferable and specific examples thereof include a methyl group, an ethyl group, a propyl group, an isopropyl group, an n-butyl group, an isobutyl group, a t-butyl group, a pentyl group, a hexyl group, or the like. An alkyl group may further have a substituent.

As an aryl group, for example, an aryl group having 6 to 20 carbon atoms is preferable and specific examples thereof include a phenyl group, a xylyl group, a toluoyl group, a cumenyl group, a naphthyl group, an anthracenyl group or the like.

As an alkoxy group, for example, an alkoxy group having 1 to 10 carbon atoms is preferable and specific examples thereof include a methoxy group, an ethoxy group, a propoxy group, a butoxy group or the like.

Examples of the halogen atom include a fluorine atom, a chlorine atom, a bromine atom and an iodine atom, a fluorine atom or a chlorine atom is preferable and a fluorine atom is most preferable.

Examples of the alkylcarbonyl group include a group formed by a combination of a group exemplified as an alkyl group described above and a carbonyl group.

Examples of the arylcarbonyl group include a group formed by a combination of a group exemplified as an aryl group described above and a carbonyl group.

Examples of the ester group include a group formed by a combination of —COO-group and a group exemplified as an alkyl group described above.

Examples of the ether group include a group formed by a combination of —O-group and any two of groups exemplified as an alkyl group described above. In any one of alkyl groups, one of hydrogen atoms is replaced with a single bond to form an alkylene group. In addition, each of two alkyl groups here may be the same as or different from each other.

A substituent which is represented by $R_2$ may further include a substituent. Preferred examples of the substituent which can be further include, include an alkyl group, a halogen atom, an alkoxy group, a cycloalkyl group, a hydroxyl group, a nitro group, an acyl group, an acyloxy group, an acylamino group, a sulfonylamino group, an alkylthio group, an arylthio group, an aralkylthio group, a thiophene carbonyloxy group, a thiophenemethyl carbonyloxy group, a heterocyclic residue such as a pyrrolidone residue or the like and a substituent having 12 or less carbon atoms is preferable.

A substituent which is represented by $R_3$ is preferably a hydrogen atom or a group which is represented by $-COOR_4$ or $-SO_2R_5$, $R_3$ is more preferably a hydrogen atom or a group which is represented by $-COOR_4$ and is particularly preferably a group which is represented by $-COOR_4$. Herein, $R_4$ and $R_5$ represent an alkyl group, an aryl group, an aralkyl group, an alkenyl group or a cycloalkyl group. These groups may further have a substituent and examples of the substituent include an alkyl group, an alkoxy group, an aryl group, a hydroxyl group, a halogen atom, a nitro group, an alkylcarbonyl group, an arylcarbonyl group, a group formed by a combination of these groups and an ester group or an ether group or the like. Among these, an alkyl group, an alkoxy group and an aryl group are preferable.

Examples of the alkyl group and the aryl group of $R_4$ and $R_5$ include the same groups included as examples of the alkyl group and the aryl group of $R_2$ described above.

As an aralkyl group of $R_4$ and $R_5$, for example, those of which the number of carbon atoms is preferably 7 to 15 and specific examples include a benzyl group or the like.

As the alkenyl group of $R_4$ and $R_5$, a group in which one of carbon-carbon single bonds of a group exemplified as an alkyl group of $R_2$ described above is replaced with a double bond is included.

As a cycloalkyl group of $R_4$ and $R_5$, for example, a cycloalkyl group having 3 to 10 carbon atoms is preferable and specific examples include a cyclobutyl group, a cyclopentyl group, a cyclohexyl group, a norbornyl group, an adamantyl group or the like.

A carbon atom in $R_4$ which is bonded to —COO group in —$COOR_4$ is preferably a tertiary carbon atom. Here, "tertiary carbon atom" means that the number of other carbon atoms bonded to a focused carbon atom is three. Therefore, "an carbon atom in $R_4$ bonded to —COO group is a tertiary carbon atom" means that a three remaining bonds included in carbon atom in $R_4$ bonded to —COO group other than a bond, which is needed for being bonded to —COO group, are respectively bonded to carbon atoms.

$R_4$ is preferably an alkyl group, the number of carbon atoms is preferably 4 or more and the number of carbon atoms is more preferably 5 or more. As such $R_4$, a t-alkyl group is preferable and a t-amyl group is more preferable.

$R_5$ is preferably an alkyl group or aryl group and is more preferably an aryl group.

n is preferably 0 to 2, is more preferably 0 or 1 and is particularly preferably 0.

In an actinic ray-sensitive or radiation-sensitive resin composition used as a chemical amplification type resist, by combining with an acid diffusion control agent having functions for controlling diffusion phenomenon of an acid generated from an acid generator in a resist film and inhibiting an undesirable chemical reaction in the non-exposed region, the storage stability of a resin composition is improved and the resolution as a resist is improved. Furthermore, it is known that the line width variation in a resist pattern due to the change of post exposure delay (PED) from the exposure to the development process can be controlled and the process stability is improved. The inventors have found that various performance as a resist is significantly improved by using a nitrogen-containing compound (N) described above and have reached the completion of the present invention as a result of extensive studies of an acid diffusion control agent in an actinic ray-sensitive or radiation-sensitive resin composition.

Therefore, by the nitrogen-containing compound (N) being contained in a composition of the present invention, in a case of using the composition of the present invention to form a pattern, it is thought that a pattern shape becomes a rectangular shape and furthermore, the sensitivity, the resolution and DOF are improved.

The nitrogen-containing compound (N), for example, is a compound which is represented by any of the general formulae as below.

[Chem. 5]

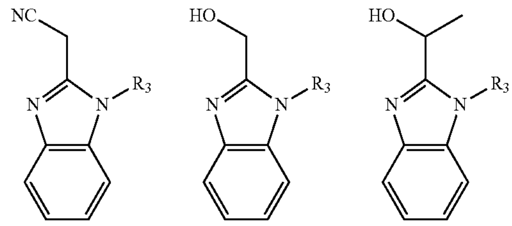

-continued

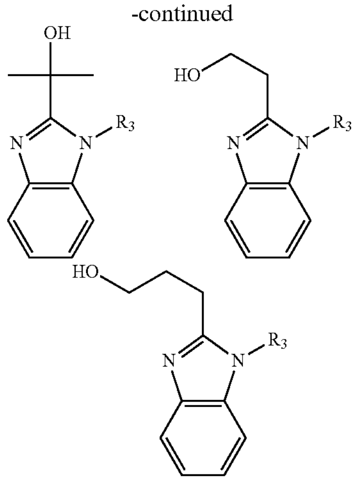

In each general formula described above, $R_3$ is as defined in the general formula (N1) described above.

Specific examples of the nitrogen-containing compound (N) are shown below, but the present invention is not limited thereto.

[Chem. 6]

(AM-1)

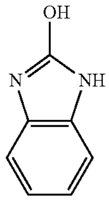

(AM-2)

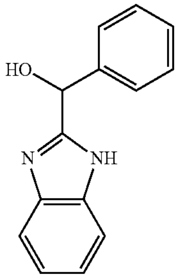

(AM-3)

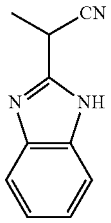

(AM-4)

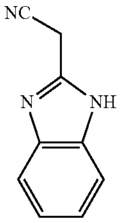

-continued
(AM-5)
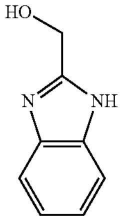
(AM-6)
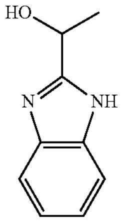
(AM-7)
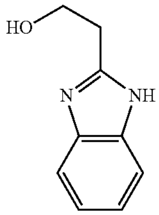
(AM-8)
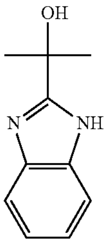
(AM-9)
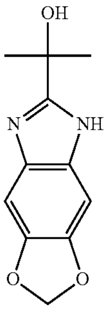
(AM-10)
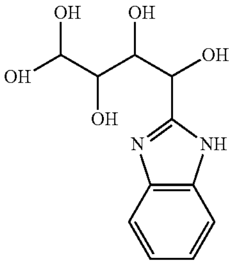
-continued
(AM-11)
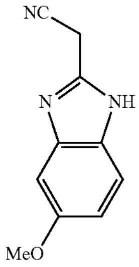
(AM-12)
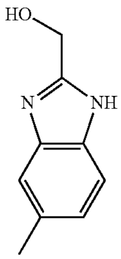
(AM-13)
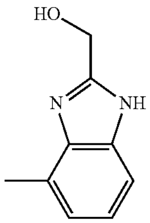
(AM-14)
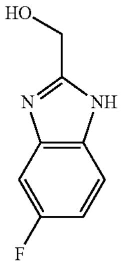
(AM-15)
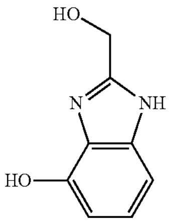
(AM-16)
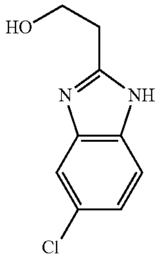

-continued
(AM-17)
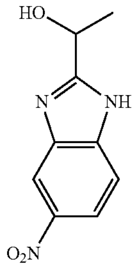
(AM-18)
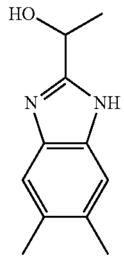
(AM-19)
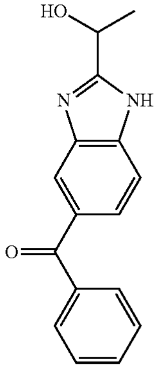
(AM-20)
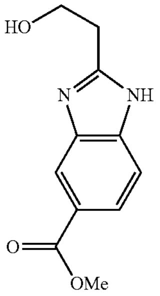
(AM-21)
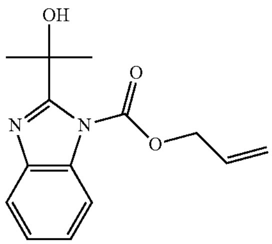
-continued
(AM-22)
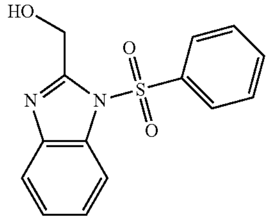
(AM-23)
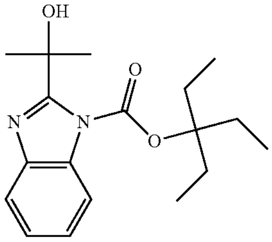
(AM-24)
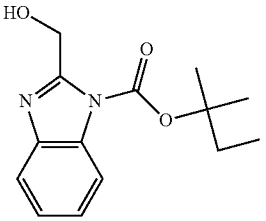
(AM-25)
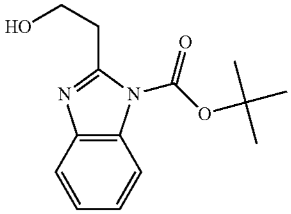
(AM-26)
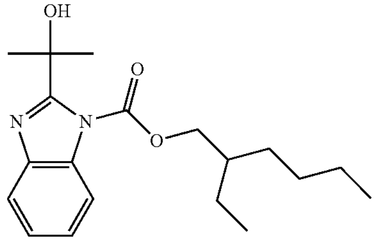
(AM-27)
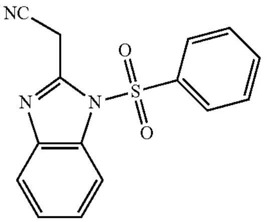
(AM-28)
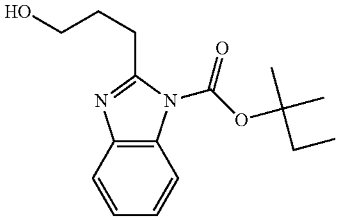

-continued
(AM-29)
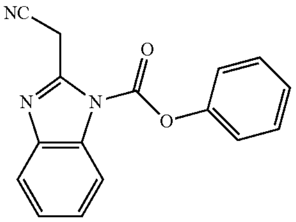
(AM-30)
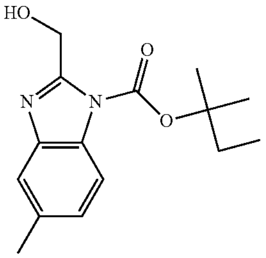
[Chem. 7]
(AM-31)
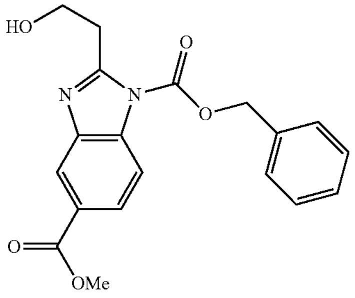
(AM-32)
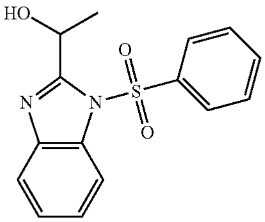
(AM-33)
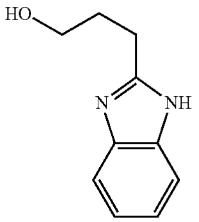
(AM-34)
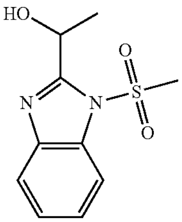
-continued
(AM-35)
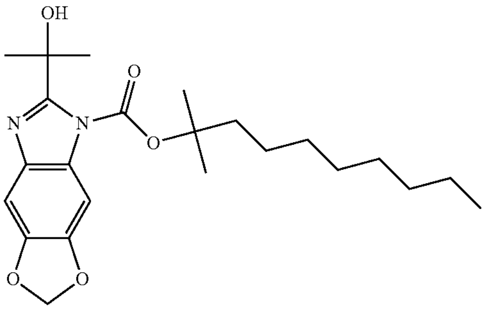
(AM-36)
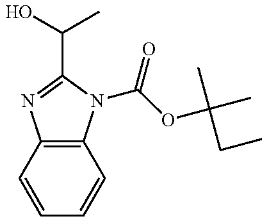
(AM-37)
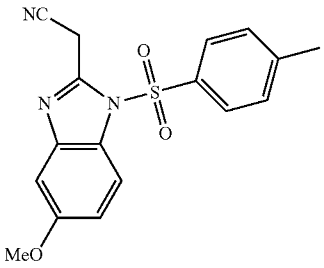
(AM-38)
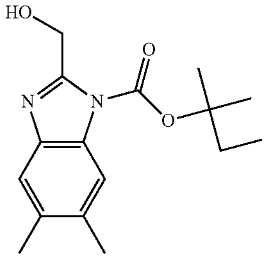
(AM-39)
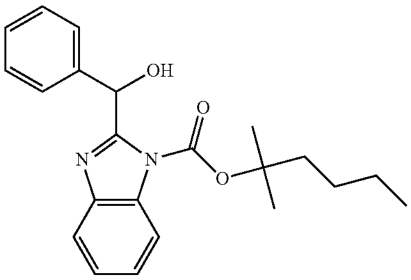
(AM-40)
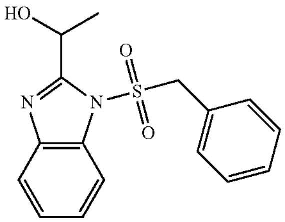

-continued
(AM-41)
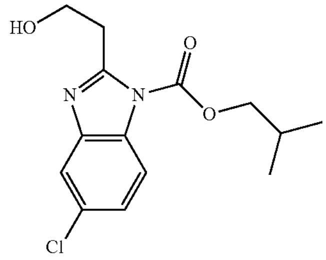
(AM-42)
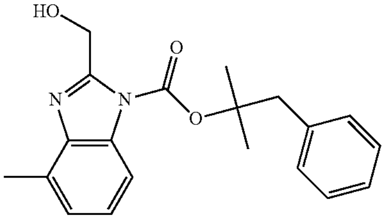
(AM-43)
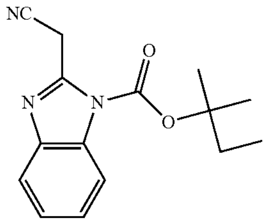
(AM-44)
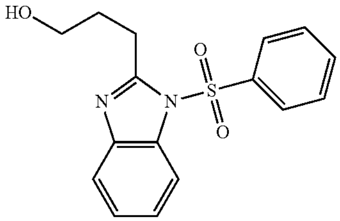
(AM-45)
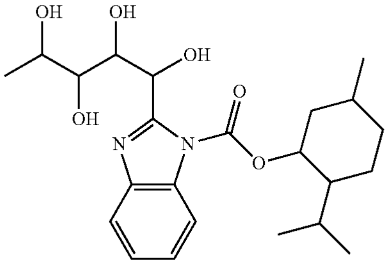
(AM-46)
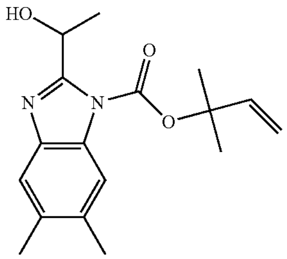
-continued
(AM-47)
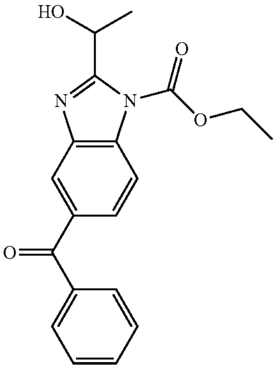
(AM-48)
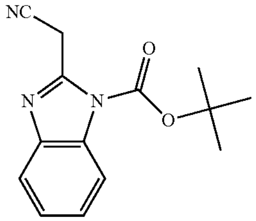
(AM-49)
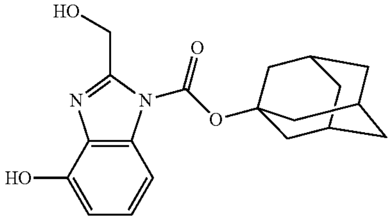
(AM-50)
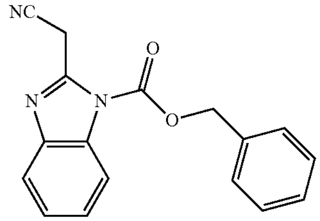
(AM-51)
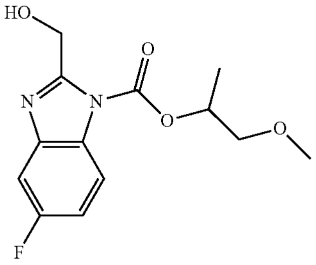
(AM-52)
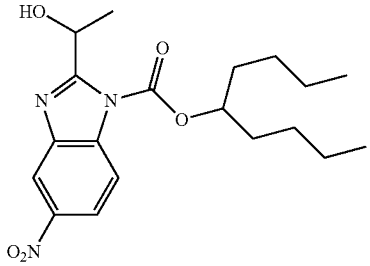

-continued

[Chem. 7-2]

(AM-53)

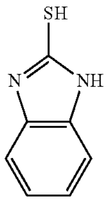

(AM-54)

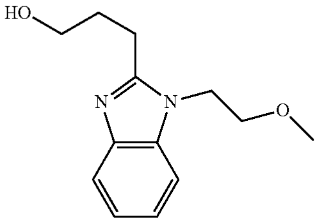

The molecular weight of the nitrogen-containing compound (N) is preferably 2,000 or less, more preferably 1,000 or less, further preferably 750 or less and most preferably 500 or less.

The nitrogen-containing compound (N) described above may be used alone or may be used in combination of two or more kinds thereof. The nitrogen-containing compound (N) is preferably a non-ionic compound.

The content of the nitrogen-containing compound (N) in the present invention is preferably 0.001 to 20% by mass, more preferably 0.001 to 10% by mass and particularly preferably 0.01 to 5% by mass based on the total solid contents of the composition.

[2] Resin (Ab) in which the Polarity Changes by Action of an Acid

The composition according to the present invention may contain a resin (Ab) in which the polarity changes due to the action of an acid that generates by irradiation with actinic rays or radiation. The resin (Ab) is a resin of which the solubility with respect to a developer changes (increases or decreases) due to the action of an acid that generates by irradiation with actinic rays or radiation. Examples of the developer include a developer such as an alkali developer or a developer which is set an organic solvent as a main component (also referred to as an "organic-based developer") described later. In a case of performing a negative-tone development using a developer containing an organic solvent, the resin (Ab) is a resin of which the polarity increases by the action of an acid and the degree of solubility with respect to a developer containing an organic solvent decreases, and in a case of performing a positive-tone development using an alkali developer, the resin (Ab) is a resin of which the polarity increases by the action of an acid and the degree of solubility with respect to an alkali developer increases. The composition according to the present invention preferably contains a resin of which the alkali solubility changes (increases or decreases) by the action of an acid which generates by irradiation with actinic rays or radiation as a resin (Ab).

The resin (Ab) is preferably insoluble or slightly soluble with respect to an alkali developer.

The resin (Ab) preferably has a repeating unit having an acid-decomposable group.

Examples of the acid-decomposable group include groups in which a hydrogen atom of an alkali-soluble group such as a carboxyl group, a phenolic hydroxyl group, a sulfonic acid group, and a thiol group is protected with a group leaving by the action of an acid.

Examples of the group leaving by the action of an acid include $-C(R_{36})(R_{37})(R_{38})$, $-C(R_{36})(R_{37})(OR_{39})$, $-C(=O)-O-C(R_{36})(R_{37})(R_{38})$, $-C(R_{01})(R_{02})(OR_{39})$, $-C(R_{01})(R_{02})-C(=O)-O-C(R_{36})(R_{37})(R_{38})$, and the like.

In the formulae, $R_{36}$ to $R_{39}$ each independently represent an alkyl group, a cycloalkyl group, an aryl group, an aralkyl group, or an alkenyl group. $R_{36}$ and $R_{37}$ may be bonded to each other to form a ring. $R_{01}$ to $R_{02}$ each independently represent a hydrogen atom, an alkyl group, a cycloalkyl group, an aryl group, an aralkyl group, or an alkenyl group.

In one embodiment, the resin (Ab) preferably contains a repeating unit represented by the following general formula (AI) as a repeating unit having an acid-decomposable group.

[Chem. 8]

(AI)

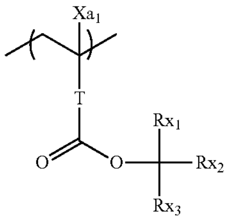

In the general formula (AI), $Xa_1$ represents a hydrogen atom, a methyl group or a group represented by $-CH_2-R_9$. $R_9$ represents a hydroxyl group or a monovalent organic group, for example, includes an alkyl group having 1 to 5 carbon atoms or an acyl group, is preferably an alkyl group having 1 to 3 carbon atoms and further preferably a methyl group. $Xa_1$ is preferably a hydrogen atom, a methyl group, a trifluoromethyl group, or a hydroxymethyl group.

T represents a single bond or a divalent connecting group.

$Rx_1$ to $Rx_3$ each independently represent an alkyl group (linear or branched) or a cycloalkyl group (monocyclic or polycyclic).

At least two members out of $Rx_1$ to $Rx_3$ may be bonded to each other to form a cycloalkyl group (monocyclic or polycyclic).

Examples of the divalent connecting group of T include an alkylene group, —COO-Rt-, —O-Rt- or the like. In the formulae, Rt represents an alkylene group or a cycloalkylene group.

T is preferably a single bond or —COO-Rt-. Rt is preferably an alkylene group having 1 to 5 carbon atoms and more preferably $-CH_2-$ or $-(CH_2)_3-$.

The alkyl group of $Rx_1$ to $Rx_3$ is preferably an alkyl group having 1 to 4 carbon atoms such as a methyl group, an ethyl group, an n-propyl group, an isopropyl group, an n-butyl group, an isobutyl group, and a t-butyl group.

The cycloalkyl group of $Rx_1$ to $Rx_3$ is preferably a monocyclic cycloalkyl group such as a cyclopentyl group and a cyclohexyl group, or a polycyclic cycloalkyl group such as a norbornyl group, a tetracyclodecanyl group, a tetracyclododecanyl group, and an adamantyl group.

The cycloalkyl group formed by the bonding of at least two members out of $Rx_1$ to $Rx_3$ is preferably a monocyclic cycloalkyl group such as a cyclopentyl group and a cyclohexyl group, or a polycyclic cycloalkyl group such as a norbornyl group, a tetracyclodecanyl group, a tetracyclododecanyl group, and an adamantyl group.

An embodiment where $Rx_1$ is a methyl group or an ethyl group, and $Rx_2$ and $Rx_3$ are bonded to each other to form the above-described cycloalkyl group is preferable.

The respective groups above may have a substituent, and examples of the substituent include an alkyl group (having 1 to 4 carbon atoms), a halogen atom, a hydroxyl group, an alkoxy group (having 1 to 4 carbon atoms), a carboxyl group and an alkoxycarbonyl group (having 2 to 6 carbon atoms), and the number of carbon atoms is preferably 8 or less.

In another embodiment, the resin (Ab) preferably contains at least one kind of repeating units represented by the following general formulae (A1) and (A2)

[Chem. 9]

(A1)

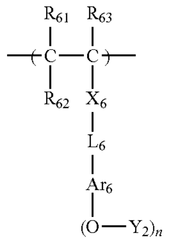

(A2)

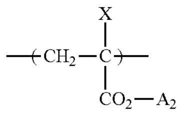

In the general formula (A1), $R_{61}$, $R_{62}$ and $R_{63}$ each independently represent a hydrogen atom, an alkyl group, a cycloalkyl group, a halogen atom, a cyano group or an alkoxycarbonyl group. However, $R_{62}$ may be bonded to $Ar_6$ to form a ring, and in this case, $R_{62}$ represents a single bond or an alkylene group.

$X_6$ represents a single bond, —COO—, or —$CONR_{64}$—. $R_{64}$ represents a hydrogen atom or an alkyl group.

$L_6$ represents a single bond or an alkylene group.

$Ar_6$ represents a (n+1)-valent aromatic ring group and in a case of being bonded to $R_{62}$ to form a ring, represents a (n+2)-valent aromatic ring group.

In a case of n=1, $Y_2$ represents a group leaving by the action of an acid and in a case of n≥2, $Y_2$'s each independently represent a hydrogen atom or a group leaving by the action of an acid. However, at least one of $Y_2$'s represents a group leaving by the action of an acid.

n represents an integer of 1 to 4.

The general formula (A1) will be described in more detail.

Examples of the alkyl group of $R_{61}$ to $R_{63}$ in the general formula (A1) preferably include an alkyl group having 20 or less carbon atoms such as a methyl group, an ethyl group, a propyl group, an isopropyl group, an n-butyl group, a sec-butyl group, a hexyl group, a 2-ethylhexyl group, an octyl group, a dodecyl group, which may have a substituent, and more preferably include an alkyl group having 8 or less carbon atoms.

Examples of the alkyl group included in an alkoxycarbonyl group are preferably the same as an alkyl group of $R_{61}$ to $R_{63}$ described above.

A cycloalkyl group may be a monocyclic type or polycyclic type and preferably include a monocyclic type cycloalkyl group having 3 to 8 carbon atoms such as a cyclopropyl group, a cyclopentyl group, a cyclohexyl group, which may have a substituent.

Examples of the halogen atom include a fluorine atom, a chlorine atom, a bromine atom and an iodine atom and a fluorine atom is more preferable.

In a case where $R_{62}$ is bonded to $Ar_6$ to form a ring, $R_{62}$ represents a single bond or an alkylene group. Examples of the alkylene group in this case preferably include an alkylene group having 1 to 8 carbon atoms such as a methylene group, an ethylene group, a propylene group, a butylene group, a hexylene group and an octylene group, which may have a substituent. As a ring in which $R_{62}$ is bonded to $Ar_6$ to form, a 5-membered ring or a 6-membered ring is preferable.

Examples of the alkyl group in $R_{64}$ in —$CONR_{64}$— ($R_{64}$ represents a hydrogen atom or an alkyl group) represented by $X_6$ include the same as an alkyl group of $R_{61}$ to $R_{63}$.

As X6, a single bond, —COO— and —CONH— are preferable and a single bond and —COO— are more preferable.

Examples of the alkylene group in $L_6$ preferably include a an alkylene group having 1 to 8 carbon atoms such as a methylene group, an ethylene group, a propylene group, a butylene group, a hexylene group and an octylene group, which may have a substituent.

$Ar_6$ represents a (n+1)-valent aromatic ring group. A divalent aromatic ring group may have a substituent in a case where n is 1 and, for example, an arylene group having 6 to 18 carbon atoms such as a phenylene group, a tolylene group, a naphthylene group or, for example, a divalent aromatic ring group including a hetero ring such as thiophene, furan, pyrrole, benzothiophene, benzofuran, benzopyrrole, triazine, imidazole, benzimidazole, triazole, thiadiazole or thiazole is included as a preferred example.

Specific examples of the (n+1)-valent aromatic ring group in a case where n is an integer of 2 or more suitably include a group where arbitrary (n+1) hydrogen atoms are removed from specific examples in divalent aromatic ring groups described above.

The (n+1)-valent aromatic ring group may further have a substituent.

Examples of the substituent which an alkyl group, a cycloalkyl group, an alkoxycarbonyl, an alkylene group and (n+1)-valent aromatic ring group can have described above, include an alkyl group, a cycloalkyl group, an aryl group, an amino group, an amido group, a ureido group, a urethane group, a hydroxyl group, a carboxyl group, a halogen atom, an alkoxy group, a thioether group, an acyl group, an acyloxy group, an alkoxycarbonyl group, a cyano group, a nitro group or the like and the number of carbon atoms of the substituent is preferably 10 or less.

n is preferably 1 or 2 and more preferably 1.

n Y2's each independently represent a hydrogen atom or a group leaving by the action of an acid. However, at least one of n represents a group leaving by the action of an acid.

Examples of Y2 of the group leaving by the action of an acid include —$C(R_{36})(R_{37})(R_{38})$, —C(=O)—O—$C(R_{36})(R_{37})(R_{38})$, —$C(R_{01})(R_{02})(OR_{39})$, —$C(R_{01})(R_{02})$—C(=O)—O—$C(R_{36})(R_{37})(R_{38})$, —$CH(R_{36})(Ar)$, or the like.

In the formulae, $R_{36}$ to $R_{38}$ each independently represent an alkyl group, a cycloalkyl group, a monovalent aromatic ring group, a group formed by a combination of an alkylene group and a monovalent aromatic ring group, or an alkenyl group. $R_{36}$ and $R_{37}$ may be bonded to each other to form a ring.

$R_{01}$ and $R_{02}$ each independently represent a hydrogen atom, an alkyl group, a cycloalkyl group, a monovalent aromatic ring group, a group formed by a combination of an alkylene group and a monovalent aromatic ring group, or an alkenyl group.

Ar represents a monovalent aromatic ring group.

An alkyl group in $R_{36}$ to $R_{38}$, $R_{01}$ and $R_{02}$ is preferably an alkyl group having 1 to 8 carbon atoms and, for example, a methyl group, an ethyl group, a propyl group, an n-butyl group, a sec-butyl group, a hexyl group, an octyl group, or the like is included.

A cycloalkyl group in $R_{36}$ to $R_{38}$, $R_{01}$ and $R_{02}$ may be a monocyclic type or polycyclic type. As a monocyclic type, a cycloalkyl group having 3 to 8 carbon atoms is preferable and, for example, a cyclopropyl group, a cyclobutyl group, a cyclopentyl group, a cyclohexyl group, a cyclooctyl group, or the like is included. As a polycyclic type, a cycloalkyl group having 6 to 20 carbon atoms is preferable and, for example, an adamantyl group, a norbornyl group, an isobornyl group, a camphanyl group, a dicyclopentyl group, an α-pinanyl group, a tricyclodecanyl group, a tetracyclododecyl group, an androstanyl group, or the like is included. Incidentally, parts of carbon atoms in the cycloalkyl group may be substituted with heteroatoms such as an oxygen atom.

A monovalent aromatic ring group of $R_{36}$ to $R_{38}$, $R_{01}$, $R_{02}$ and Ar is preferably a monovalent aromatic ring group having 6 to 10 carbon atoms and, for example, an aryl group such as a phenyl group, a naphthyl group or anthryl group or a divalent aromatic ring group including a hetero ring such as thiophene, furan, pyrrole, benzothiophene, benzofuran, benzopyrrole, triazine, imidazole, benzimidazole, triazole, thiadiazole or thiazole is included.

As a group formed by a combination of an alkylene group and a monovalent aromatic ring group of $R_{36}$ to $R_{38}$, $R_{01}$ and $R_{02}$, an aralkyl group having 7 to 12 carbon atoms is preferable and, for example, a benzyl group, a phenethyl group, a naphthylmethyl group or the like is included.

An alkenyl group in $R_{36}$ to $R_{38}$, $R_{01}$ and $R_{02}$ is preferably an alkenyl group having 2 to 8 carbon atoms and, for example, a vinyl group, an allyl group, a butenyl group, a cyclohexenyl group, or the like is included.

A ring in which $R_{36}$ and $R_{37}$ are bonded to each other to form may be a monocyclic type or polycyclic type. As a monocyclic type, a cycloalkyl structure having 3 to 8 carbon atoms is preferable and, for example, a cyclopropane structure, a cyclobutane structure, a cyclopentane structure, a cyclohexane structure, a cycloheptane structure, a cyclooctane structure, or the like is included. As a polycyclic type, a cycloalkyl structure having 6 to 20 carbon atoms is preferable and, for example, an adamantane structure, a norbornane structure, a dicyclopentane structure, a tricyclodecane structure, a tetracyclododecane structure, or the like is included. Incidentally, parts of carbon atoms in the cycloalkyl structure may be substituted with heteroatoms such as an oxygen atom.

The respective groups above as $R_{36}$ to $R_{38}$, $R_{01}$, $R_{02}$ and Ar may have a substituent, and examples of the substituent include an alkyl group, a cycloalkyl group, an aryl group, an amino group, an amido group, a ureido group, a urethane group, a hydroxyl group, a carboxyl group, a halogen atom, an alkoxy group, a thioether group, an acyl group, an acyloxy group, an alkoxycarbonyl group, a cyano group, a nitro group, or the like and the number of carbon atoms of the substituent is preferably 8 or less.

As $Y_2$ of the group leaving by the action of an acid, a structure represented by the following general formula (VI-A) is more preferable.

[Chem. 10]

(VI-A)

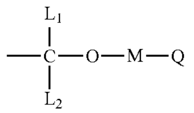

Here, $L_1$ and $L_2$ each independently represent a hydrogen atom, an alkyl group, a cycloalkyl group, a monovalent aromatic ring group or a group formed by a combination of an alkylene group and a monovalent aromatic ring group.

M represents a single bond or a divalent connecting group.

Q represents an alkyl group, a cycloalkyl group which may include a heteroatom, a monovalent aromatic ring group which may include a heteroatom, an amino group, an ammonium group, a mercapto group, a cyano group or an aldehyde group.

At least two of Q, M, $L_1$ may be bonded to form a ring (preferably a 5-membered or a 6-membered ring).

An alkyl group as $L_1$ and $L_2$, for example, is an alkyl group having 1 to 8 carbon atoms, and specific examples preferably include a methyl group, an ethyl group, a propyl group, an n-butyl group, a sec-butyl group, a hexyl group or an octyl group.

A cycloalkyl group as $L_1$ and $L_2$, for example, is a cycloalkyl group having 3 to 15 carbon atoms, and specific examples include a cyclopentyl group, a cyclohexyl group, a norbornyl group, an adamantyl group, or the like as a preferable example.

A monovalent aromatic ring group as $L_1$ and $L_2$, for example, is an aryl group having 6 to 15 carbon atoms, and specific examples include a phenyl group, a tolyl group, a naphthyl group, an anthryl group, or the like as a preferable example.

A group formed by a combination of an alkylene group and a monovalent aromatic ring group as $L_1$ and $L_2$, for example, is a group having 6 to 20 carbon atoms, and an aralkyl group such as a benzyl group or phenethyl group is included.

A divalent connecting group as M, for example, is an alkylene group (for example, a methylene group, an ethylene group, a propylene group, a butylene group, a hexylene group, an octylene group, or the like), a cycloalkylene group (for example, a cyclopentylene group, a cyclohexylene group, an adamantylene group, or the like), an alkenylene group (for example, a vinylene group, a propenylene group, a butenylene group, or the like), a divalent aromatic ring group (for example, a phenylene group, a tolylene group, a naphthylene group, or the like), —S—, —O—, —CO—, $—SO_2—$, $—N(R_0)—$ and a divalent connecting group formed by a combination of a plurality of these groups. $R_0$ is a hydrogen atom or an alky group (for example, it is an alkyl group having 1 to 8 carbon atoms, and specific examples are a methyl group, an ethyl group, a propyl group, an n-butyl group, a sec-butyl group, a hexyl group, an octyl group, or the like).

An alkyl group as Q is the same as each group as $L_1$ and $L_2$ described above.

As an aliphatic hydrocarbon ring group which does not have a heteroatom and a monovalent aromatic ring group which does not have a heteroatom in a cycloalkyl group which may include a heteroatom and a monovalent aromatic ring group which may have a heteroatom as Q, a cycloalkyl group, a monovalent aromatic ring group and the like as $L_1$ and $L_2$ described above are included, and the number of carbon atoms is preferably 3 to 15.

Examples of the cycloalkyl group including a heteroatom and the monovalent aromatic ring group including a heteroatom include a group having a heterocycle structure such as thiirane, cyclothiolane, thiophene, furan, pyrrole, benzothiophene, benzofuran, benzopyrrole, triazine, imidazole, benzimidazole, triazole, thiadiazole, thiazole or pyrrolidone, however, as long as a group has a structure which is generally called a heterocycle (a ring formed by carbon atoms and heteroatoms or a ring formed by heteroatoms), it is not limited thereto.

Examples of the ring in which at least two of Q, M and $L_1$ may be bonded to form include a case where at least two of Q, M and $L_1$ are bonded to form, for example, a propylene group or a butylene group and a 5-membered or a 6-membered ring containing an oxygen atom is formed.

Each group represented by $L_1$, $L_2$, M and Q in the general formula (VI-A) may have a substituent, for example, a substituent which is described as a substituent which may be included in $R_{36}$ to $R_{38}$, $R_{01}$, $R_{02}$ and Ar described before is included, and the number of carbon atoms of a substituent is preferably 8 or less.

As a group represented by -M-Q, a group which is configured by 1 to 30 carbon atoms is preferable and a group which is configured by 5 to 20 carbon atoms is more preferable.

A repeating unit represented by the general formula (A1) particularly preferably have a structure represented by the following general formula (A1').

[Chem. 11]

(A1')

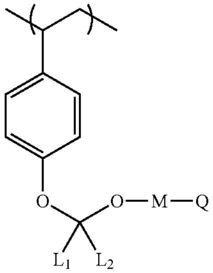

L1, L2, M and Q in the general formula (A1') is as defined in the general formula (VI-A) described above.

Specific examples of the repeating unit represented by the general formula (A1) are shown below, but the present invention is not limited thereto.

[Chem. 12-1]

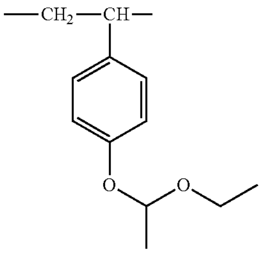

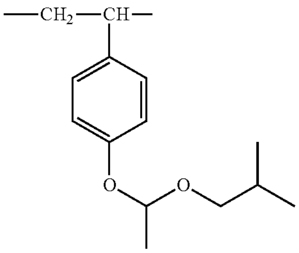

-continued

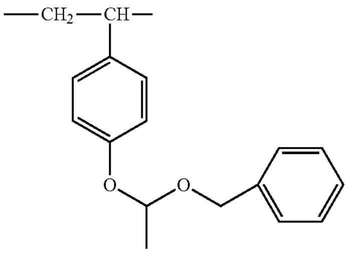

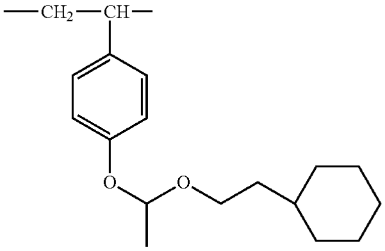

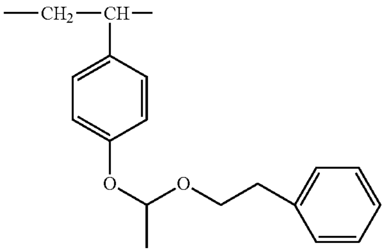

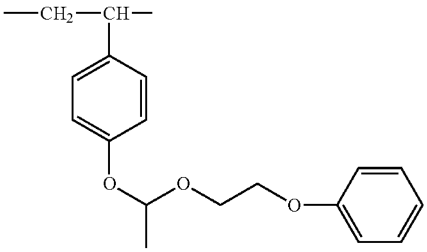

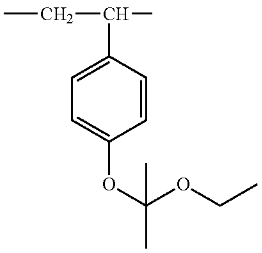

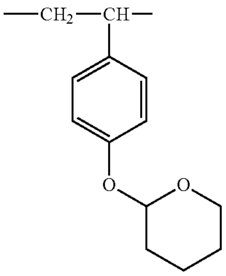

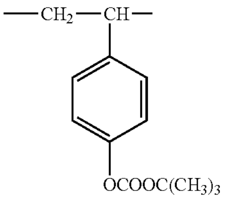

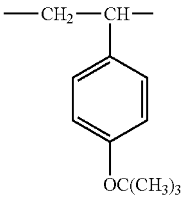

-continued
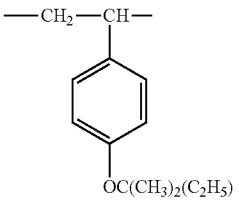
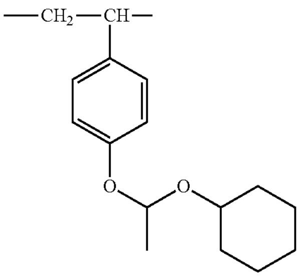
[Chem. 12-2]
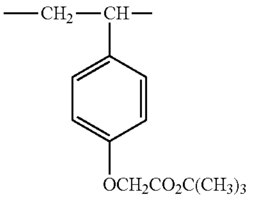
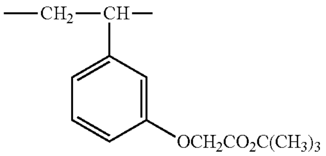
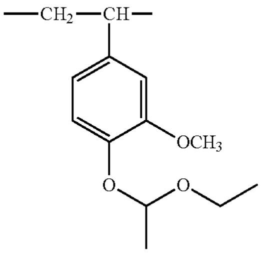
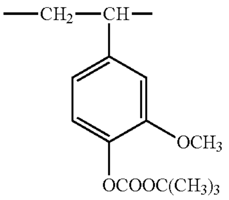
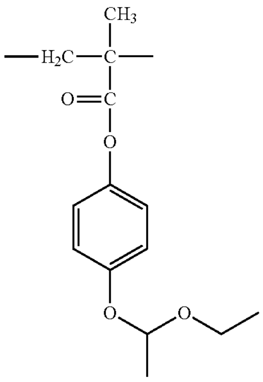
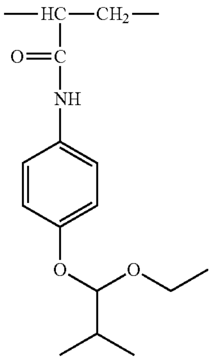
[Chem. 12-3]
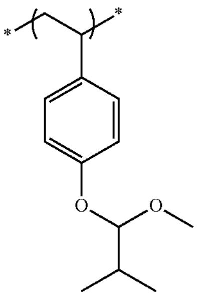
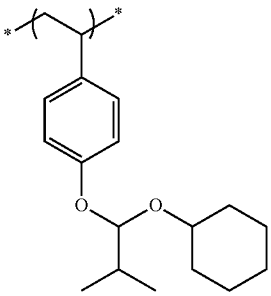
-continued
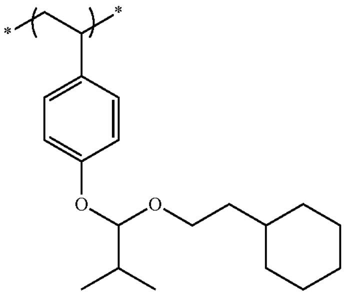
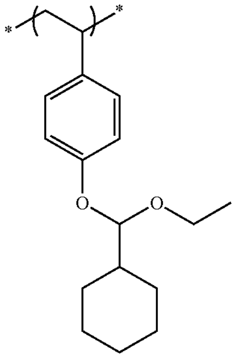
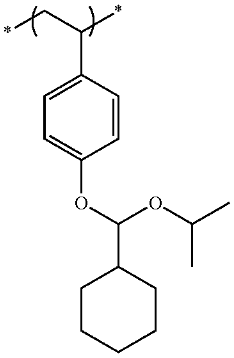
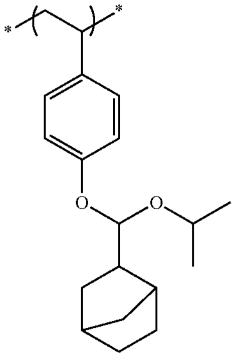
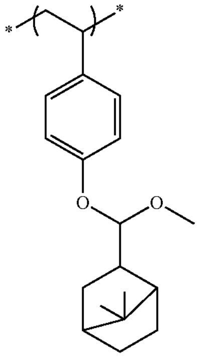
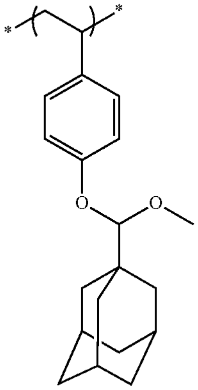
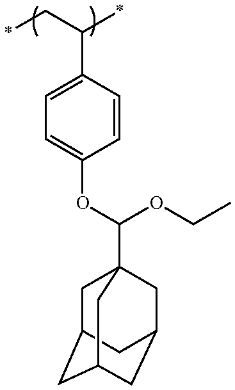

-continued

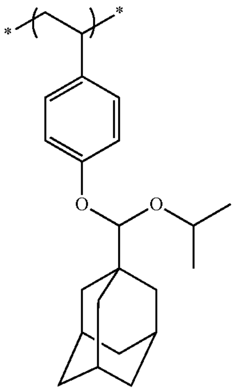
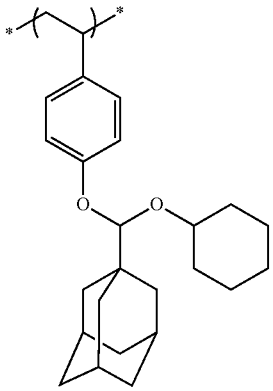
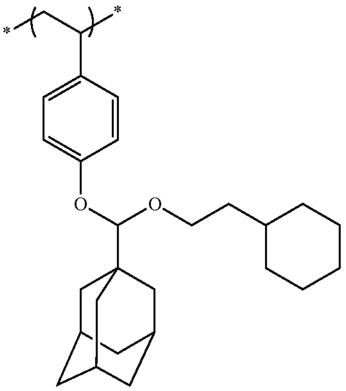
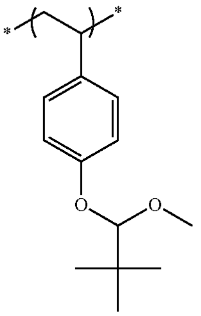
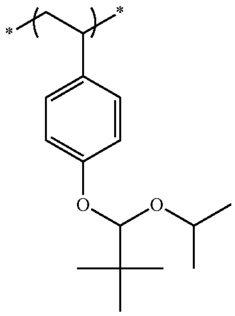
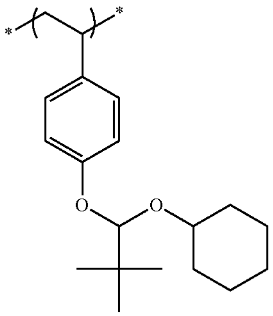
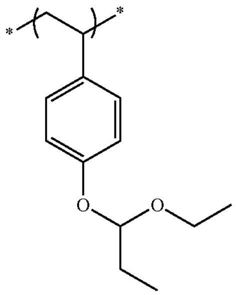
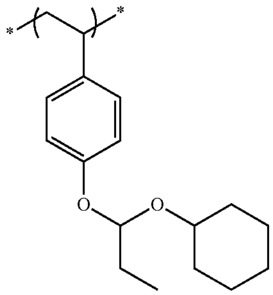

-continued

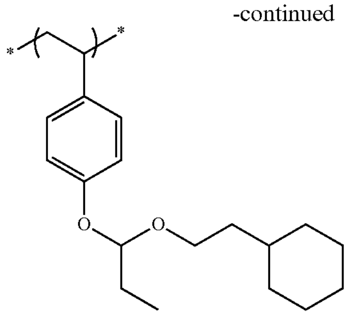
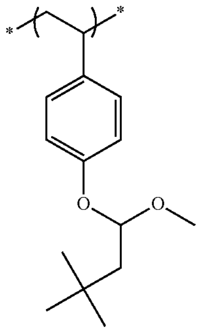
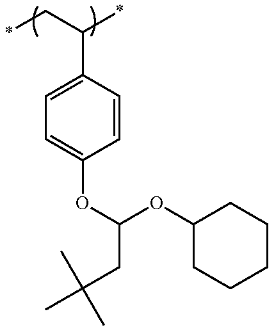
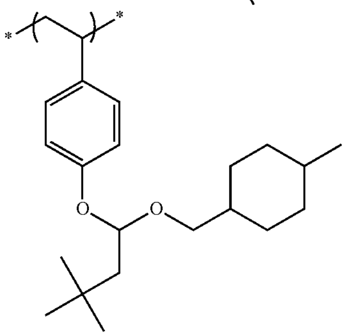
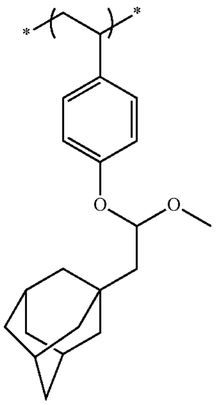
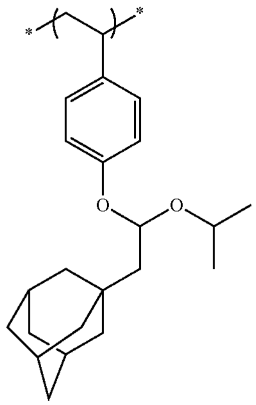
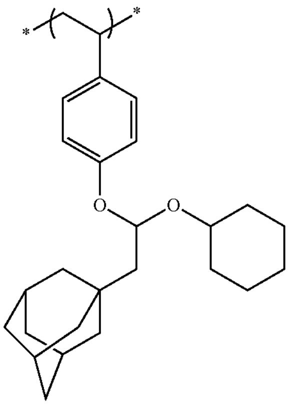

Next, the repeating unit represented by the general formula (A2) will be described.

X represents a hydrogen atom, an alkyl group, a hydroxyl group, an alkoxy group, a halogen atom, a cyano group, a nitro group, an acyl group, an acyloxy group, a cycloalkyl group, a cycloalkyloxy group, an aryl group, a carboxyl group, an alkyloxycarbonyl group, an alkylcarbonyloxy group, or an aralkyl group.

The alkyl group as X may have a substituent and may be either linear or branched. The linear alkyl group is preferably an alkyl group having 1 to 30 carbon atoms, more preferably 1 to 20, and examples thereof include a methyl group, an ethyl group, an n-propyl group, an n-butyl group, an n-pentyl group, an n-hexyl group, an n-heptyl group, an n-octyl group, an n-nonyl group, an n-decanyl group, or the like. The branched alkyl group is preferably an alkyl group having 3 to 30 carbon atoms, more preferably 3 to 20, and examples thereof include an i-propyl group, an i-butyl group, a t-butyl group, an i-pentyl group, a t-pentyl group, an i-hexyl group, a t-hexyl group, an i-heptyl group, a t-heptyl group, an i-octyl group, a t-octyl group, an i-nonyl group and a t-decanoyl group.

The alkoxy group as X may have a substituent, and it is, for example, an alkoxy group having 1 to 8 carbon atoms, examples of which include a methoxy group, an ethoxy group, a propoxy group, a butoxy group, a pentyloxy group, a hexyloxy group, and a cyclohexyloxy group.

Examples of the halogen atom as X include a fluorine atom, a chlorine atom, a bromine atom and an iodine atom, and a fluorine atom is preferable.

The acyl group as X may have a substituent, and it is, for example, an acyl group having 2 to 8 carbon atoms, specific examples of which preferably include a formyl group, an acetyl group, a propanoyl group, a butanoyl group, a pivaloyl group and a benzoyl group.

The acyloxy group as X may have a substituent, and it is, for example, an acyloxy groups having 2 to 8 carbon atoms, examples of which include an acetoxy group, a propionyloxy group, a butylyloxy group, a valeryloxy group, a pivaloyloxy group, a hexanoyloxy group, an octanoyloxy group, and a benzoyloxy group.

The cycloalkyl group as X may have a substituent and may be monocyclic, polycyclic, or a bridged structure. For example, the cycloalkyl group may have a bridged structure. The monocyclic type is preferably a cycloalkyl group having 3 to 8 carbon atoms, and examples thereof include a cyclopropyl group, a cyclopentyl group, a cyclohexyl group, a cyclobutyl group and a cyclooctyl group. The polycyclic cycloalkyl group includes a group having a bicyclo structure, a tricyclo structure, a tetracyclo structure, and the like and having 5 or more carbon atoms, and a cycloalkyl group having 6 to 20 carbon atoms is preferable. Examples thereof include an adamantyl group, a norbornyl group, an isobornyl group, a camphanyl group, a dicyclopentyl group, an -pinanyl group, a tricyclodecanyl group, a tetracyclododecyl group, and an androstanyl group. Further, parts of carbon atoms in the cycloalkyl group may be substituted with a heteroatom such as an oxygen atom.

The aryl group as X may have a substituent, and is preferably an aryl group having 6 to 14 carbon atoms. Examples thereof include a phenyl group, a xylyl group, a tolyl group, a cumenyl group, a naphthyl group, and an anthracenyl group.

The alkyloxycarbonyl group as X may have a substituent, and is preferably an alkyloxycarbonyl group having 2 to 8 carbon atoms. Examples thereof include a methoxycarbonyl group, an ethoxycarbonyl group, and a propoxycarbonyl group.

The alkylcarbonyloxy group as X may have a substituent, and is preferably an alkylcarbonyloxy group having 2 to 8 carbon atoms. Examples thereof include a methylcarbonyloxy group and an ethylcarbonyloxy group.

The aralkyl group as X may have a substituent, and is preferably an aralkyl group having 7 to 16 carbon atoms. Examples thereof include a benzyl group.

Examples of the substituent which an alkyl group, an alkoxy group, an acyl group, a cycloalkyl group, an aryl group, an alkyloxycarbonyl group, an alkylcarbonyloxy group, an aralkyl group as X may further have, include a hydroxyl group, a fluorine atom, a chlorine atom, a bromine atom, an iodine atom, an alkyl group, an alkoxy group, a halogen atom, a cyano group, a nitro group, an acyl group, an acyloxy group, a cycloalkyl group, an aryl group, a carboxyl group, an alkyloxycarbonyl group, an alkylcarbonyloxy group, an aralkyl group, or the like.

$A_2$ represents a group leaving by the action of an acid. That is, the repeating unit represented by the general formula (A2) is provided with a group represented by "—$COOA_2$" as the acid-decomposable group. Examples of $A_2$ include the same as those described above for $Y_2$ in the general formula (A1).

$A_2$ is preferably a hydrocarbon group (preferably having 20 or less carbon atoms, and more preferably having 4 to 12 carbon atoms), and more preferably a t-butyl group, a t-amyl group, or a hydrocarbon group having an alicyclic structure (for example, an alicyclic group itself, and a group having the alkyl group substituted with an alicyclic group).

$A_2$ is preferably a tertiary alkyl group or a tertiary cycloalkyl group.

The alicyclic structure may be monocyclic or polycyclic. Specific examples thereof include groups having a monocyclo structure, a bicyclo structure, a tricyclo structure, and a tetracyclo structure, each having 5 or more carbon atoms. The number of carbon atoms is preferably 6 to 30, and particularly preferably 7 to 25. The hydrocarbon group having the alicyclic structure may have a substituent.

Examples of the alicyclic structure are shown below.

[Chem. 13-1]

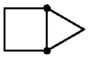
(1)

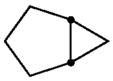
(2)

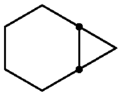
(3)

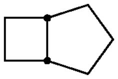
(4)

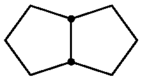
(5)

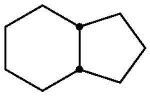
(6)

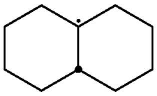
(7)

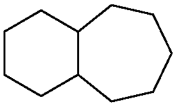
(8)

-continued
(9)
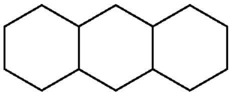
(10)
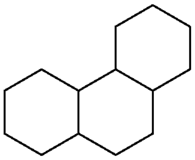
(11)
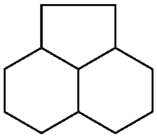
(12)
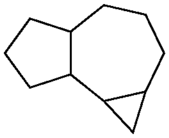
(13)
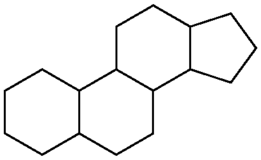
(14)
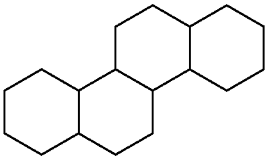
(15)
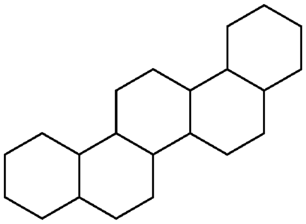
(16)
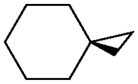
(17)
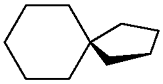
(18)
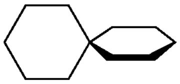
(19)
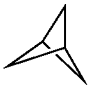
-continued
(20)
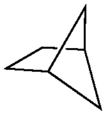
(21)
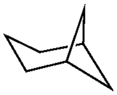
(22)
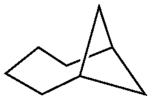
(23)
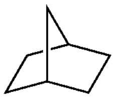
(24)
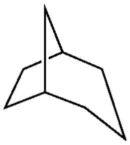
(25)
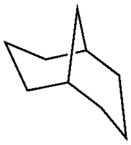
(26)
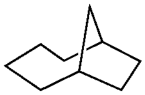
(27)
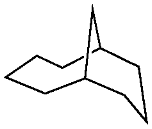
[Chem. 13-2]
(28)
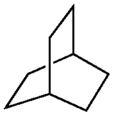
(29)
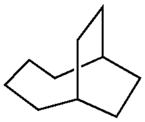
(30)
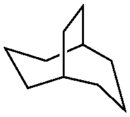
(31)
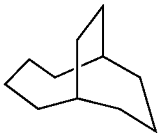

-continued (32)

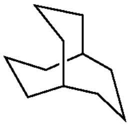

(33)

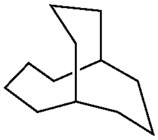

(34)

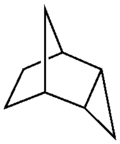

(35)

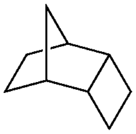

(36)

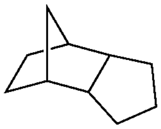

(37)

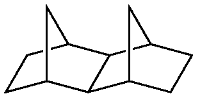

(38)

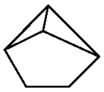

(39)

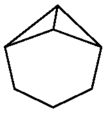

(40)

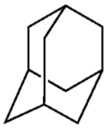

(41)

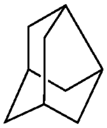

(42)

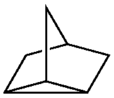

(43)

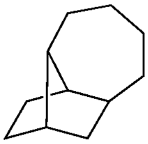

-continued (44)

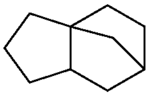

(45)

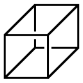

(46)

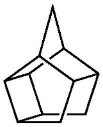

(47)

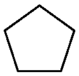

(48)

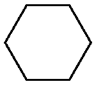

(49)

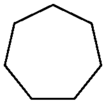

(50)

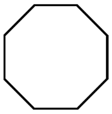

In the present invention, preferred examples of the alicyclic structure include an adamantyl group, a noradamantyl group, a decalin residue, a tricyclodecanyl group, a tetracyclododecanyl group, a norbornyl group, a cedrol group, a cyclohexyl group, a cycloheptyl group, a cyclooctyl group, a cyclodecanyl group and a cyclododecanyl group as a monovalent alicyclic group. More preferred examples thereof include an adamantyl group, a decalin residue, a norbornyl group, a cedrol group, a cyclohexyl group, a cycloheptyl group, a cyclooctyl group, a cyclodecanyl group and a cyclododecanyl group.

Examples of the substituent which these alicyclic structures may have include an alkyl group, a halogen atom, a hydroxyl group, an alkoxy group, a carboxyl group and an alkoxycarbonyl group. The alkyl group is preferably a lower alkyl group such as a methyl group, an ethyl group, a propyl group, an isopropyl group and a butyl group, and more preferably a methyl group, an ethyl group, a propyl group or an isopropyl group. The alkoxy group includes an alkoxy group having 1 to 4 carbon atoms, such as a methoxy group, an ethoxy group, a propoxy group and a butoxy group. The alkyl group and the alkoxy group each may further have a substituent. Examples of the substituent which the alkyl group and alkoxy group may further have include a hydroxyl group, a halogen atom and an alkoxy group.

A hydrocarbon group having a alicyclic structures is preferably a group showing in the general formula (pI) to the general formula (pV) described below.

[Chem. 14]

(pI)

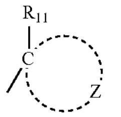

(pII)

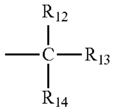

(pIII)

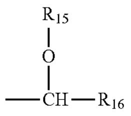

(pIV)

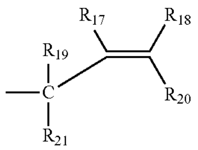

(pV)

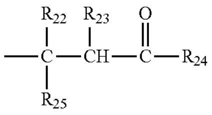

In the general formulae (pI) to (pV), $R_{11}$ represents a methyl group, an ethyl group, an n-propyl group, an isopropyl group, an n-butyl group, an isobutyl group or a sec-butyl group, and Z represents an atomic group necessary for forming an alicyclic hydrocarbon group together with the carbon atom.

$R_{12}$ to $R_{16}$ each independently represent a linear or branched alkyl group having 1 to 4 carbon atoms or an alicyclic hydrocarbon group, provided that at least one of $R_{12}$ to $R_{14}$ or either one of $R_{15}$ and $R_{16}$ represents an alicyclic hydrocarbon group.

$R_{17}$ to $R_{21}$ each independently represent a hydrogen atom, a linear or branched alkyl group or an alicyclic hydrocarbon group having 1 to 4 carbon atoms, provided that at least one of $R_{17}$ to $R_{21}$ represents an alicyclic hydrocarbon group. Further, either one of $R_{19}$ and $R_{21}$ represents a linear or branched alkyl group or an alicyclic hydrocarbon group having 1 to 4 carbon atoms.

$R_{22}$ to $R_{25}$ each independently represent a hydrogen atom, a linear or branched alkyl group or an alicyclic hydrocarbon group having 1 to 4 carbon atoms, provided that at least one of $R_{22}$ to $R_{25}$ represents an alicyclic hydrocarbon group. Further, $R_{23}$ and $R_{24}$ may be bonded to each other to form a ring.

In the general formulae (pI) to (pV), the alkyl group of $R_{12}$ to $R_{25}$ is a linear or branched alkyl group having from 1 to 4 carbon atoms, which may be substituted or unsubstituted. Examples of the alkyl group include a methyl group, an ethyl group, an n-propyl group, an isopropyl group, an n-butyl group, an isobutyl group, a sec-butyl group and a t-butyl group.

Furthermore, examples of the substituent which the alkyl group may further have include an alkoxy group having 1 to 4 carbon atoms, a halogen atom (a fluorine atom, a chlorine atom, a bromine atom, and an iodine atom), an acyl group, an acyloxy group, a cyano group, a hydroxyl group, a carboxyl group, an alkoxycarbonyl group and a nitro group.

Examples of the alicyclic hydrocarbon group in $R_{11}$ to $R_{25}$ and the alicyclic hydrocarbon group formed by Z together with the carbon atom include the same groups mentioned above as the alicyclic structure.

In one embodiment, the repeating unit represented by the general formula (A2) is preferably a repeating unit represented by the following formula.

[Chem. 15]

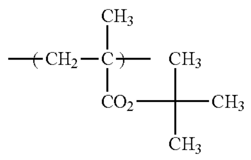

Furthermore, in another embodiment, the repeating unit represented by the general formula (A2) is also preferably a repeating unit represented by the general formula (A3) shown below.

[Chem. 16]

(A3)

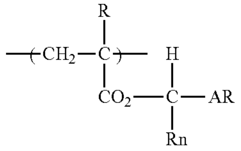

In the general formula (A3),

AR represents an aryl group.

Rn represents an alkyl group, a cycloalkyl group, or an aryl group. Rn and AR may be bonded to each other to form a non-aromatic ring.

R represents a hydrogen atom, an alkyl group, a cycloalkyl group, a halogen atom, a cyano group, or an alkyloxycarbonyl group.

The repeating unit represented by the general formula (A3) will be described in detail.

AR represents an aryl group as described above. As the aryl group of AR, those having 6 to 20 carbon atoms, such as a phenyl group, a naphthyl group, an anthryl group, or a fluorene group are preferred, and those having 6 to 15 carbon atoms are more preferred.

In the case where AR is a naphthyl group, an anthryl group, or a fluorene group, the bonding site between AR and the carbon atom to which Rn is bonded is not particularly limited. For example, when AR is a naphthyl group, the carbon atom may be bonded to the α-position or the β-position of the naphthyl group. Or when AR is an anthryl group, the carbon atom may be bonded to the 1-position, the 2-position or the 9-position of the anthryl group.

The aryl group as AR each may have one or more substituents. Specific examples of the substituent include a linear or branched alky group having 1 to 20 carbon atoms, such as a methyl group, an ethyl group, a propyl group, an isopropyl group, an n-butyl group, an isobutyl group, a t-butyl group, a pentyl group, a hexyl group, an octyl group, and a dodecyl group, an alkoxy group containing such an alkyl group moiety, a cycloalkyl group such as cyclopentyl group and cyclohexyl group, a cycloalkoxy group containing such a cycloalkyl group moiety, a hydroxyl group, a halogen atom, an aryl group, a cyano group, a nitro group, an acyl group, an acyloxy group, an acylamino group, a sulfonylamino group, an alkylthio group, an arylthio group, an aralkylthio group, a thiophenecarbonyloxy group, a thiophenemethylcarbonyloxy group, and a heterocyclic residue such as a pyrrolidone residue. The substituent is preferably a linear or branched alkyl group having 1 to 5 carbon atoms or an alkoxy group containing such an alkyl group moiety, and more preferably a paramethyl group or a paramethoxy group.

In a case where an aryl group as AR has a plurality of substituents, at least two of a plurality of substituents may be bonded to each other to form a ring. The ring is preferably a 5- to 8-membered ring, more preferably a 5- or 6-membered ring. The ring may be also a heterocycle containing a heteroatom such as an oxygen atom, a nitrogen atom and a sulfur atom in the ring members.

Furthermore, this ring may have a substituent. Examples of the substituent are the same as those described later for the further substituent which Rn may have.

Moreover, in view of the roughness performance, the repeating unit represented by the general formula (A3) preferably contains two or more aromatic rings. Usually, the number of aromatic rings contained in the repeating unit is preferably 5 or less, and more preferably 3 or less.

In addition, in view of the roughness performance, in the repeating unit represented by the general formula (A3), AR preferably contains two or more aromatic rings, and AR is more preferably a naphthyl group or a biphenyl group. Usually, the number of the aromatic rings contained in AR is preferably 5 or less, and more preferably 3 or less.

As described above, Rn represents an alkyl group, a cycloalkyl group or an aryl group.

The alkyl group of Rn may be a linear alkyl group or a branched alkyl group. The alkyl group is preferably an alky group having 1 to 20 carbon atoms, such as a methyl group, an ethyl group, a propyl group, an isopropyl group, an n-butyl group, an isobutyl group, a t-butyl group, a pentyl group, a hexyl group, a cyclohexyl group, an octyl group, and a dodecyl group. The alkyl group of Rn is preferably an alkyl group having 1 to 5 carbon atoms, and more preferably an alkyl group having 1 to 3 carbon atoms.

Examples of the cycloalkyl group of Rn include a cycloalkyl group having 3 to 15 carbon atoms, such as a cyclopentyl group and a cyclohexyl group.

The aryl group of Rn is preferably, for example, an aryl group having 6 to 14 carbon atoms, such as a phenyl group, a xylyl group, a tolyl group, a cumenyl group, a naphthyl group and an anthryl group.

Each of the alkyl group, the cycloalkyl group, and the aryl group as Rn may further have a substituent. Examples of the substituent include an alkoxy group, a hydroxyl group, a halogen atom, a nitro group, an acyl group, an acyloxy group, an acylamino group, a sulfonylamino group, dialkyl amino group, an alkylthio group, an arylthio group, an aralkylthio group, a thiophenecarbonyloxy group, a thiophenemethylcarbonyloxy group, and heterocyclic residues such as a pyrrolidone residue. Among these, an alkoxy group, a hydroxyl group, a halogen atom, a nitro group, an acyl group, an acyloxy group, an acylamino group, and a sulfonylamino group are particularly preferred.

As described above, R represents a hydrogen atom, an alkyl group, a cycloalkyl group, a halogen atom, a cyano group or an alkyloxycarbonyl group.

Examples of the alkyl group and the cycloalkyl group of R are the same as those described above for Rn. Each of these alkyl groups and cycloalkyl groups may have a substituent. Examples of this substituent are the same as those described above for Rn.

In the case where R is an alkyl group or a cycloalkyl group having a substituent, particularly preferred examples of R include a trifluoromethyl group, an alkyloxycarbonyl methyl group, an alkylcarbonyloxymethyl group, a hydroxymethyl group and an alkoxymethyl group.

The halogen atom of R includes a fluorine atom, a chlorine atom, a bromine atom and an iodine atom. Among these, the fluorine atom is particularly preferable.

As the alkyl group moiety contained in the alkyloxycarbonyl group of R, for example, the configuration described above as the alkyl group of R may be employed.

Rn and AR are preferably bonded to each other to form a non-aromatic ring and, in particular, this can further improve the roughness performance.

The non-aromatic ring which may be formed by the mutual bonding of Rn and AR is preferably a 5- to 8-membered ring, and more preferably a 5- or 6-membered ring.

The non-aromatic ring may be an aliphatic ring or a heterocycle containing a heteroatom such as an oxygen atom, a nitrogen atom and a sulfur atom, as a ring member.

The non-aromatic ring may have a substituent. Examples of the substituent are the same as those described above with respect to the further substituent which Rn may have.

Specific examples of the monomer corresponding to a repeating unit represented by the general formula (A2) and specific examples of the repeating unit are illustrated below, but the present invention is not limited thereto.

[Chem. 17-1]

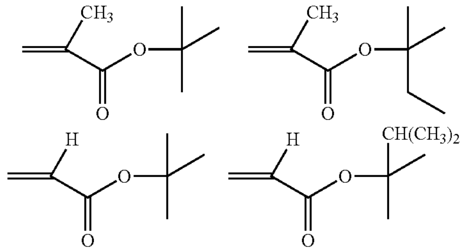

[Chem. 17-2]

1

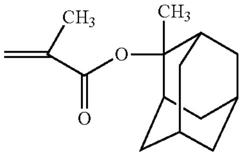

3

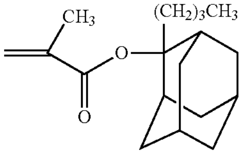

5

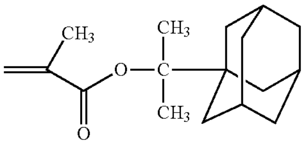

-continued
6
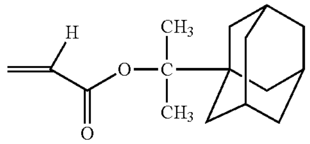
8
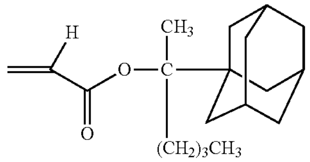
9
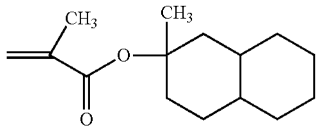
11
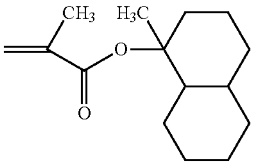
14
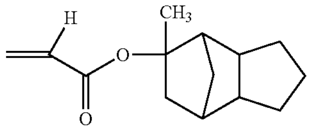
15
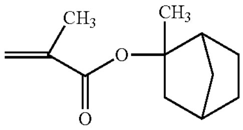
[Chem. 17-3]
17
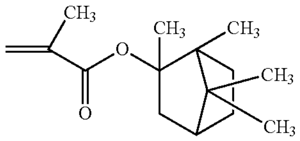
19
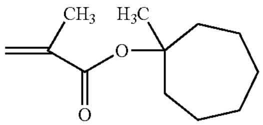
22
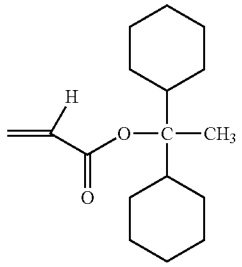
-continued
23
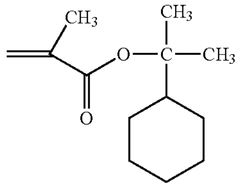
25
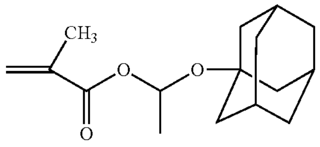
28
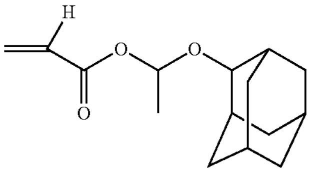
29
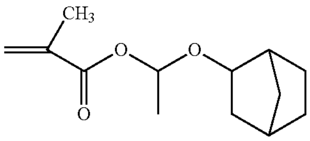
32
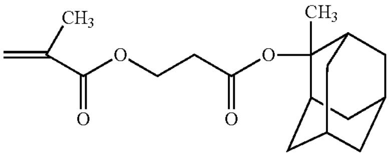
[Chem. 17-4]
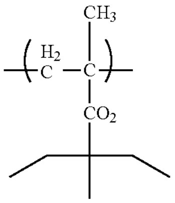
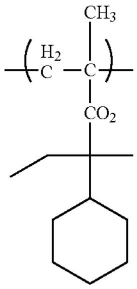
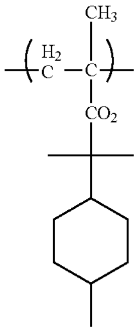
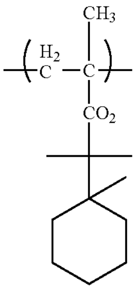
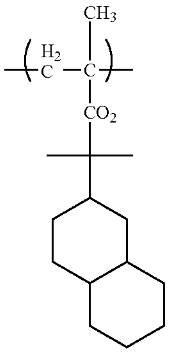
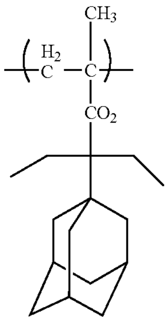

-continued
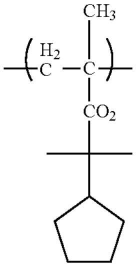
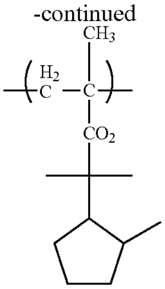
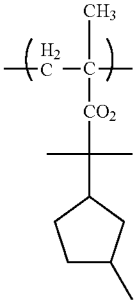
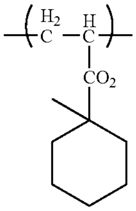
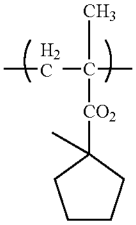
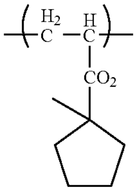
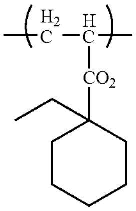
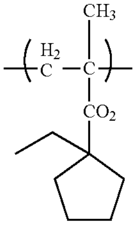
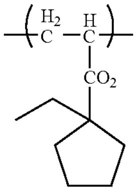
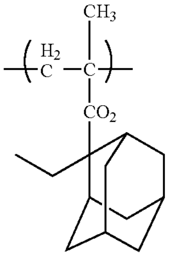
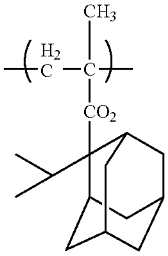
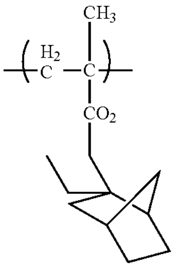
[Chem. 17-5]
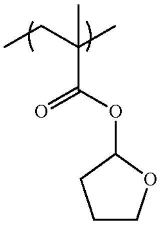
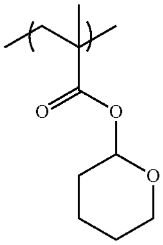
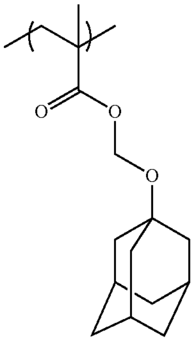
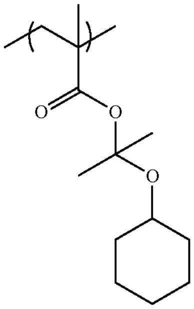
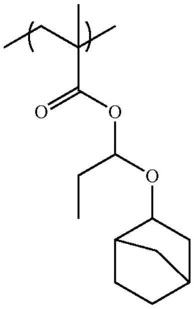
-continued
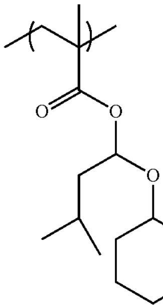
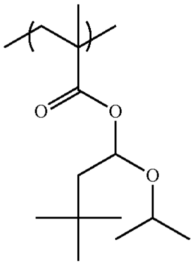
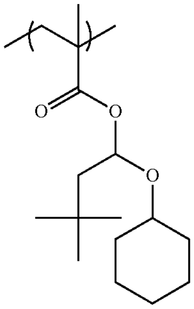
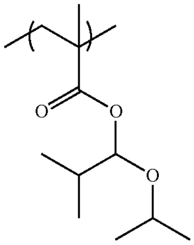
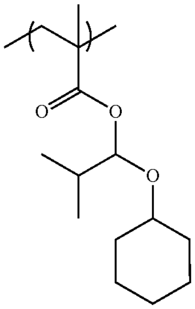
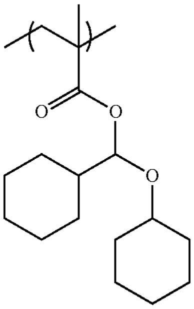
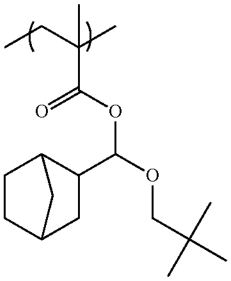
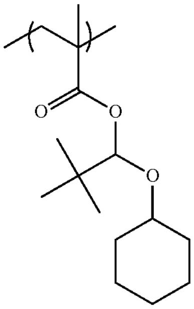
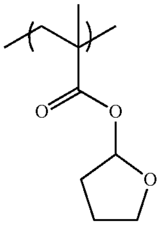
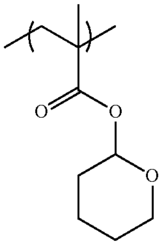
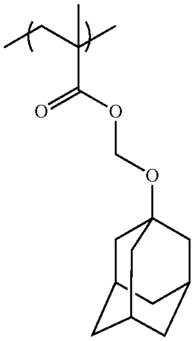

-continued
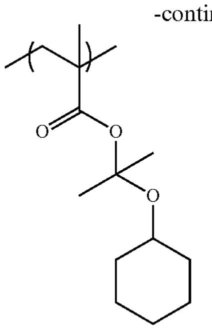
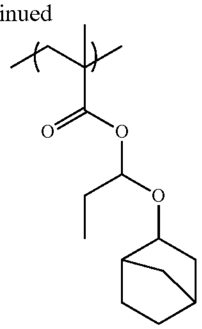
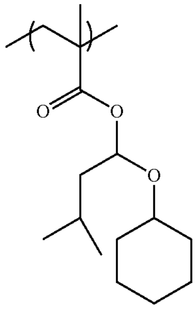
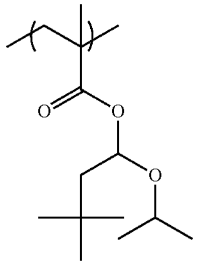
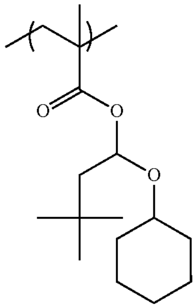
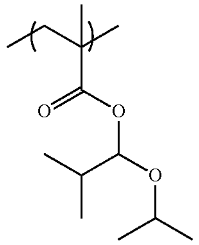
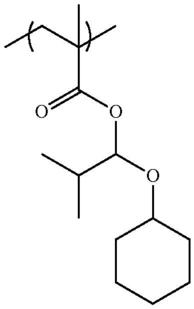
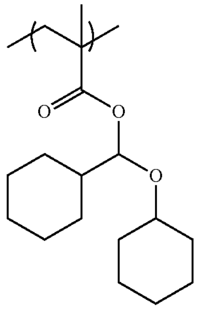
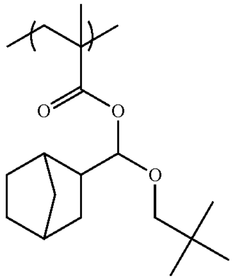
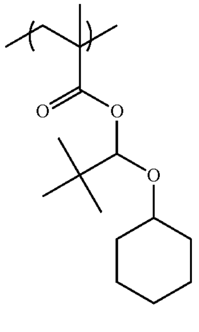
Specific examples of the repeating unit represented by the general formula (A3) are illustrated below, but the present invention is not limited thereto.
[Chem. 18-1]
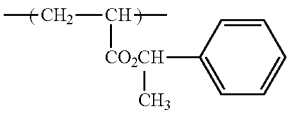
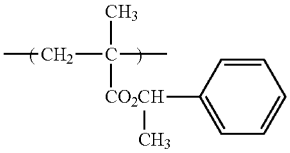
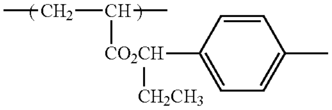
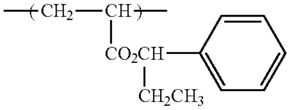
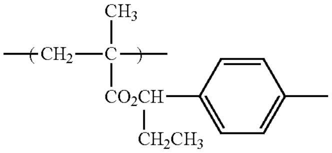
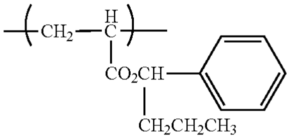
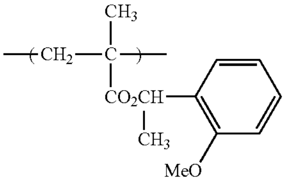
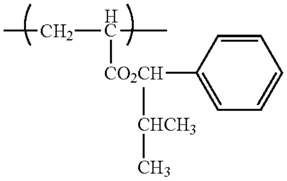
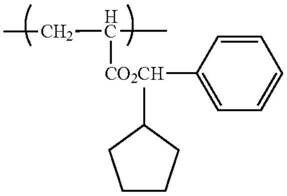
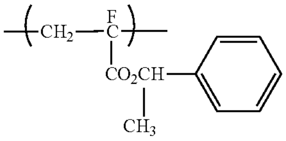
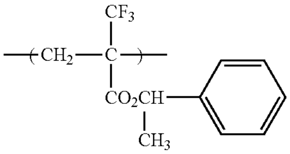
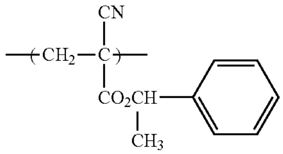
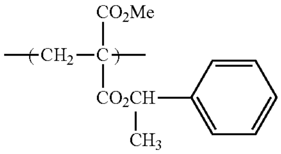
[Chem. 18-2]
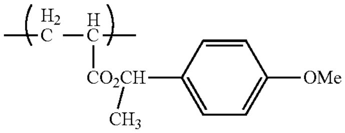

-continued
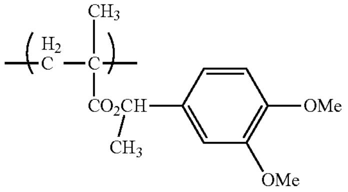
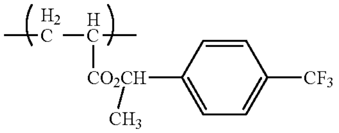
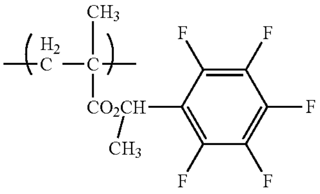
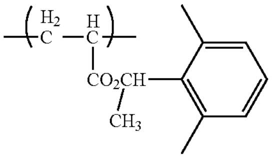
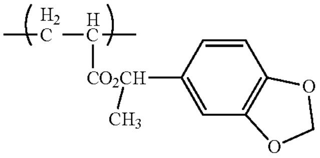
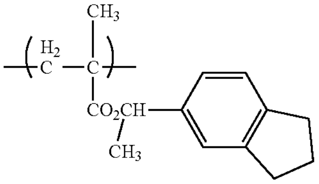
[Chem. 18-3]
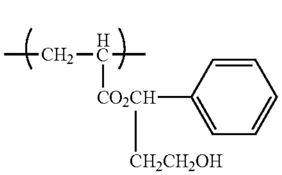
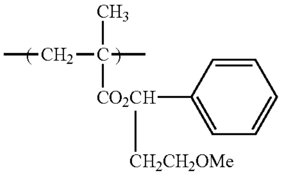
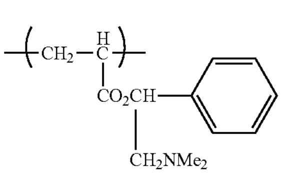
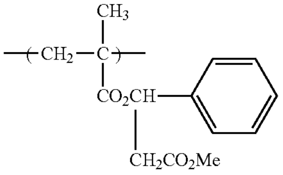
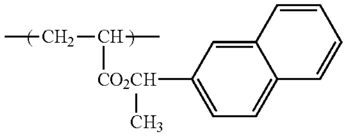
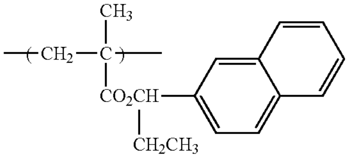
-continued
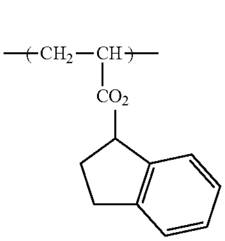
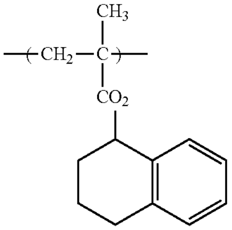
[Chem. 18-4]
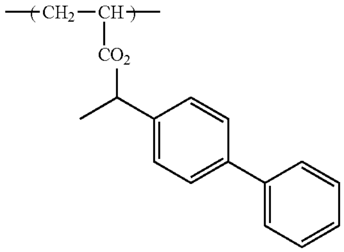
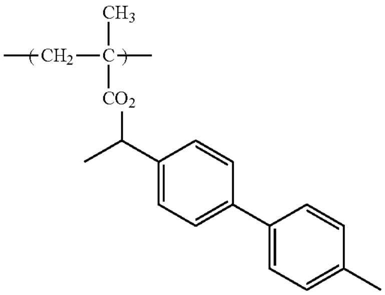
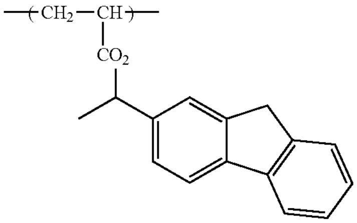
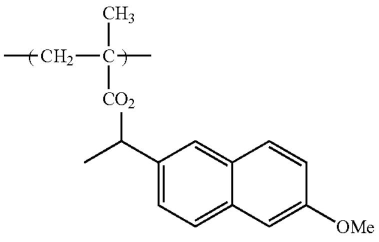
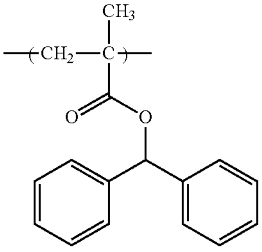
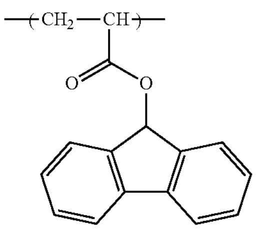

-continued

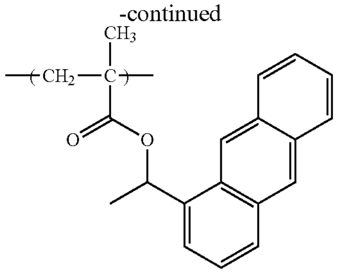

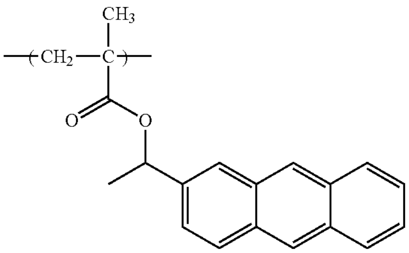

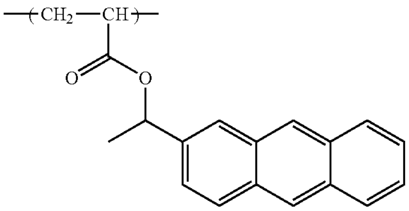

[Chem. 18-5]

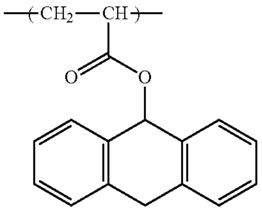

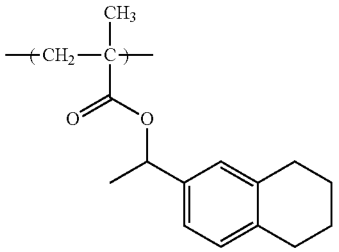

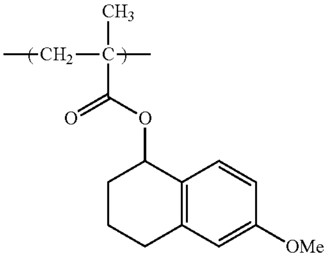

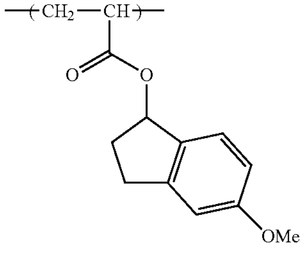

The resin (Ab) may further contain a repeating unit represented by the following general formula (A5).

[Chem. 19]

(A5)

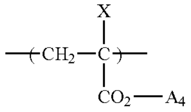

In the formula (A5),

X represents a hydrogen atom, an alkyl group, a hydroxyl group, an alkoxy group, a halogen atom, a cyano group, a nitro group, an acyl group, an acyloxy group, a cycloalkyl group, an aryl group, a carboxyl group, an alkyloxycarbonyl group, an alkylcarbonyloxy group, or an aralkyl group.

$A_4$ represents a hydrocarbon group incapable of leaving by the action of an acid.

In the general formula (A5), examples of the hydrocarbon group incapable of leaving by the action of an acid of $A_4$ include hydrocarbon groups other than the above-described acid-decomposable groups, for example, an alkyl group not leaving by the action of an acid (preferably having 1 to 15 carbon atoms), a cycloalkyl group incapable of leaving by the action of an acid (preferably having 3 to 15 carbon atoms), and an aryl group incapable of leaving by the action of an acid (preferably having 6 to 15 carbon atoms).

The hydrocarbon group incapable of leaving by the action of an acid of $A_4$ may be further substituted with a hydroxyl group, an alkyl group, a cycloalkyl group, an aryl group, or the like.

Specific examples of the repeating unit represented by the general formula (A5) are illustrated below, but the present invention is not limited thereto.

[Chem. 20]

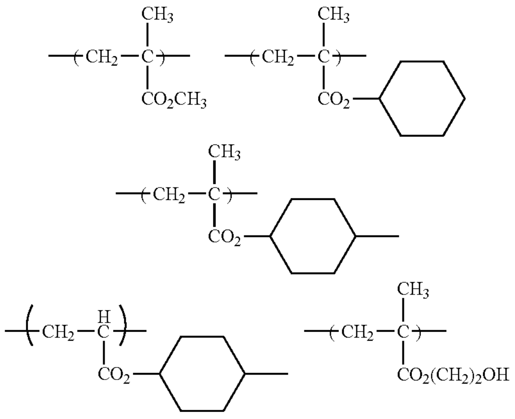

It is also preferable for the resin (Ab) to further have a repeating unit represented by the general formula (A6).

[Chem. 21]

(A6)

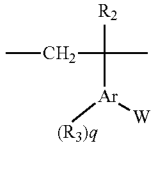

In the general formula (A6), $R_2$ represents a hydrogen atom, a methyl group, a cyano group, a halogen atom, or a perfluoro group having 1 to 4 carbon atoms.

$R_3$ represents a hydrogen atom, an alkyl group, a cycloalkyl group, a halogen atom, an aryl group, an alkoxy group, or an acyl group.

q represents an integer of 0 to 4.

Ar represents a (q+2)-valent aromatic ring.

W represents a group incapable of decomposing by the action of an acid, or a hydrogen atom.

The aromatic ring represented by Ar is preferably a benzene ring, a naphthalene ring, or an anthracene ring, and more preferably a benzene ring.

W represents a group incapable of decomposing under the action of an acid (also referred to as an "acid-stable group"), examples thereof include groups other than the above-described acid-decomposable groups, and specific examples thereof include a halogen atom, an alkyl group, a cycloalkyl group, an alkenyl group, an aryl group, an acyl group, an alkylamide group, an arylamidomethyl group, and an arylamide group. The acid-stable group is preferably an acyl group or an alkylamide group, more preferably an acyl group, an alkylcarbonyloxy group, an alkyloxy group, a cycloalkyloxy group, or an aryloxy group.

In the acid-stable group of W, the alkyl group is preferably one having 1 to 4 carbon atoms, such as a methyl group, an ethyl group, a propyl group, an n-butyl group, a sec-butyl group, and a t-butyl group; the cycloalkyl group is preferably one having 3 to 10 carbon atoms, such as a cyclopropyl group, a cyclobutyl group, a cyclohexyl group, and an adamantyl group; the alkenyl group is preferably one having 2 to 4 carbon atoms, such as a vinyl group, a propenyl group, an allyl group, and a butenyl group; the alkenyl group is preferably one having 2 to 4 carbon atoms, such as a vinyl group, a propenyl group, an allyl group, and a butenyl group; and the aryl group is preferably one having 6 to 14 carbon atoms, such as a phenyl group, a xylyl group, a tolyl group, a cumenyl group, a naphthyl group, and an anthracenyl group. W may be at any position of the benzene ring, but is preferably at the meta- or para-position of the styrene skeleton, and particularly preferably at the para position.

Specific examples of the repeating unit represented by the general formula (A6) are shown below, but the present invention is not limited thereto.

[Chem. 22]

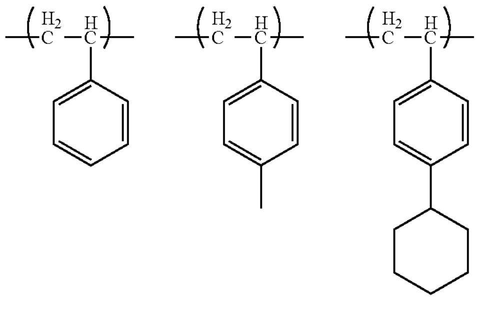

-continued

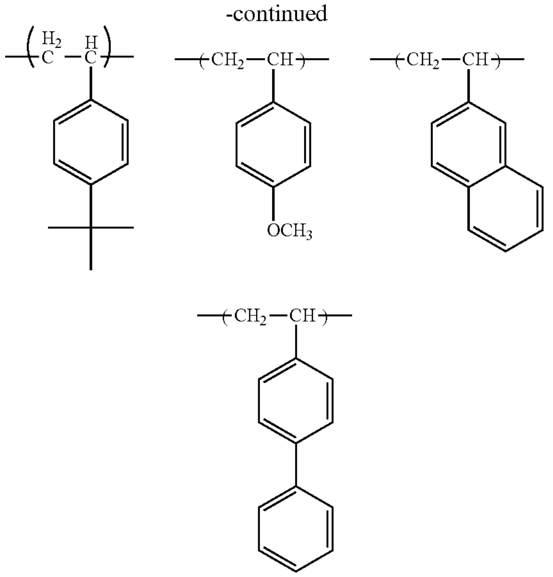

The content of the repeating units having the acid-decomposable groups in the resin (Ab) is preferably from 5 to 95% by mole, more preferably from 10 to 60% by mole, and particularly preferably 15 to 50% by mole, based on all the repeating units.

Furthermore, the resin (Ab) may be copolymerized with other appropriate polymerizable monomers to incorporate an alkali-soluble group, for example, a phenolic hydroxyl group or a carboxyl group for the purpose of maintaining good developability with an alkali developer, or may be copolymerized with other appropriate hydrophobic polymerizable monomers such as alkyl acrylate and alkyl methacrylate for the purpose of enhancing the film quality.

In one embodiment, the resin (Ab) preferably contains a repeating unit represented by the following general formula (A).

[Chem. 23]

(A)

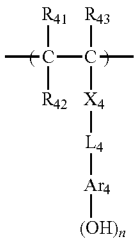

In the formula (A), $R_{41}$, $R_{42}$ and $R_{43}$ each independently represent a hydrogen atom, an alkyl group, a cycloalkyl group, a halogen atom, a cyano group or alkoxycarbonyl group. However, $R_{42}$ may be bonded to $Ar_4$ to form a ring, in this case, $R_{42}$ represents a single bond and an alkylene group.

$X_4$ represents a single bond, —COO—, or —$CONR_{64}$— and $R_{64}$ represents a hydrogen atom, and an alkyl group.

$L_4$ represents a single bond and an alkylene group.

$Ar_4$ represents a (n+1)-valent aromatic ring group and in a case of being bonded to $R_{42}$ to form a ring, represents a (n+2)-valent aromatic ring group.

n represents an integer of 1 to 4.

Specific examples of the substituent which an alkyl group, a cycloalkyl group, a halogen atom and an alkoxycarbonyl group of $R_{41}$, $R_{42}$ and $R_{43}$ can have in the formula (A) include, for example, an alkyl group, a cycloalkyl group, an aryl group, an amino group, an amido group, a ureido group, a urethane group, a hydroxyl group, a carboxyl group, a halogen group, an alkoxy group, a thioether group, an acyl group, an acyloxy group, an alkoxycarbonyl group, a cyano group, a nitro group, or the like and the number of carbon atoms of the substituent is preferably 10 or less.

$Ar_4$ represents a (n+1)-valent aromatic ring group. As a divalent aromatic ring group in a case where n is 1, for example, an arylene group having 6 to 18 carbon atoms such as a phenylene group, a tolylene group, a naphthylene group, an anthracenylene group or, for example, an aromatic ring group including a hetero ring such as thiophene, furan, pyrrole, benzothiophene, benzofuran, benzopyrrole, triazine, imidazole, benzimidazole, triazole, thiadiazole or thiazole is included as a preferred example. The divalent aromatic ring group may further have a substituent.

Specific examples of the (n+1)-valent aromatic ring group in a case where n is an integer of 2 or more suitably include a group where arbitrary (n−1) hydrogen atoms are removed from specific examples of divalent aromatic ring groups described above.

The (n+1)-valent aromatic ring group may further have a substituent.

Examples of the substituent which an alkyl group, a cycloalkyl group, an alkoxycarbonyl, an alkylene group and (n+1)-valent aromatic ring group can have described above include an alkyl group, an alkoxy group such as, a methoxy group, an ethoxy group, a hydroxyethoxy group, a propoxy group, a hydroxypropoxy group, a butoxy group, or an aryl group such as a phenyl group.

Examples of the alkyl group of $R_{64}$ in $—CONR_{64}—$ ($R_{64}$ represents a hydrogen atom or an alkyl group) represented by $X_4$ include the same as an alkyl group of $R_{61}$ to $R_{63}$ in the general formula (A1) described above.

As $X_4$, a single bond, —COO— and —CONH— are preferable and a single bond and —COO— are more preferable.

Examples of the alkylene group in $L_4$ preferably include an alkylene group having 1 to 8 carbon atoms such as a methylene group, an ethylene group, a propylene group, a butylene group, a hexylene group or an octylene group, which may have a substituent.

As $Ar_4$, an aromatic ring group having 6 to 18 carbon atoms which may have a substituent is more preferable and a benzene ring group, a naphthalene ring group and a biphenylene ring group are particularly preferable.

A repeating unit (A) is preferably provided with a hydroxystyrene structure. That is, $Ar_4$ is preferably a benzene ring group.

Hereinafter, specific examples of the repeating unit (A) represented by the general formula (A) are shown, but the present invention is not limited thereto.

[Chem. 24]

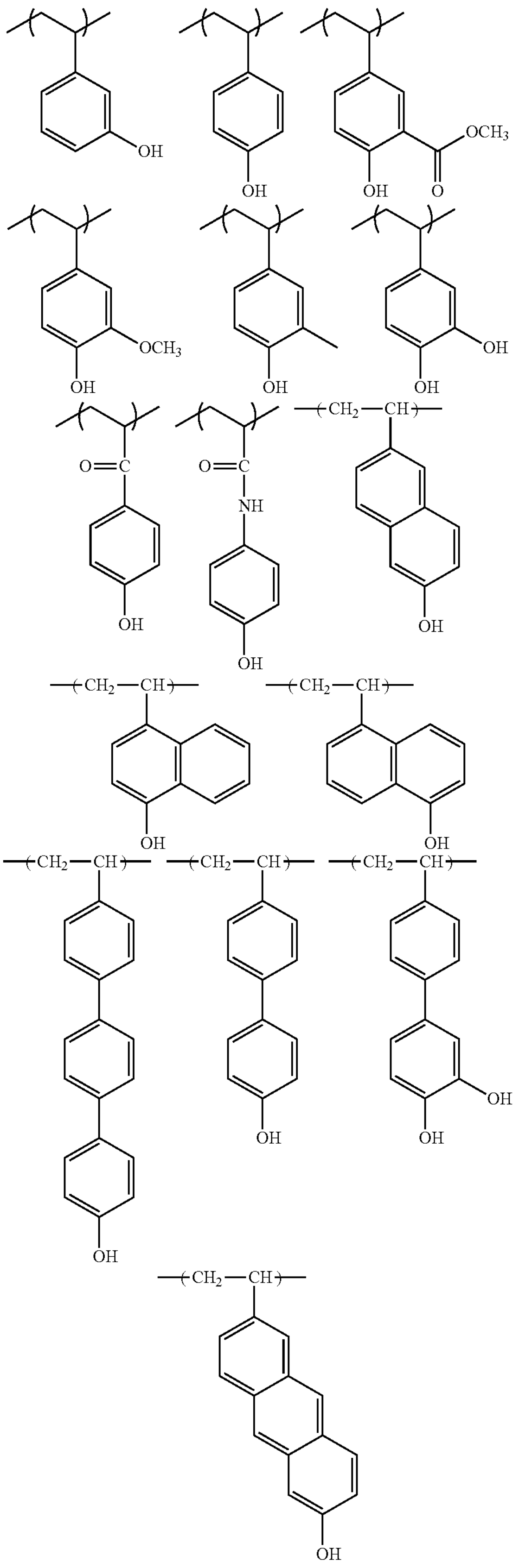

In one embodiment, a resin (Ab) preferably include at least a repeating unit represented by the following formula as a repeating unit represented by the general formula (A).

[Chem. 25]

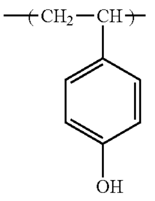

The content of repeating unit represented by the general formula (A) in the resin (Ab) is preferably from 0 to 90% by mole, more preferably from 5 to 80% by mole, still more preferably from 10 to 70% by mole, and particularly preferably from 20 to 60% by mole, based on all the repeating units in the resin (Ab).

In one embodiment, the resin (Ab) may contain a repeating unit (B) including a structural moiety capable of decomposing by irradiation with actinic rays or radiation to generate an acid (hereinafter referred to as an "acid-generating repeating unit (B)" or a "repeating unit (B)").

The structural moiety may be, for example, a structural moiety capable of decomposing by irradiation with actinic rays or radiation to generate an acid anion in the repeating unit (B), or a structural moiety capable of discharging an acid anion to generate a cation structure in the repeating unit (B).

Furthermore, this structural moiety is preferably, for example, an ionic structural moiety including a sulfonium salt structure or an iodonium salt structure.

This structural moiety may be, for example, the same structural moiety as a structural moiety represented by A in the general formulae (B1), (B2), and (B3) shown below.

In one embodiment, it is preferable that the repeating unit (B) be at least one selected from the group consisting of repeating units of the following general formulae (B1), (B2) and (B3). Among these, the repeating unit represented by the following general formula (B1) or (B3) is more preferred, and the repeating unit represented by the following general formula (B1) is particularly preferred.

[Chem. 26]

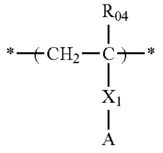

(B1)

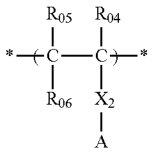

(B2)

-continued

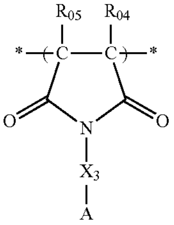

(B3)

In the general formulae (B1), (B2) and (B3),

A represents a structural moiety capable of decomposing by irradiation with actinic rays or radiation to generate an acid anion.

$R_{04}$, $R_{05}$ and $R_{07}$ to $R_{09}$ each independently represent a hydrogen atom, an alkyl group, a cycloalkyl group, a halogen atom, a cyano group, or an alkoxycarbonyl group.

$R_{06}$ represents a cyano group, a carboxyl group, —CO—$OR_{25}$ or —CO—$N(R_{26})(R_{27})$. $R_{25}$ represents an alkyl group, a cycloalkyl group, an alkenyl group, a cycloalkenyl group, an aryl group or an aralkyl group. $R_{26}$ and $R_{27}$ each independently represent a hydrogen atom, an alkyl group, a cycloalkyl group, an alkenyl group, a cycloalkenyl group, an aryl group or an aralkyl group. $R_{26}$ and $R_{27}$ may be bonded to each other to form a ring together with a nitrogen atom.

$X_1$, $X_2$ and $X_3$ each independently represent a single bond, an arylene group, an alkylene group, a cycloalkylene group, —O—, —$SO_2$—, —CO—, —$N(R_{33})$—, or a divalent connecting group formed by a combination of two or more of these. $R_{33}$ represents a hydrogen atom, an alkyl group, a cycloalkyl group, an alkenyl group, a cycloalkenyl group, an aryl group, or an aralkyl group.

A represents a structural moiety capable of decomposing by irradiation with actinic rays or radiation to generate an acid anion, and specific examples thereof include a photoinitiator for photocationic polymerization, a photoinitiator for photoradical polymerization, a photo-achromatic agent and photo-discoloring agent for coloring materials, structural moieties contained in generally known compounds that generate an acid by light, employed in microresists or the like.

Furthermore, A is preferably an ionic structural moiety with a sulfonium salt structure or an iodonium salt structure. In particular, A is preferably any of the groups represented by the following general formulae (ZI) and (ZII).

[Chem. 27]

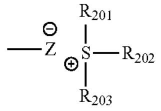

ZI

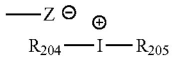

ZII $R_{201}$, $R_{202}$ and $R_{203}$ in the general formula (ZI) each independently represent an organic group.

In the general formula (ZII), $R_{204}$ and $R_{205}$ each independently represent an aryl group, an alkyl group or a cycloalkyl group.

The number of carbon atoms of each of the organic groups as $R_{201}$, $R_{202}$ and $R_{203}$ is generally in the range of 1 to 30, preferably 1 to 20. Two members of $R_{201}$ to $R_{203}$ may be bonded to each other to form a ring structure, and the ring within the same may contain an oxygen atom, a sulfur atom, an ester bond, an amide bond, or a carbonyl group. Examples of the group formed by bonding of two members out of $R_{201}$ to $R_{203}$ include an alkylene group such as a butylene group and a pentylene group.

$Z^-$ represents the acid anion generated by decomposition by irradiation with actinic rays or radiation. $Z^-$ is preferably a normucleophilic anion. Examples of the normucleophilic anion include a sulfonate anion, a carboxylate anion, a sulfonylimido anion, a bis(alkylsulfonyl)imido anion, and a tris(alkylsulfonyl)methyl anion.

Furthermore, the normucleophilic anion means an anion whose capability of inducing a nucleophilic reaction is extremely low. By using the nucleophilic anion, time course decomposition by intramolecular nucleophilic reaction can be inhibited. This would realize an enhancement of the time course stability of the resin and the composition.

Moreover, examples of the structural portion capable of generating an acid by irradiation with actinic rays or radiation include the structural moiety destined for a sulfonic acid precursor that is introduced in each of the following photo-acid generators. Examples of the photo-acid generators include the following compounds (1) to (3).

(1) Compounds photolyzed to generate a sulfonic acid whose representative is an iminosulfonate or the like, as described in M. Tunooka et al., Polymer Preprints Japan, 35(8); G. Berner et al., J. Rad. Curing, 13(4); W. J. Mijs et al., Coating Technol., 55(697), 45 (1983); H. Adachi et al., Polymer Preprints Japan, 37(3); EP0199,672B, EP84515B, EP199,672B, EP044,115B, and EP0101,122B; U.S. Pat. No. 618,564B, U.S. Pat. No. 4,371,605B and U.S. Pat. No. 4,431,774B; JP1989-18143A (JP-S64-18143A), JP1990-245756A (JP-H02-245756A), and JP1992-365048A (JP-H04-365048A); etc.

(2) Disulfone compounds as described in JP1986-166544A (JP-S61-166544A), etc.

(3) Compounds capable of generating an acid by light, as described in V. N. R. Pillai, Synthesis, (1), 1 (1980); A. Abad et al., Tetrahedron Lett., (47) 4555 (1971); D. H. R. Barton et al., J. Chem. Soc., (C), 329 (1970); U.S. Pat. No. 3,779,778B, EP126,712B; etc.

Specific examples of the repeating units (B) are shown below, but the scope of the present invention is not limited thereto.

[Chem. 28-1]

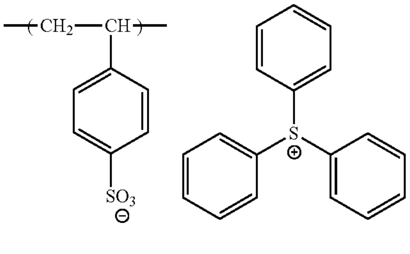

-continued

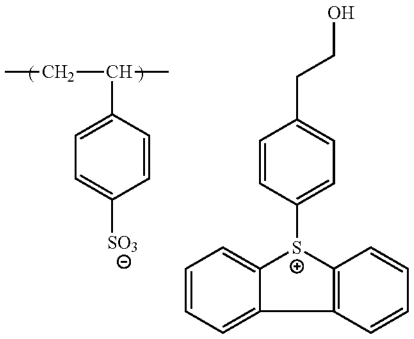

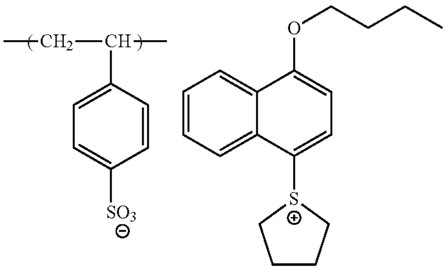

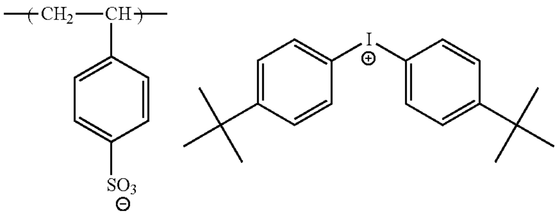

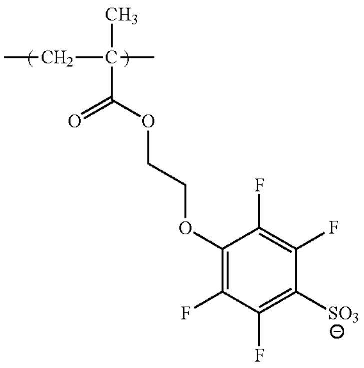

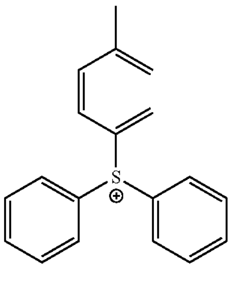

-continued
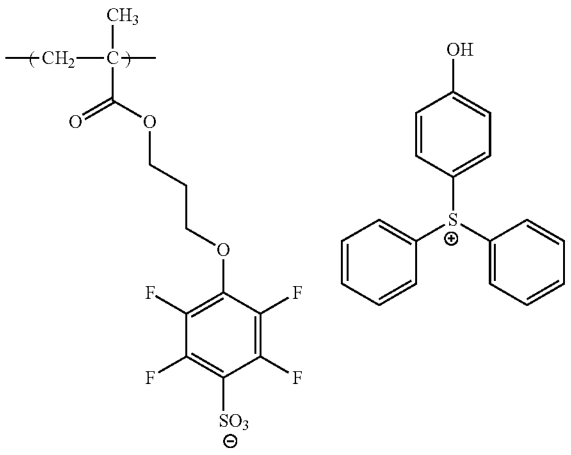
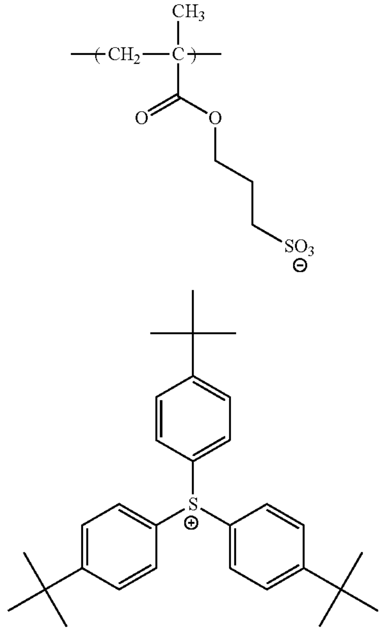
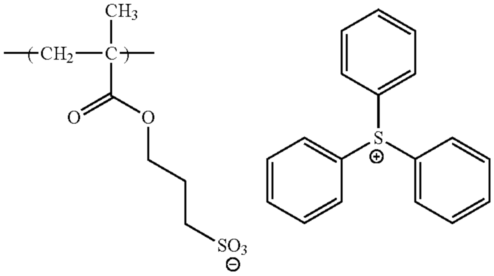
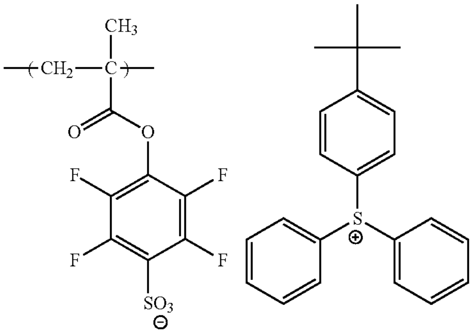
-continued
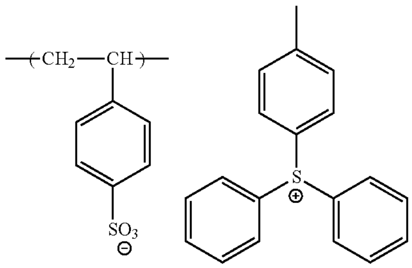
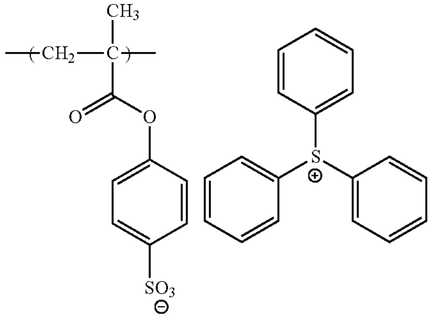
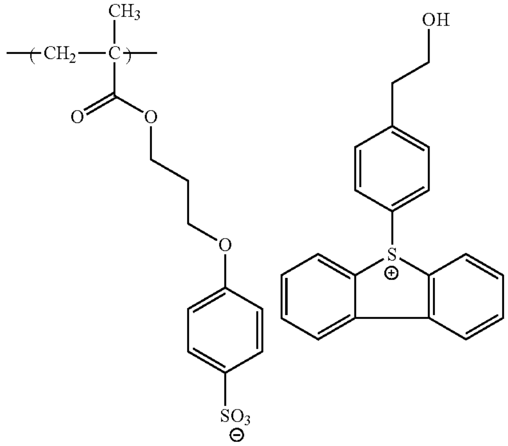
[Chem. 28-2]
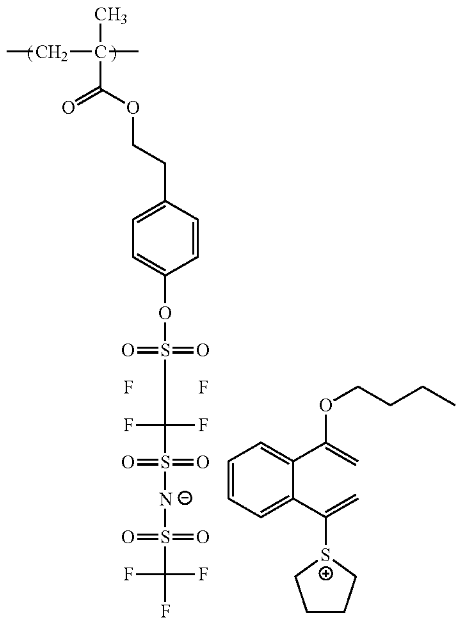

-continued
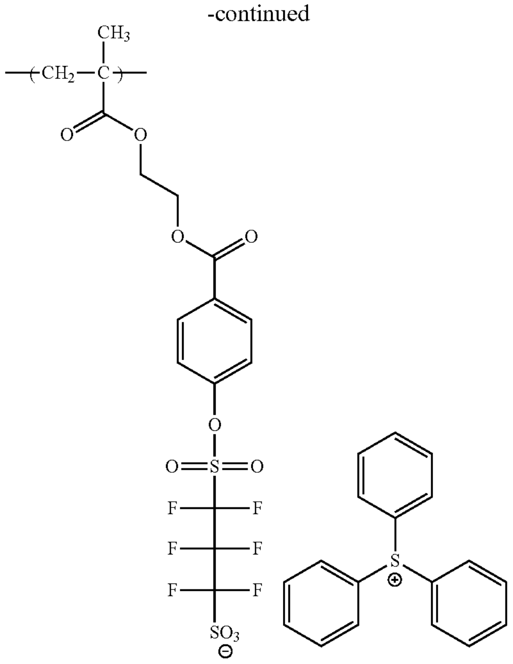
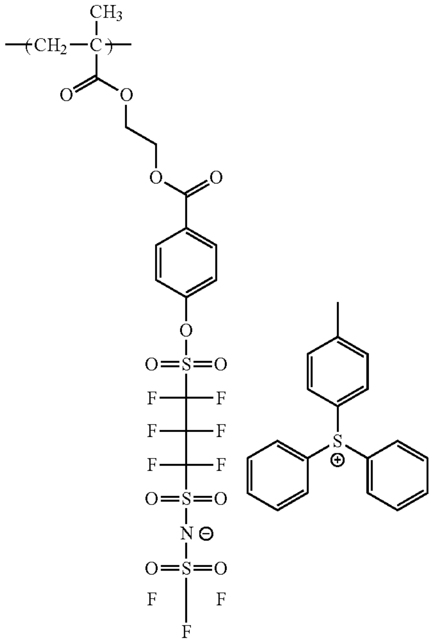
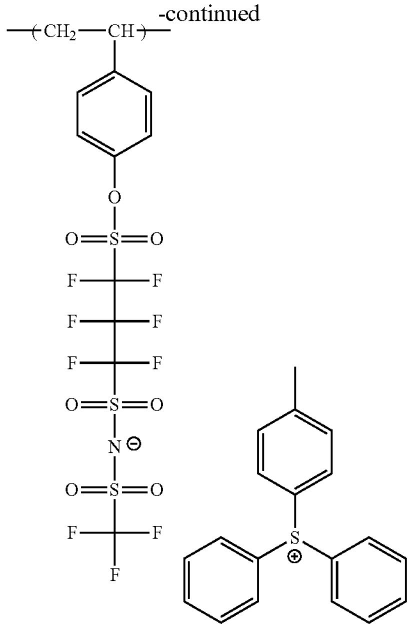
-continued
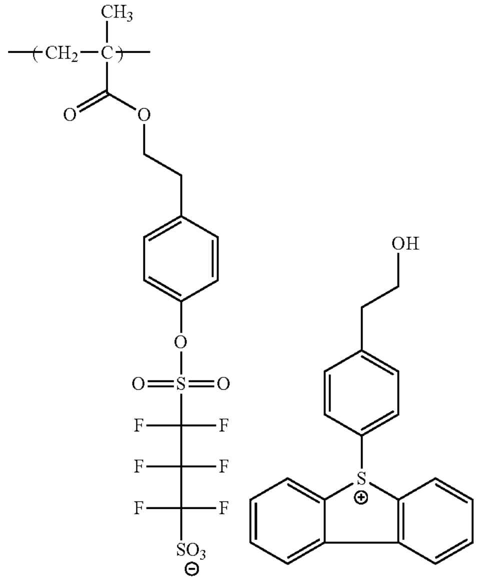
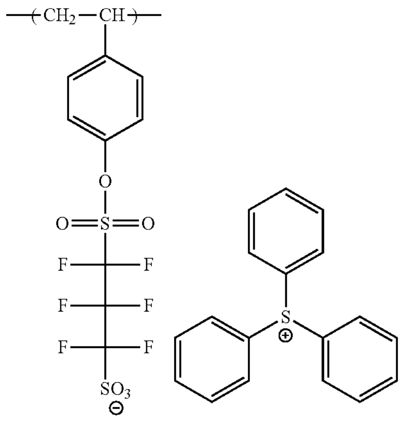

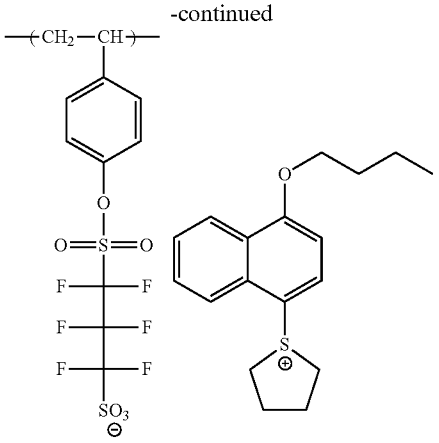
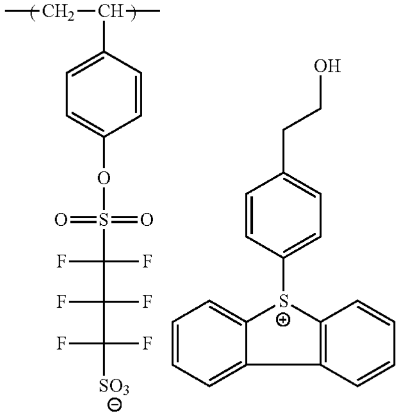
[Chem. 28-3]
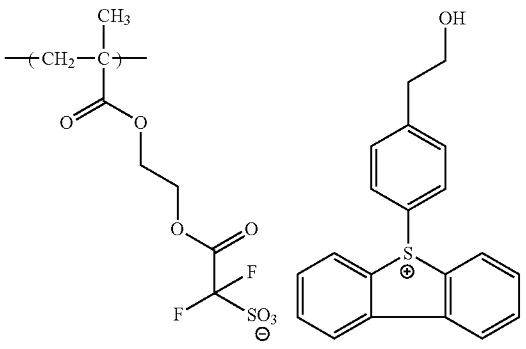
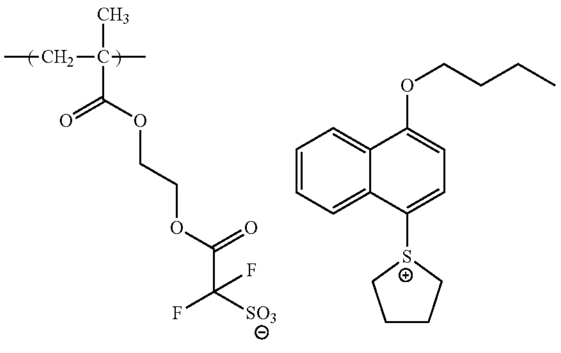
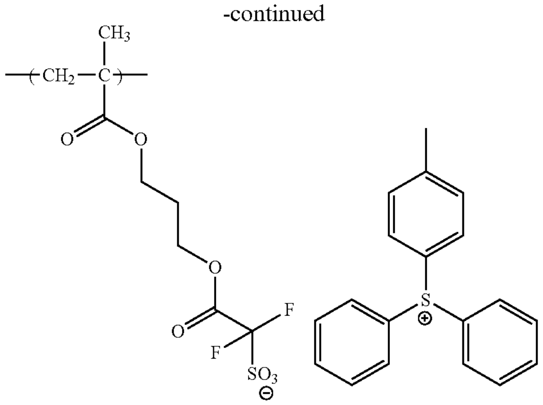
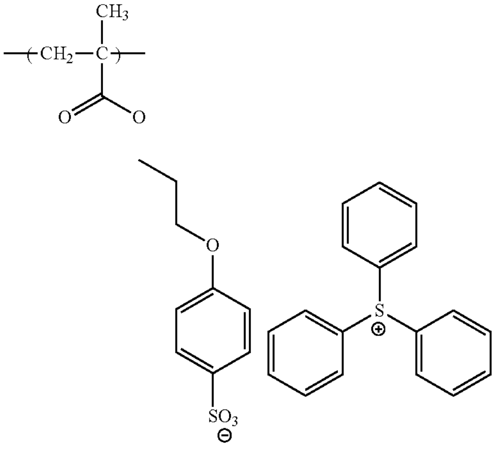
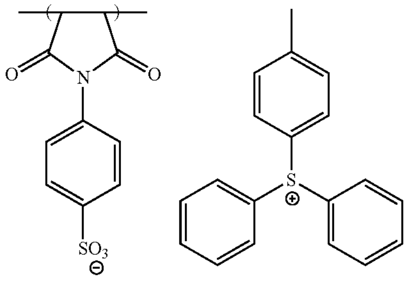
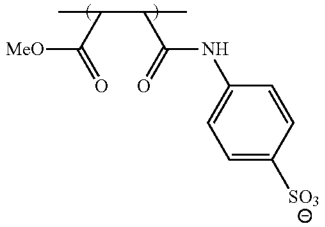
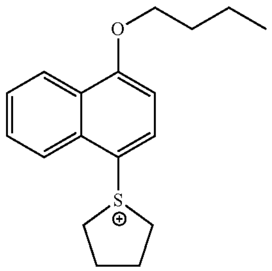

-continued
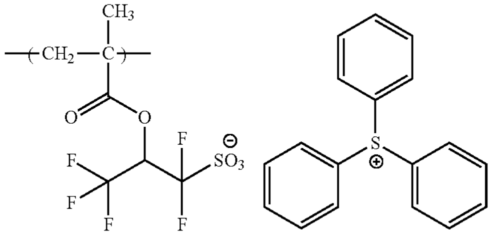
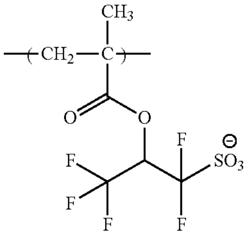
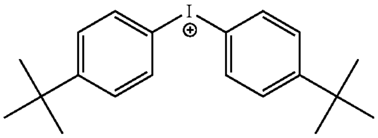
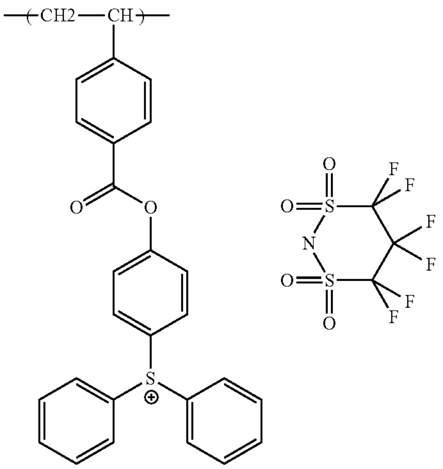
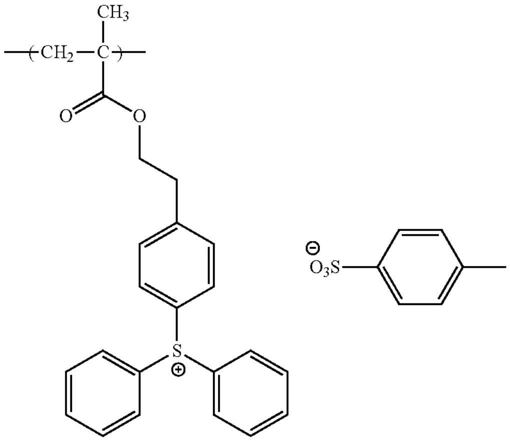
-continued
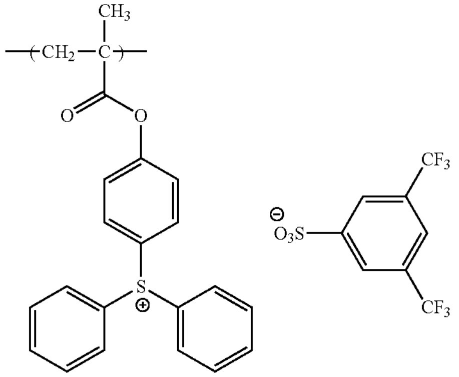
[Chem. 28-4]
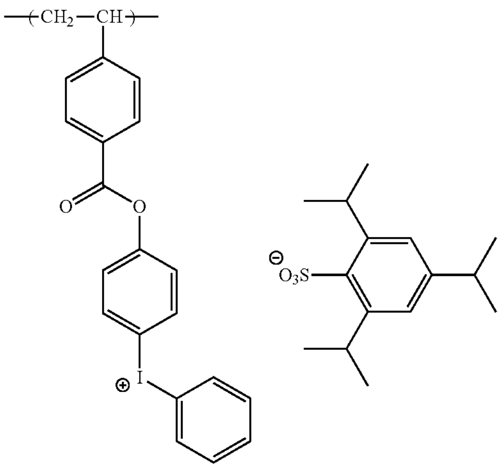
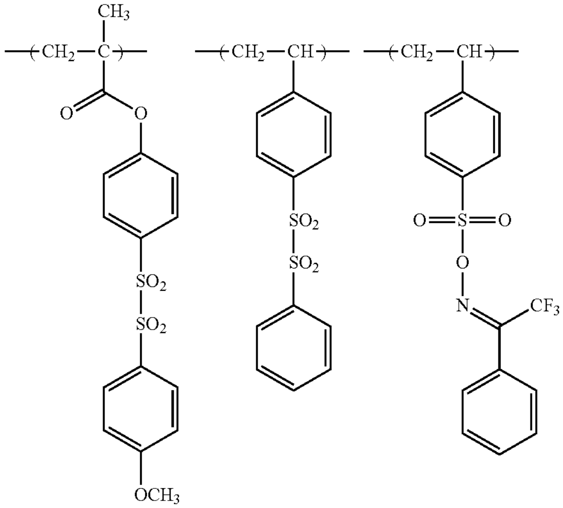

-continued
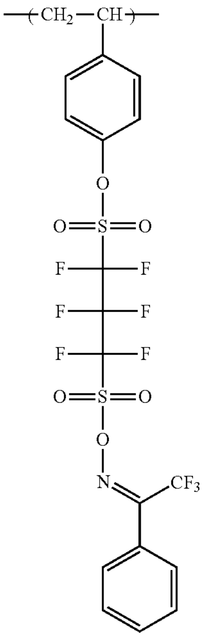
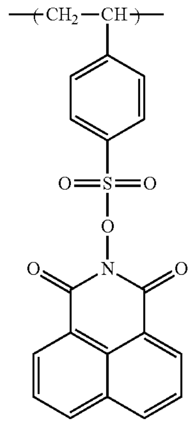
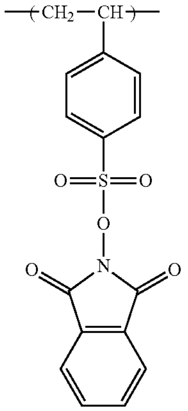
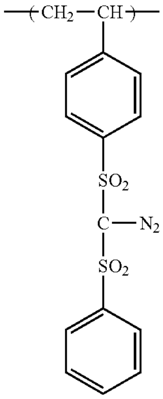
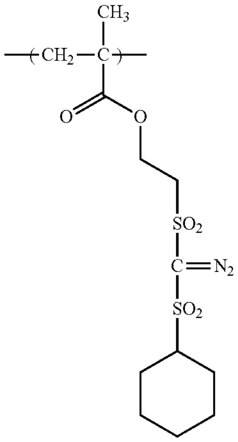
-continued
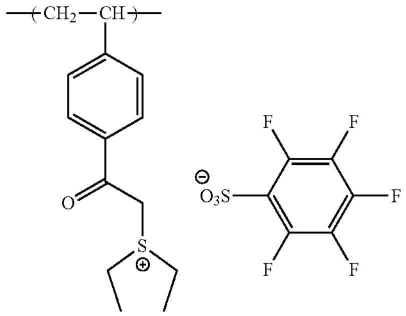
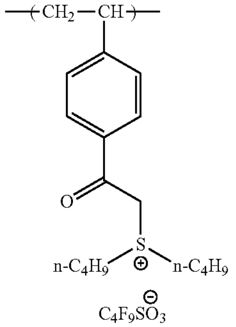
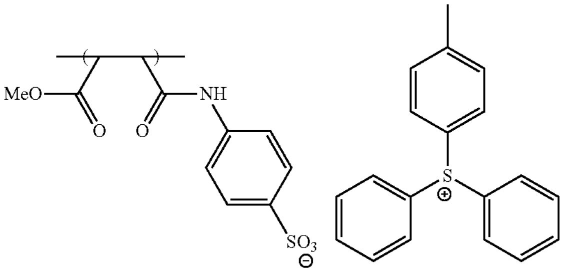
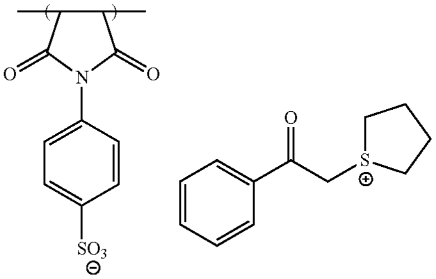
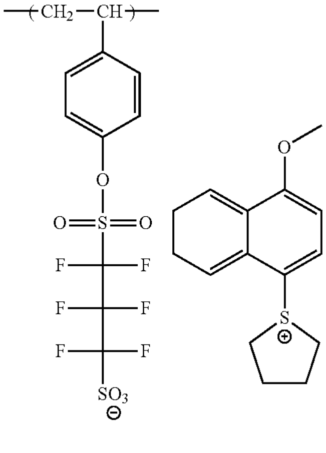

-continued

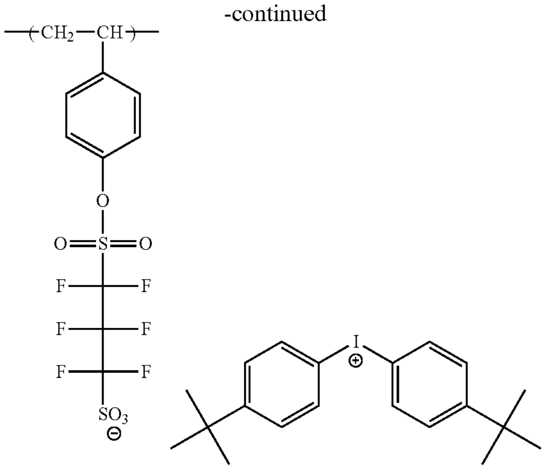

In the case where the resin (Ab) contains the repeating unit (B), the content of the repeating units (B) in the resin (Ab) is preferably from 0.1 to 80% by mole, more preferably from 0.5 to 60% by mole, and still more preferably from 1 to 40% by mole, based on all the repeating units in the resin (Ab)

In addition, when a resin composition of the present invention is exposed with ArF excimer laser, in view of the transparency with respect to ArF excimer laser, a resin not having an aromatic ring as a resin (Ab) is preferably used.

A resin suitable for ArF excimer laser exposure (also hereinafter referred to as a resin (A')) will be described below.

Examples of acid-decomposable group contained in the resin (A') include the same groups as set forth in the resin (Ab), and preferred examples of the repeating unit containing an acid-decomposable group include repeating units represented by the general formula (A2).

The content of the repeating units having an acid-decomposable group is preferably from 20 to 50% by mole, and more preferably from 25 to 45% by mole, based on all the repeating units in the resin (A').

The resin (A') is also preferably one having a repeating unit containing at least one kind of group selected from a lactone group, a hydroxyl group, a cyano group, and an alkali-soluble group.

The content of the repeating units having a lactone group is preferably from 15 to 60% by mole, more preferably from 20 to 50% by mole, and still more preferably from 30 to 50% by mole, based on all the repeating units in the resin (A').

Specific examples of the repeating unit having a lactone group are shown below, but the present invention is not limited thereto.

[Chem. 29-1]

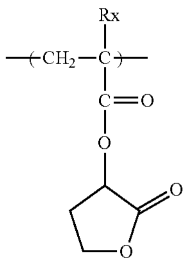
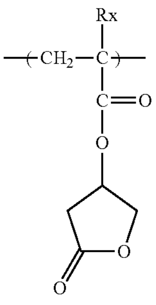
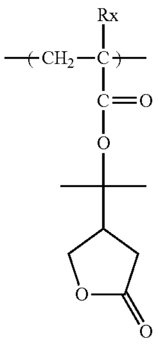

-continued

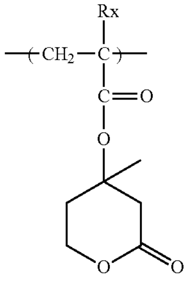
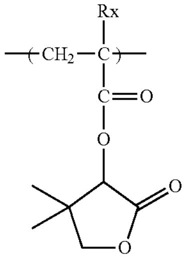
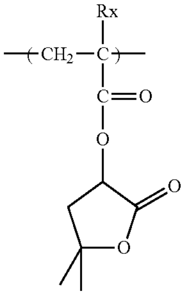

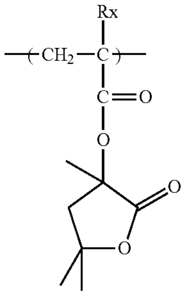
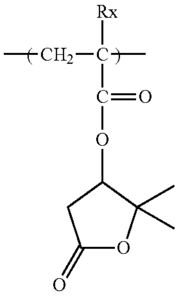

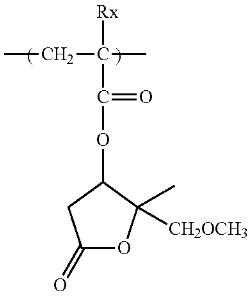
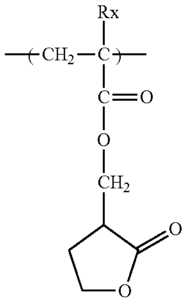

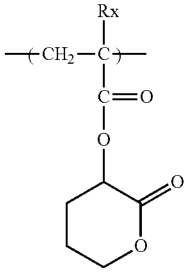
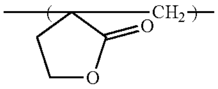

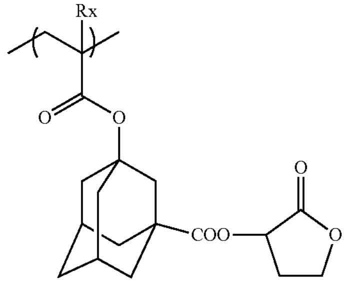

(In the formulae, Rx is H, $CH_3$, $CH_2OH$ or $CF_3$.)

-continued
[Chem. 29-2]
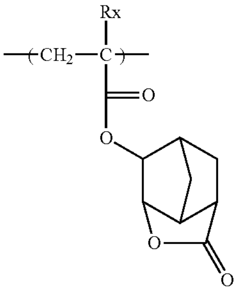
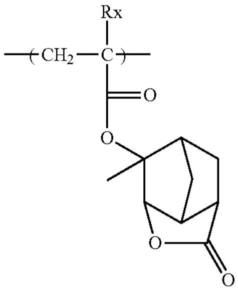
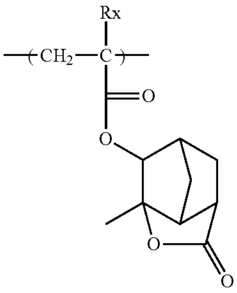
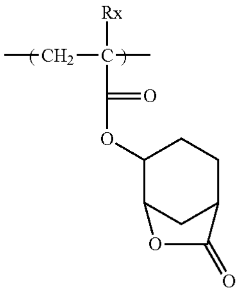
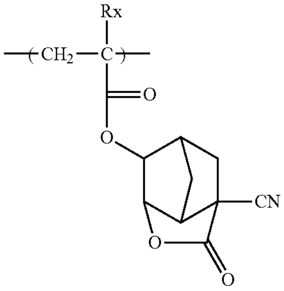
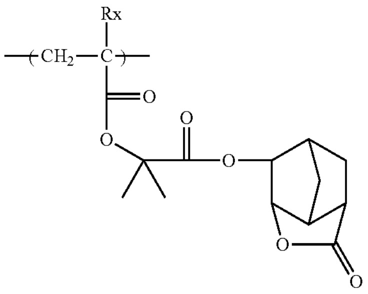
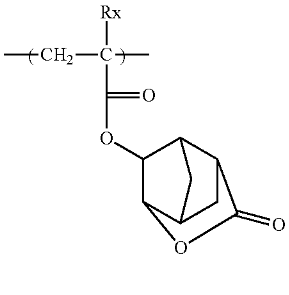
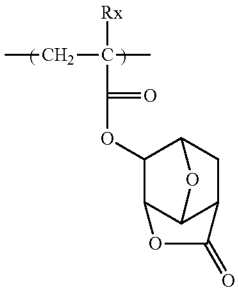
-continued
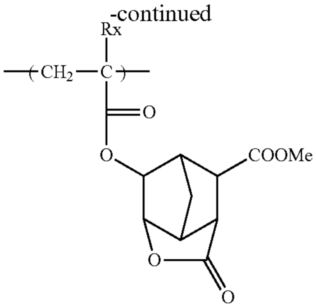
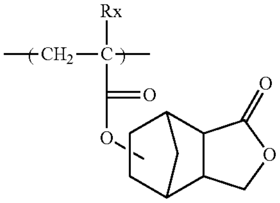
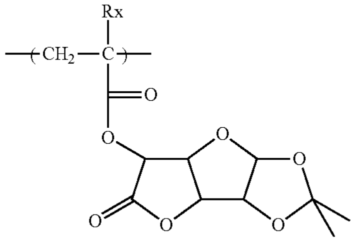
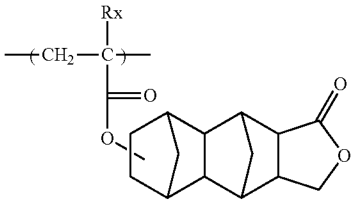
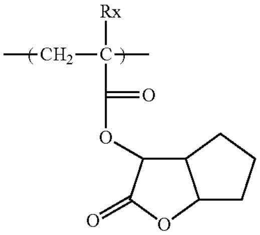
(In the formulae, Rx is H, $CH_3$, $CH_2OH$ or $CF_3$.)
[Chem. 29-3]
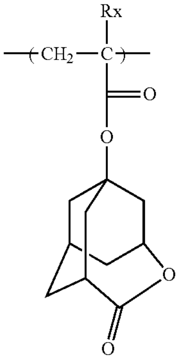
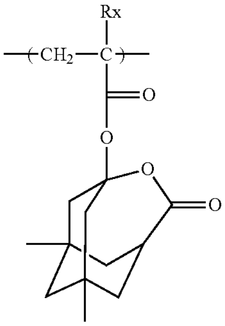

-continued

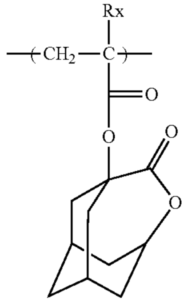

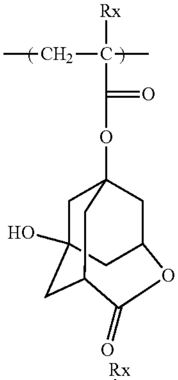

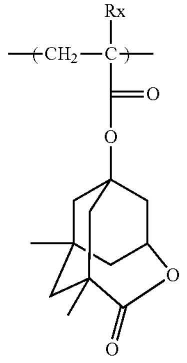

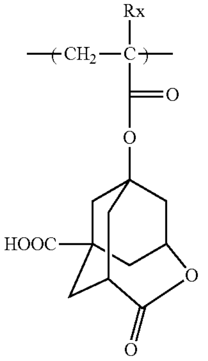

(In the formulae, Rx is H, $CH_3$, $CH_2OH$ or $CF_3$.)

The resin (A') preferably has a repeating unit containing a hydroxyl group or a cyano group. This increases the adherence to a substrate and affinity to a developer. The repeating unit having a hydroxyl group or a cyano group is preferably a repeating unit having an alicyclic hydrocarbon structure substituted with a hydroxyl group or a cyano group. The alicyclic hydrocarbon structure in the alicyclic hydrocarbon structure substituted with a hydroxyl group or a cyano group is preferably an adamantyl group, a diamantyl group and a norbornane group.

The content of the repeating units having a hydroxyl group or a cyano group is preferably from 5 to 40% by mole, more preferably from 5 to 30% by mole, and still more preferably from 10 to 25% by mole, based on all the repeating units in the resin (A').

Specific examples of the repeating unit having a hydroxyl group or a cyano group are shown below, but the present invention is not limited thereto.

[Chem. 30]

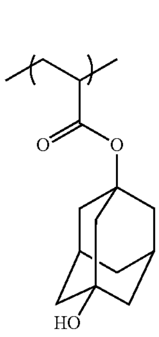

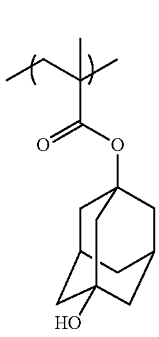

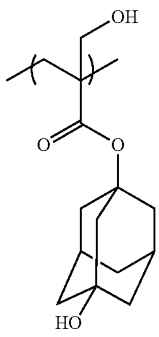

-continued

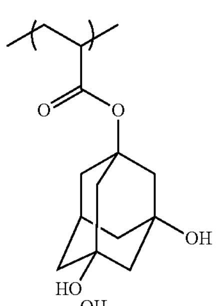

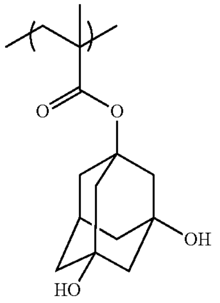

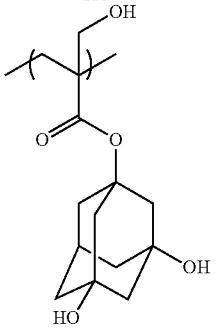

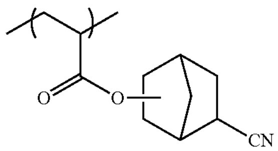

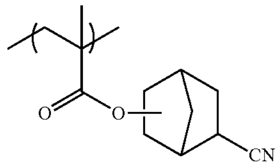

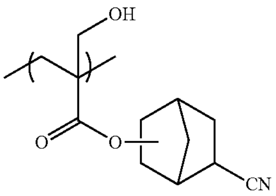

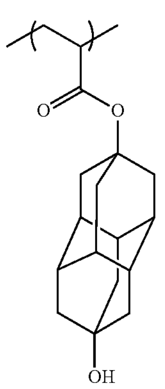

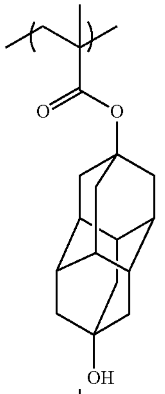

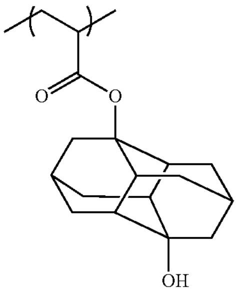

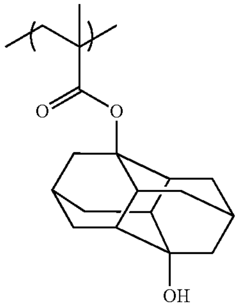

The resin (A') preferably has a repeating unit having an alkali-soluble group. Examples of the alkali-soluble group include a carboxyl group, a sulfonamide group, a sulfonylimide group, a bissulfonylimide group, and an aliphatic alcohol (for example, a hexafluoroisopropanol group) with the α-position being substituted with an electron-withdrawing group, and more preferably has a repeating unit having a carboxyl group. By virtue of containing the repeating units having an alkali-soluble group, the resolution increases in the usage of forming contact holes. As the repeating unit having an alkali-soluble group, a repeating unit in which an alkali-soluble group is directly bonded to the main chain of a resin such as a repeating unit by an acrylic acid or a methacrylic acid, a repeating unit in which an alkali-soluble group is bonded to the main chain of a resin by a connecting group, and a repeating unit in which a polymerization initiator or a chain transfer agent having an alkali-soluble group is used in the polymerization to be introduced into the end of a polymer chain are all preferred, and the connecting group may have a monocyclic or polycyclic hydrocarbon structure. A repeating unit of acrylic acid or methacrylic acid is particularly preferred.

The content of the repeating units having an alkali-soluble group is preferably from 0 to 20% by mole, more preferably from 3 to 15% by mole, and still more preferably from 5 to 10% by mole, based on the entire repeating units in the resin (A').

Specific examples of the repeating unit having an alkali-soluble group are shown below, but the present invention is not limited thereto.

[Chem. 31]

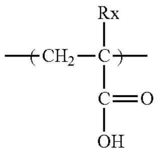

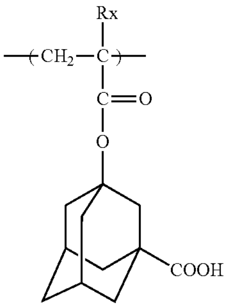

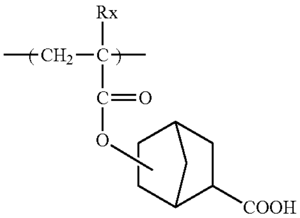

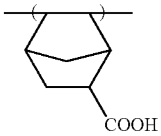

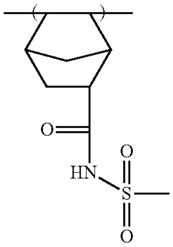

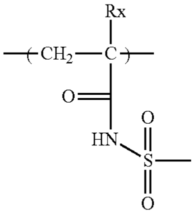

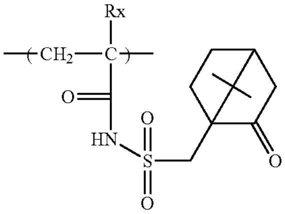

-continued

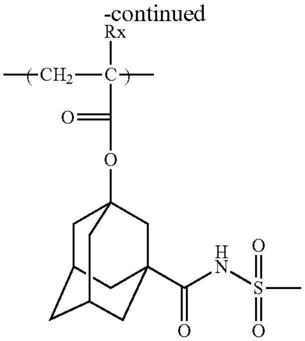

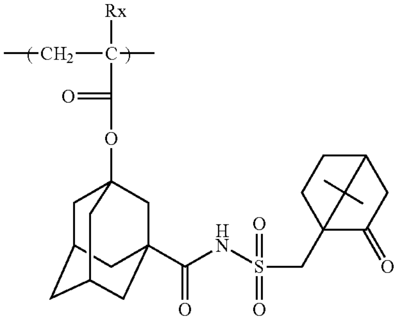

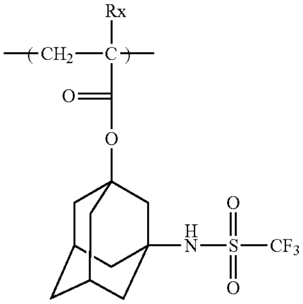

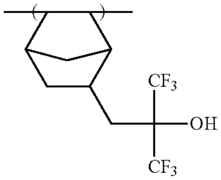

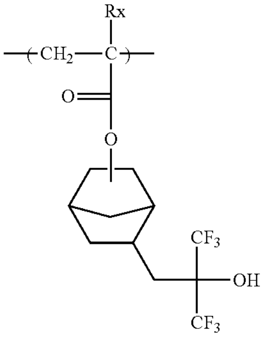

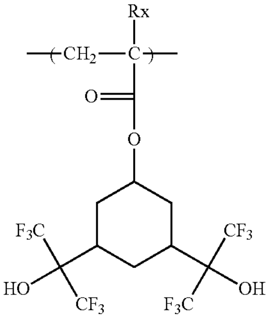

(In the formulae, Rx is H, $CH_3$, $CF_3$ or $CH_2OH$)

The resin (A') may further have an alicyclic hydrocarbon structure and may have a repeating unit which does not show acid-decomposability. This can reduce the elution of low molecular components from a resist film the immersion liquid upon immersion liquid exposure. Examples of the repeating unit include repeating units of 1-adamantyl (meth) acrylate, diamantyl (meth)acrylate, tricyclodecanyl (meth)acrylate, or cyclohexyl (meth)acrylate.

The resin (Ab) may be used in combination of two or more kinds thereof.

The addition amount of the resin (Ab) in terms of a total amount is usually from 10 to 99% by mass, preferably from 20 to 99% by mass, and particularly preferably from 30 to 99% by mass, based on the total solid contents of the composition of the present invention. In addition, the amount of residual monomers and oligomer components in the resin (Ab) is preferably from 0 to 10% by mass, more preferably from 0 to 5% by mass and further preferably from 0 to 1% by mass. When these conditions are satisfied, a resist composition free from time course change of foreign substances in a liquid or sensitivity or the like can be obtained.

The weight average molecular weight (Mw) of the resin (Ab) is each preferably in the range of 1,000 to 200,000. In views of the dissolution rate in an alkali and the sensitivity of the resin itself it is preferably 200,000 or less. The degree of dispersion (Mw/Mn) of the resin (Ab) is preferably from 1.0 to 3.0, more preferably from 1.0 to 2.5 and particularly preferably from 1.0 to 2.0.

The weight average molecular weight (Mw) of the resin is more preferably in a range of from 1,000 to 100,000, particularly preferably in a range of from 1,000 to 50,000 and most preferably in a range of from 1,000 to 25,000.

Here, the weight average molecular weight is defined in terms of a polystyrene equivalent value by gel permeation chromatography (carrier: tetrahydrofuran (THF)). Specifically, the weight average molecular weight (Mw) and the number average molecular weight (Mn) of the resin (Ab) may be obtained by using, for example, an HLC-8120 (manufactured by Tosoh Corporation) using TSK gel Multipore HXL-M columns (manufactured by Tosoh Corporation, 7.8 mm ID×30.0 cm) and THF (tetrahydrofuran) as an eluent.

The resin (Ab) having a dispersity of 2.0 or less can be synthesized by carrying out radical polymerization using an azo-based polymerization initiator. More preferably, the resin (Ab) having a dispersity of 1.0 to 1.5 can be synthesized by, for example, living radical polymerization.

The resin (Ab) is preferably polymerized by a known anion polymerization method, a radical polymerization method, or the like. For example, the resin (Ab) can be synthesized by using a method disclosed in JP2010-13428A.

Specific examples of the resin (Ab) are shown below, but the present invention is not limited thereto.

[Chem. 32-1]

(Ab-1)

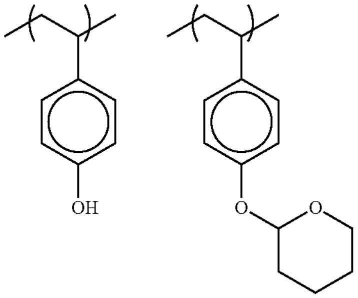

(Ab-2)

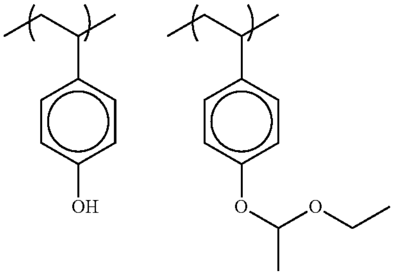

-continued (Ab-3)

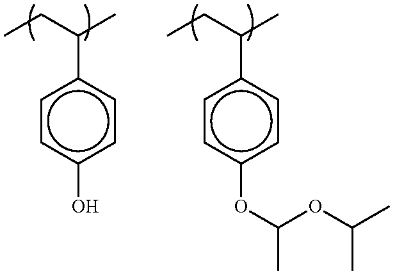

(Ab-4)

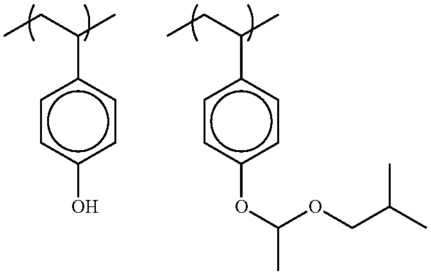

(Ab-5)

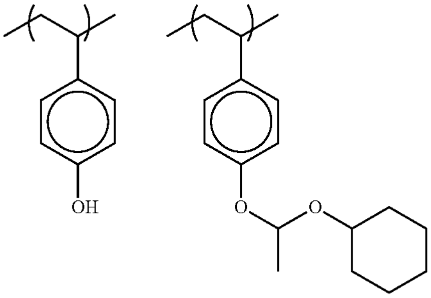

(Ab-6)

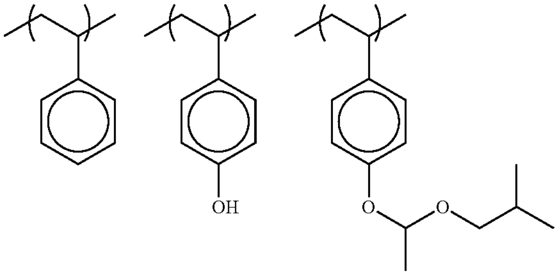

(Ab-7)

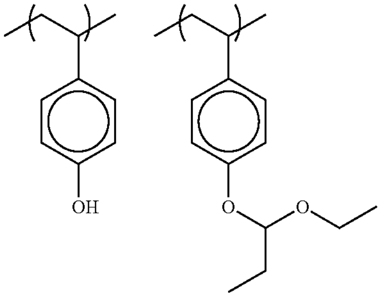

-continued
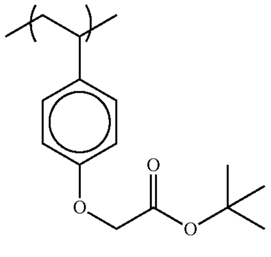
(Ab-8)
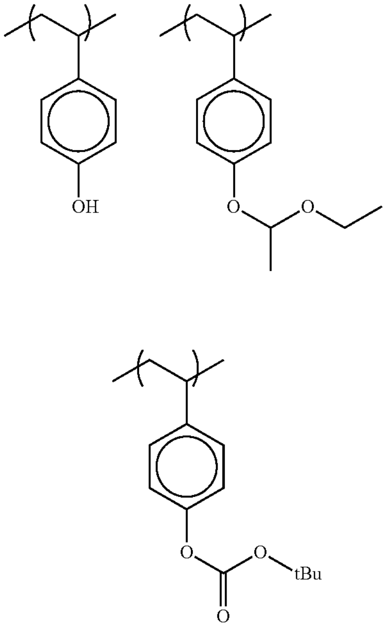
(Ab-9)
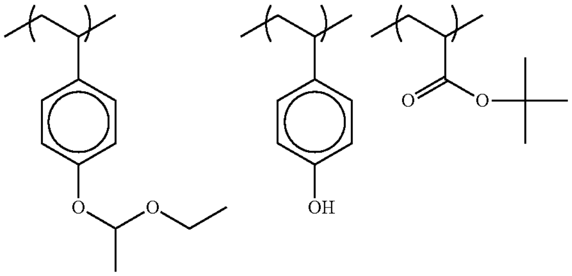
(Ab-10)
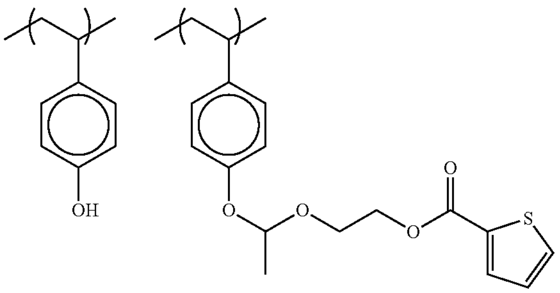
-continued
(Ab-11)
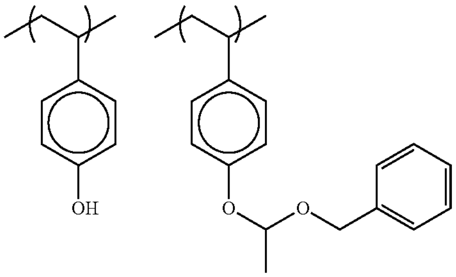
(Ab-12)
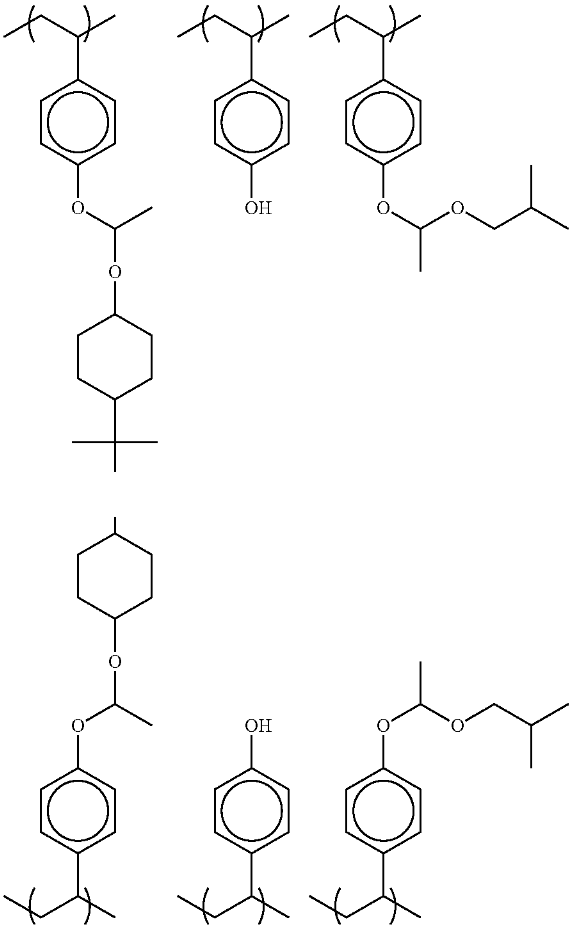
[Chem. 32-2]
(Ab-13)
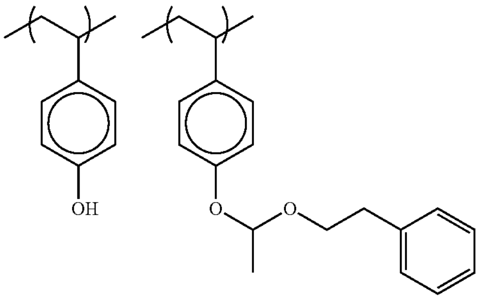

-continued
(Ab-14)
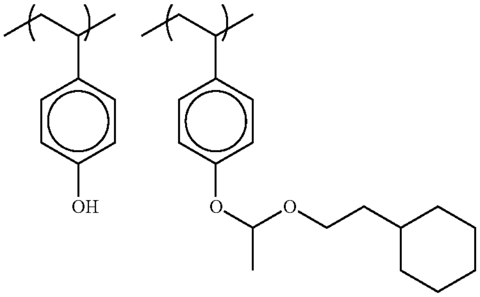
(Ab-16)
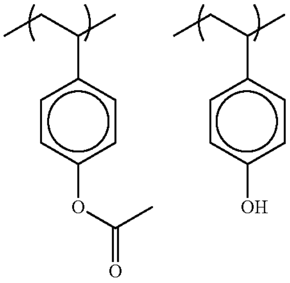
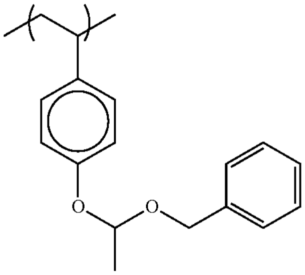
(Ab-17)
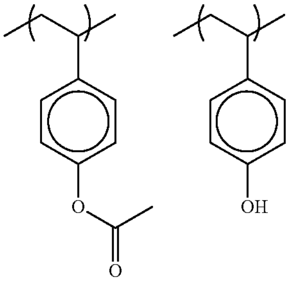
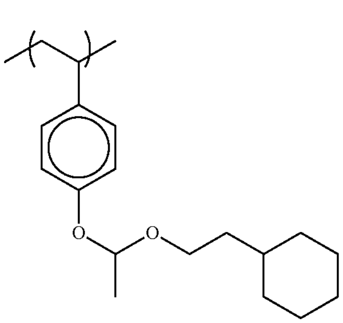
-continued
(Ab-19)
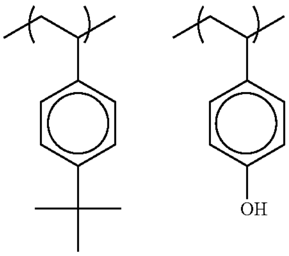
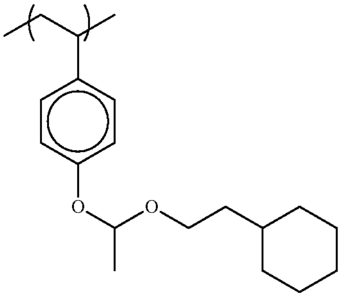
(Ab-20)
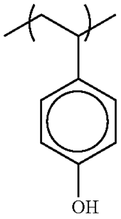
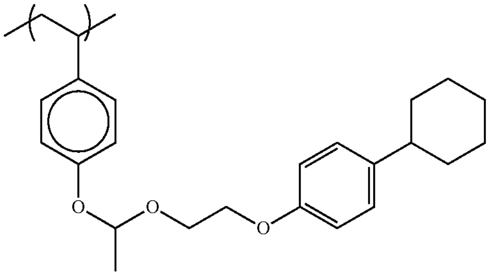
(Ab-21)
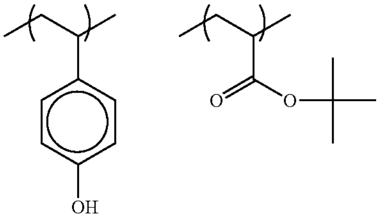
(Ab-22)
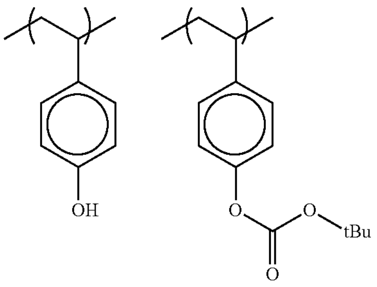

-continued
(Ab-23)
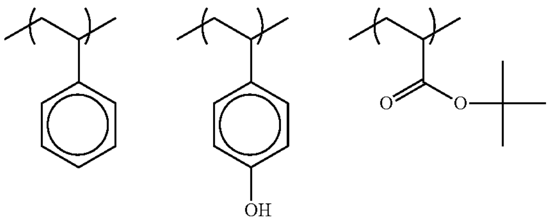
(Ab-24)
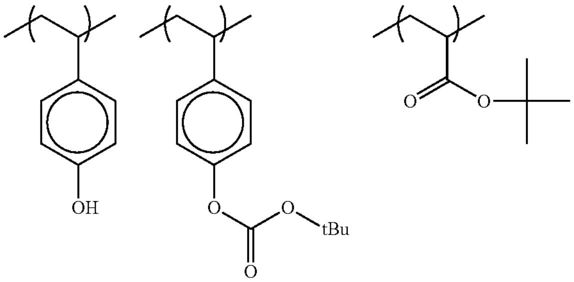
(Ab-25)
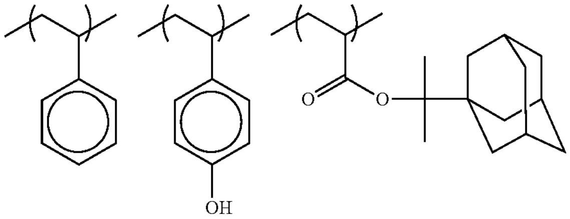
(Ab-26)
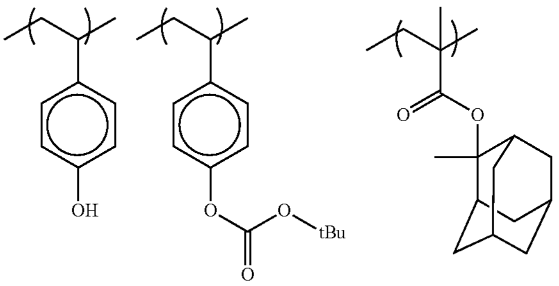
[Chem. 32-3]
(Ab-27)
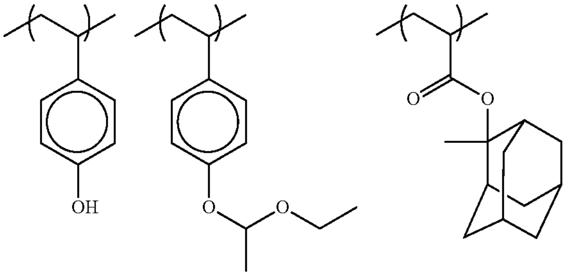
-continued
(Ab-28)
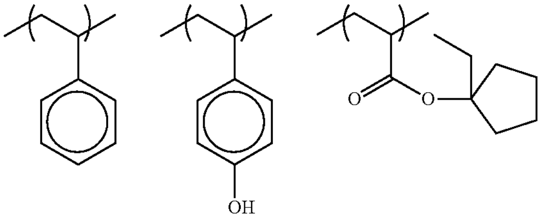
(Ab-29)
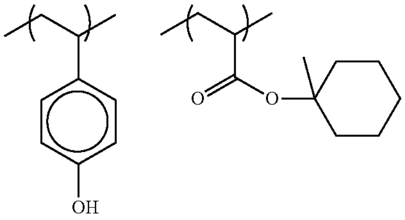
[Chem. 32-4]
(Ab-30)
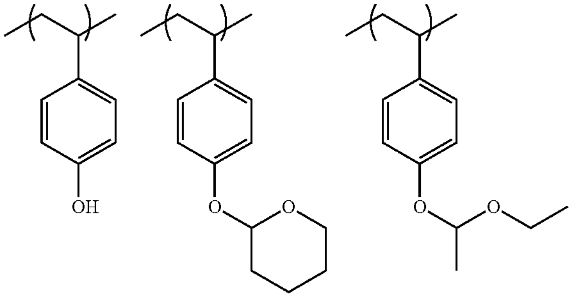
(Ab-31)
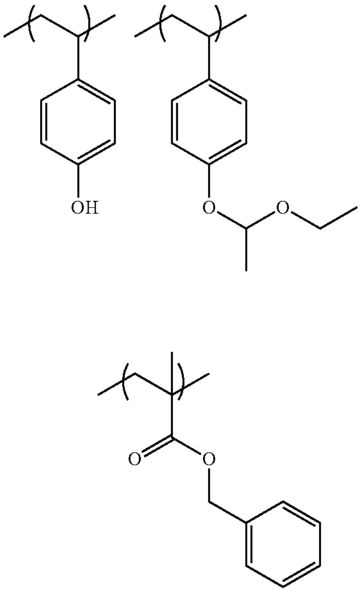

-continued
(Ab-32)
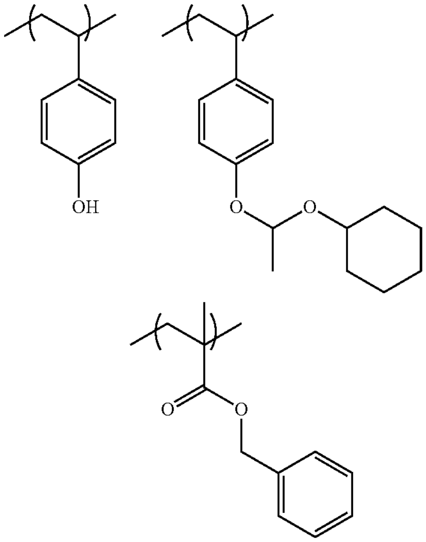
[Chem. 32-5]
(Ab-33)
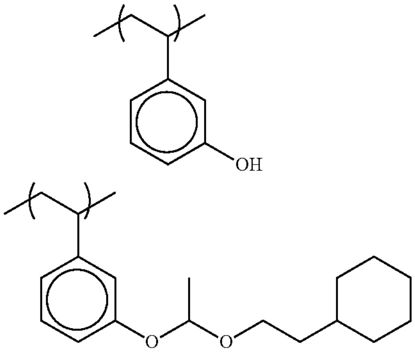
(Ab-34)
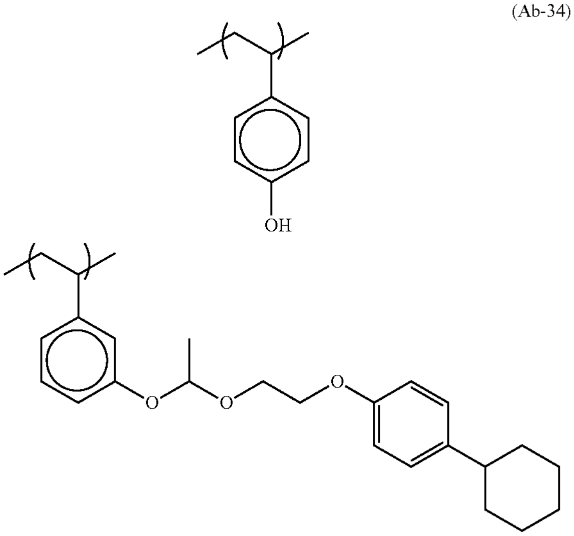
(Ab-35)
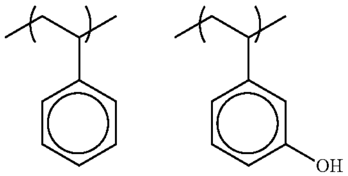
-continued
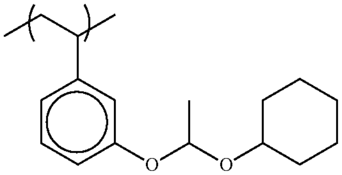
(Ab-36)
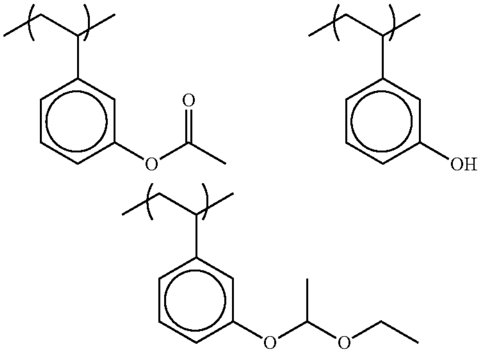
(Ab-37)
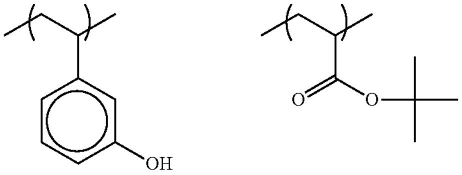
(Ab-38)
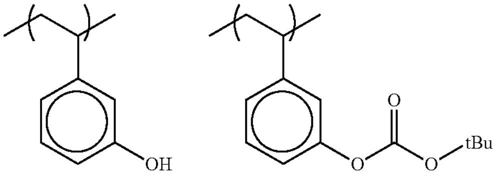
(Ab-39)
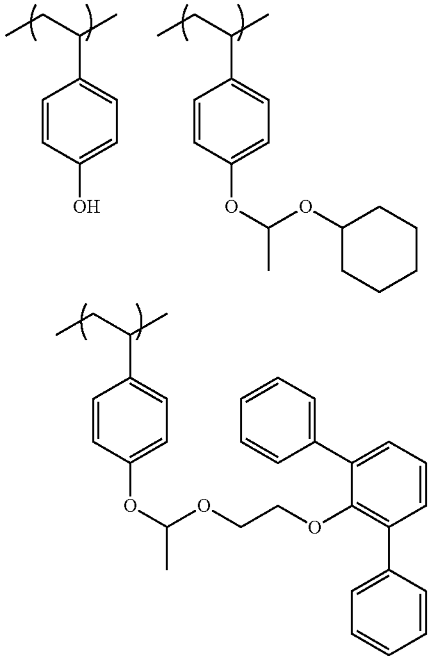

-continued
(Ab-40)
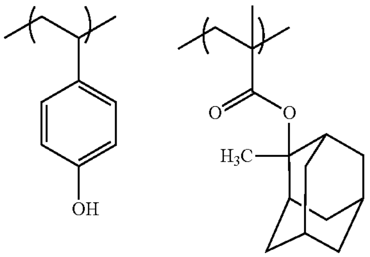
(Ab-41)
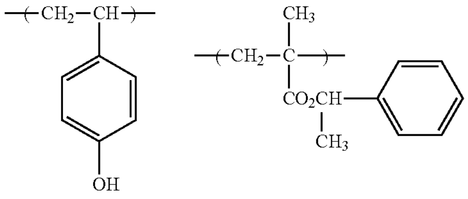
(Ab-42)
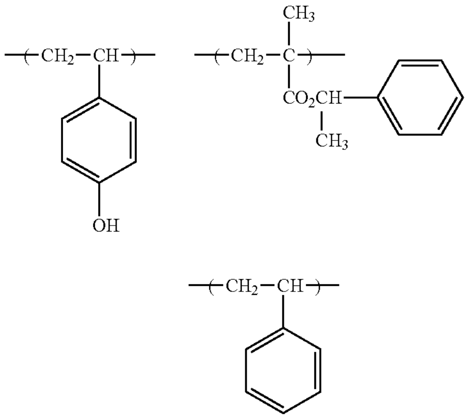
[Chem. 32-6]
(Ab-43)
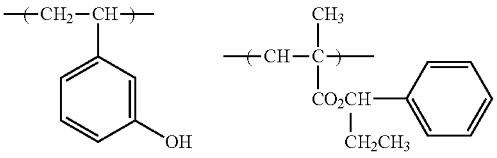
(Ab-52)
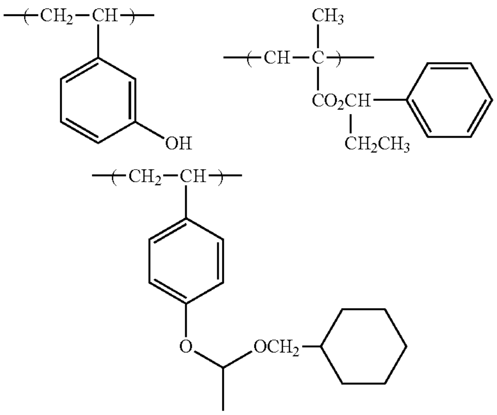
-continued
(Ab-53)
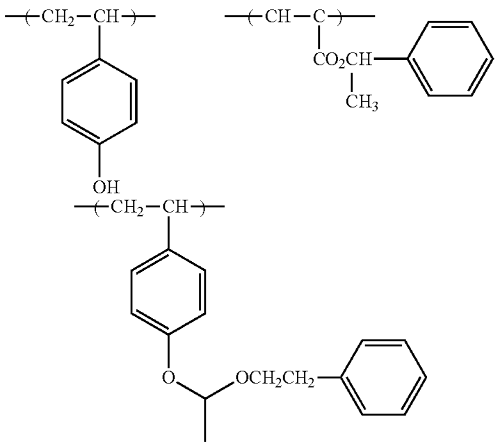
(Ab-56)
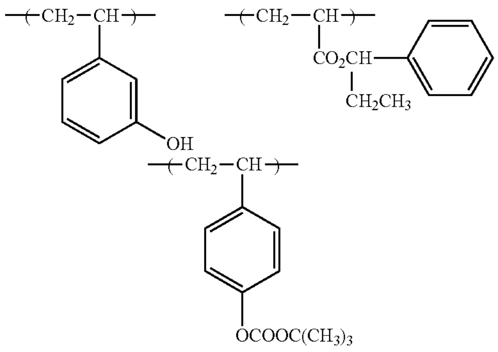
[Chem. 32-7]
(Ab-57)
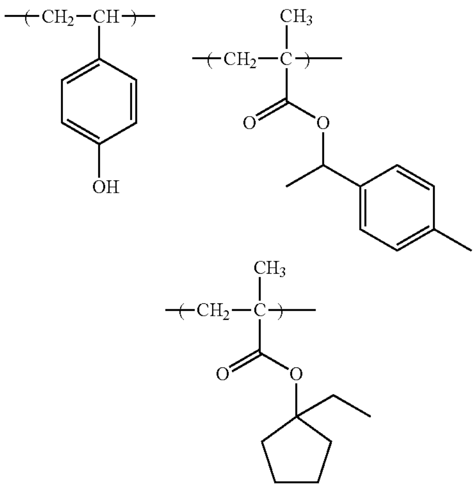
(Ab-58)
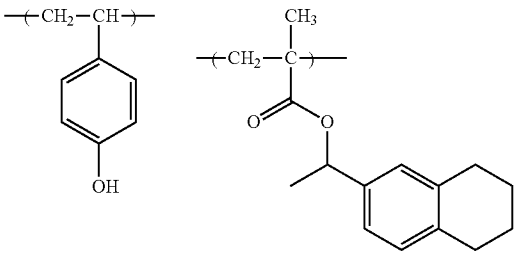

-continued
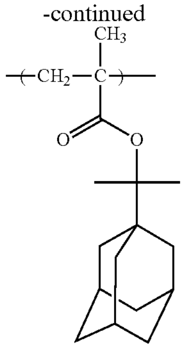
(Ab-59)
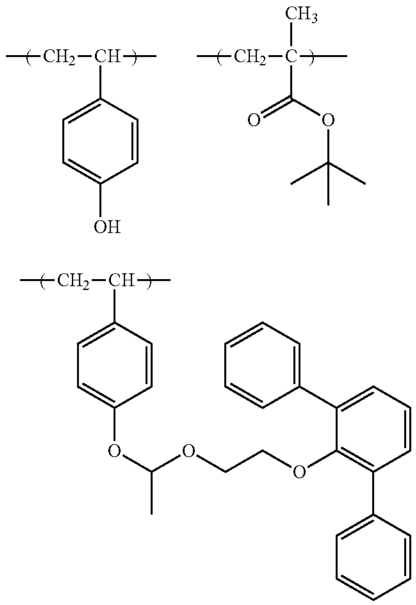
(Ab-60)
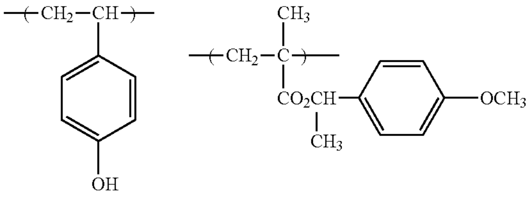
(Ab-61)
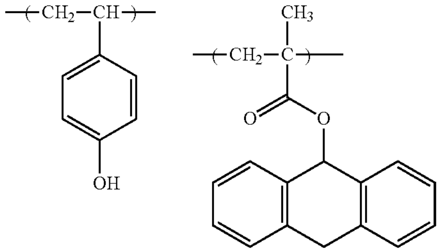
(Ab-62)
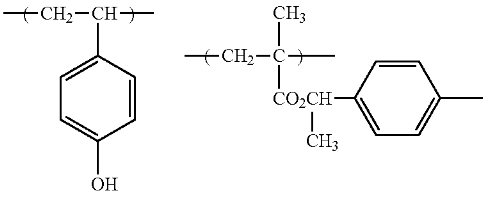
-continued
[Chem. 32-8]
(Ab-68)
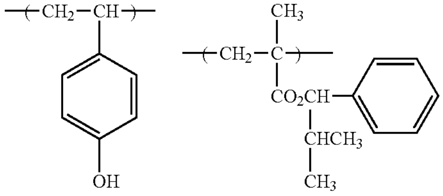
(Ab-71)
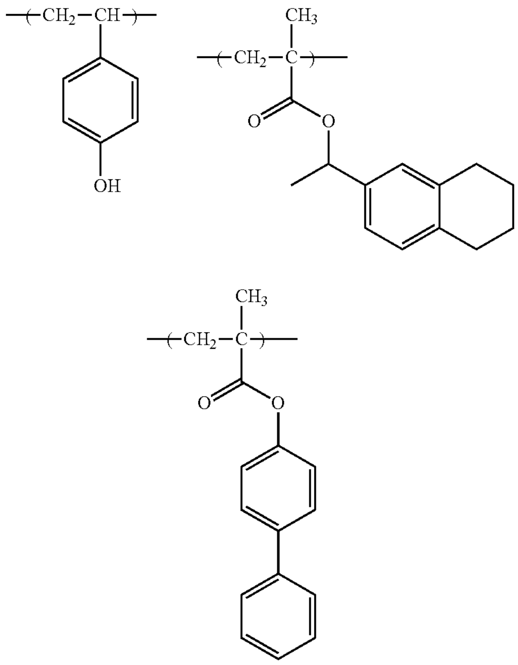
(Ab-73)
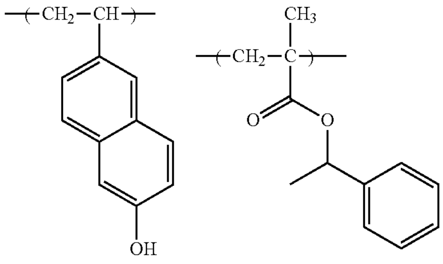
[Chem. 32-9]
(Ab-74)
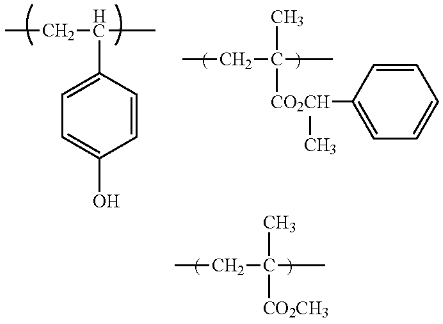

-continued
(Ab-76)
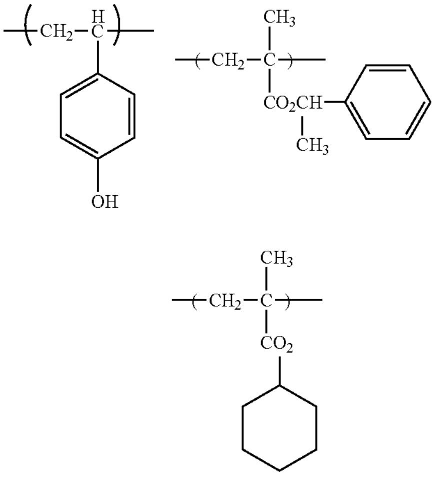
(Ab-80)
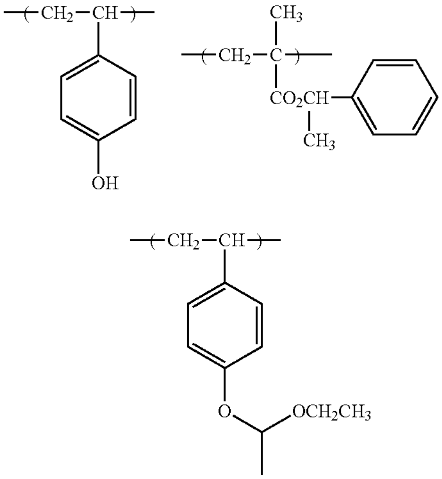
(Ab-81)
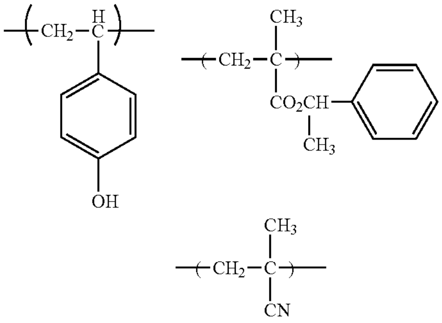
[Chem. 32-10]
(Ab-87)
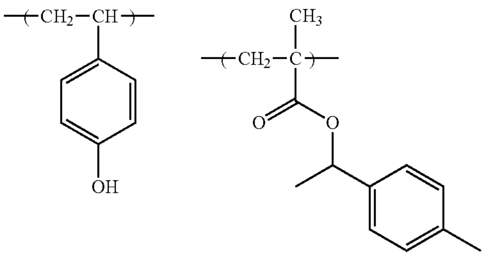
-continued
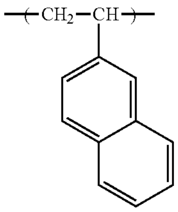
(Ab-88)
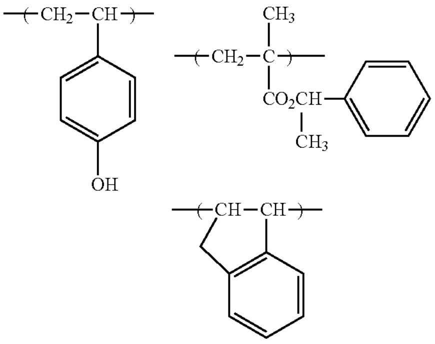
[Chem. 32-11]
(Ab-90)
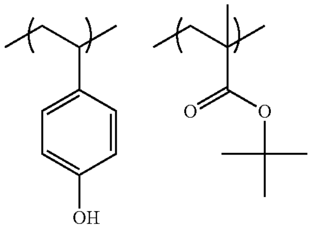
(Ab-91)
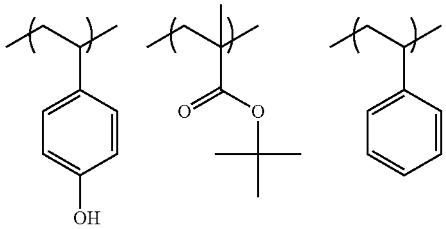
(Ab-92)
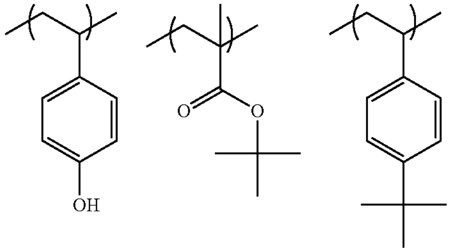
(Ab-93)
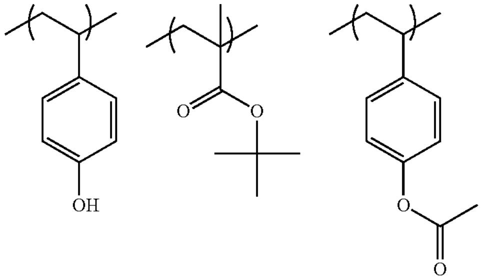

-continued
(Ab-94)
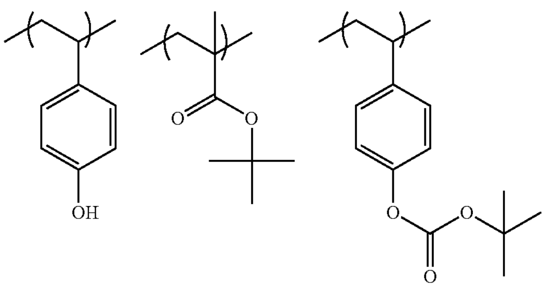
(Ab-95)
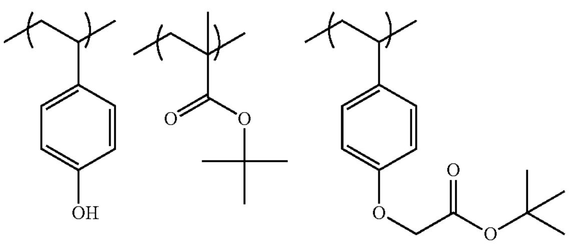
(Ab-96)
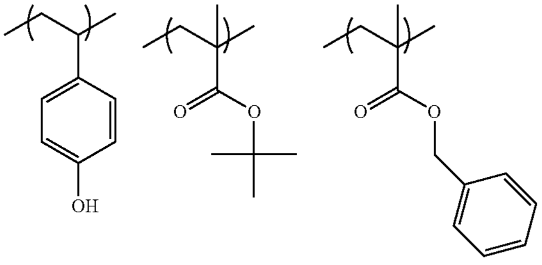
(Ab-97)
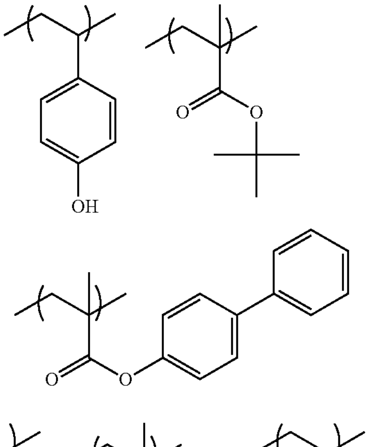
(Ab-101)
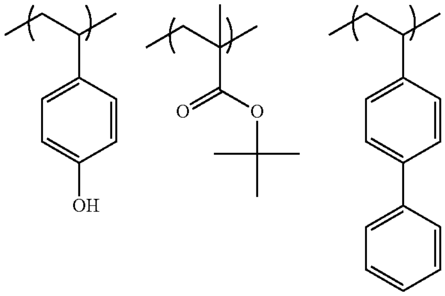
-continued
(Ab-102)
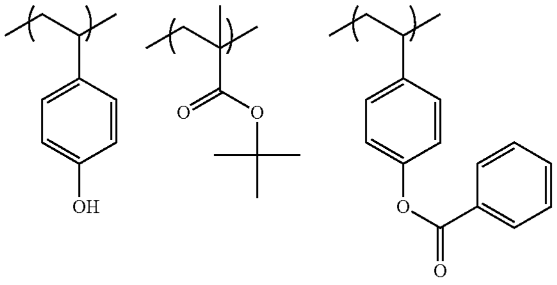
[Chem. 32-12]
(Ab-105)
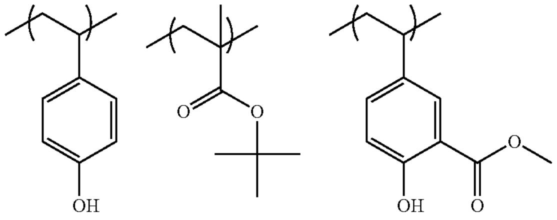
(Ab-106)
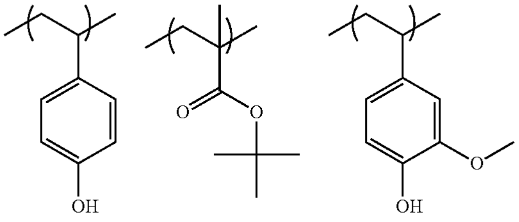
(Ab-120)
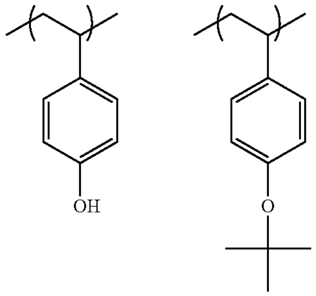
(Ab-121)
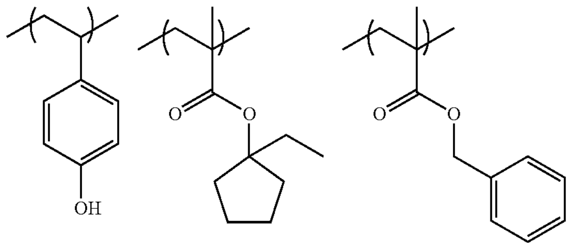

-continued
[Chem. 32-13]
(Ab-125)
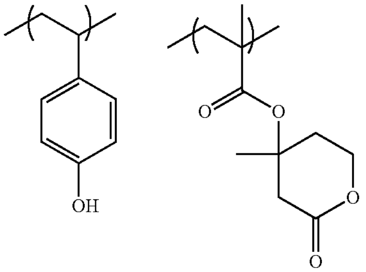
(Ab-126)
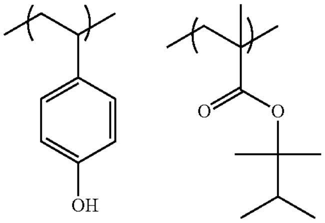
(Ab-127)
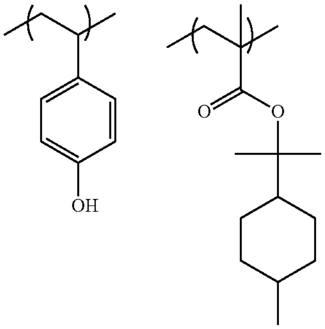
(Ab-128)
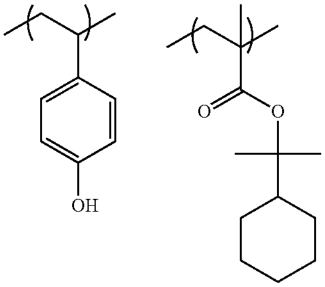
(Ab-129)
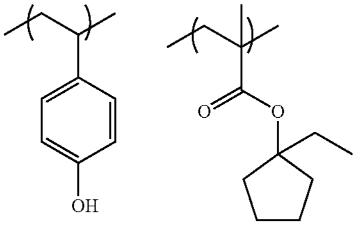
-continued
(Ab-130)
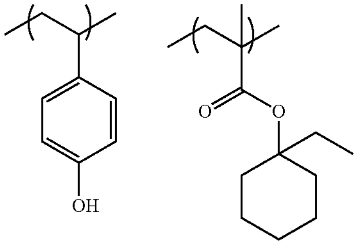
(Ab-133)
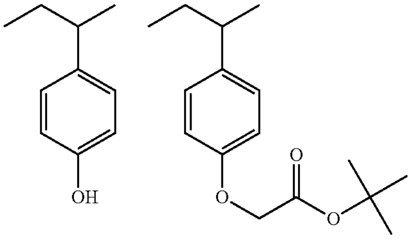
(Ab-134)
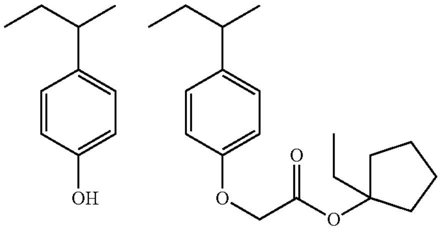
(Ab-135)
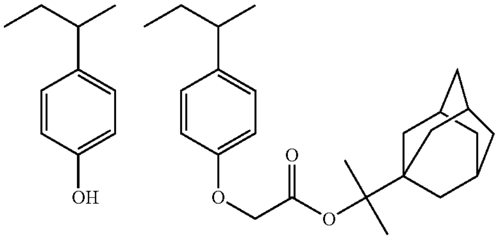
(Ab-136)
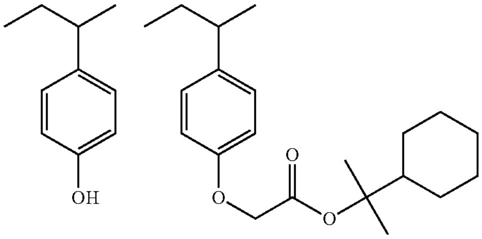
(Ab-137)
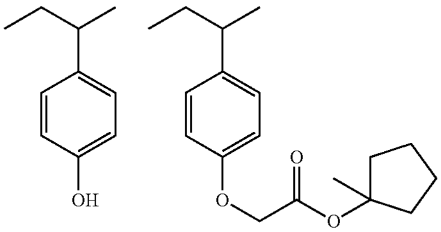

-continued
(Ab-138)
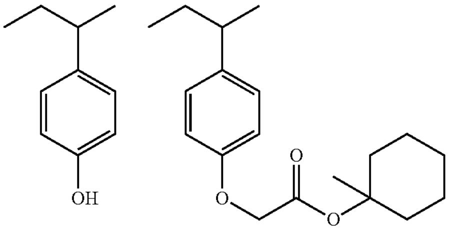
[Chem. 32-14]
(Ab-139)
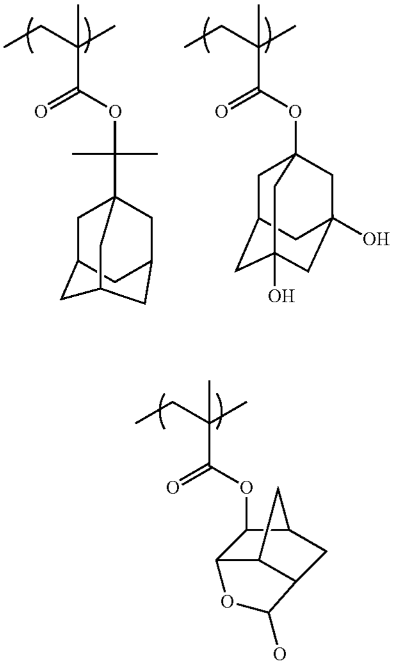
(Ab-140)
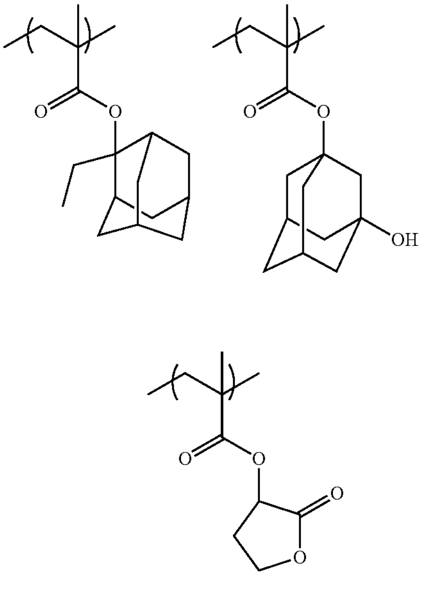
-continued
(Ab-141)
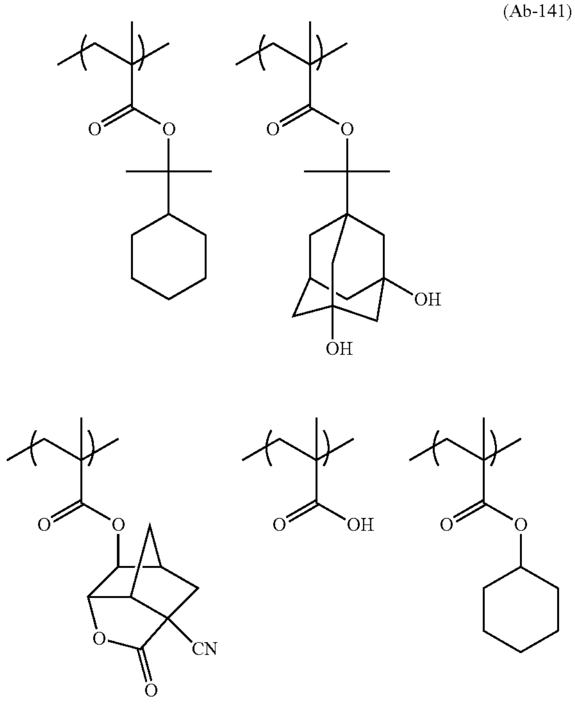
(Ab-142)
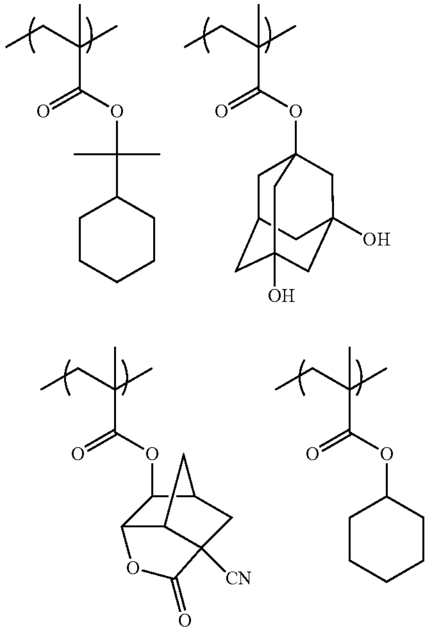
(Ab-143)
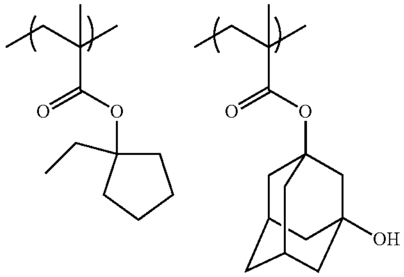

-continued
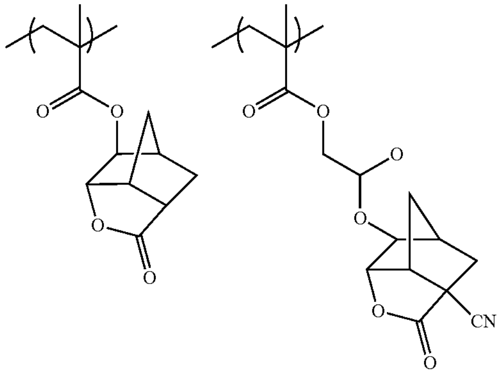
(Ab-144)
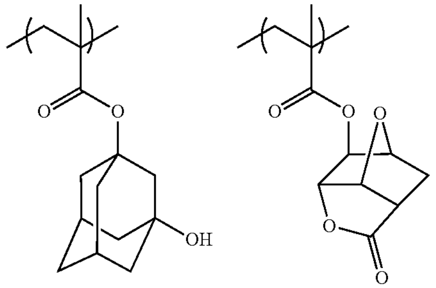
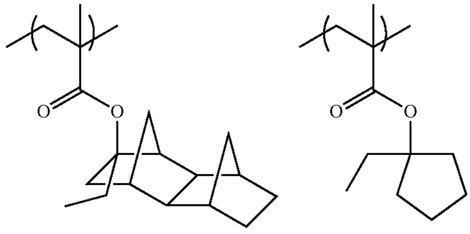
(Ab-145)
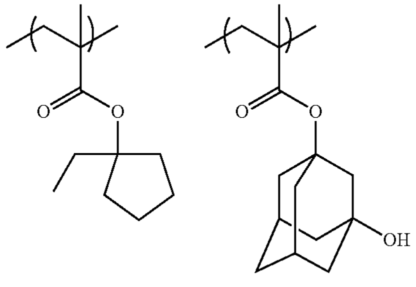
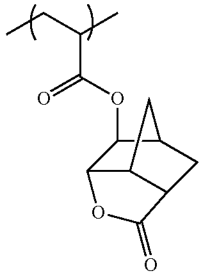
-continued
(Ab-146)
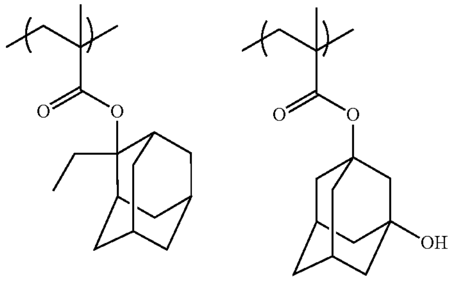
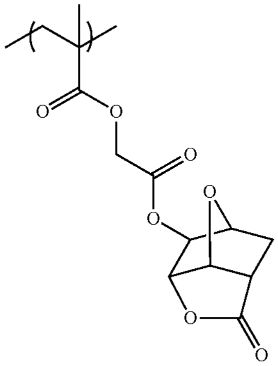
(Ab-147)
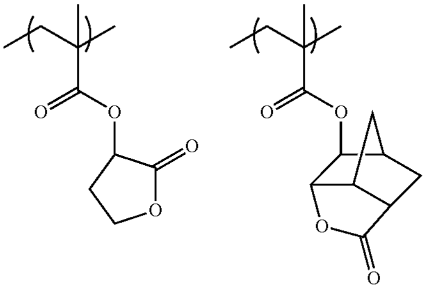
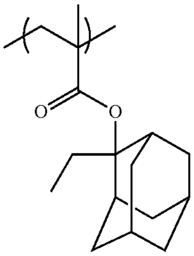
(Ab-148)
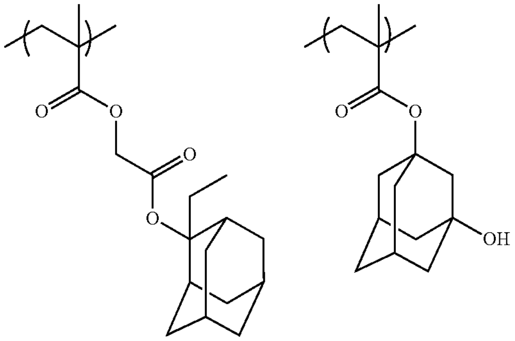

-continued
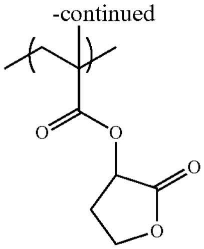
[Chem. 32-15]
(Ab-157)
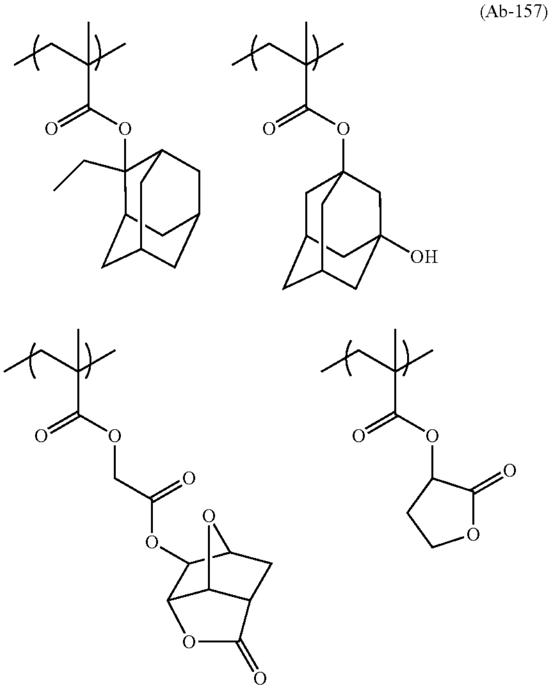
(Ab-158)
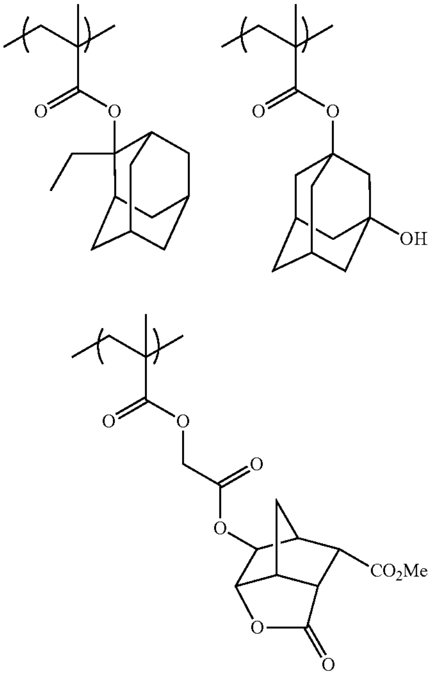
-continued
(Ab-159)
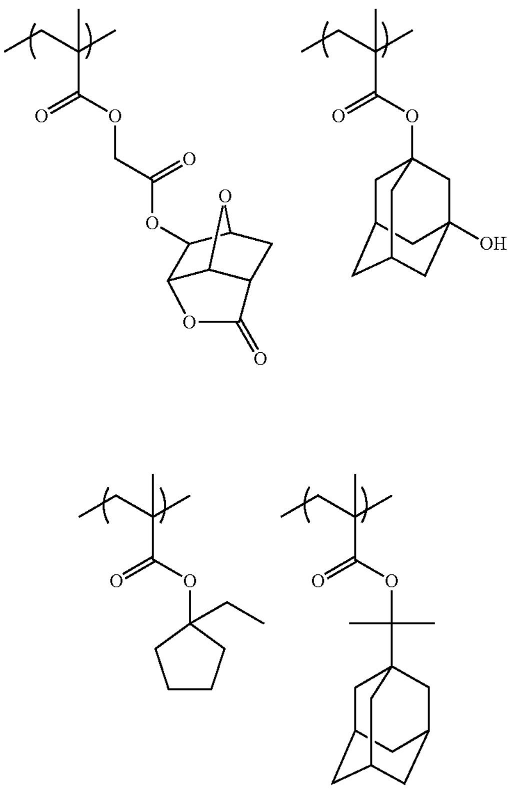
(Ab-160)
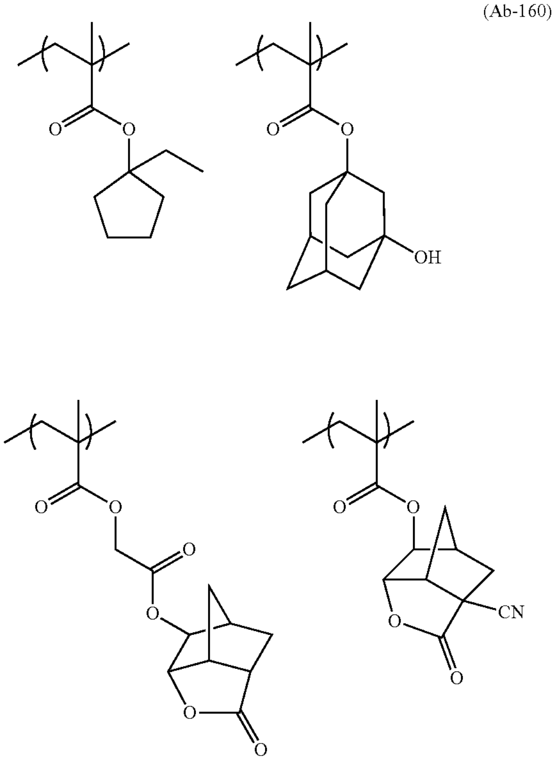

-continued
(Ab-161)
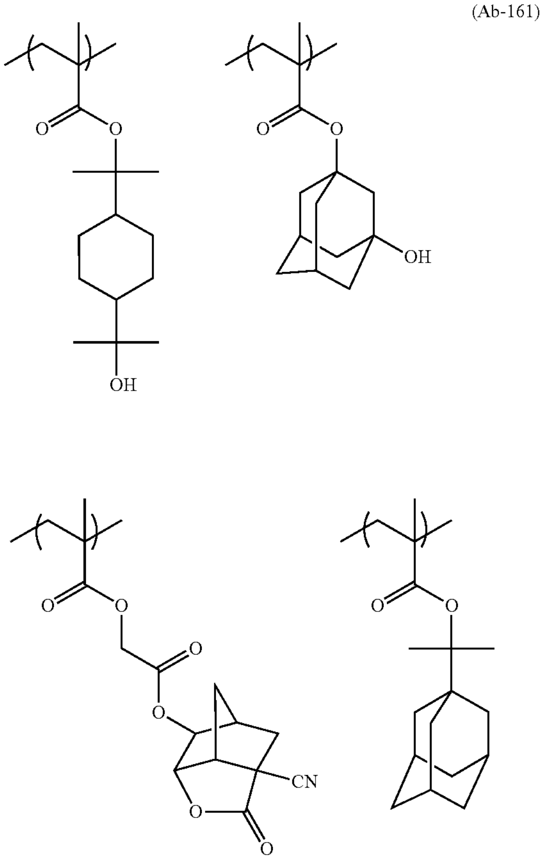
(Ab-162)
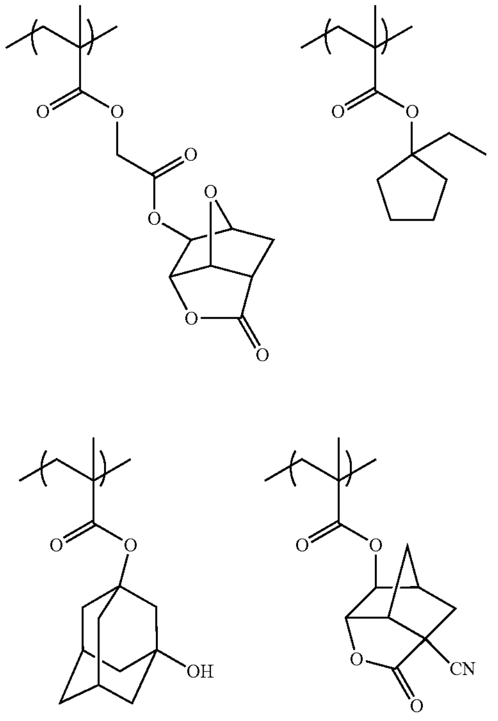
-continued
(Ab-163)
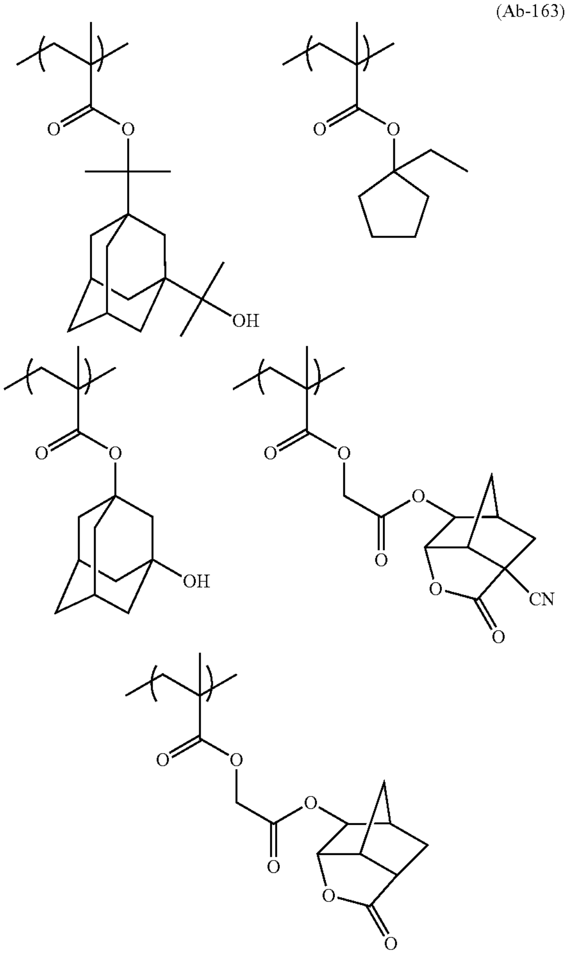
[Chem. 32-16]
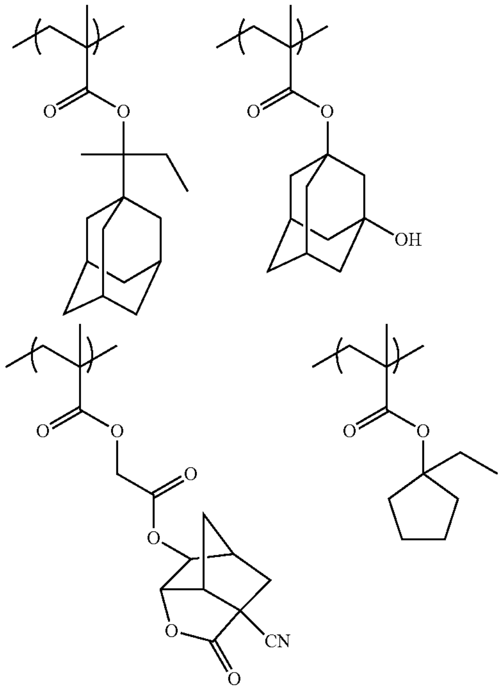

-continued
[Chem. 32-17]
(Ab-165)
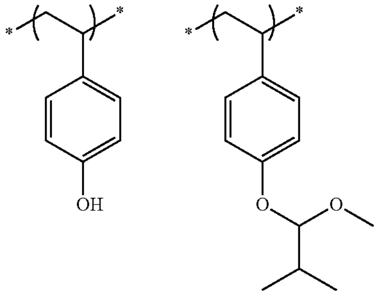
(Ab-166)
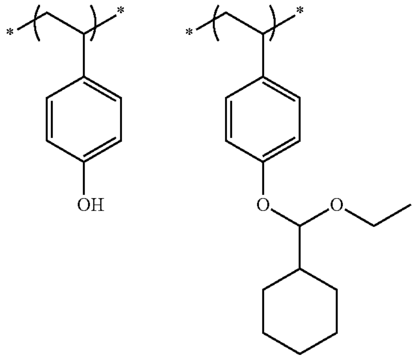
(Ab-167)
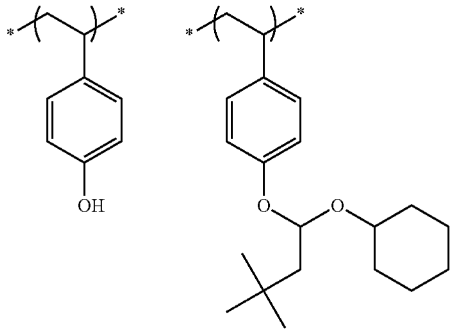
(Ab-168)
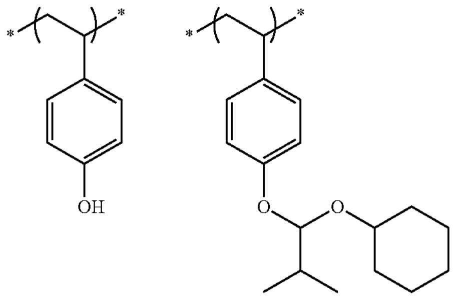
-continued
(Ab-169)
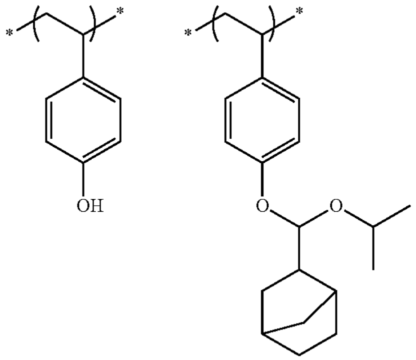
(Ab-170)
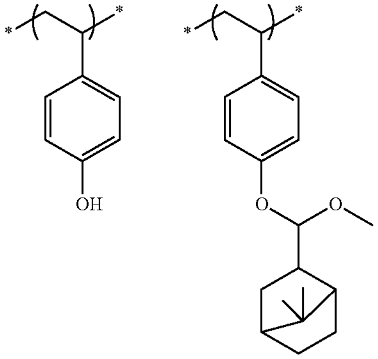
(Ab-171)
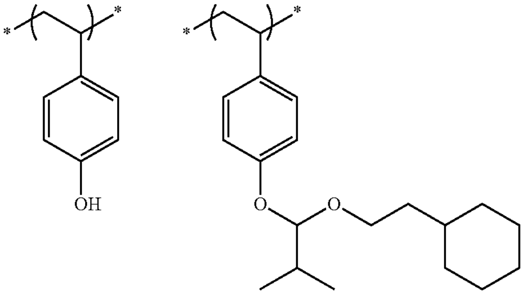
(Ab-172)
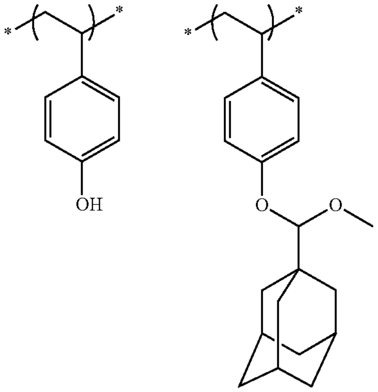

-continued
(Ab-173)
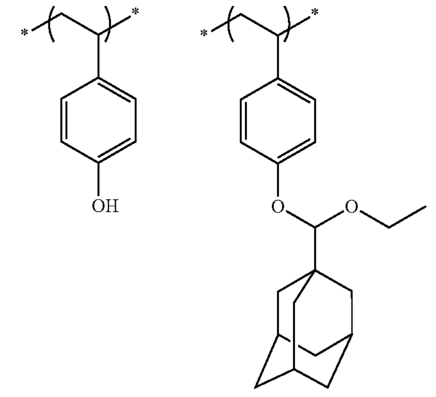
(Ab-174)
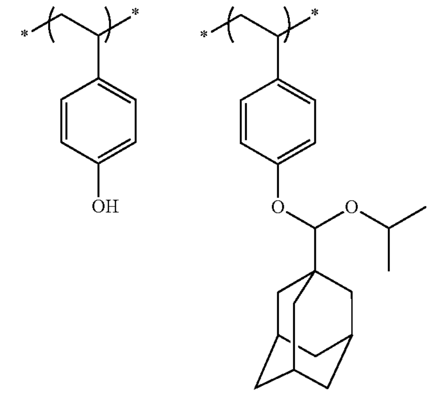
(Ab-175)
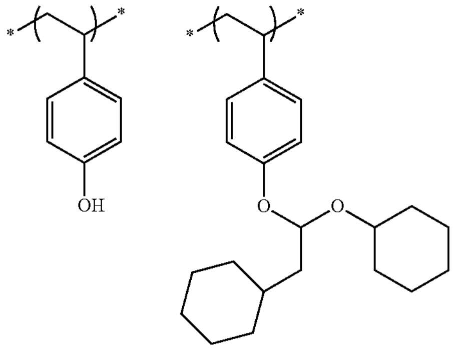
(Ab-176)
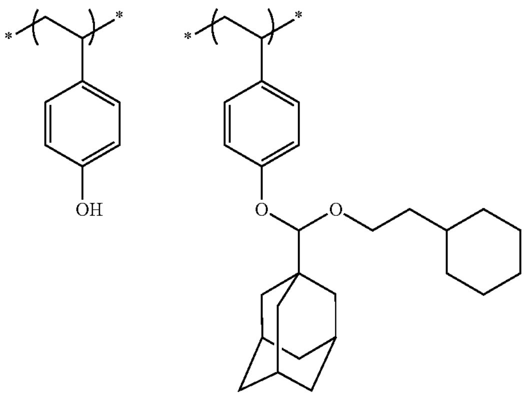
-continued
[Chem. 32-18]
(Ab-177)
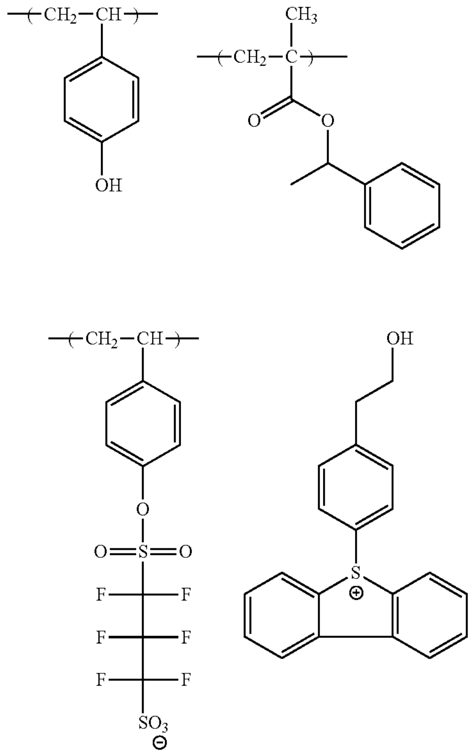
(Ab-178)
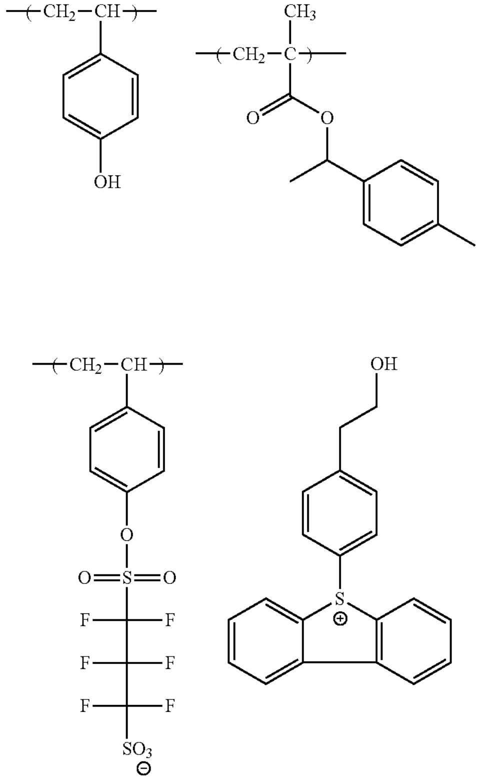

-continued
(Ab-179)
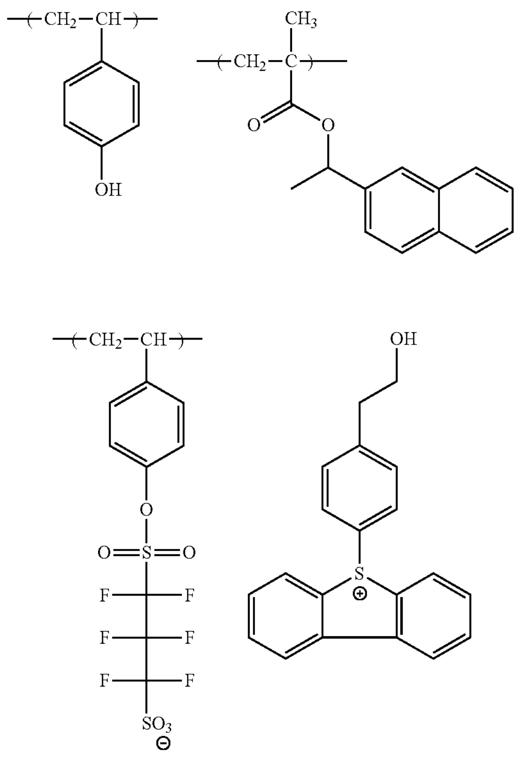
(Ab-180)
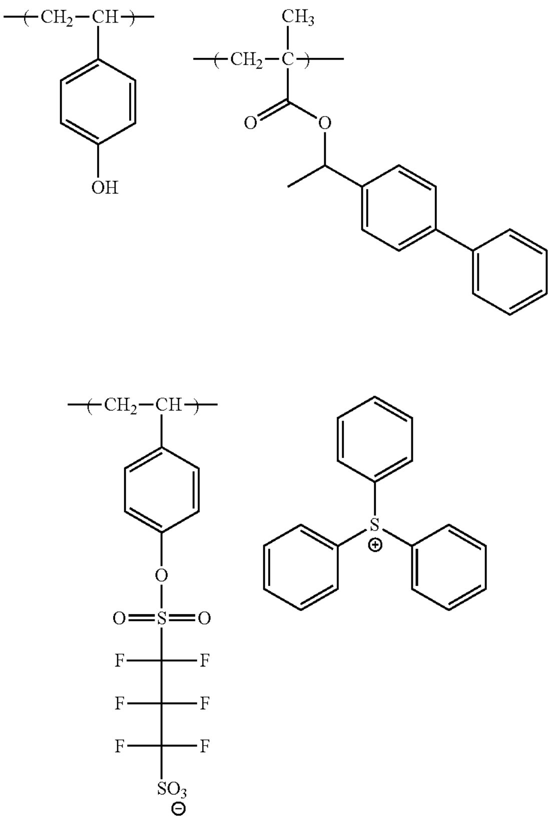
-continued
(Ab-182)
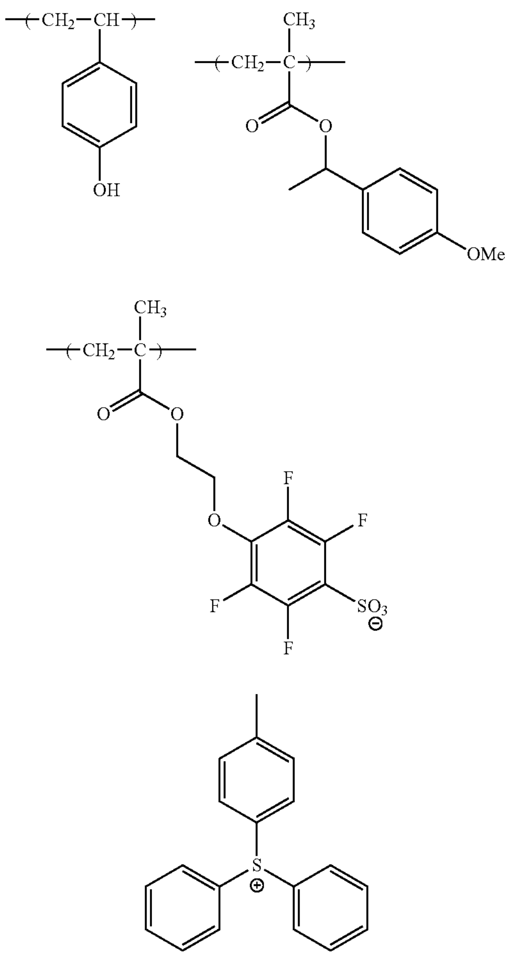
(Ab-183)
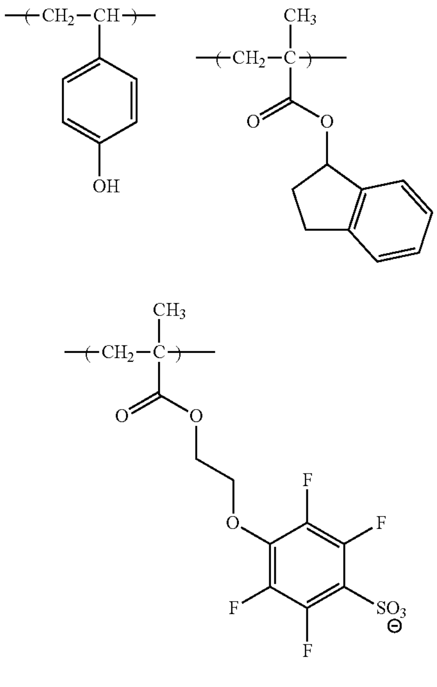

-continued
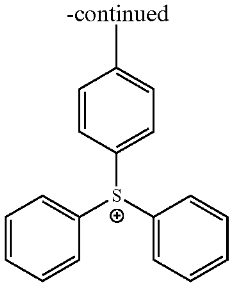
[Chem. 32-19]
(Ab-185)
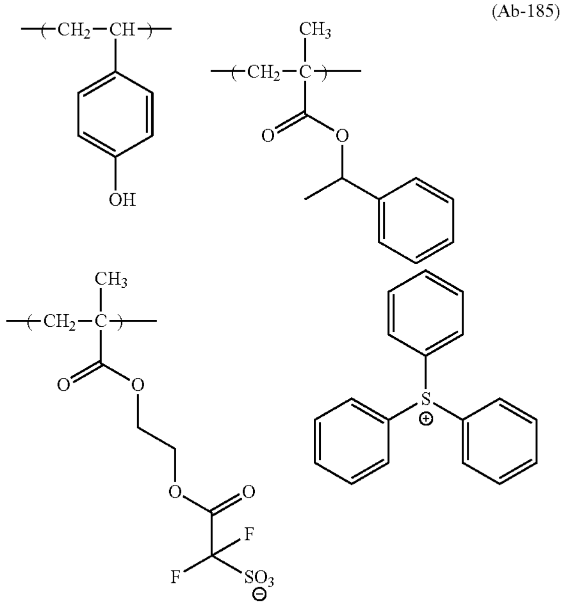
(Ab-186)
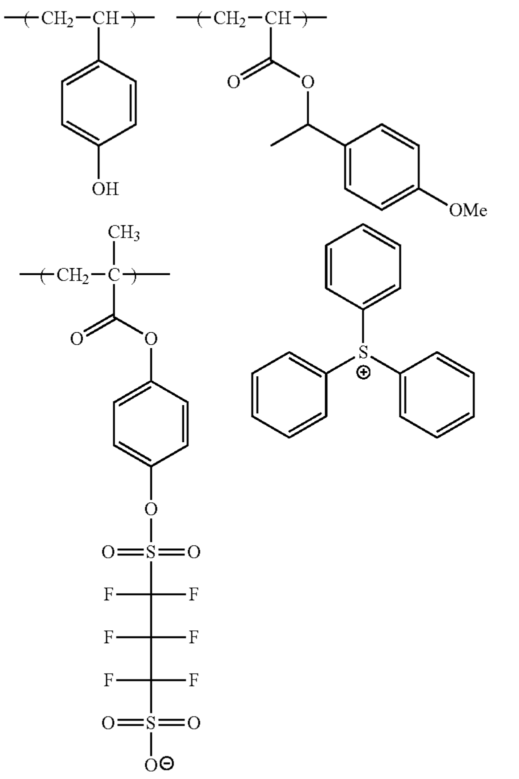
-continued
(Ab-187)
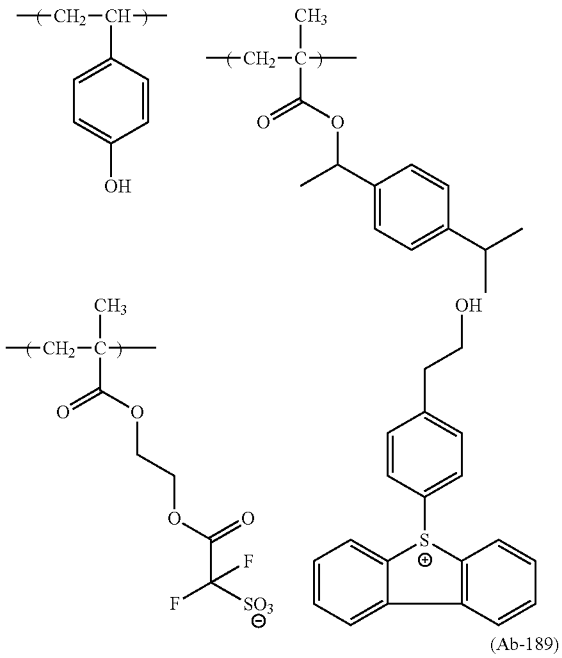
(Ab-189)
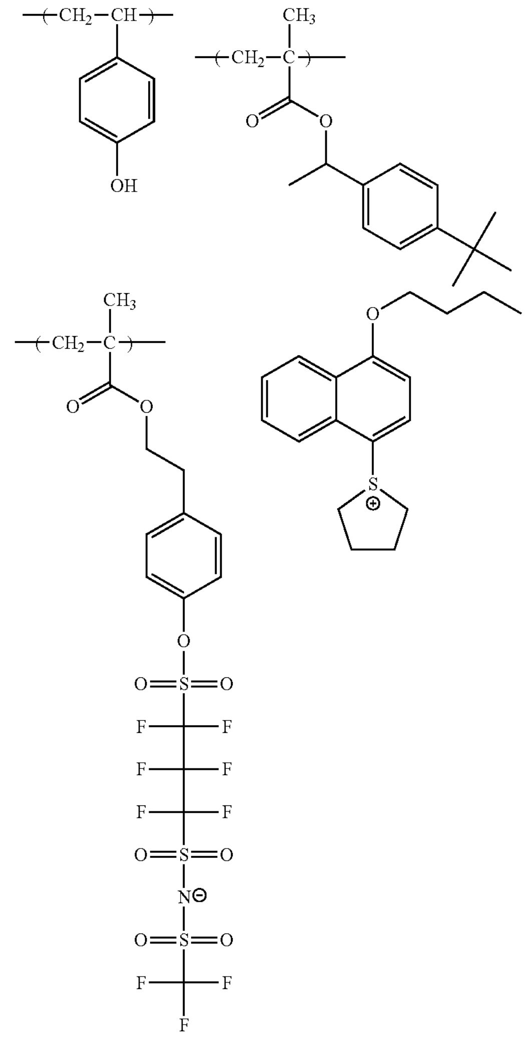

-continued
(Ab-190)
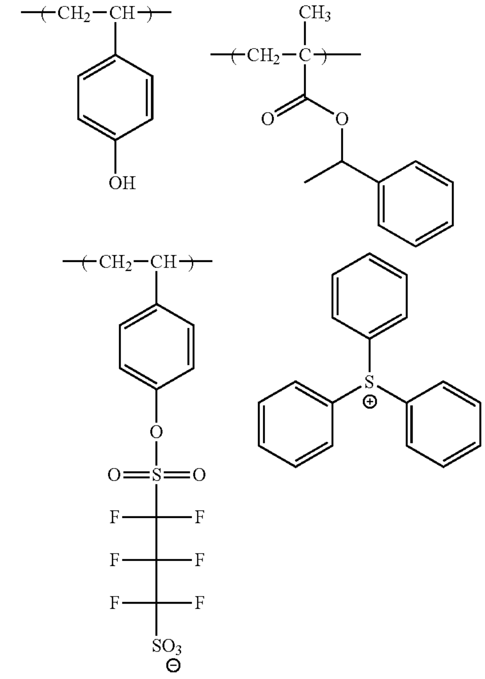
[Chem. 32-20]
(Ab-193)
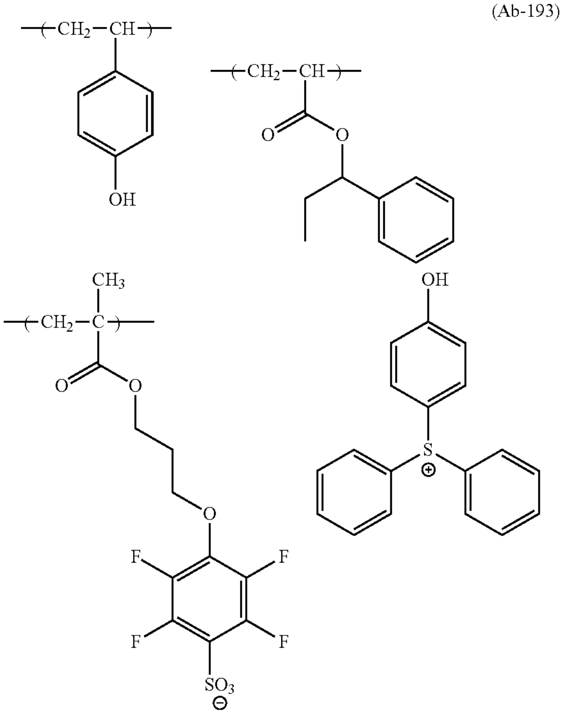
(Ab-194)
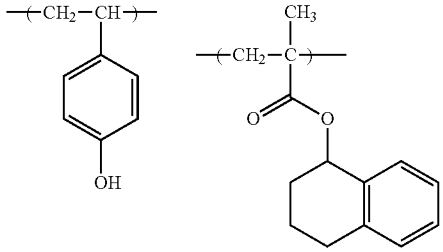
-continued
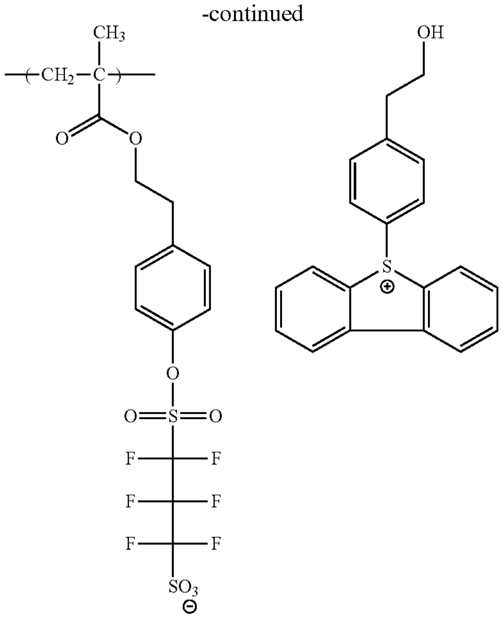
(Ab-195)
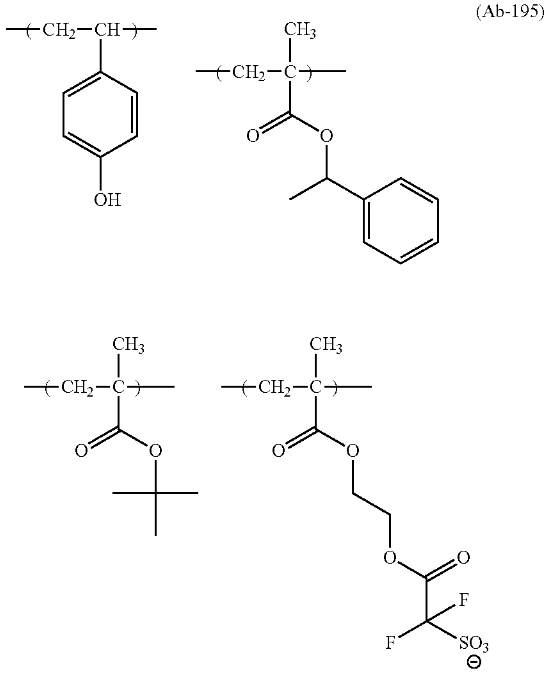
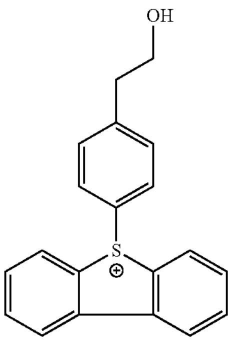

-continued
(Ab-197)
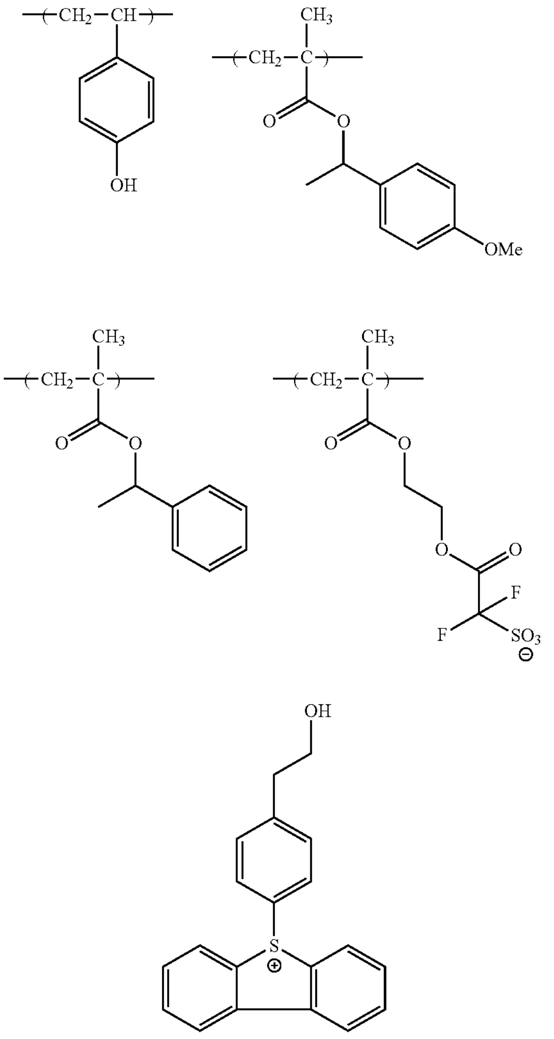
(Ab-198)
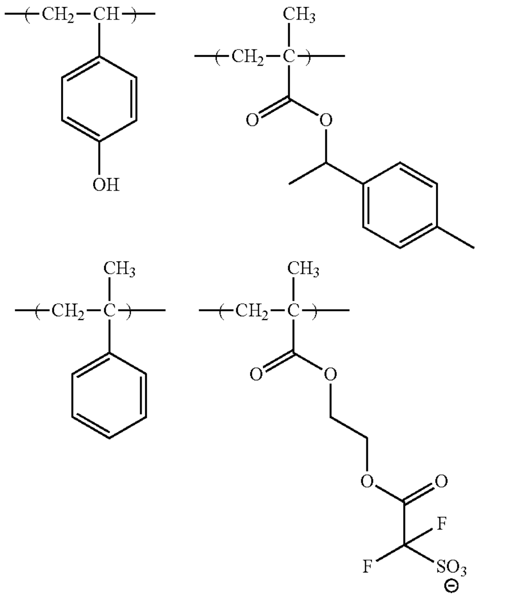
-continued
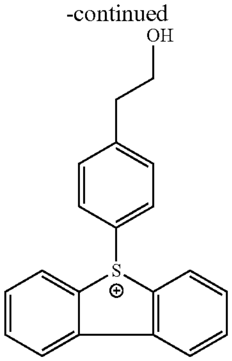
[Chem. 32-21]
(Ab-199)
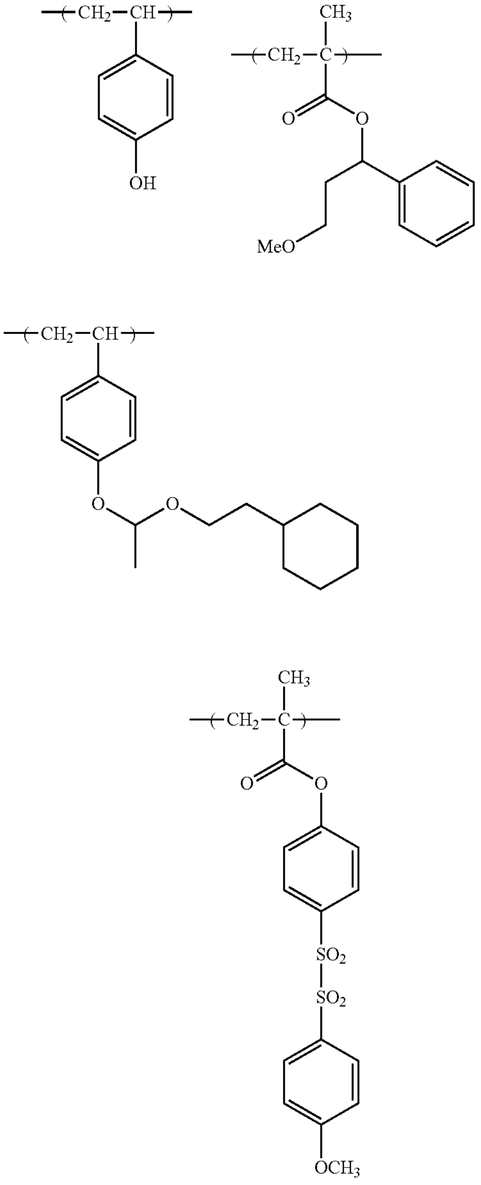

-continued
(Ab-201)
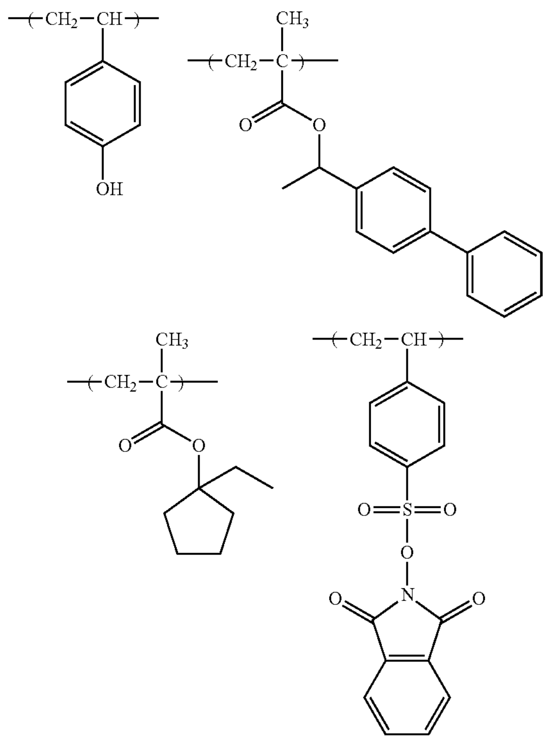
(Ab-202)
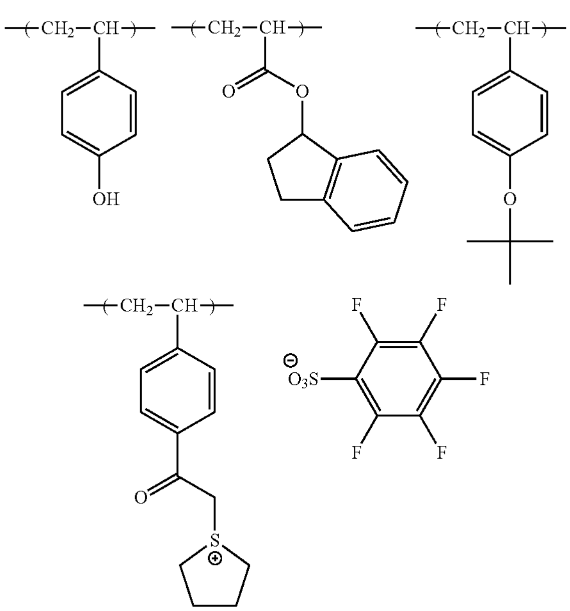
(Ab-203)
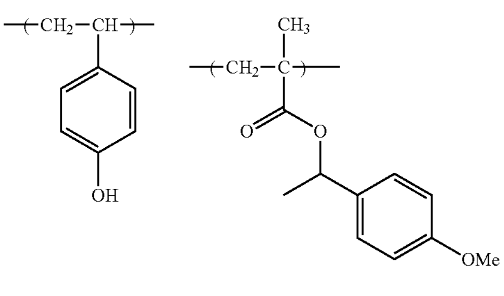
-continued
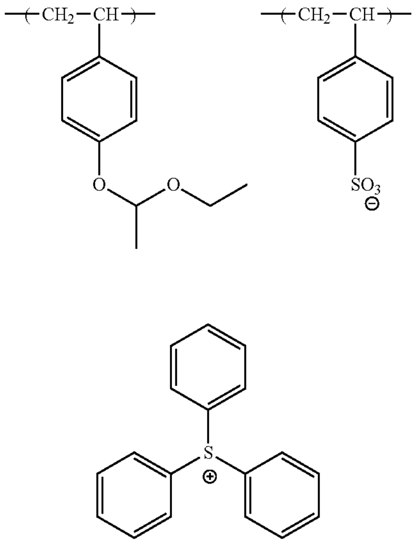
[Chem. 32-22]
(Ab-204)
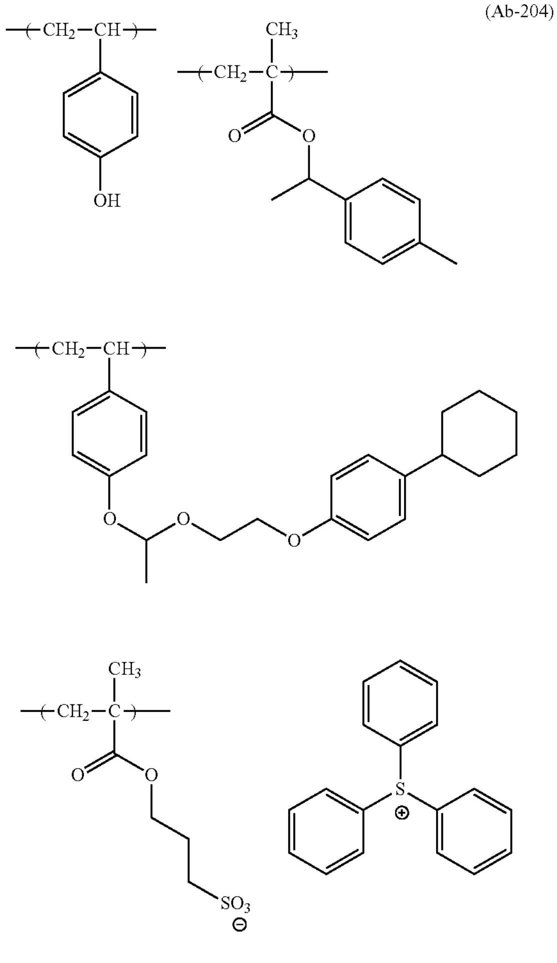

-continued
(Ab-206)
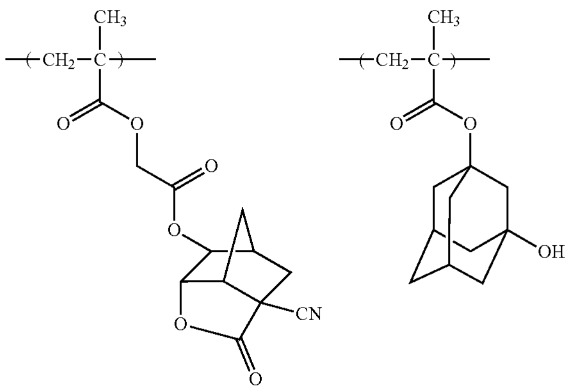
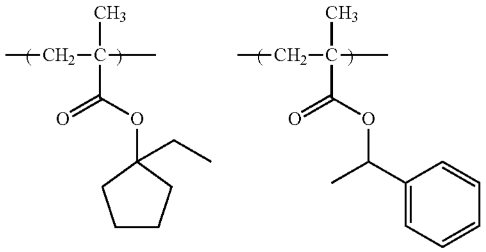
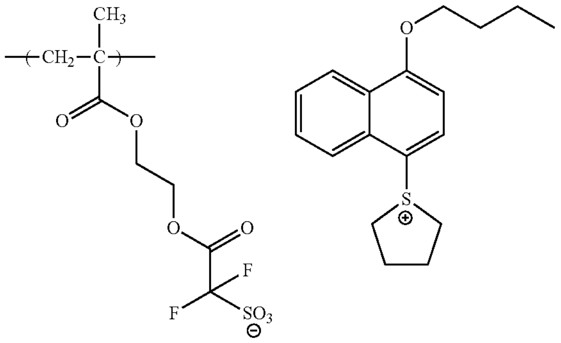
(Ab-207)
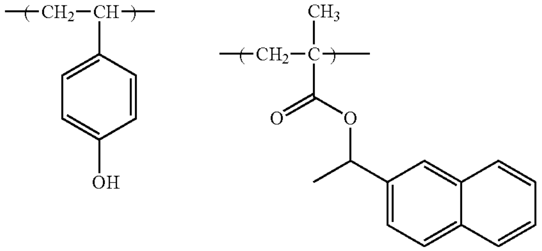
-continued
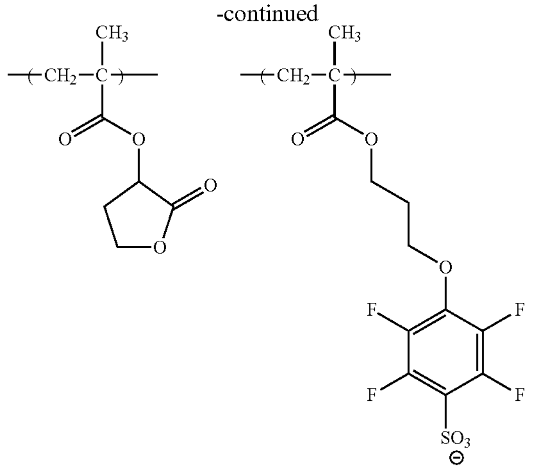
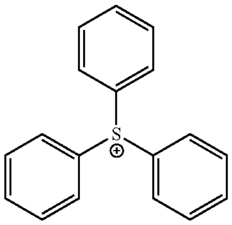
[Chem. 32-23]
(Ab-208)
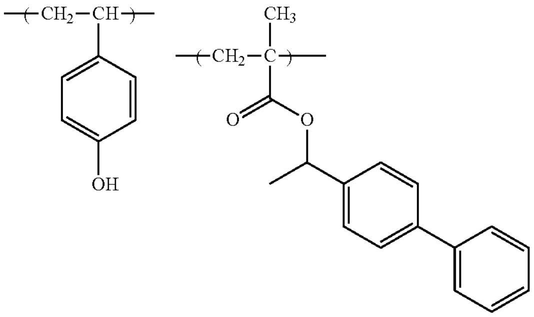
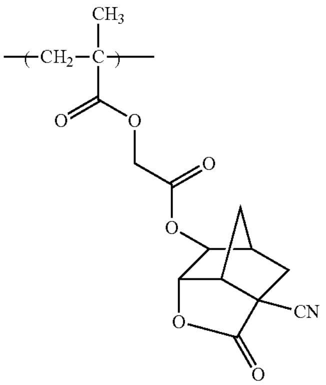

-continued
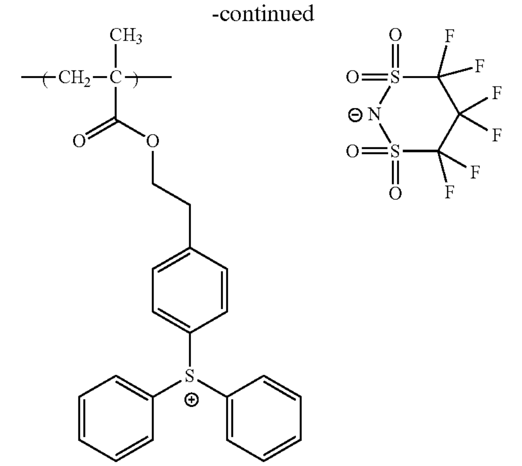
(Ab-209)
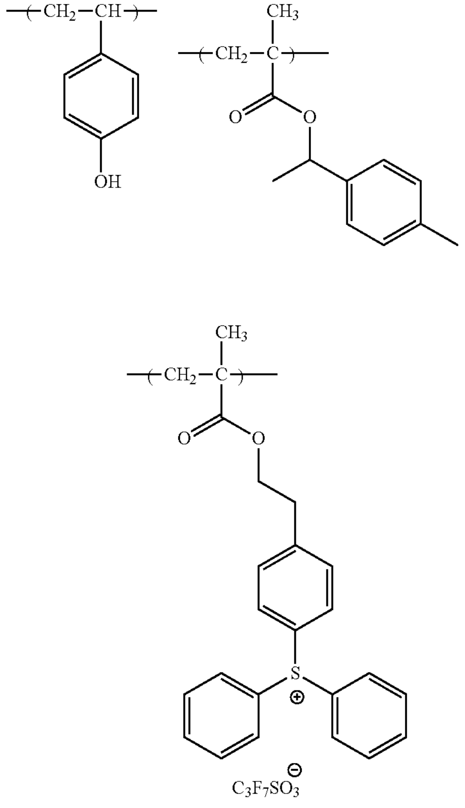
(Ab-210)
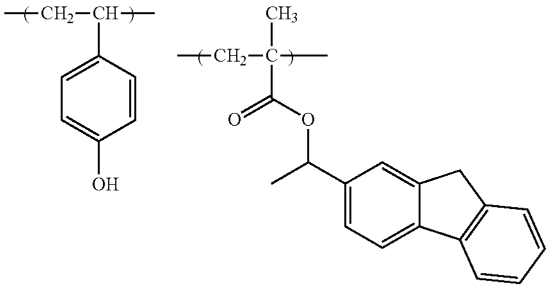
-continued
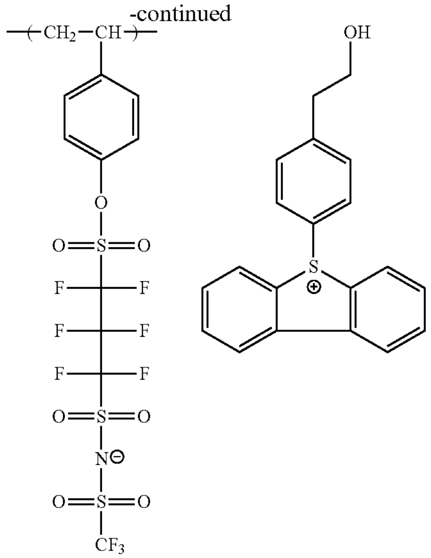
(Ab-212)
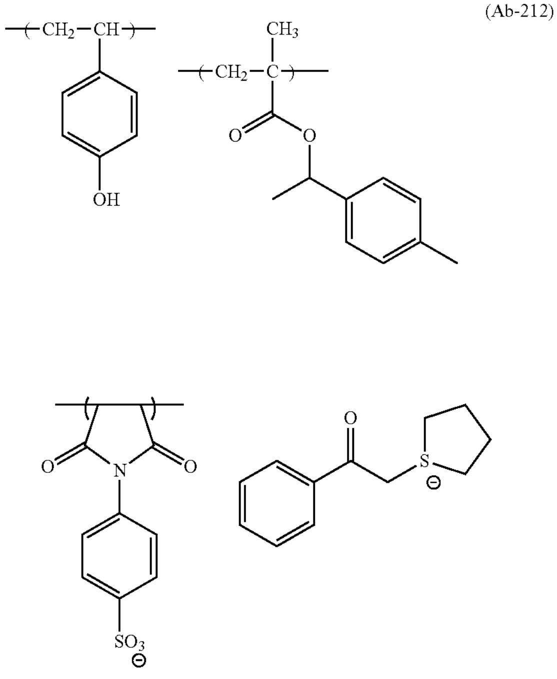
(Ab-213)
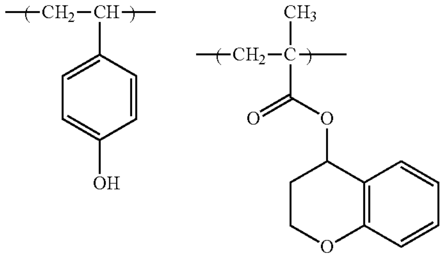

-continued
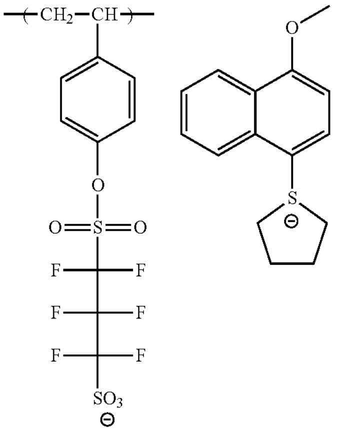
[Chem. 32-24]
(Ab-214)
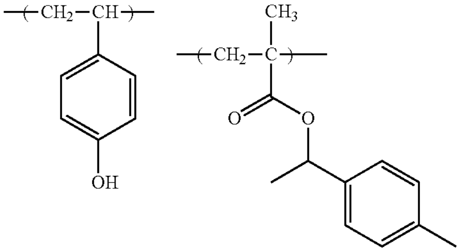
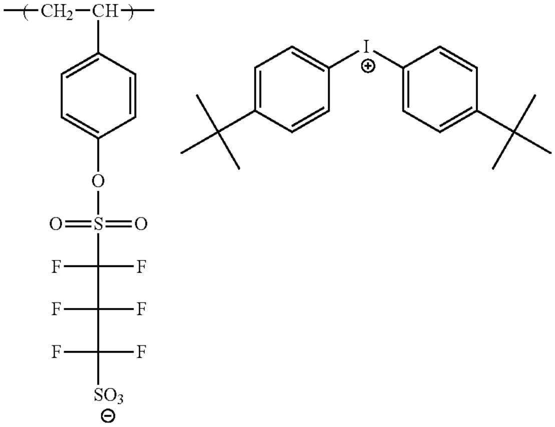
(Ab-216)
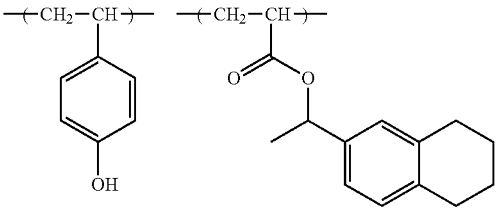
-continued
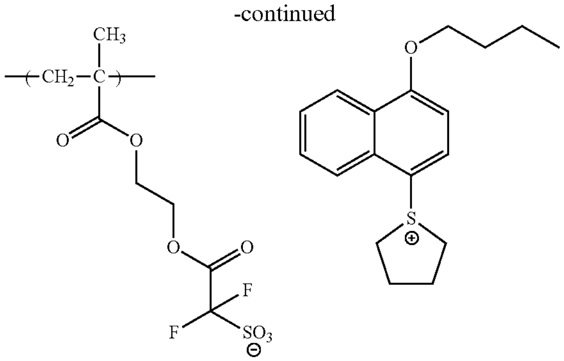
(Ab-217)
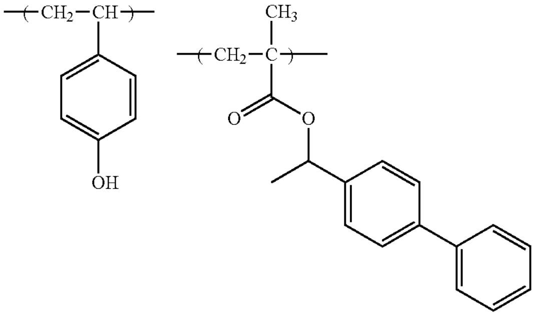
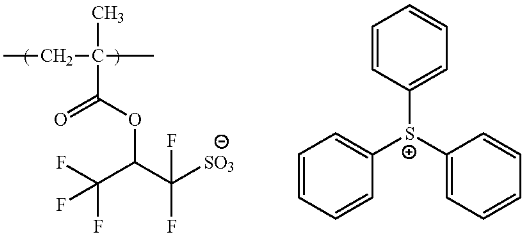
(Ab-218)
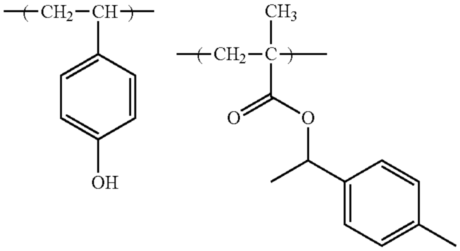
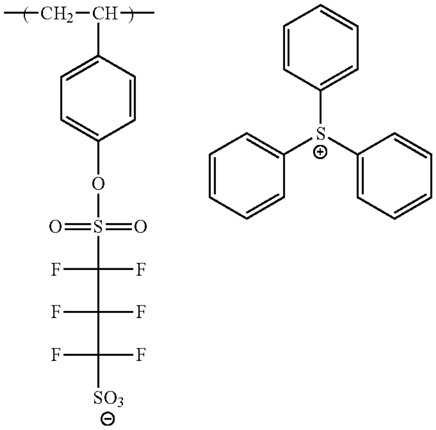

-continued
[Chem. 32-25]
(Ab-219)
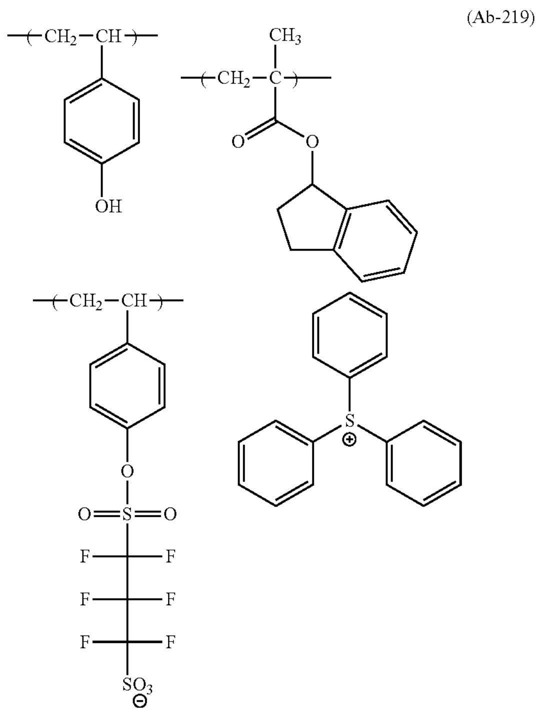
(Ab-220)
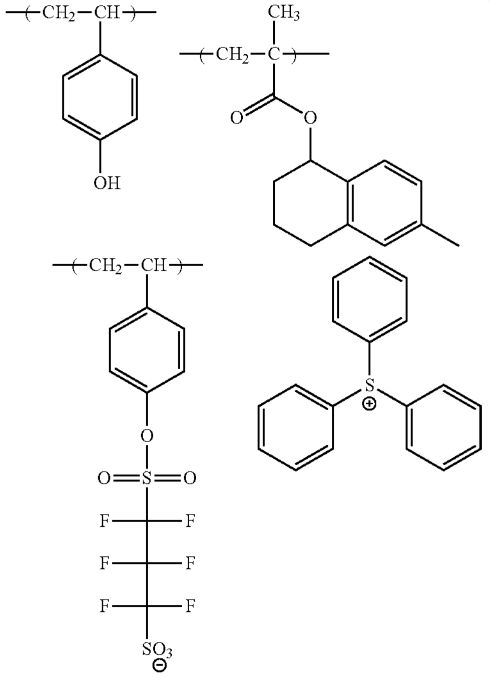
(Ab-221)
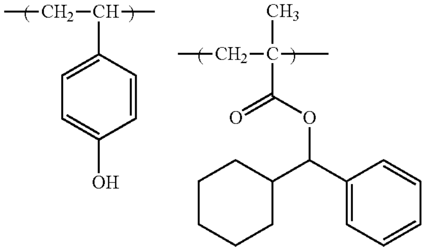
-continued
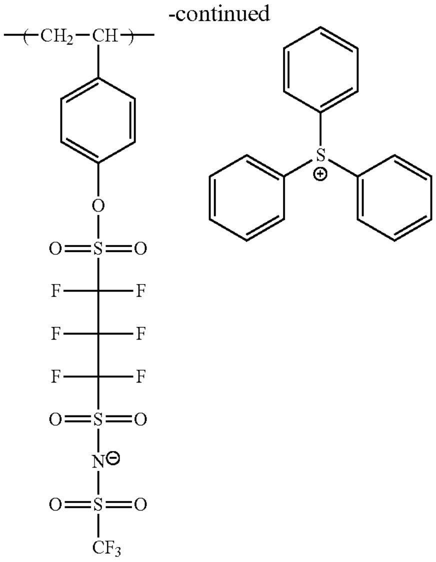
(Ab-222)
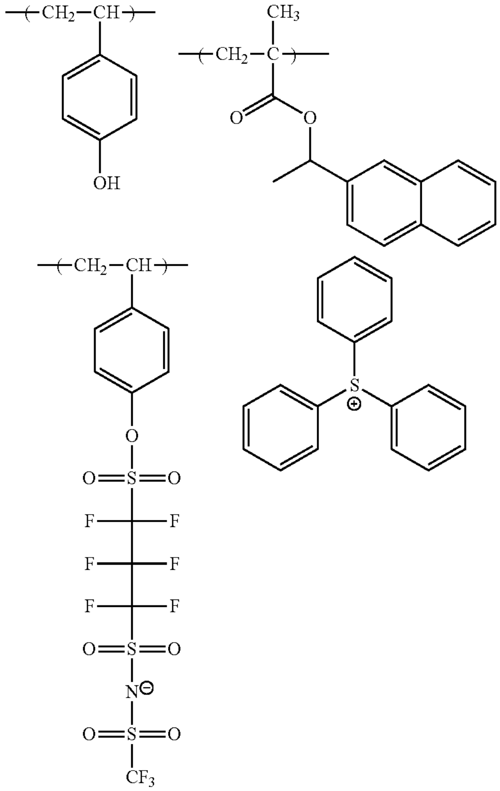
(Ab-223)
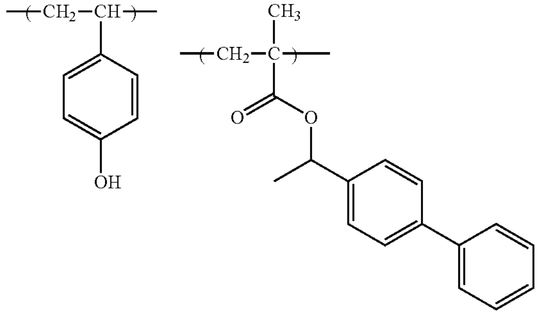

-continued
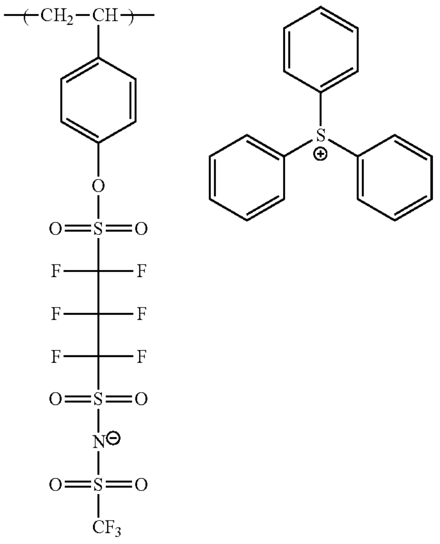
[Chem. 32-26]
(Ab-226)
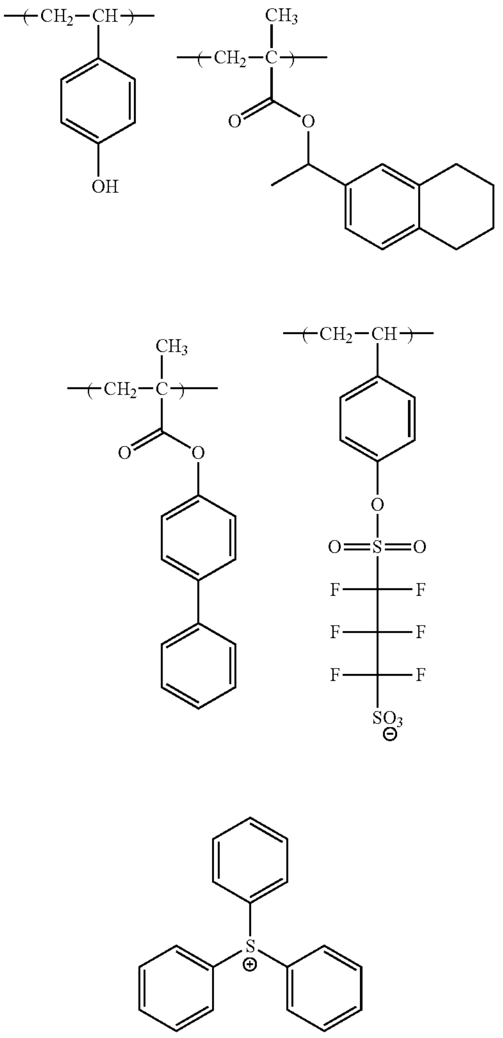
-continued
(Ab-227)
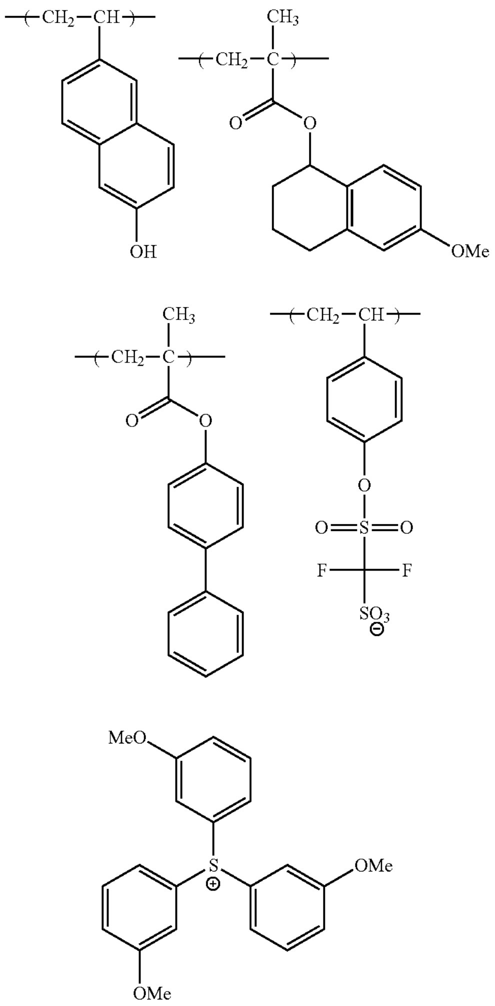
(Ab-228)
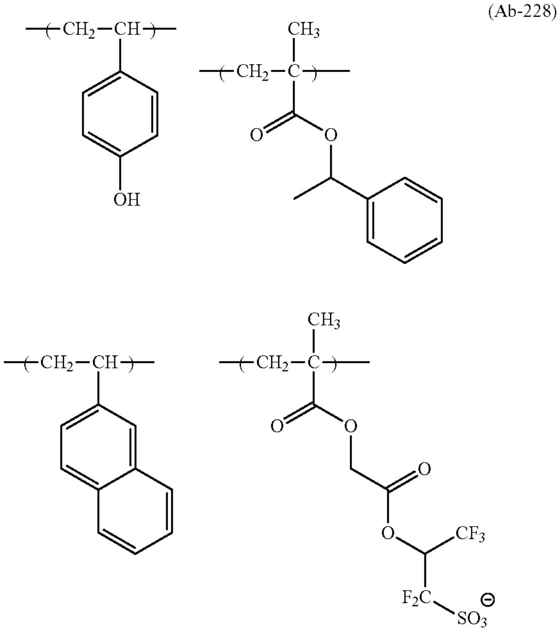

-continued
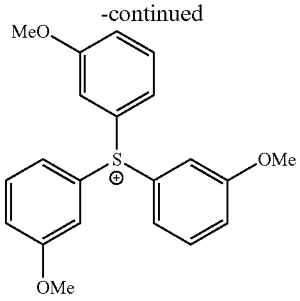
[Chem. 32-27]
(Ab-230)
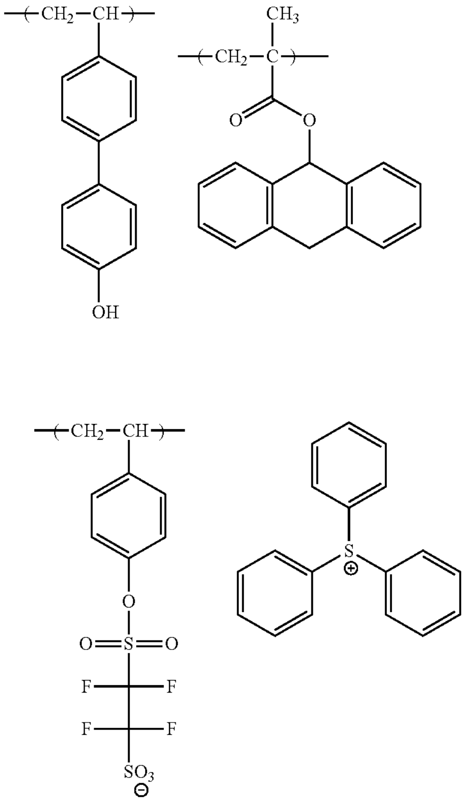
(Ab-231)
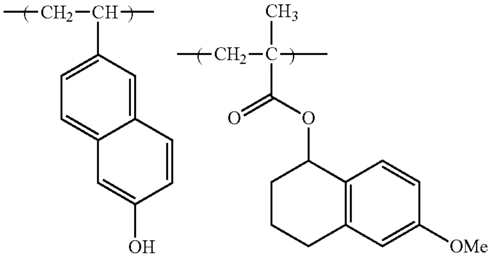
-continued
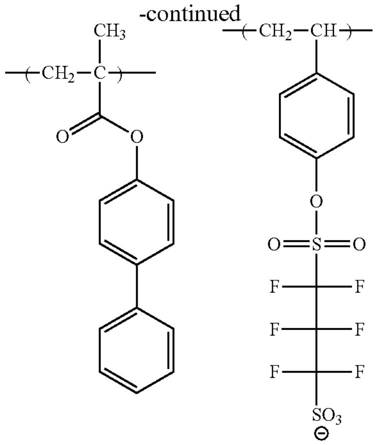
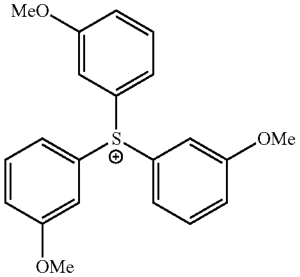
(Ab-232)
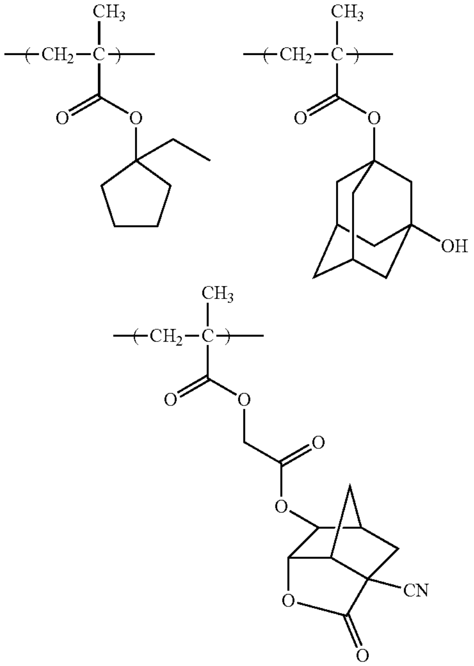
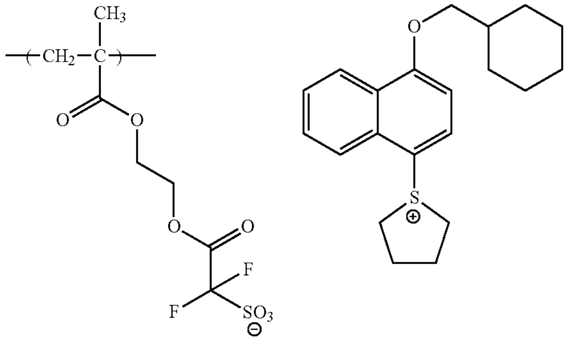

-continued
(Ab-233)
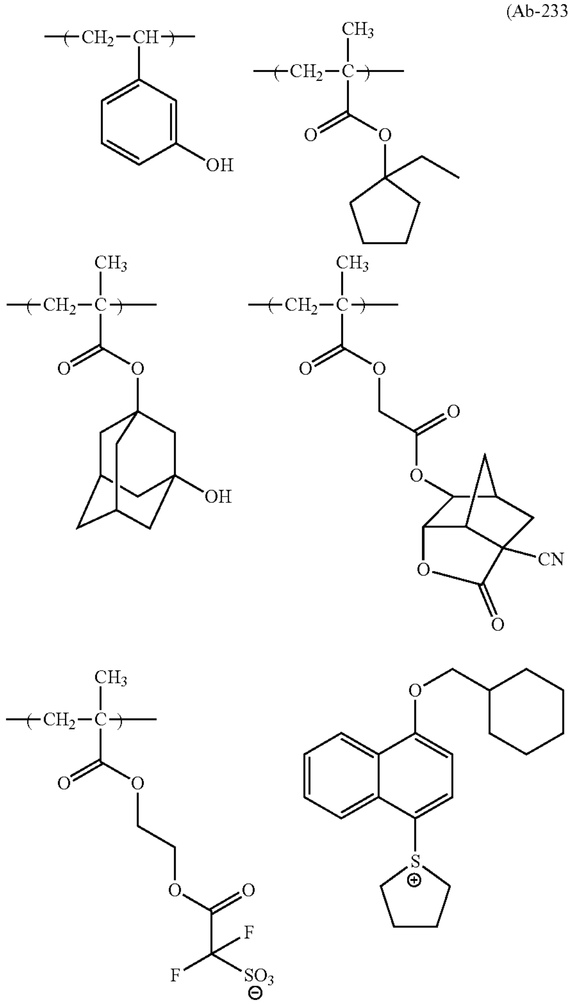
[Chem. 32-28]
(Ab-234)
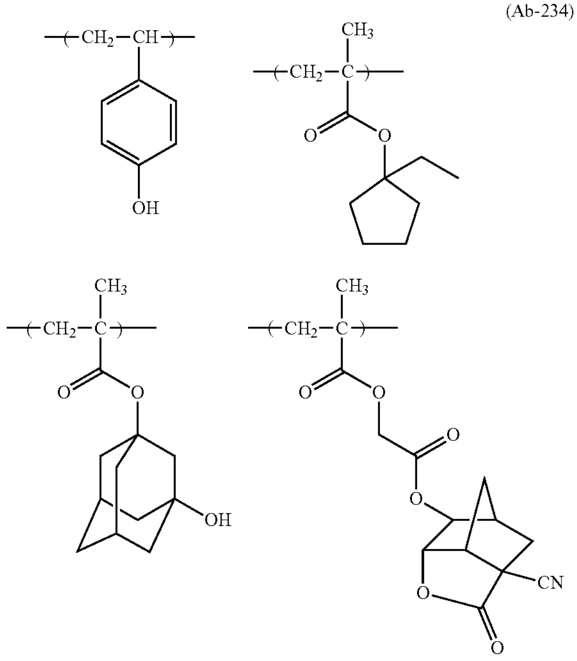
-continued
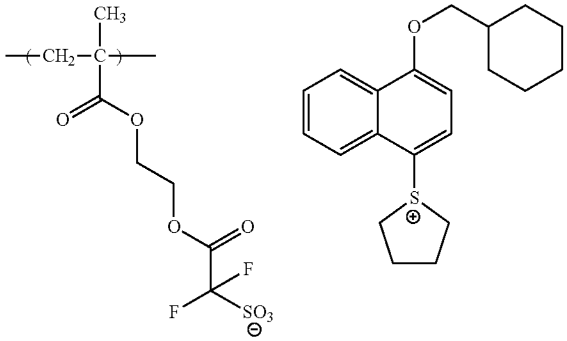
(Ab-236)
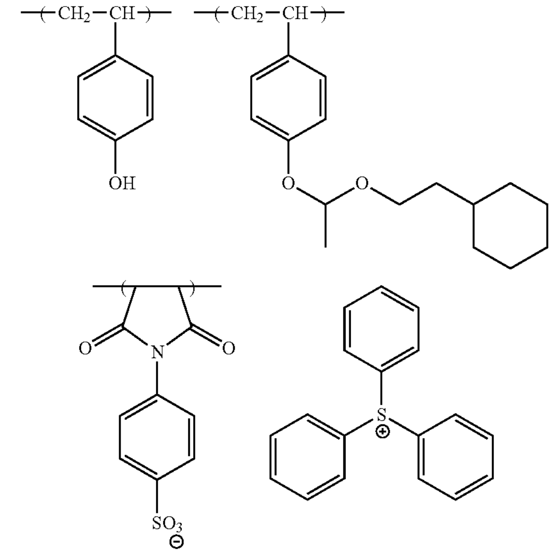
(Ab-237)
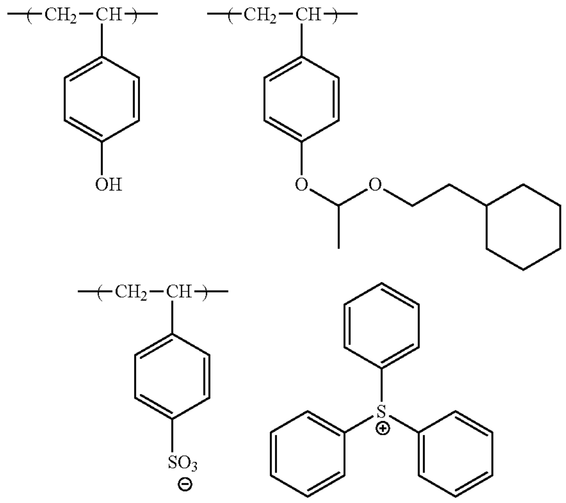
(Ab-238)
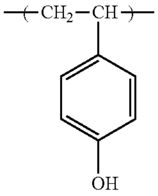

-continued
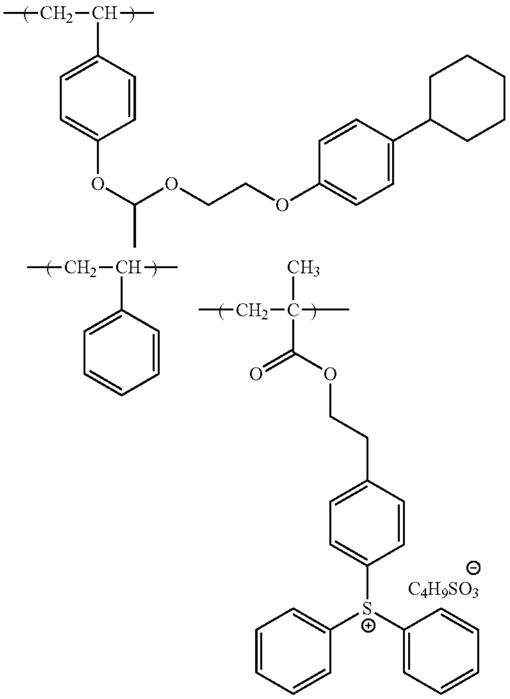
[Chem. 32-29]
(Ab-239)
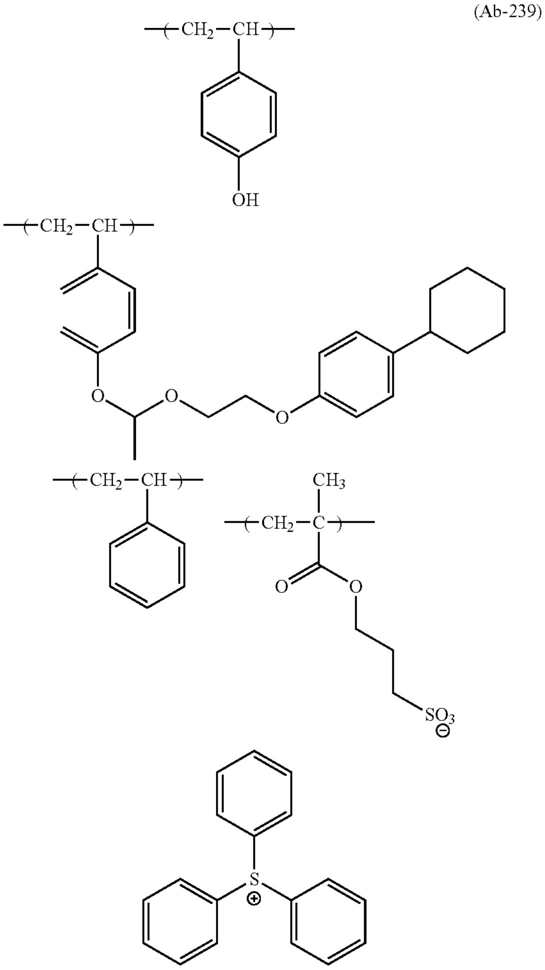
-continued
(Ab-240)
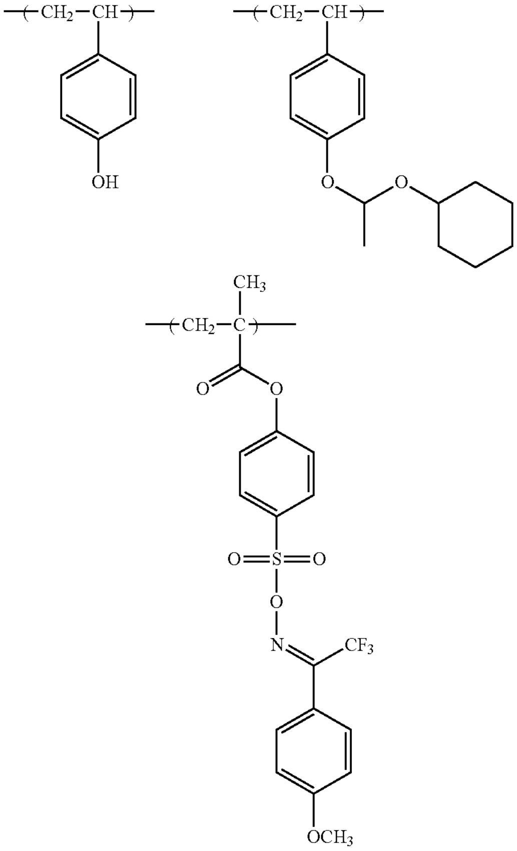
(Ab-241)
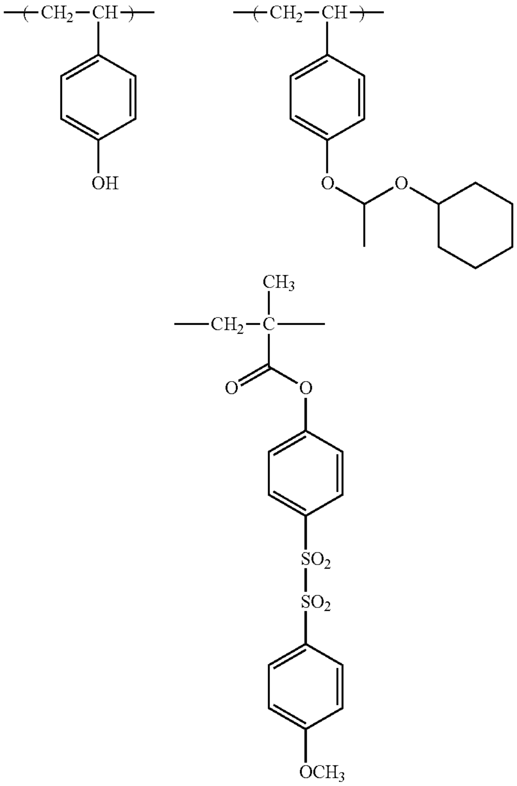

-continued
(Ab-242)
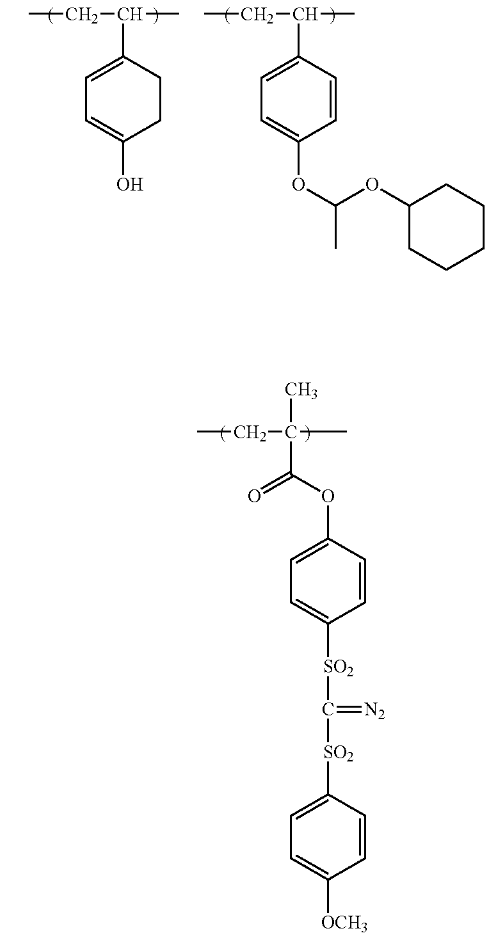
(Ab-243)
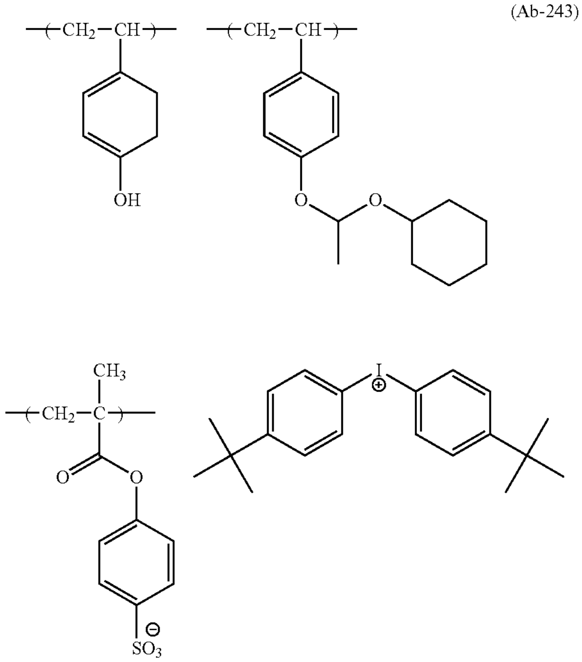
-continued
(Ab-244)
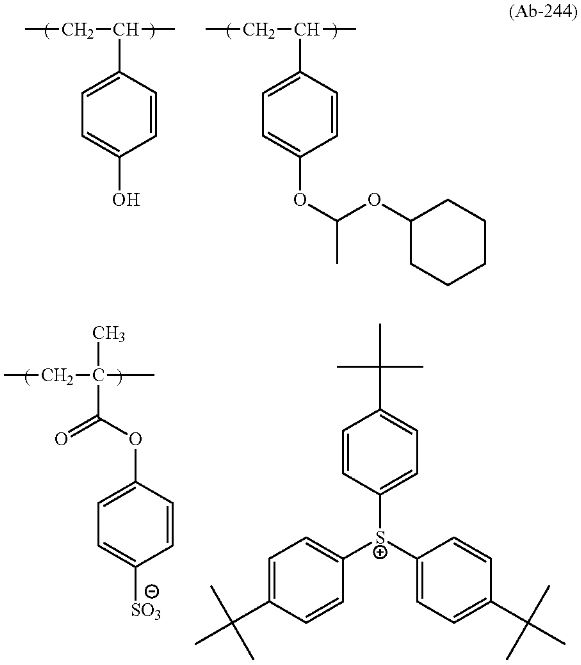
[Chem. 32-30]
(Ab-245)
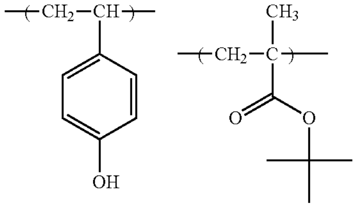
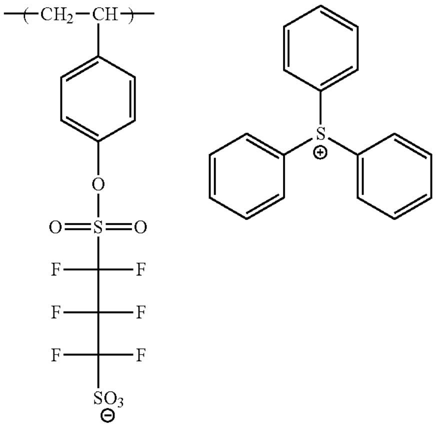
(Ab-247)
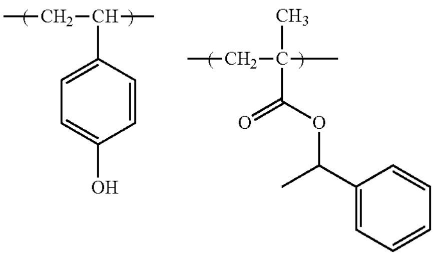

-continued
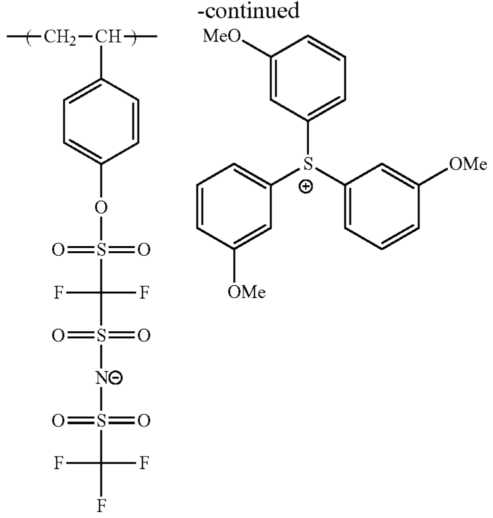
(Ab-248)
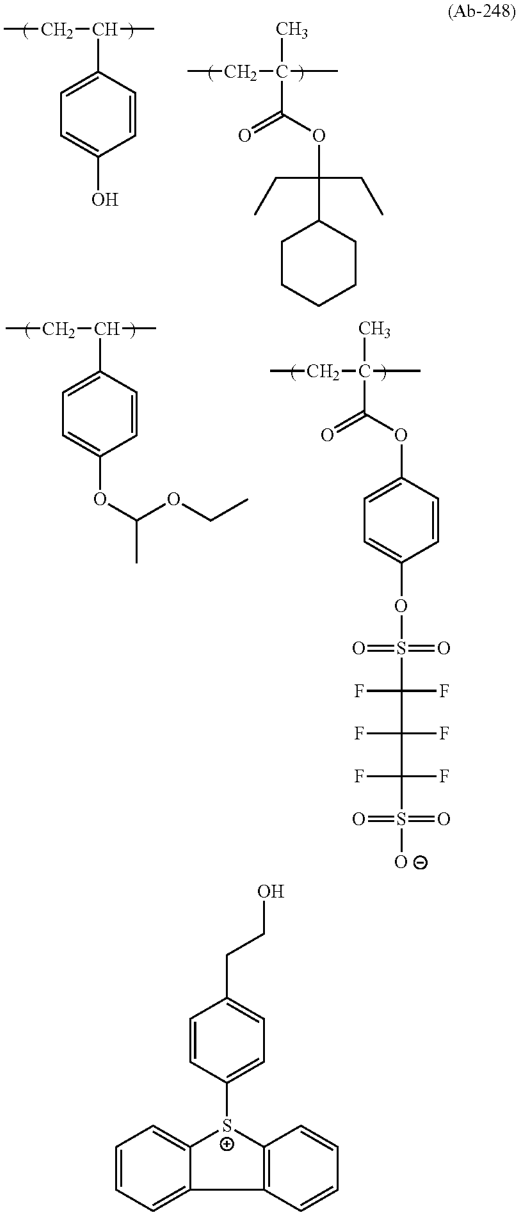
-continued
[Chem. 32-31]
(Ab-249)
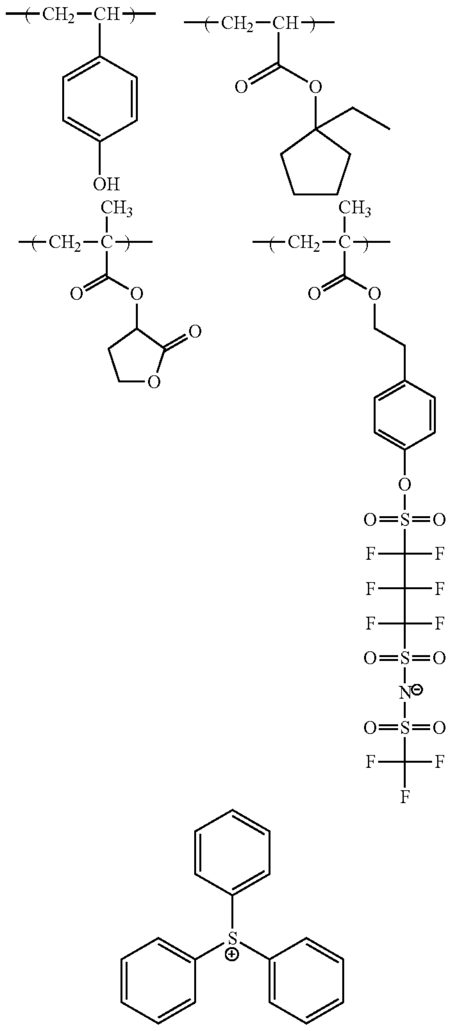
(Ab-250)
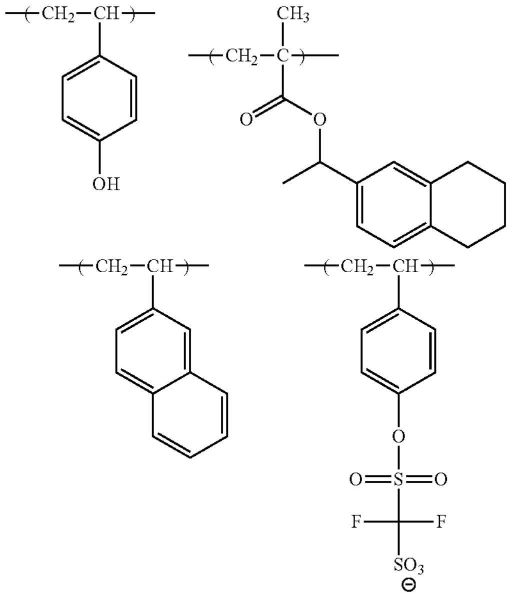

-continued
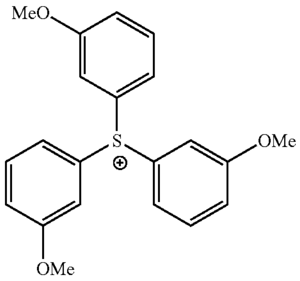
(Ab-251)
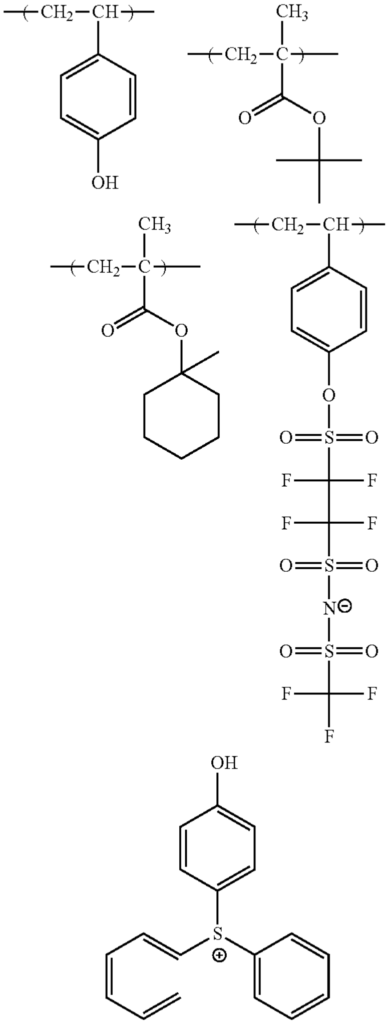
[Chem. 32-32]
(Ab-253)
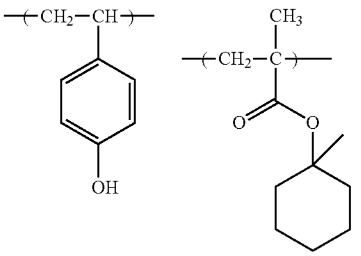
-continued
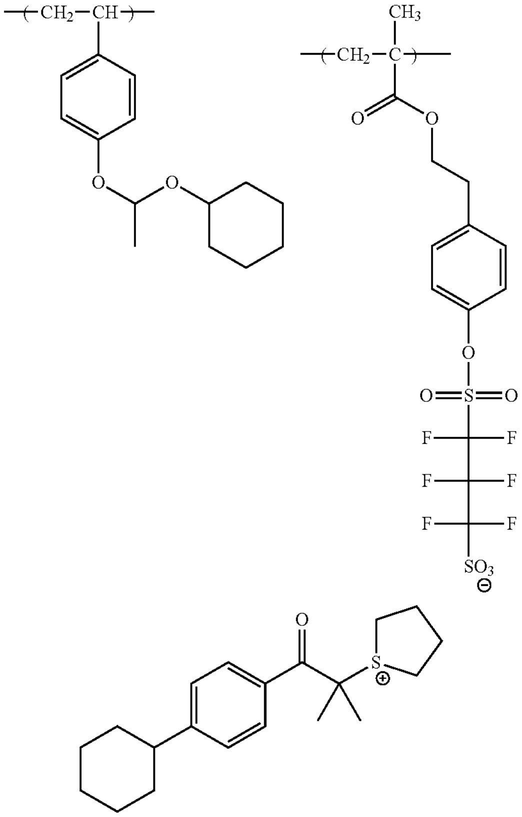
(Ab-255)
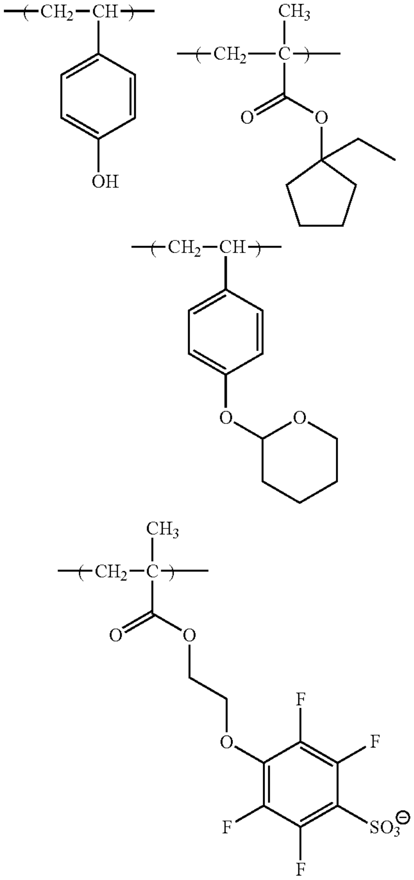

-continued
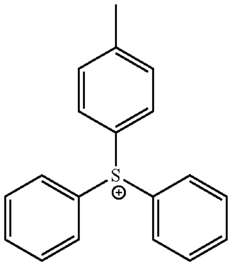
(Ab-256)
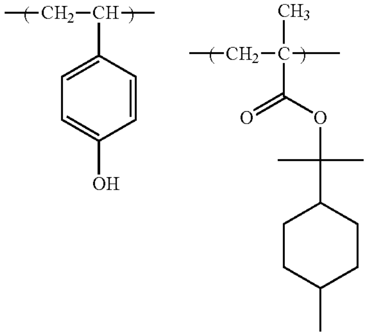
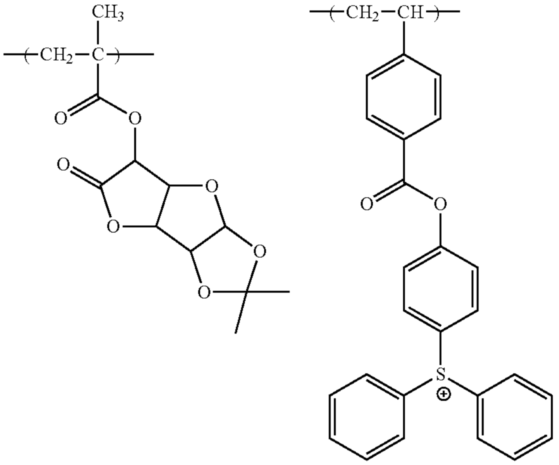
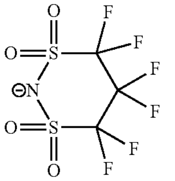
(Ab-259)
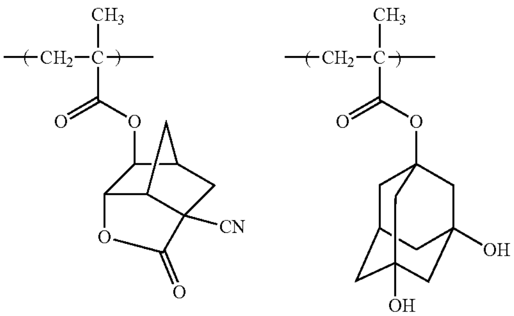
-continued
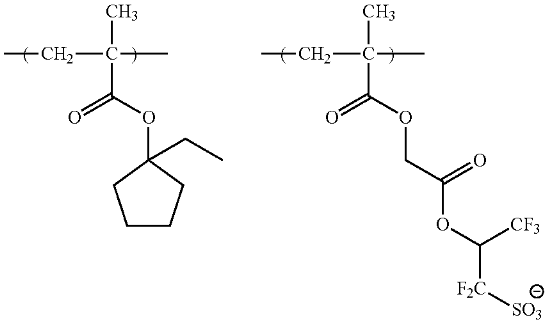
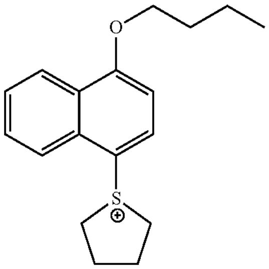
(Ab-260)
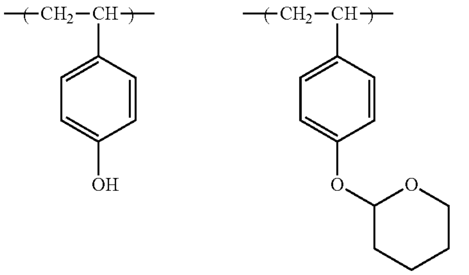
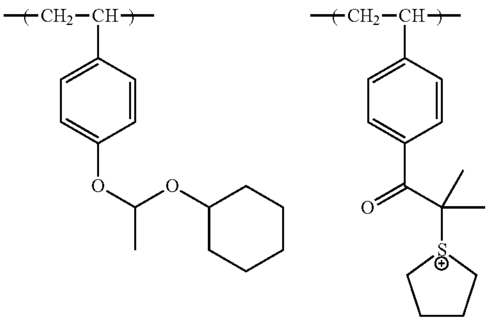
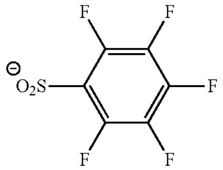

-continued
[Chem. 32-33]
(Ab-261)
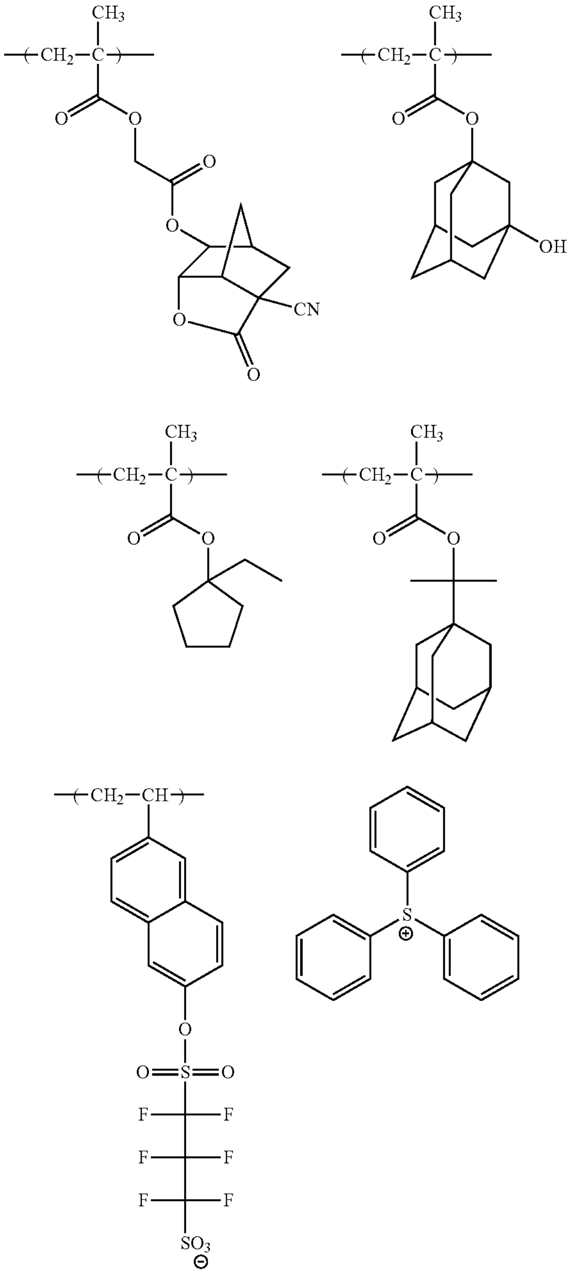
(Ab-262)
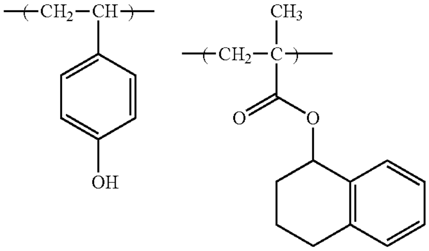
-continued
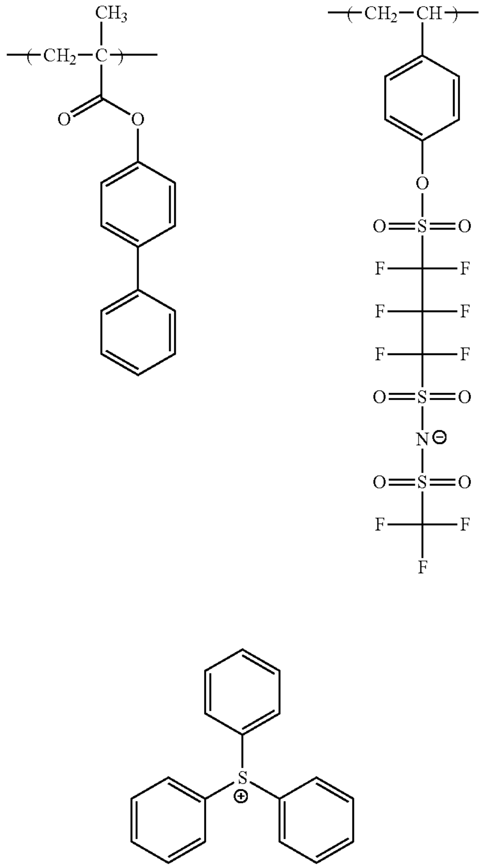
[Chem. 32-34]
(Ab-263)
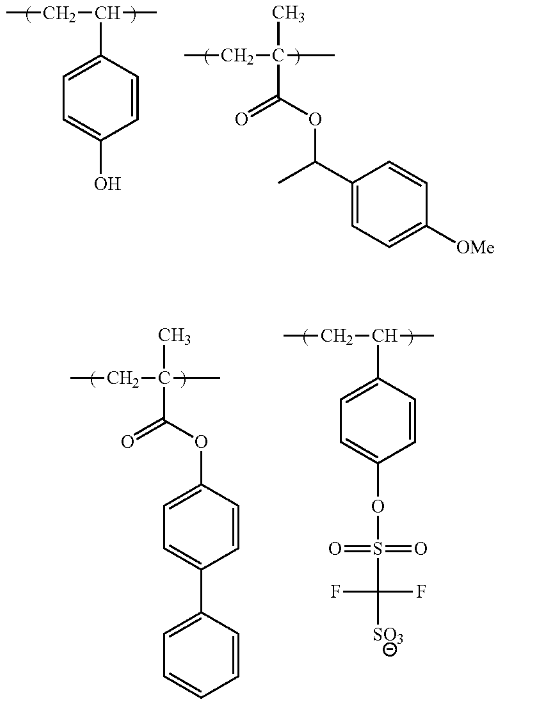

-continued
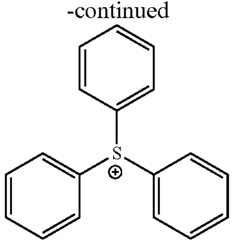
(Ab-264)
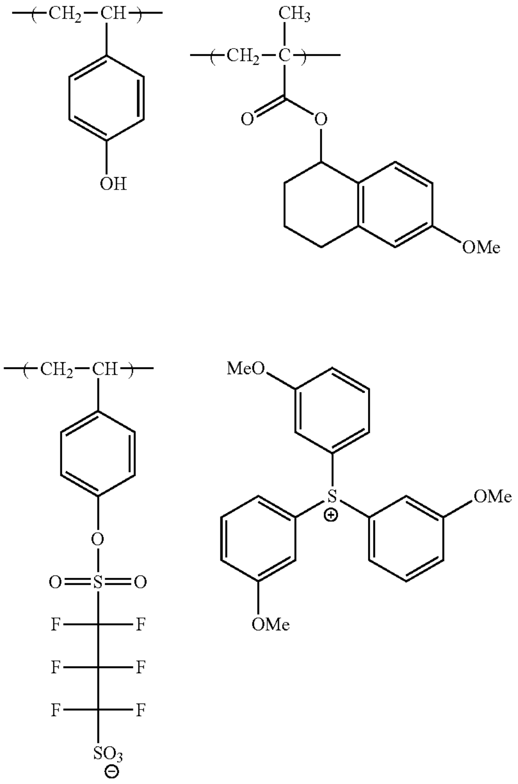
(Ab-265)
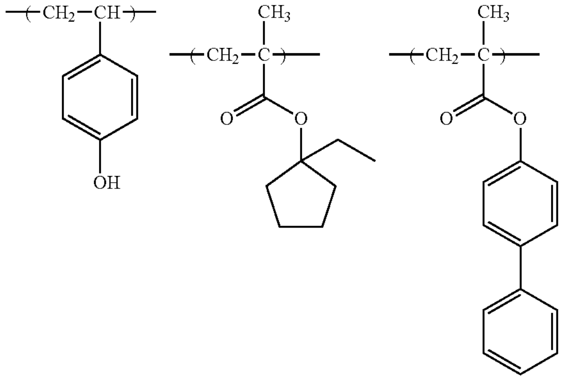
-continued
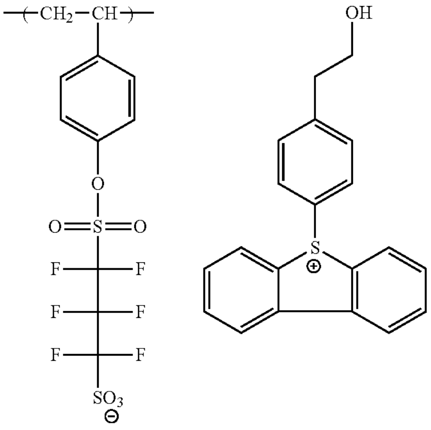
(Ab-267)
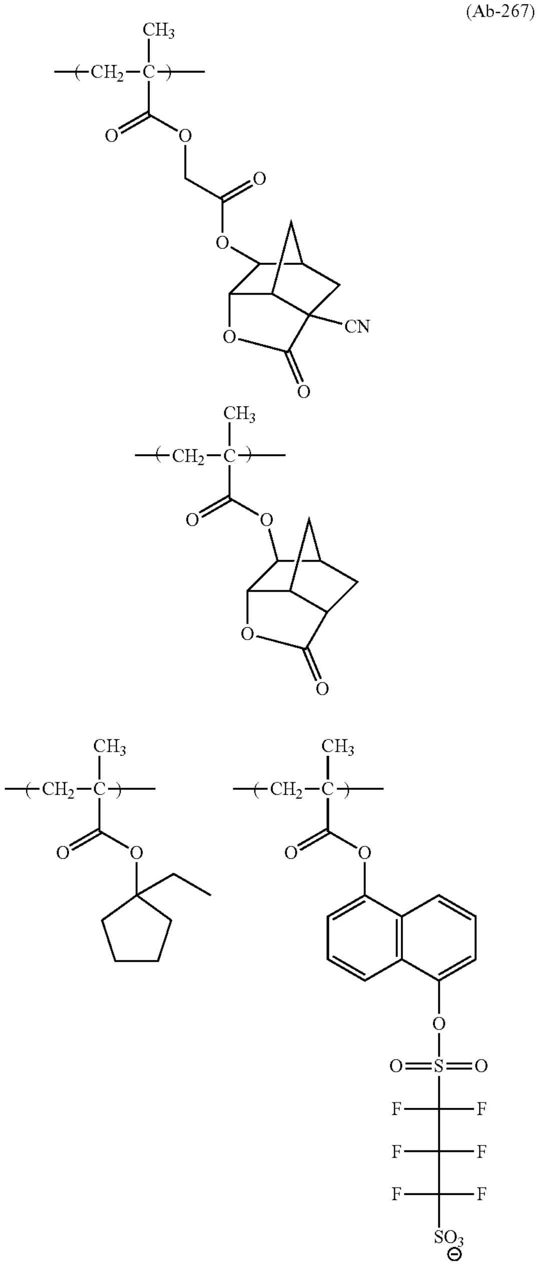

-continued
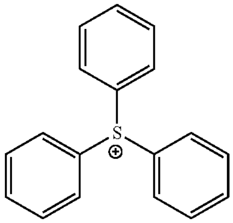
[Chem. 32-35]
(Ab-268)
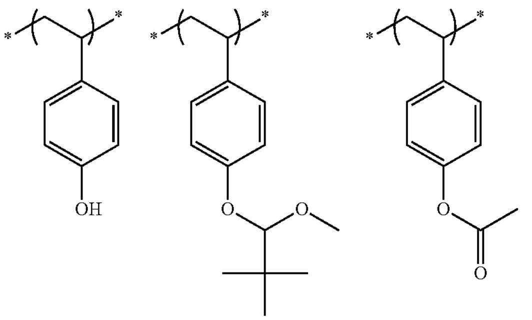
(Ab-269)
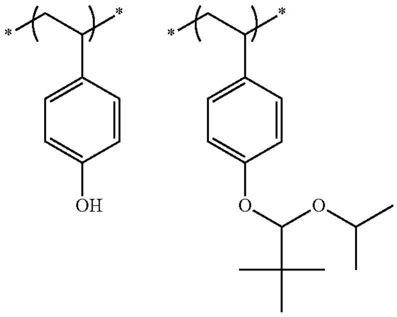
(Ab-270)
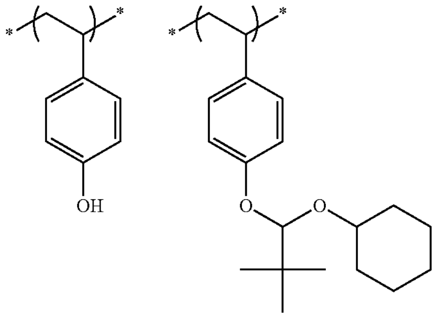
(Ab-271)
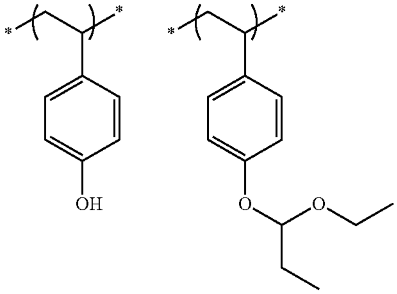
-continued
(Ab-272)
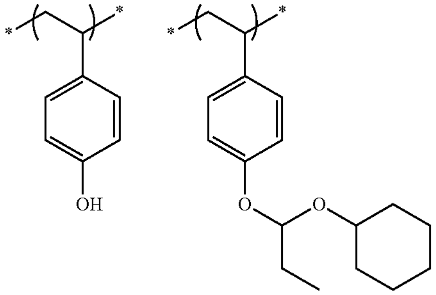
(Ab-273)
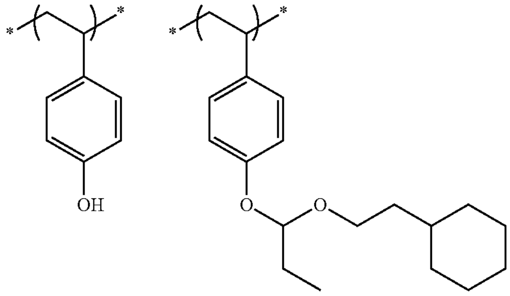
(Ab-274)
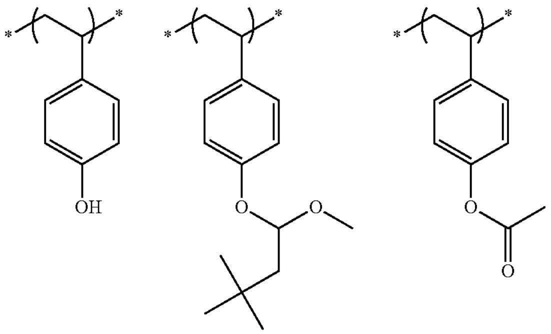
(Ab-275)
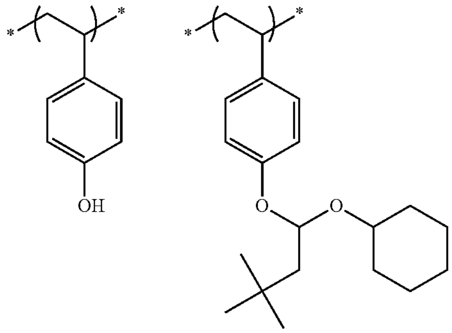
(Ab-276)
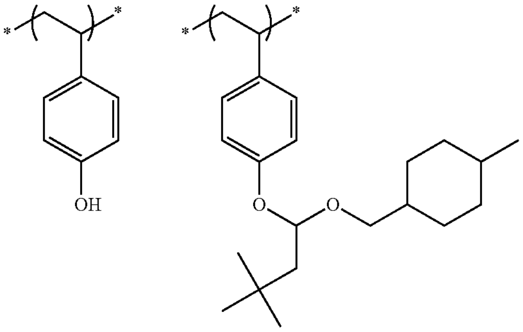

-continued
(Ab-277)
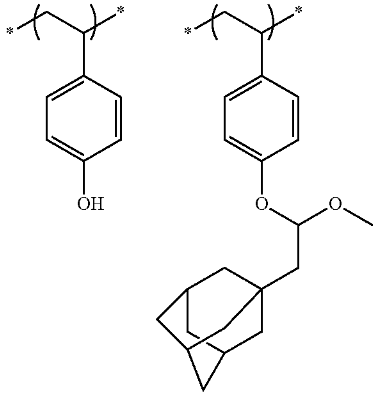
(Ab-278)
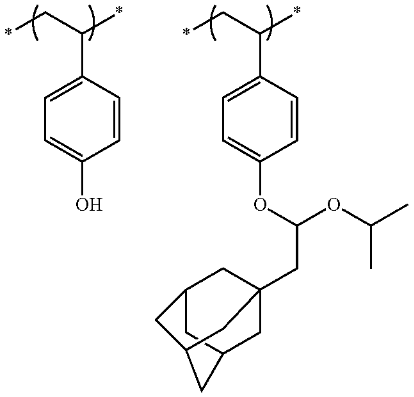
(Ab-279)
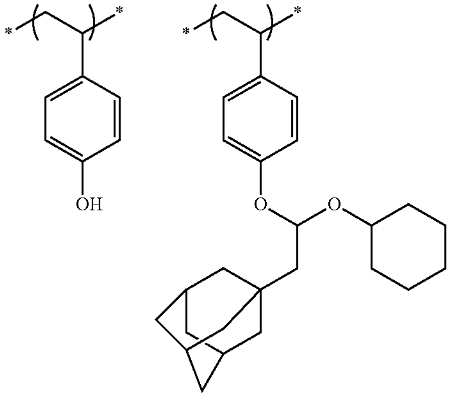
(Ab-280)
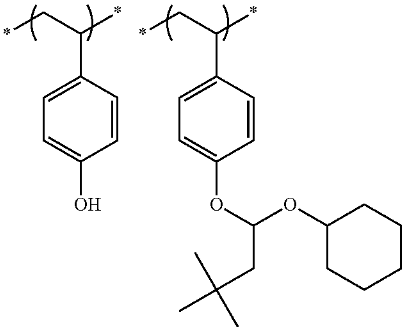
-continued
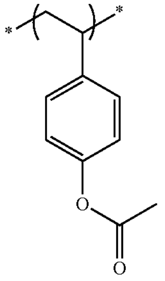
(Ab-281)
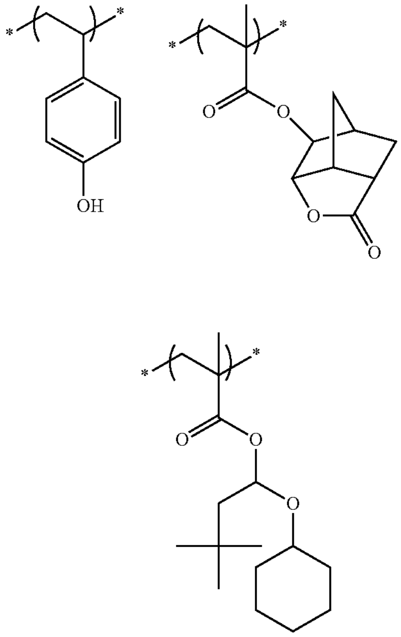
(Ab-282)
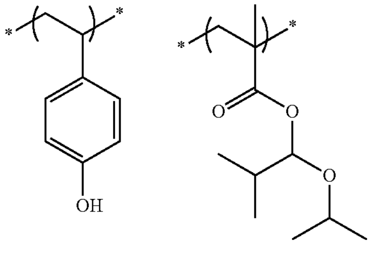
(Ab-283)
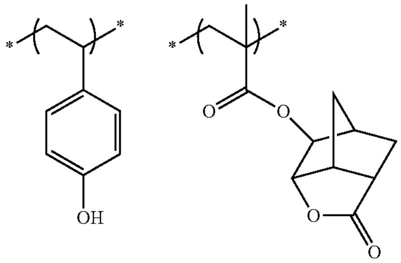

-continued
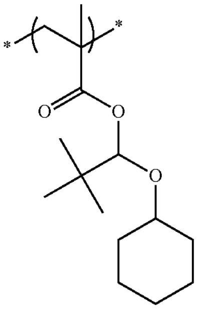
[Chem. 32-36]
(Ab-284)
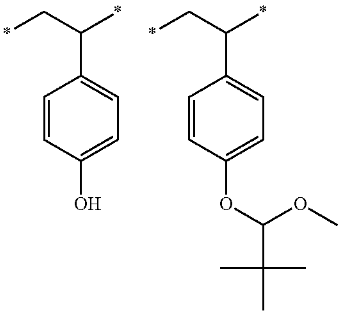
(Ab-285)
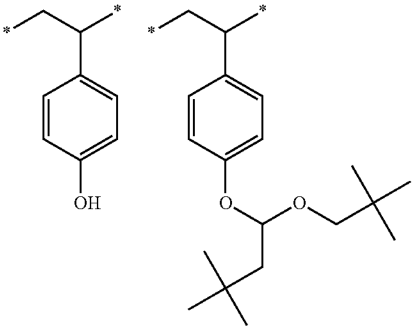
(Ab-286)
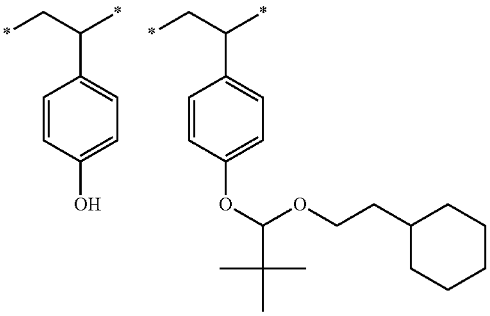
-continued
(Ab-287)
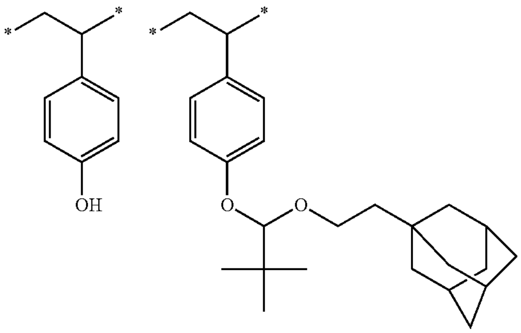
(Ab-288)
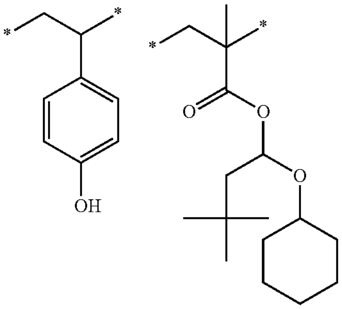
(Ab-289)
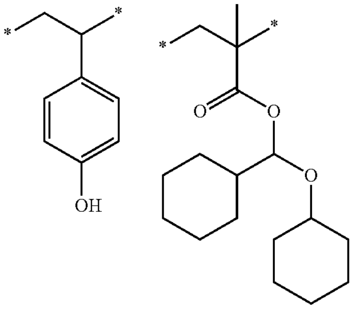
(Ab-290)
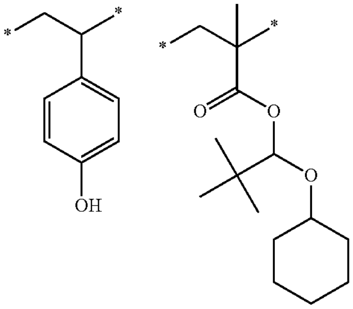
(Ab-291)
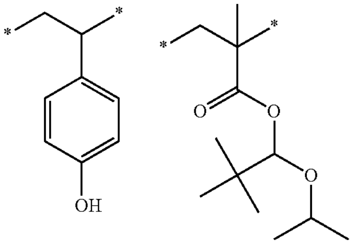

-continued
(Ab-292)
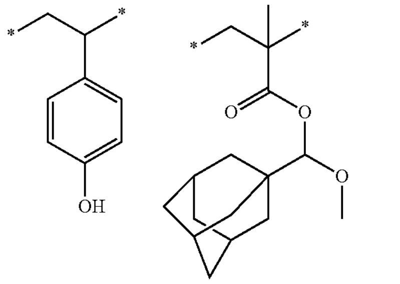
(Ab-293)
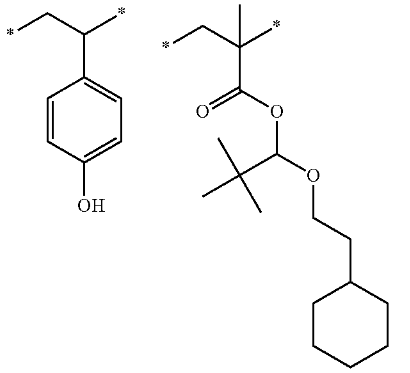
(Ab-294)
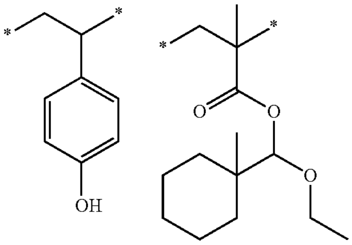
(Ab-295)
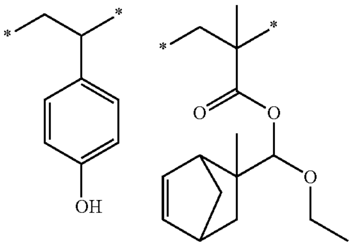
(Ab-296)
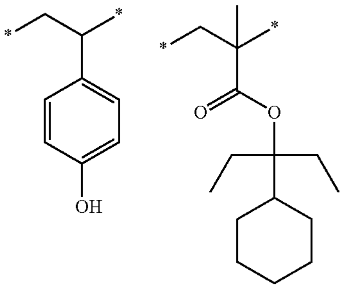
-continued
(Ab-297)
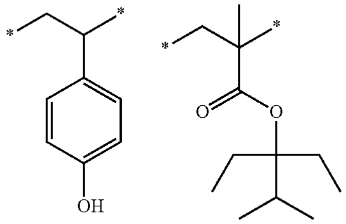
(Ab-298)
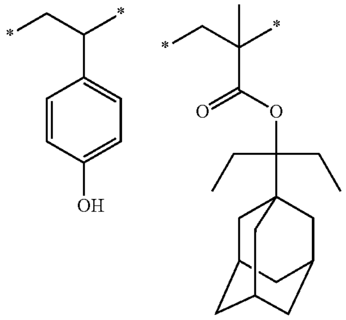
(Ab-299)
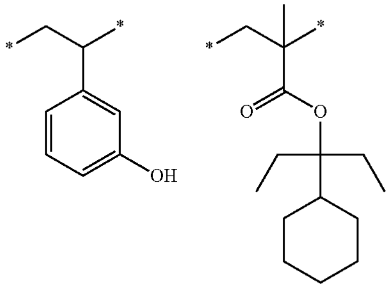
(Ab-300)
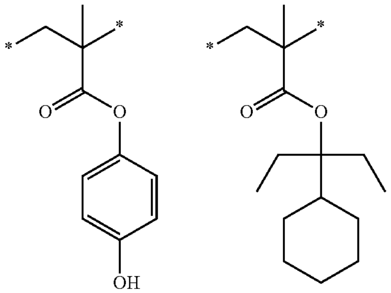
(Ab-301)
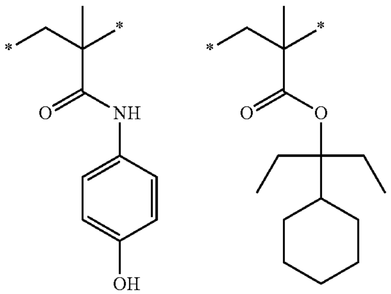

-continued
[Chem. 32-37]
(Ab-302)
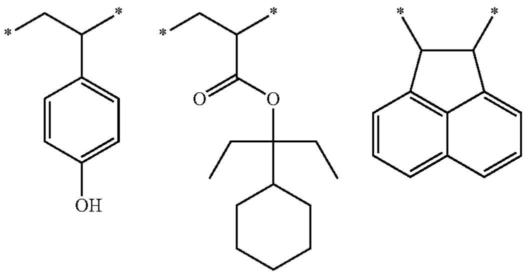
(Ab-303)
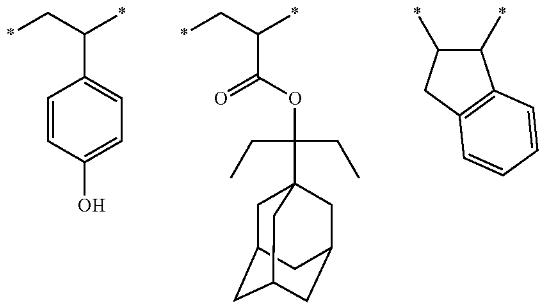
(Ab-304)
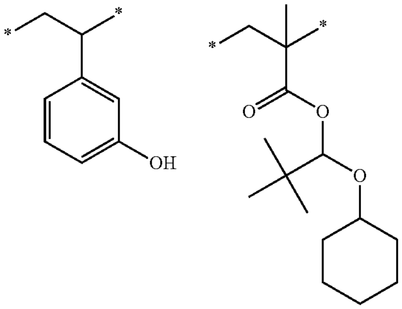
(Ab-305)
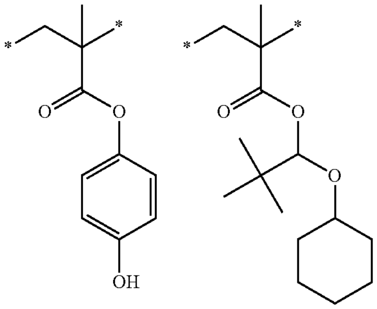
(Ab-306)
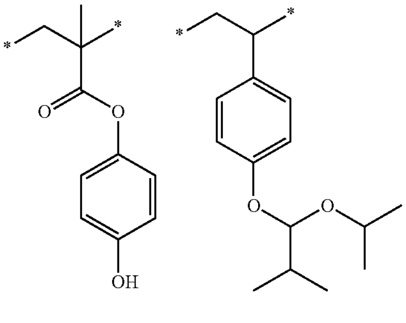
-continued
(Ab-307)
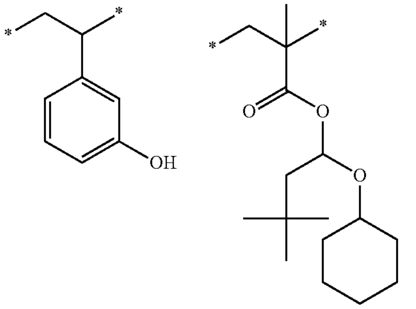
(Ab-308)
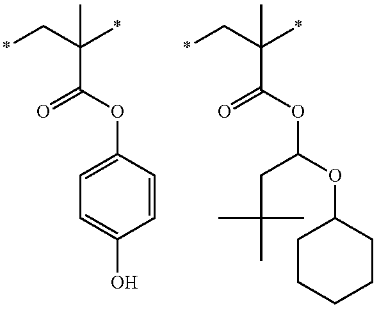
(Ab-309)
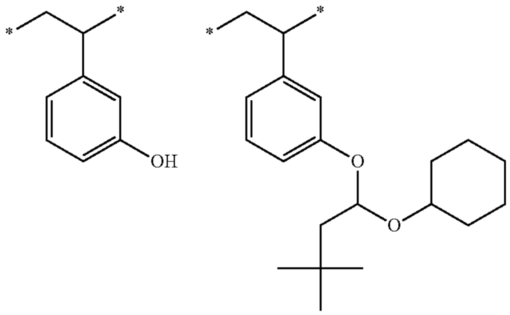
(Ab-310)
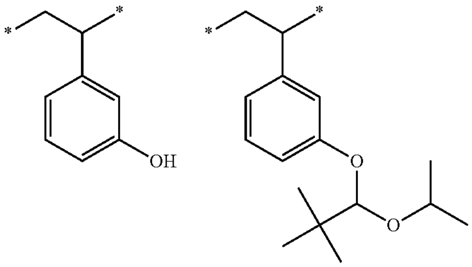
(Ab-311)
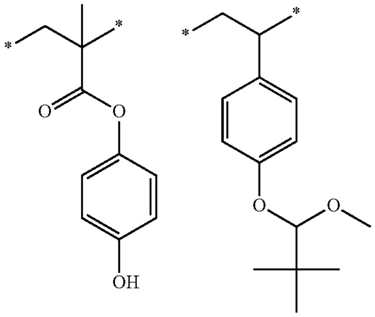
In the case where the resin (Ab) contains no acid-generating repeating unit (B), the content of the fluorine atom-containing repeating unit is preferably 1% by mole or less, and more preferably, the repeating unit contains no fluorine atom. In the case where the resin (Ab) has a repeating unit (B), the repeating unit is a repeating unit other than the repeating unit (B), and the content of the fluorine atom-containing repeating unit is more preferably 1% by mole or less, and most preferably, the repeating unit contains no fluorine atom.

[3] Compound Capable of Generating an Acid by Irradiation with Actinic Rays or Radiation The composition of the present invention may further include a compound capable of generating an acid by irradiation with actinic rays or radiation (also hereinafter referred to a "photo-acid generator").

As such a photo-acid generator, photoinitiators for photocation polymerization, photoinitiators for photo-radical polymerization, photodecoloring agents, photo-discoloring agents, known compounds that generate an acid by irradiation with actinic rays or radiation, which are used in microresists, or the like, mixtures thereof may be suitably selected and used. Examples thereof include onium salts such as a sulfonium salt and an iodonium salt, and diazodisulfone compounds such as bis(alkylsulfonyl)diazomethane.

Preferred examples of the photo-acid generator include the compounds represented by the following general formulae (ZI), (ZII) and (ZIII).

[Chem. 33]

(ZI)

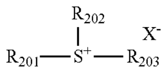

(ZII)

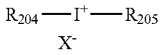

(ZIII)

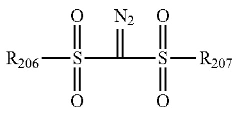

In the general formula (ZI), $R_{201}$, $R_{202}$ and $R_{203}$ each independently represent an organic group. The number of carbon atoms of the organic group as $R_{201}$, $R_{202}$ and $R_{203}$ is, for example, from 1 to 30, and preferably from 1 to 20.

Two members out of $R_{201}$ to $R_{203}$ may be bonded to each other via a single bond or a connecting group to form a ring structure. In this case, examples of the connecting group include an ether bond, a thioether bond, an ester bond, an amide bond, a carbonyl group, a methylene group, and an ethylene group. Examples of the group formed by combining two members out of $R_{20}1$ to $R_{203}$ include alkylene groups such as a butylene group and a pentylene group.

$X^-$ represents a non-nucleophilic anion. Examples of $X^-$ include a sulfonate anion, a bis(alkylsulfonyl)amide anion, a tris(alkylsulfonyl)methide anion, $BF_4^-$, $PF_6^-$, and $SbF_6^-$. $X^-$ is preferably an organic anion containing a carbon atom. Preferred examples of the organic anions include organic anions represented by the following AN1 to AN3.

[Chem. 34]

AN1

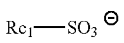

-continued

AN2

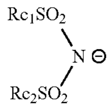

AN3

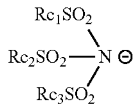

In the formulae AN1 to AN3, $Rc_1$ to $Rc_3$ each independently represent an organic group. Examples of the organic group include an organic group having 1 to 30 carbon atoms, and the organic group is preferably an alkyl group, an aryl group, or a group formed by connecting a plurality of these groups through a connecting group. Examples of the connecting group include a single bond, —O—, —$CO_2$—, —S—, —$SO_3$— and —$SO_2N(Rd_1)$—. Here, $Rd_1$ represents a hydrogen atom or an alkyl group and may form a ring structure together with the alkyl group or aryl group to which $Rd_1$ is bonded.

The organic group of $Rc_1$ to $Rc_3$ may be an alkyl group substituted with a fluorine atom or a fluoroalkyl group at the 1-position, or a phenyl group substituted with a fluorine atom or a fluoroalkyl group. By containing a fluorine atom or a fluoroalkyl group, the acidity of an acid generated by irradiation with light can be increased. This can improve the sensitivity of an actinic ray-sensitive or radiation-sensitive resin composition. Incidentally, each of $Rc_1$ to $Rc_3$ may be bonded to another alkyl group, aryl group, or the like to form a ring structure.

Furthermore, preferred examples of $X^-$ include a sulfonate anion represented by the following general formula (SA1) or (SA2).

[Chem. 35]

(SA 1)

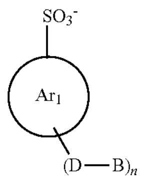

In the formula (SA1), $Ar_1$ represents an aryl group, and may further have a substituent other than a -(D-B) group.

n represents an integer of 1 or more. n is preferably from 1 to 4, more preferably from 2 to 3, and most preferably 3.

D represents a single bond or a divalent connecting group. This divalent connecting group is an ether group, a thioether group, a carbonyl group, a sulfoxide group, a sulfone group, a sulfonic acid ester group, or an ester group.

B represents a hydrocarbon group.

[Chem. 36]

(SA2)

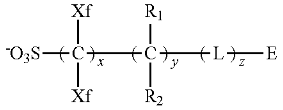

In the formula (SA2),

Xf's each independently represent a fluorine atom, or an alkyl group with at least one hydrogen atom being substituted with a fluorine atom.

$R_1$ and $R_2$ each independently represent a hydrogen atom, a fluorine atom, an alkyl group, or an alkyl group with at least one hydrogen atom being substituted with a fluorine atom, and in the case where a plurality of $R_1$'s and $R_2$'s are present, they may be the same as or different from each other.

L represents a single bond or a divalent connecting group, and in the case where a plurality of L's are present, they may be the same as or different from each other. The divalent connecting group is preferably any of an arylene group, an alkylene group, a cycloalkylene group, —O—, —$SO_2$—, —CO— or —$N(R_{34})$—. Moreover, $R_{34}$ represents a hydrogen atom, an alkyl group, a cycloalkyl group, an alkenyl group, a cycloalkenyl group, an aryl group or an aralkyl group.

E represents a group having a cyclic structure.

x represents an integer of 1 to 20, y represents an integer of 0 to 10, and z represents an integer of 0 to 10.

Examples of the sulfonate anion represented by the general formula (SA1) or (SA2) include the following.

[Chem. 37]

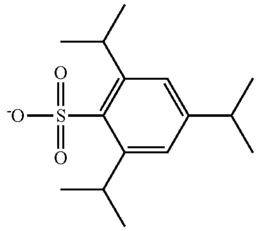

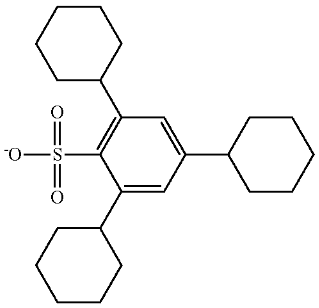

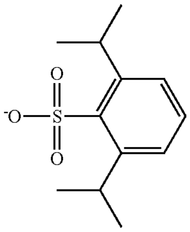

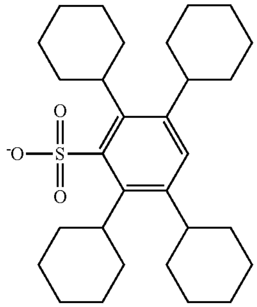

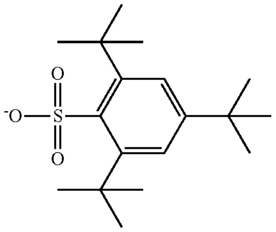

-continued

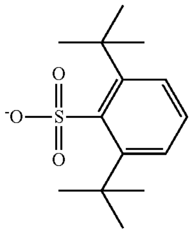

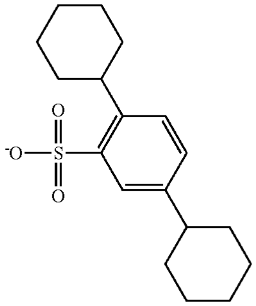

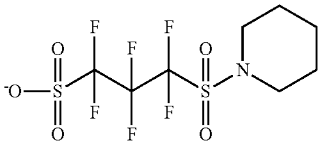

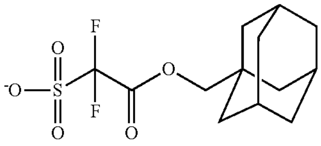

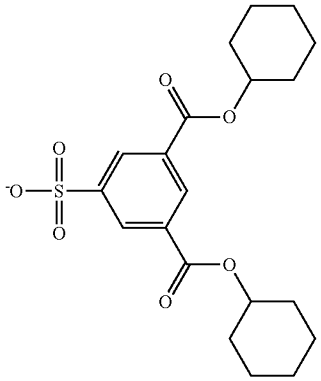

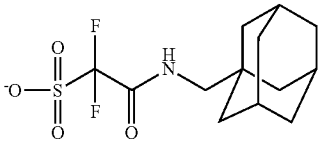

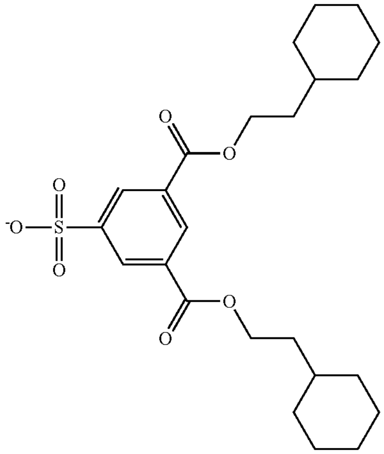

-continued

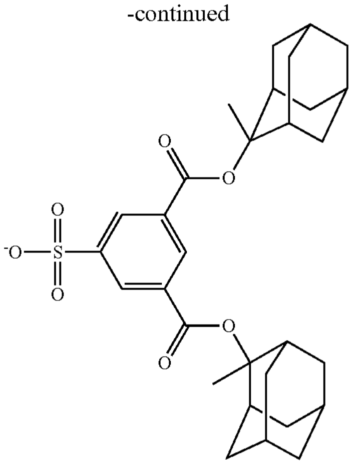

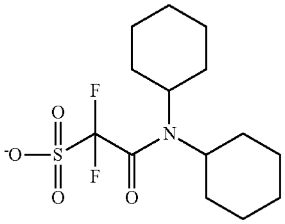

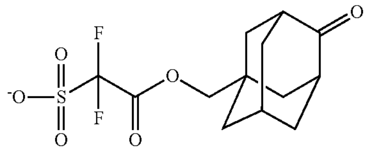

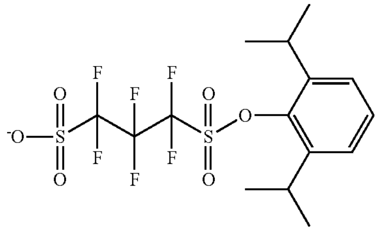

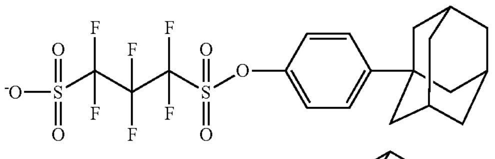

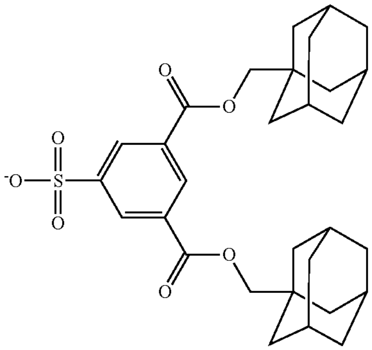

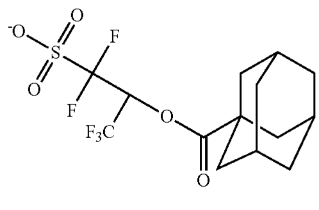

-continued

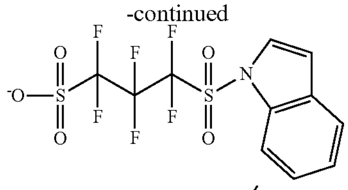

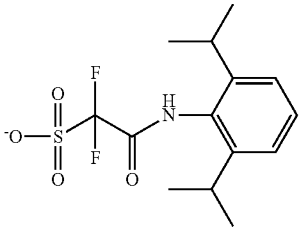

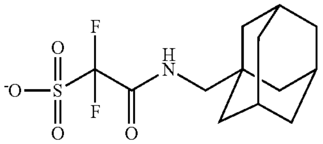

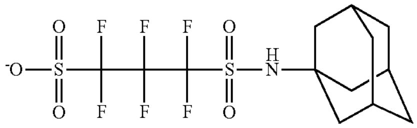

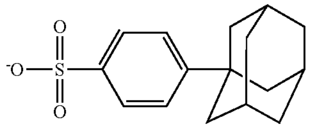

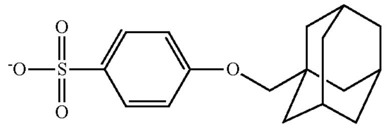

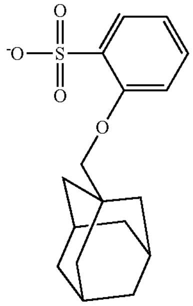

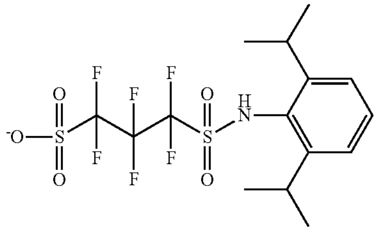

As the photo-acid generator, a compound having a plurality of structures represented by the general formula (ZI) may be also used. For example, the compound may be a compound having a structure where at least one of $R_{201}$ to $R_{203}$ in a compound represented by the general formula (ZI) is bonded to at least one of $R_{201}$ to $R_{203}$ of another compound represented by the general formula (ZI).

The general formulae (ZII) and (ZIII) will be described below.

In the general formulae (ZII) and VIM, $R_{204}$ to $R_{207}$ each independently represent an aryl group, an alkyl group, or a cycloalkyl group. The aryl group, the alkyl group, and the cycloalkyl group may have a substituent.

Moreover, $X^-$ in the general formula (ZII) is the same as $X^-$ in the general formula (ZI).

Other preferred examples of the photo-acid generator include the compounds represented by the following general formula (ZIV), (ZV), or (ZVI).

[Chem. 38]

ZIV $Ar_3—SO_2—SO_2—Ar_4$

ZV

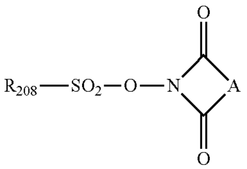

ZVI

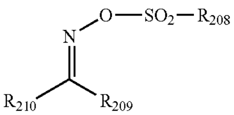

In the general formulae (ZIV) to (ZVI), $Ar_3$ and Ar4 each independently represent a substituted or unsubstituted aryl group.

$R_{208}$'s of the general formulae (ZV) and (ZVI) each independently represent an alkyl group, a cycloalkyl group or an aryl group. These alkyl groups, cycloalkyl groups, and aryl groups may or may not be substituted.

These groups are preferably substituted with a fluorine atom. This can increase the strength of the acid generated from the photo-acid generator.

$R_{209}$ and $R_{210}$ each independently represent an alkyl group, a cycloalkyl group, an aryl group, or an electron-withdrawing group. The alkyl group, the cycloalkyl group, the aryl group, and the electron-withdrawing group may or may not be substituted.

Preferred examples of $R_{209}$ include a substituted or unsubstituted aryl group.

Preferred examples of $R_{210}$ include an electron-withdrawing group. Examples of this electron-withdrawing group include a cyano group and a fluoroalkyl group.

A represents an alkylene group, an alkenylene group, or an arylene group. The alkylene group, the alkenylene group, and the arylene group may have a substituent.

Moreover, as the photo-acid generator, a compound having a plurality of structures represented by the general formula (ZVI) is also preferred. Examples of the compound include a compound having a structure where $R_{209}$ or $R_{210}$ in a compound represented by the general formula (ZVI) is bonded to $R_{209}$ or $R_{210}$ in another compound represented by the general formula (ZVI).

As a photo-acid generator, compounds represented by the general formulae (ZI) to (ZIII) are more preferable and a compound represented by the general formula (ZI) is further preferable.

As the acid generator used in the present invention, a compound having a group capable of decomposing by the action of an acid to increase the solubility in an alkali developer can also be preferably used. Examples of such an acid generator include the compounds described in JP2005-97254A and JP2007-199692A, and the like.

Specific examples of the photo-acid generator are shown below, but the present invention is not limited thereto.

[Chem. 39-1]

B-1

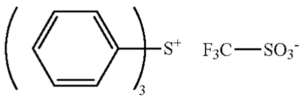

B-2

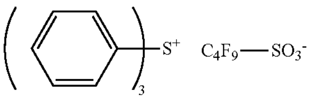

B-3

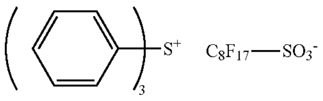

B-4

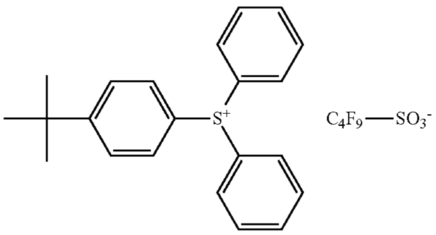

B-5

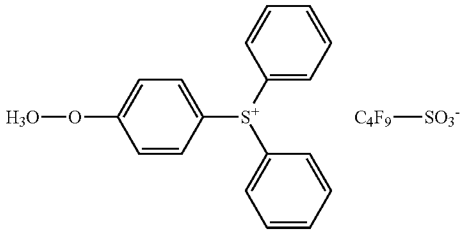

B-6

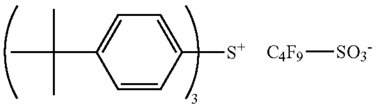

-continued
B-8
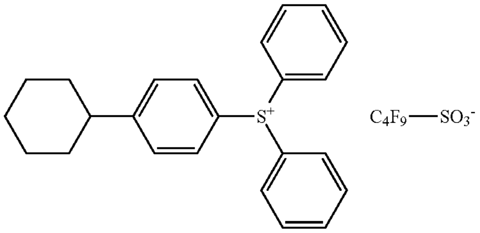
B-9
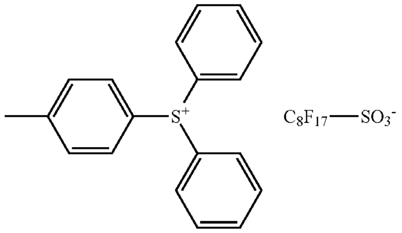
B-10
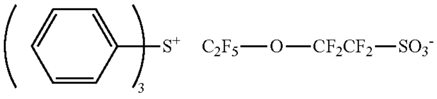
[Chem. 39-2]
B-12
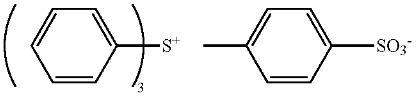
B-13
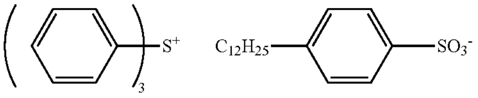
B-14
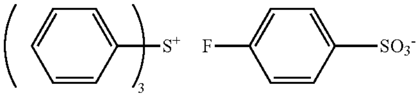
[Chem. 39-3]
B-16
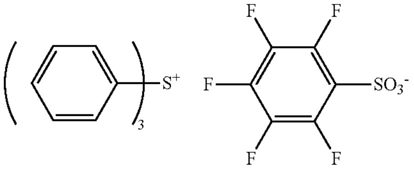
B-17
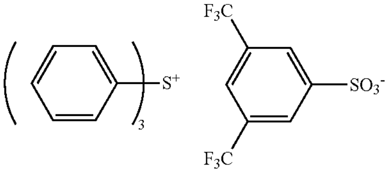
B-18
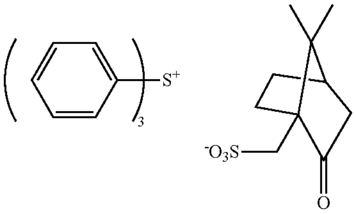
B-19
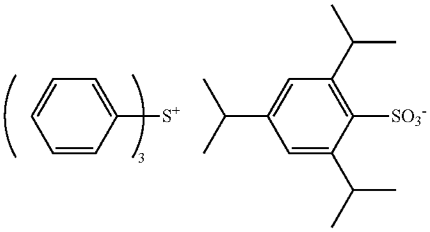
B-20
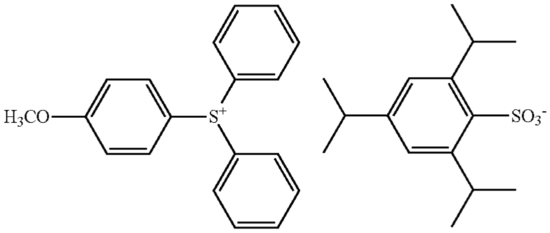
B-21
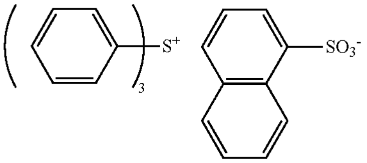

-continued
[Chem. 39-4]
B-22
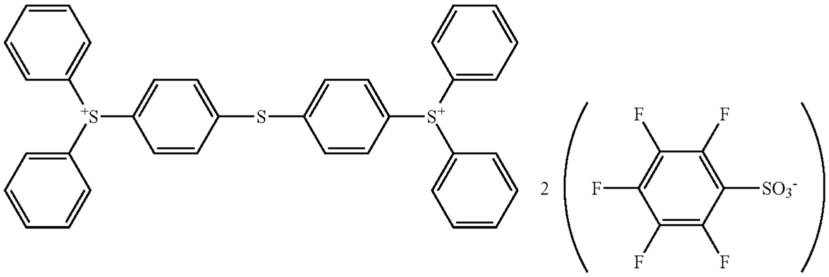
B-23
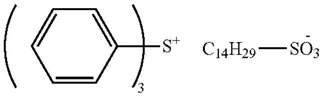
B-25
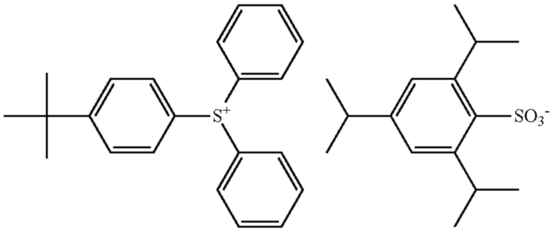
B-26
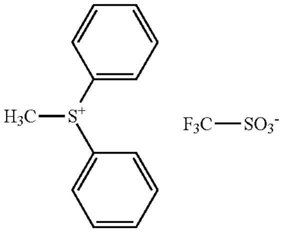
B-27
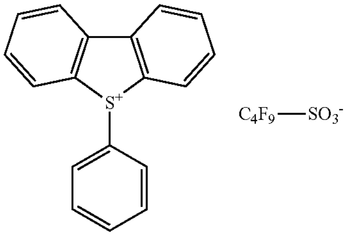
[Chem. 39-5]
B-28
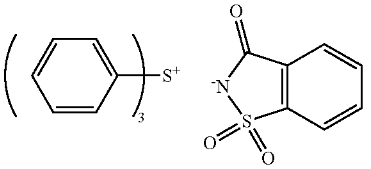
B-29
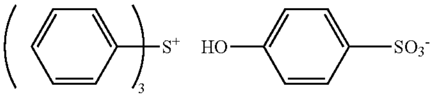
B-30
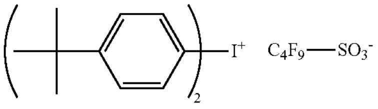
B-31
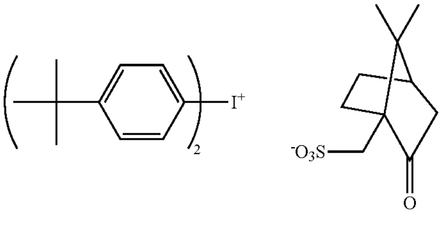
B-32
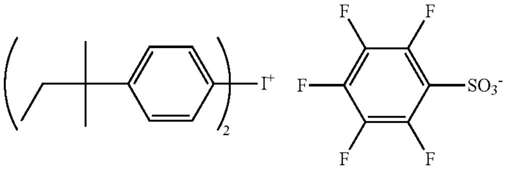
B-33
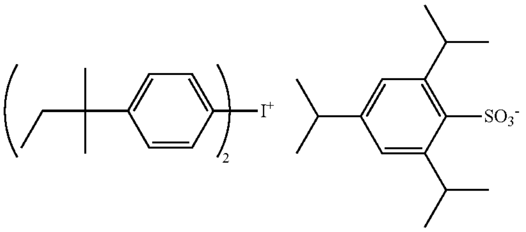

-continued
[Chem. 39-6]
B-34
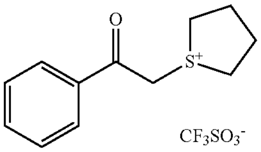
B-35
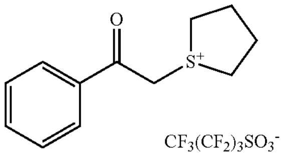
B-36
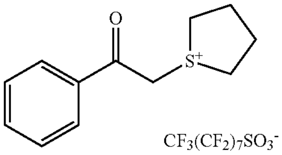
B-37
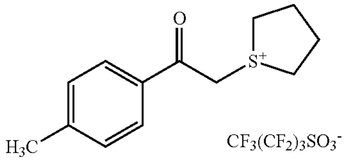
B-38
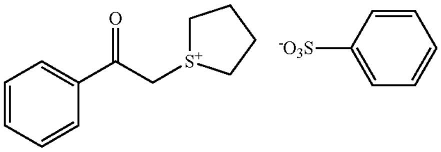
B-39
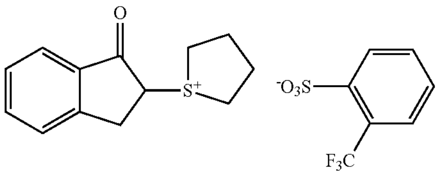
B-40
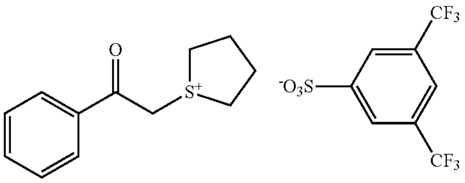
B-41
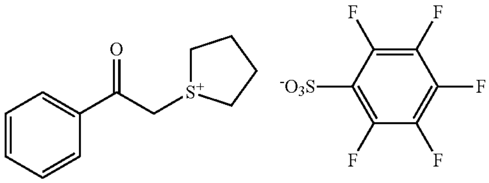
B-42
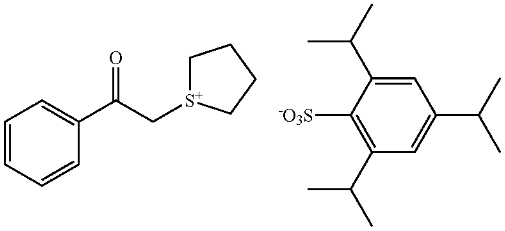
B-43
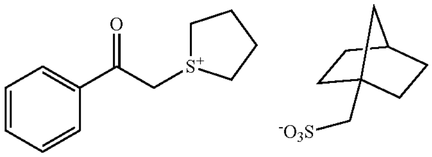
[Chem. 39-7]
B-44
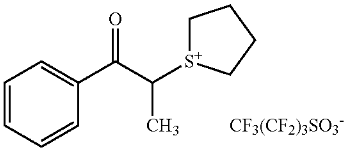
B-45
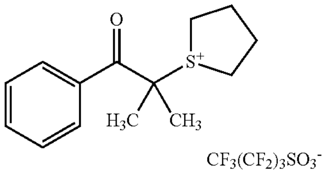
B-47
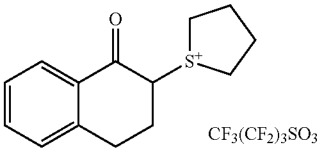
B-50
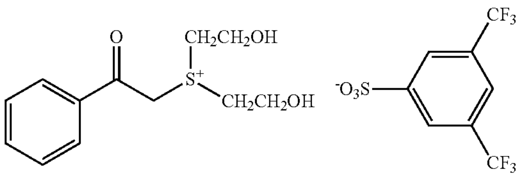
B-54
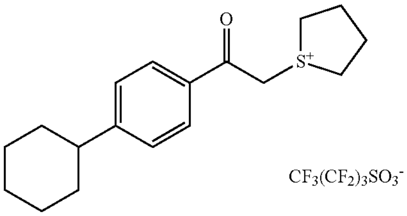
B-55
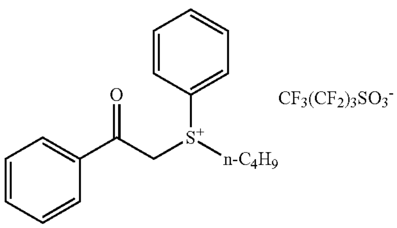

-continued
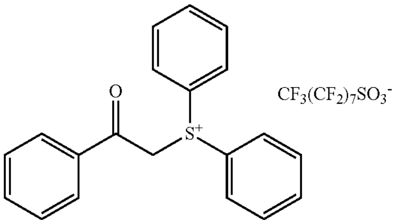
B-56
[Chem. 39-8]
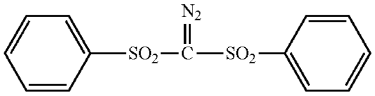
B-57
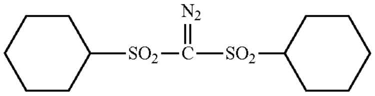
B-58
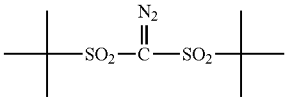
B-59
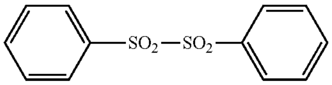
B-64
[Chem. 39-9]
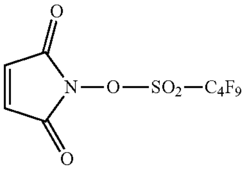
B-67
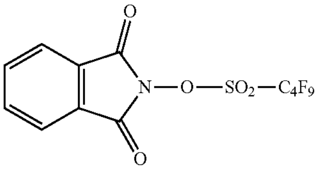
B-69
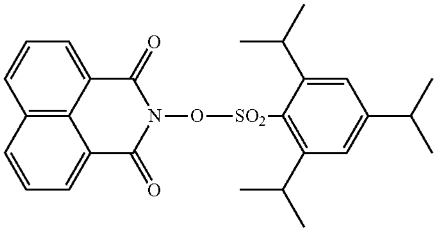
B-71
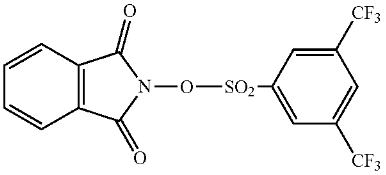
B-72
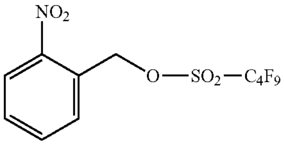
B-75
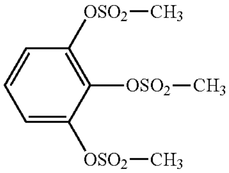
B-76
[Chem. 39-10]
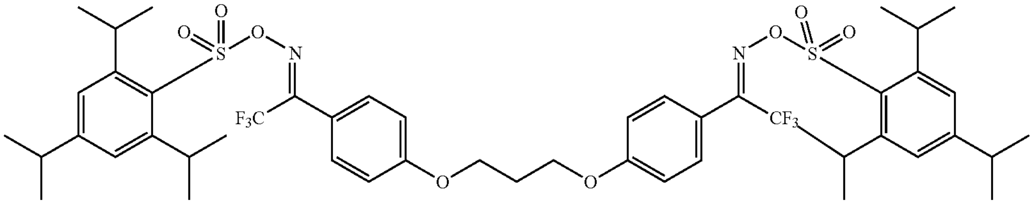
B-78
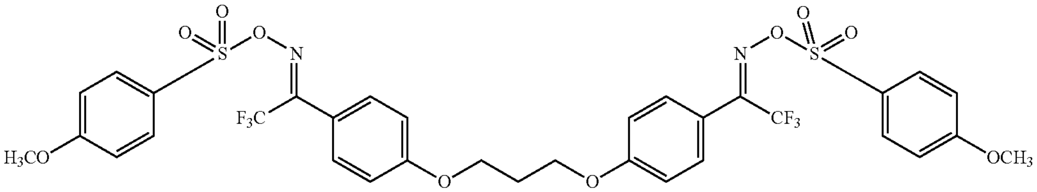
B-79

-continued
B-80
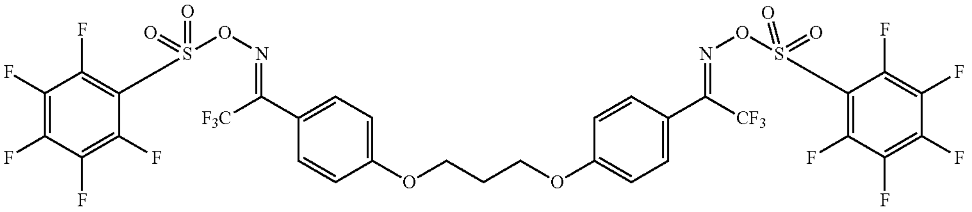
B-81
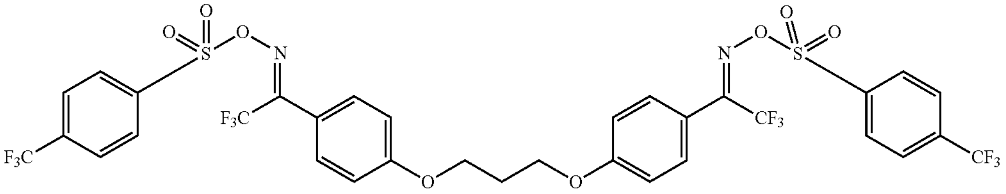
B-82
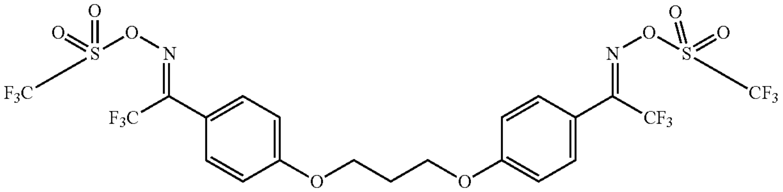
B-83
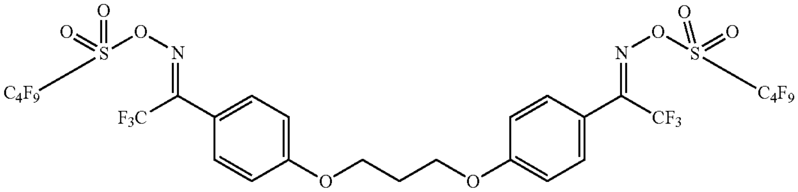
[Chem. 39-11]
B-84
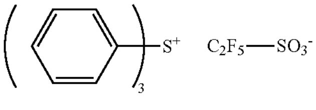
B-86
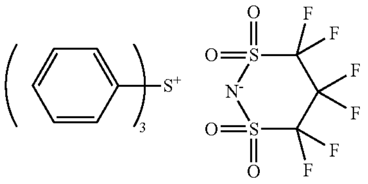
B-88
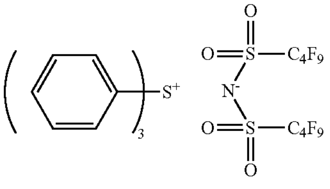
B-90
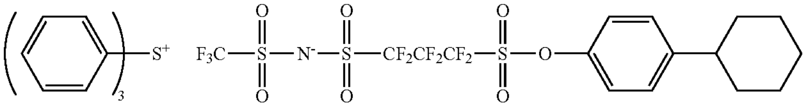
B-92
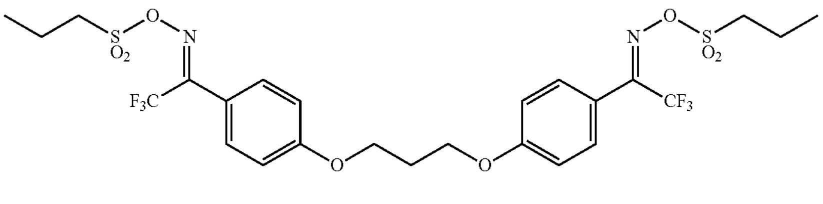

-continued
[Chem. 39-12]
B-97
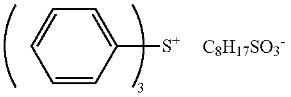
B-101
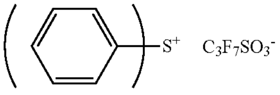
B-102
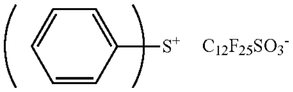
B-104
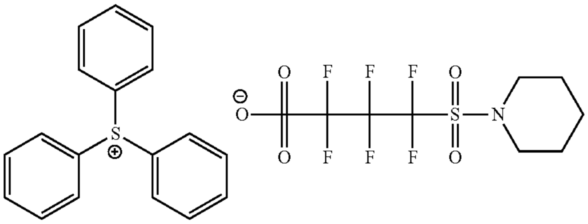
[Chem. 39-13]
B-105
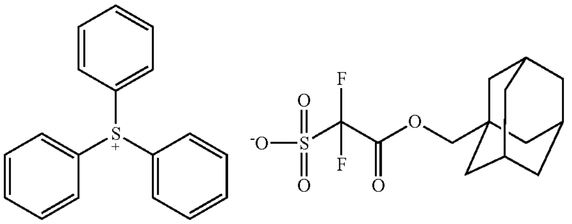
B-106
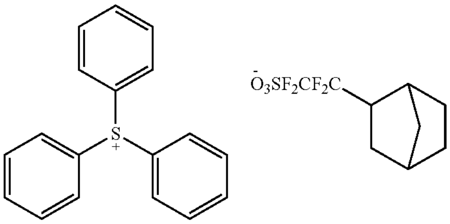
B-107
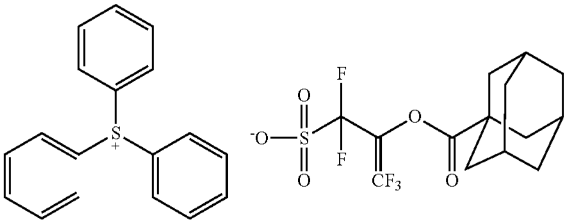
B-108
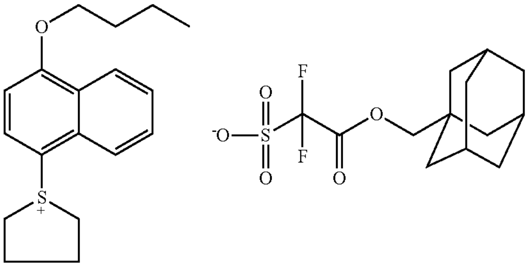
B-109
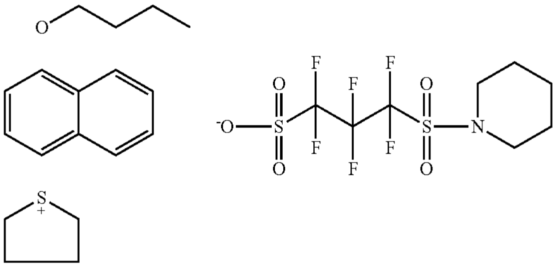
B-110
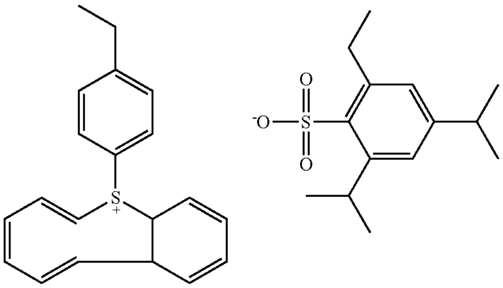
B-107
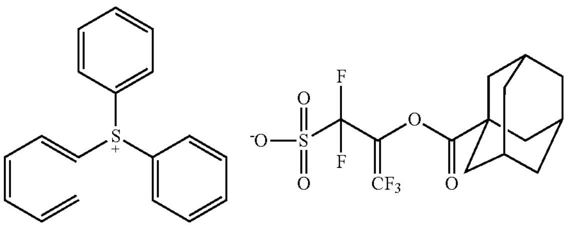

-continued
B-108
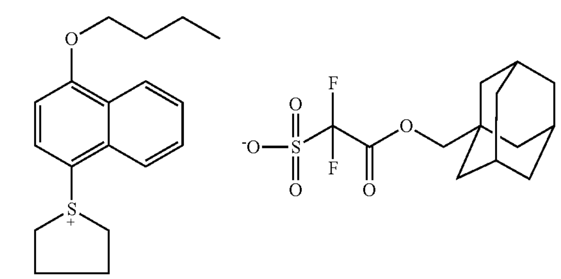
B-109
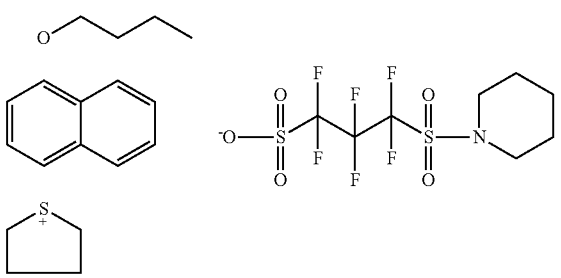
B-111
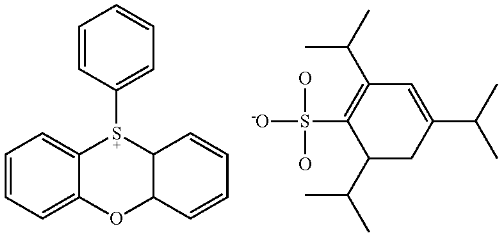
B-112
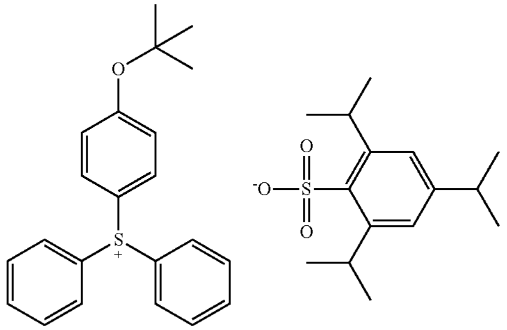
B-113
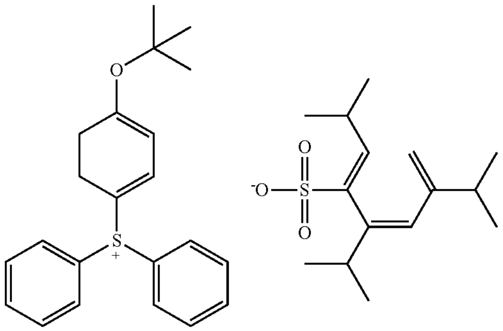
B-114
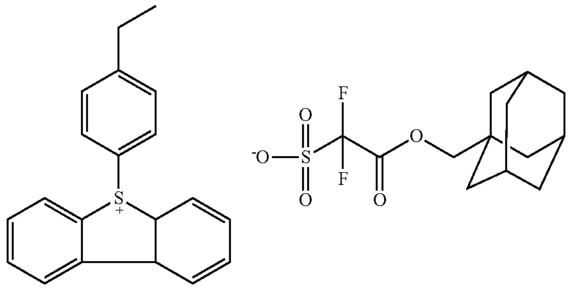
B-115
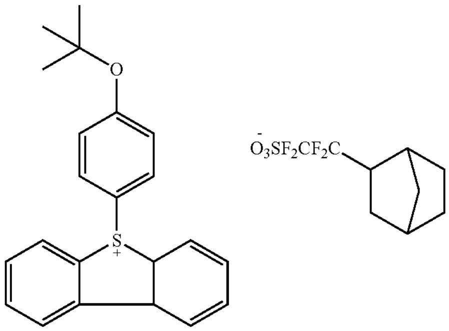
B-116
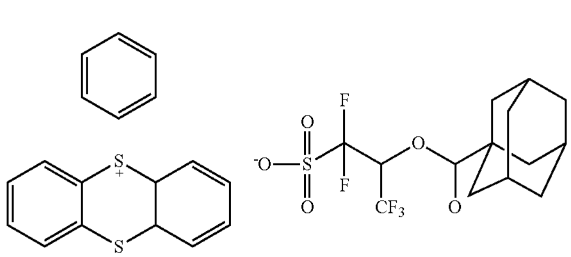

-continued
B-117
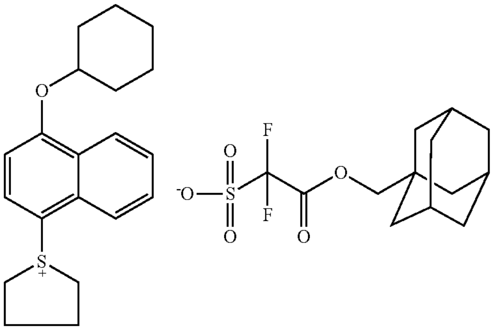
B-118
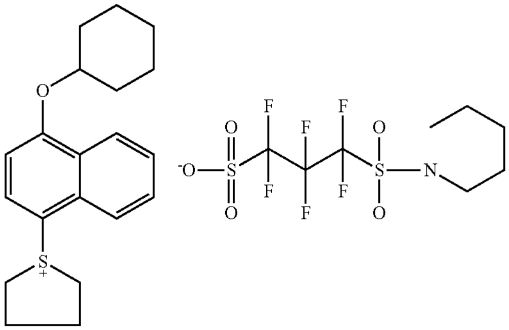
B-119
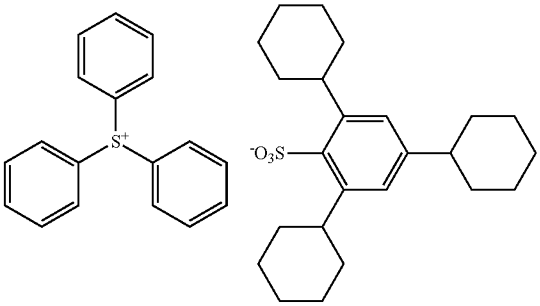
B-120
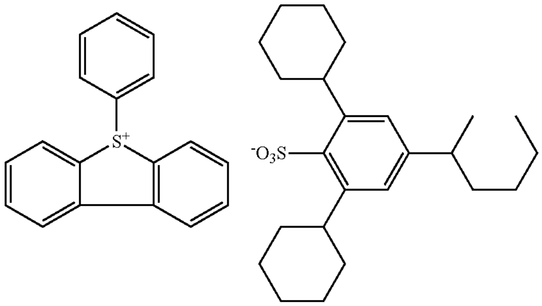
[Chem. 39-14]
B-121
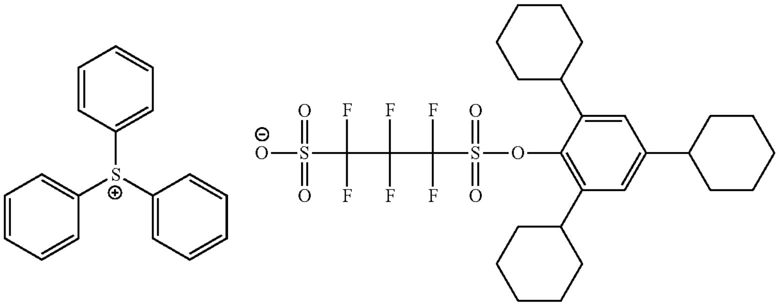
B-122
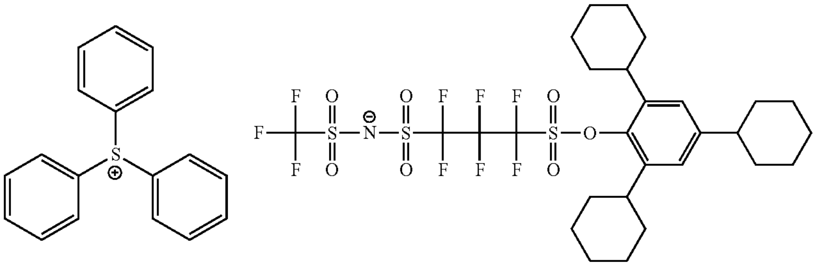
B-123
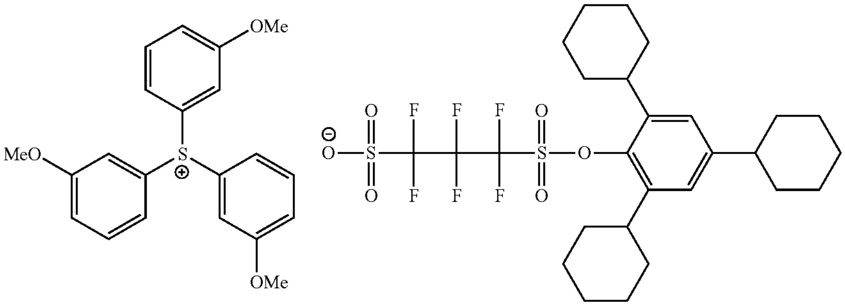

-continued
B-124
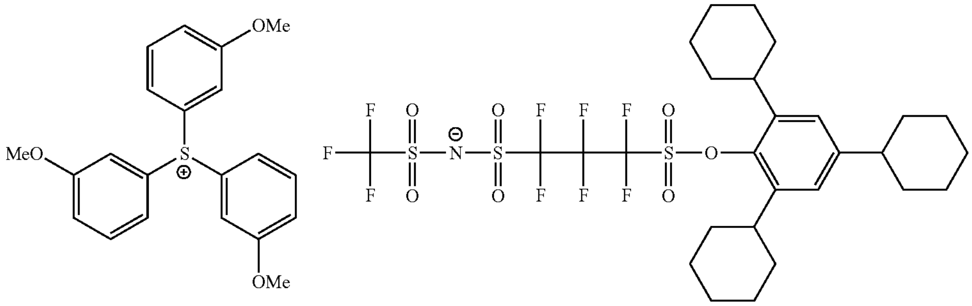
B-125
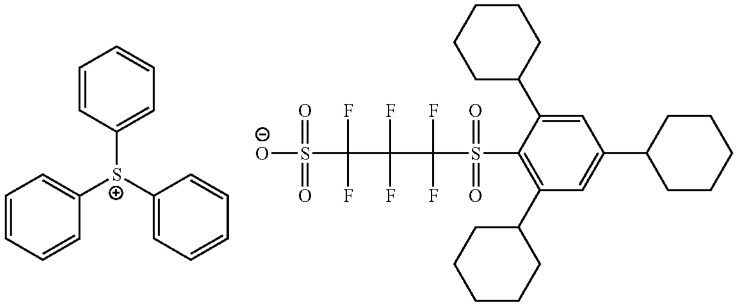
B-126
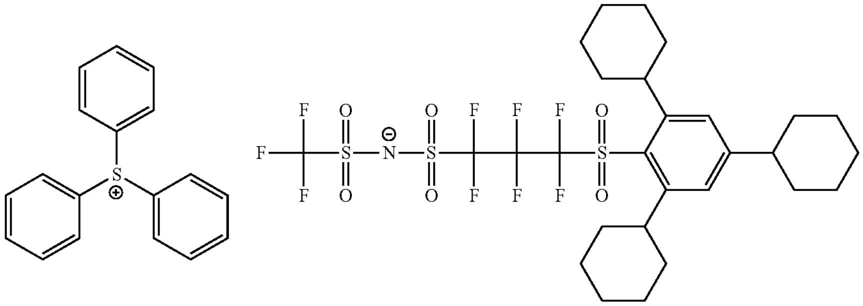
B-127
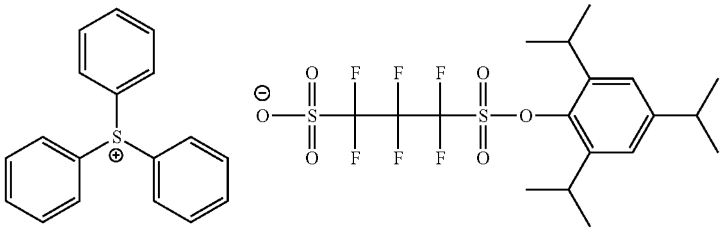
B-128
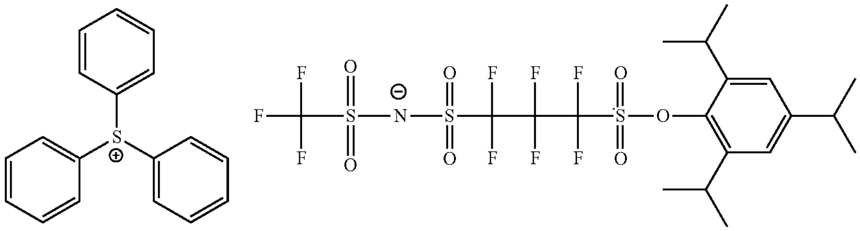

-continued
B-129
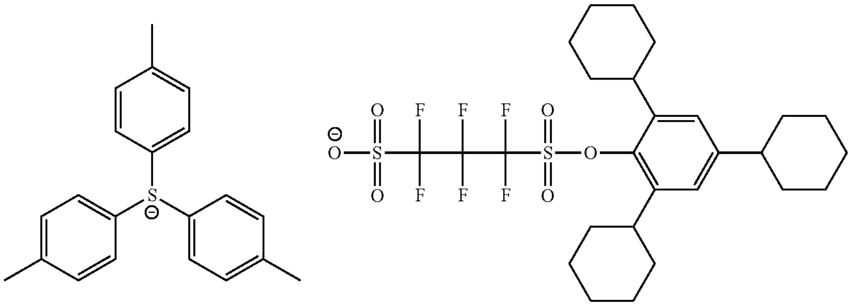
B-130
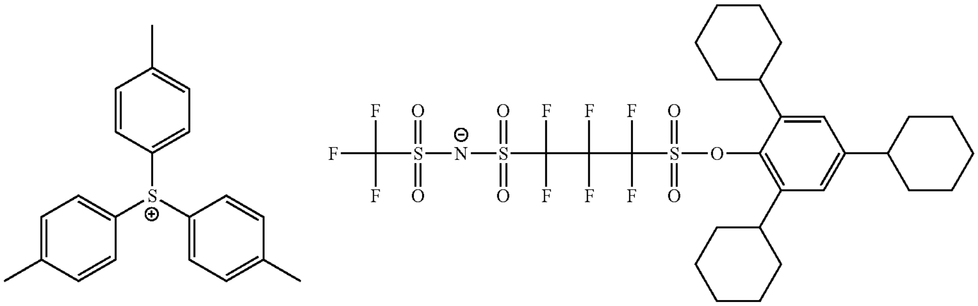
[Chem. 39-15]
B-131
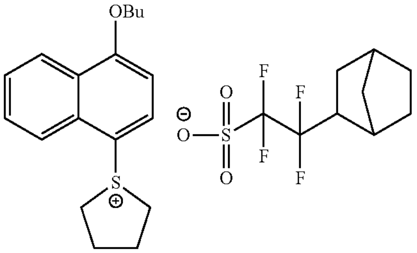
B-132
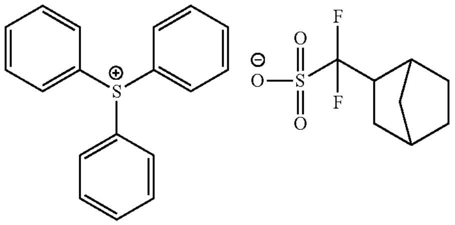
B-134
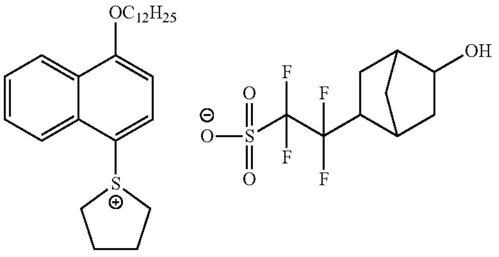
B-136
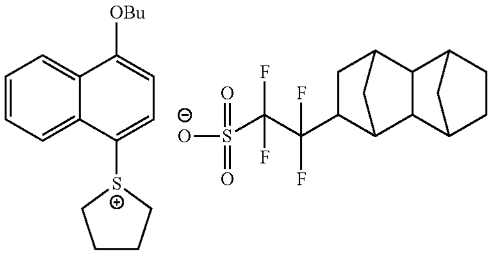
B-138
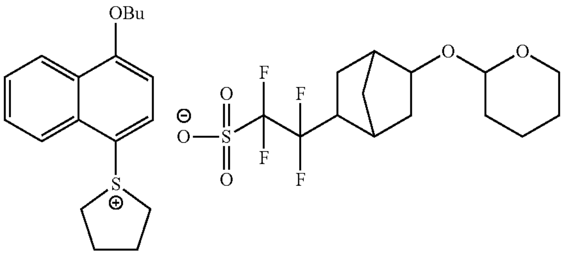
B-140
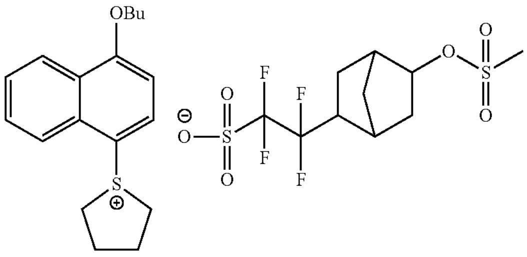

-continued
B-142
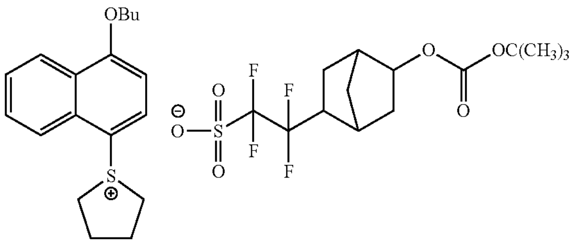
B-144
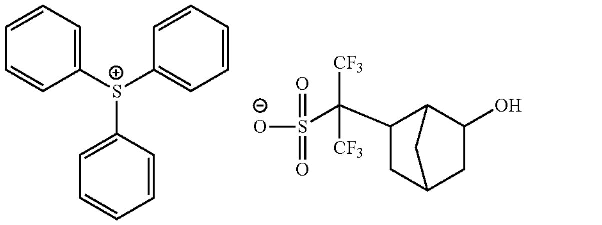
[Chem. 39-16]
B-146
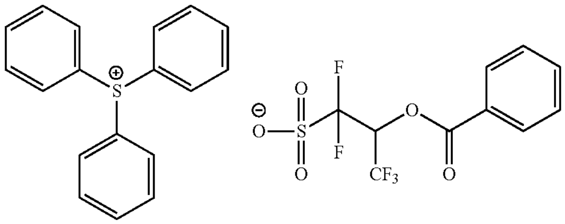
B-148
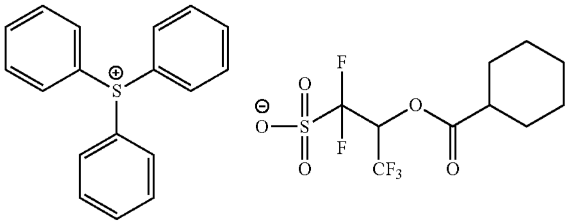
B-149
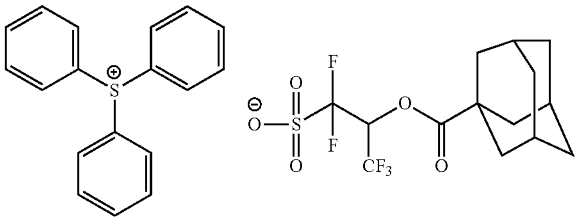
B-150
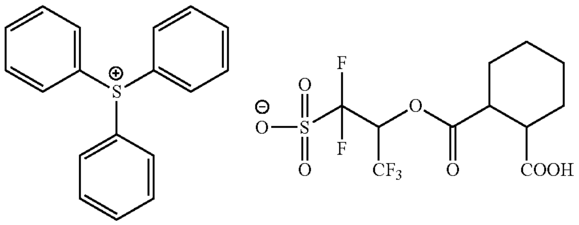
B-152
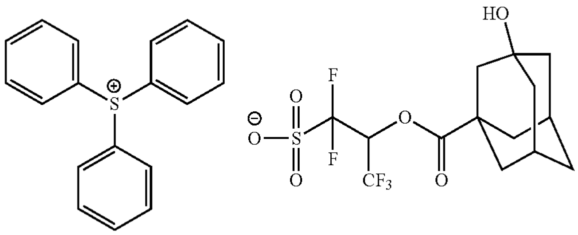
B-154
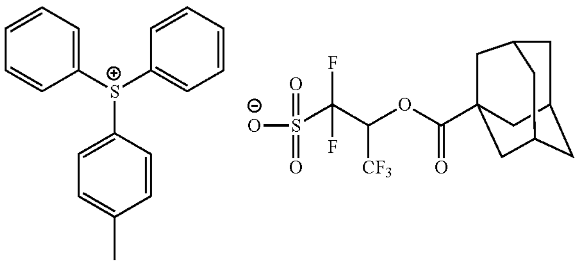
B-156
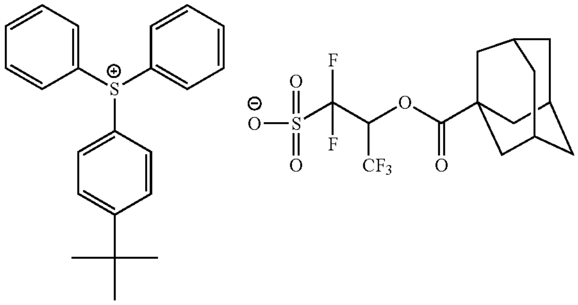

-continued
[Chem. 39-17-1]
B-158
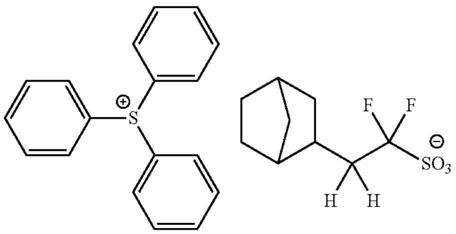
B-161
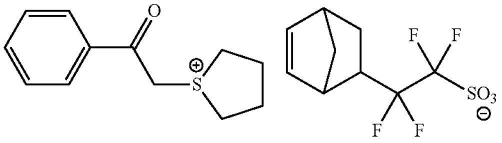
B-162
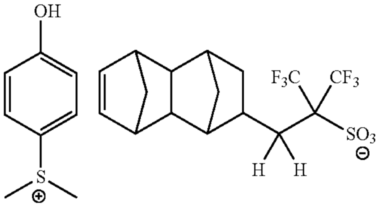
B-165
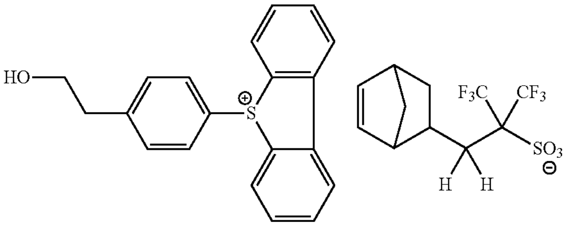
B-166
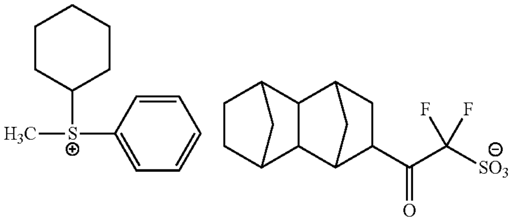
B-168
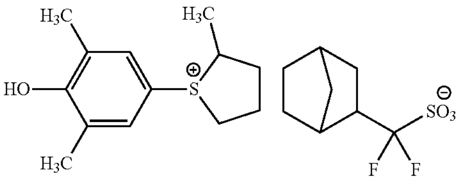
B-170
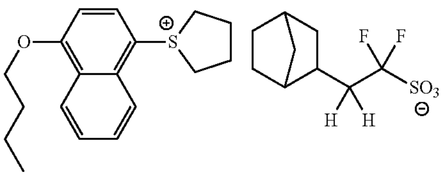
B-173
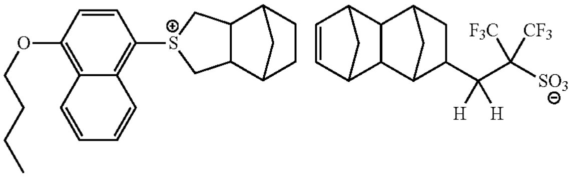
B-174
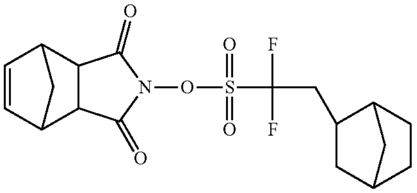
B-177
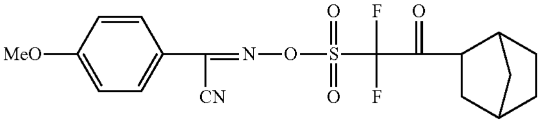
[Chem. 39-17-2]
B-179
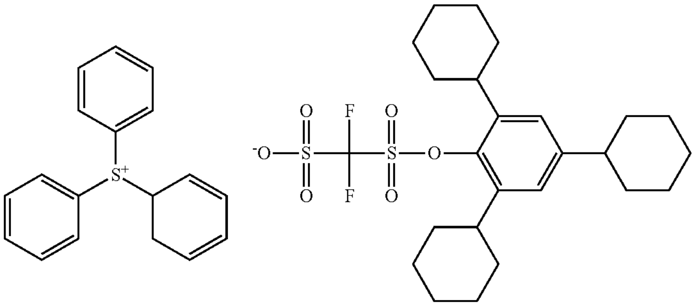

-continued
B-180
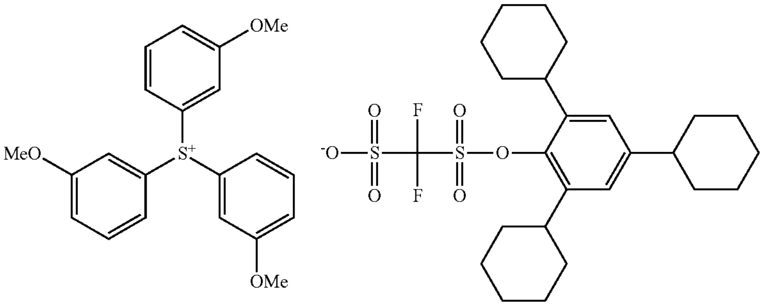
B-181
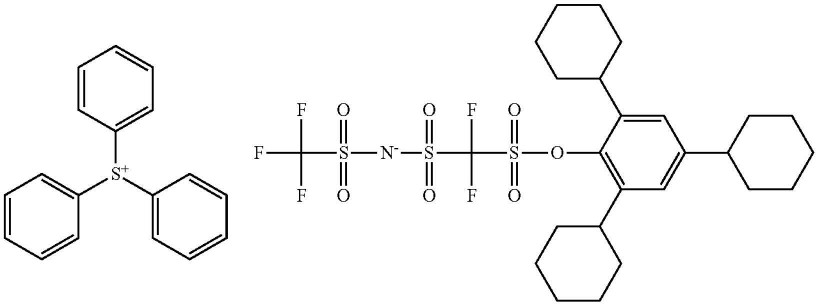
B-182
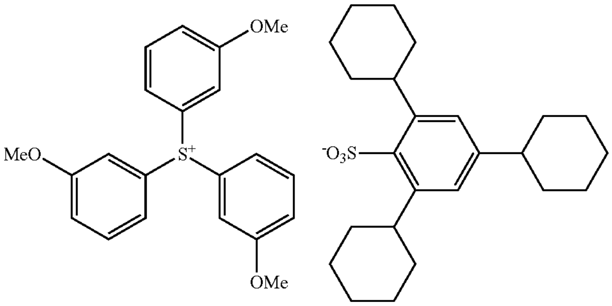
B-183
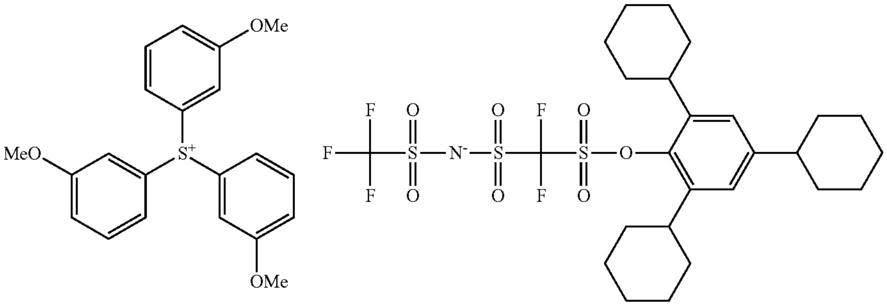
[Chem. 39-17-3]
(z128)
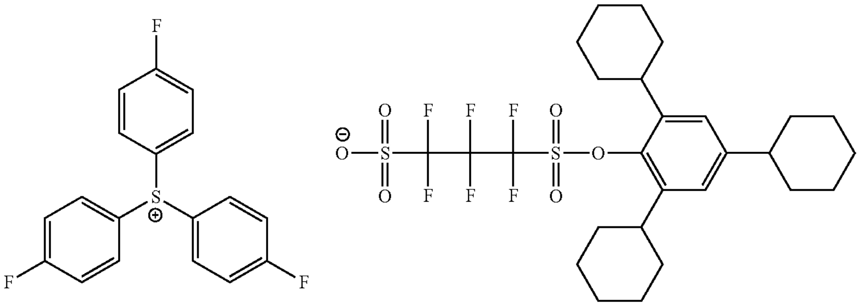

-continued
(z129)
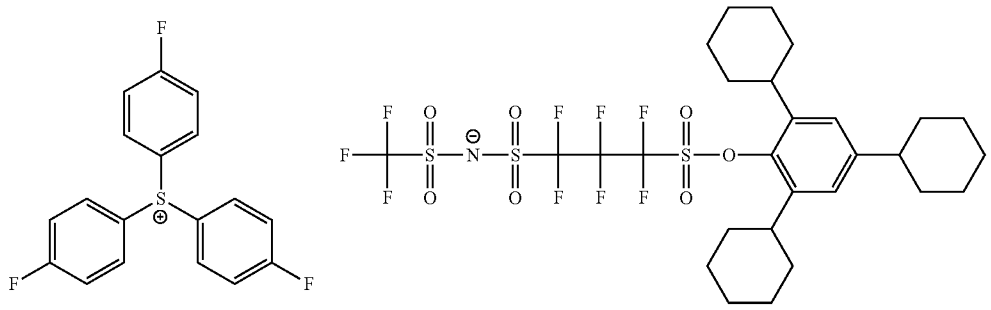
(z130)
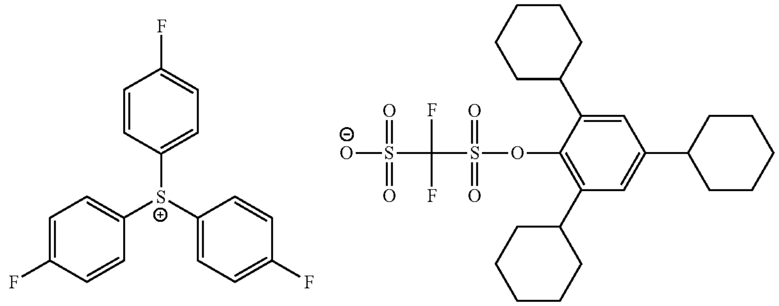
(z131)
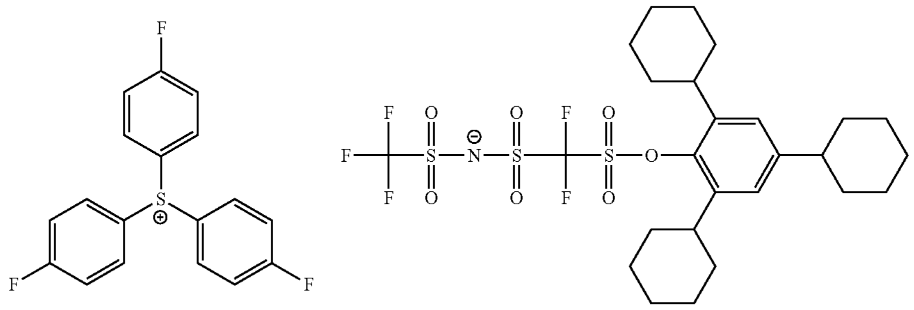
(z132)
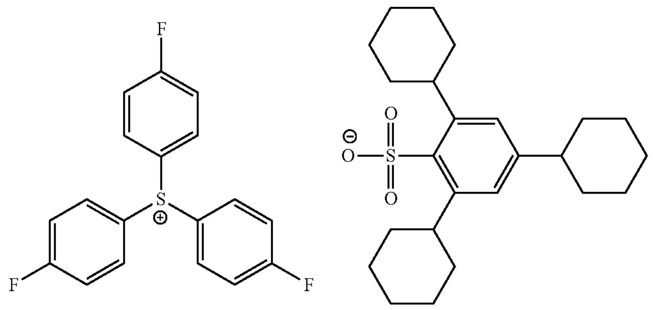
(z133)
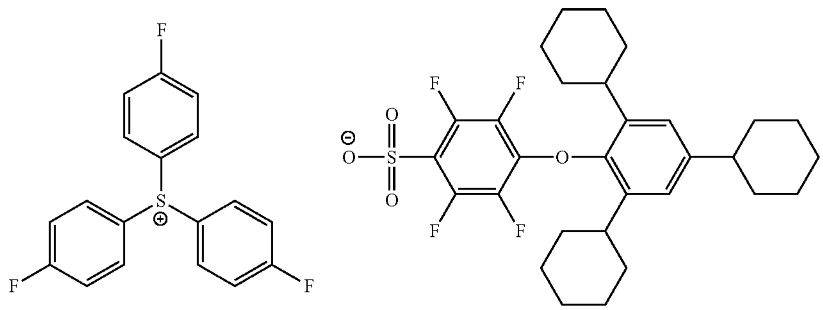

-continued
(z134)
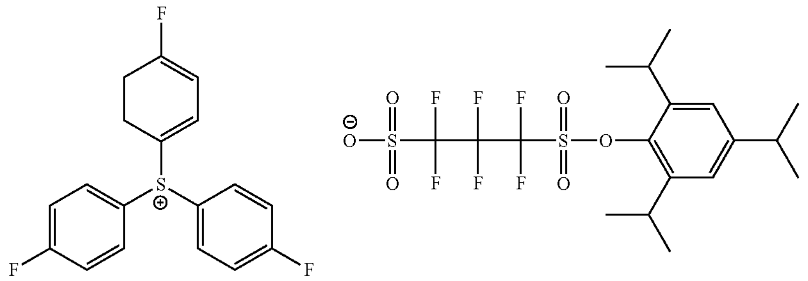
(z135)
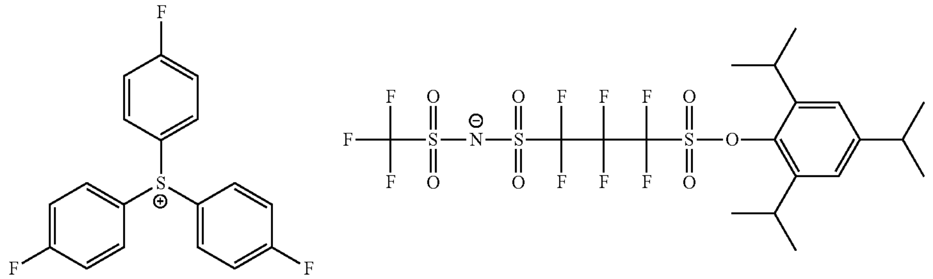
(z136)
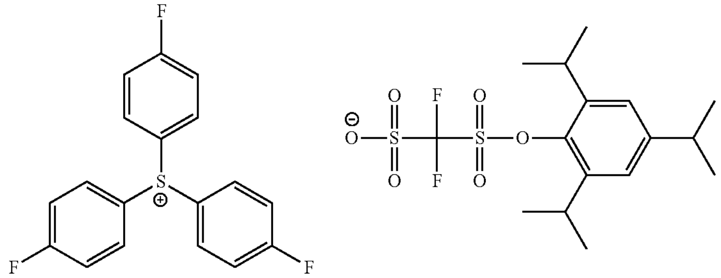
(z137)
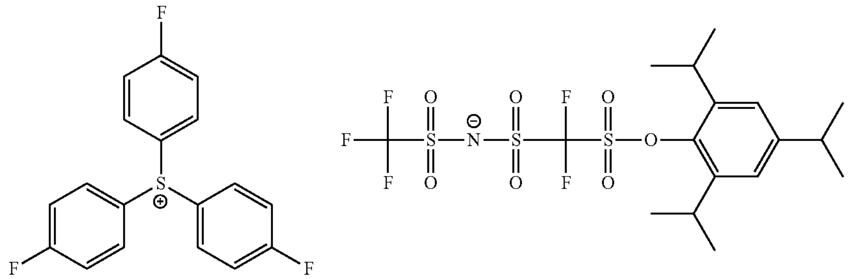
(z138)
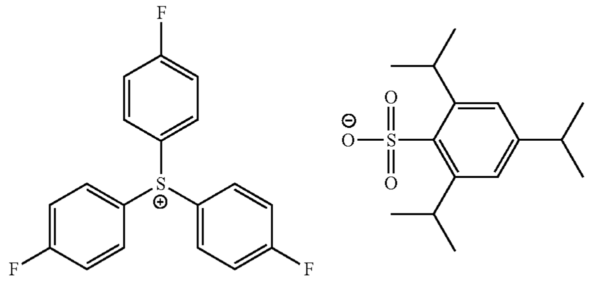

-continued
(z139)
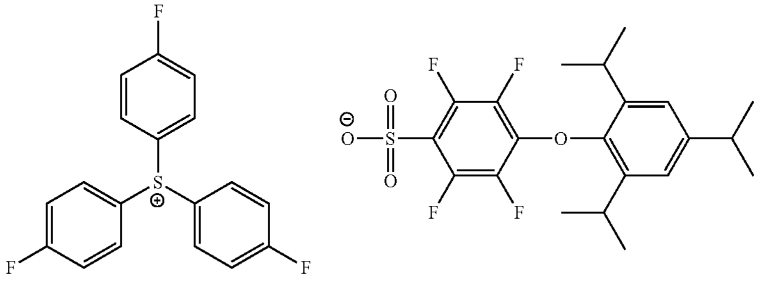
(z140)
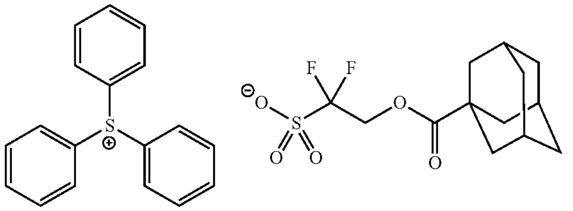
(z141)
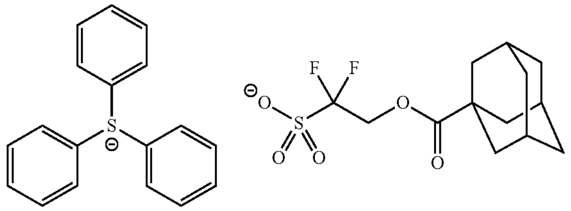
(z142)
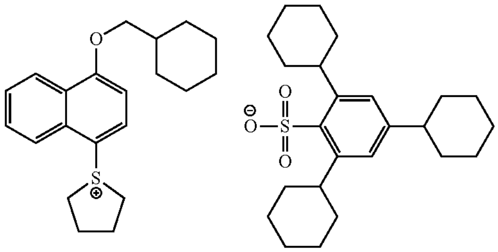
(z143)
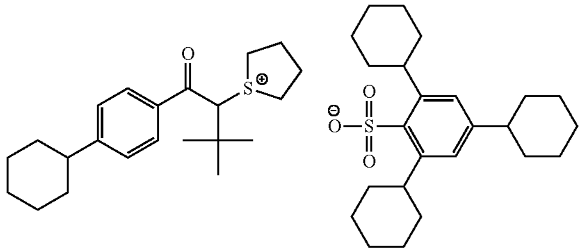
[Chem. [39-17-4]
(z140)
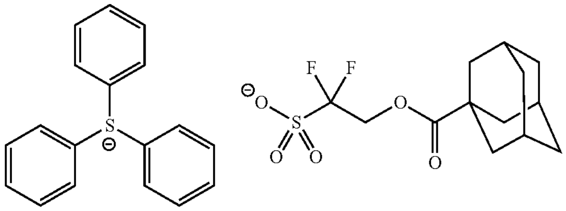
(z141)
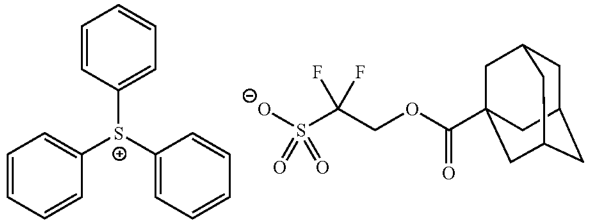
(z142)
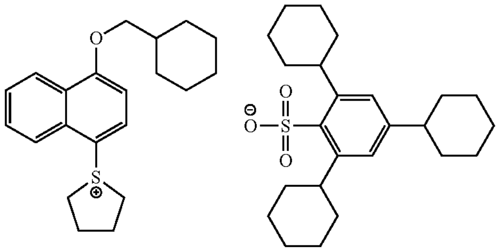
(z143)
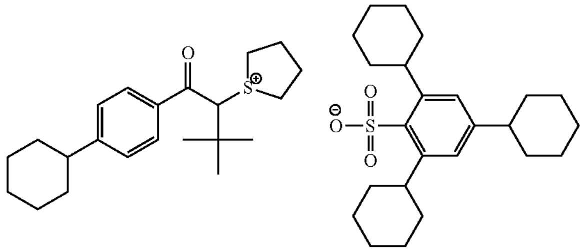

-continued
[Chem. [39-18]
(Y-1)
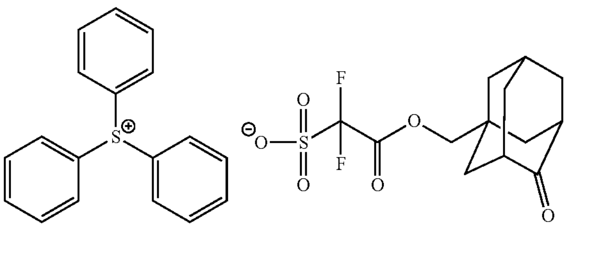
(Y-2)
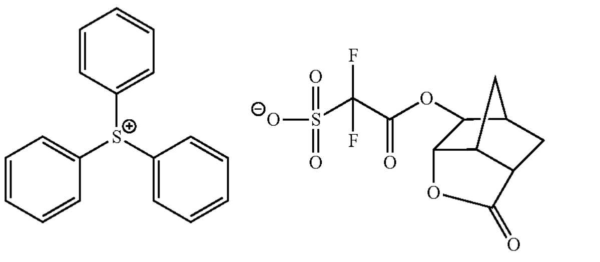
(Y-3)
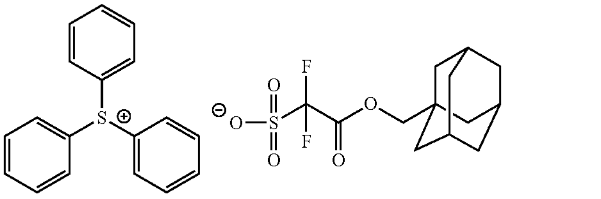
(Y-4)
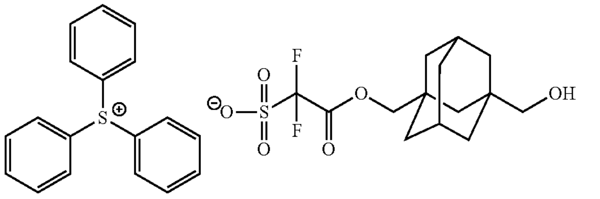
(Y-5)
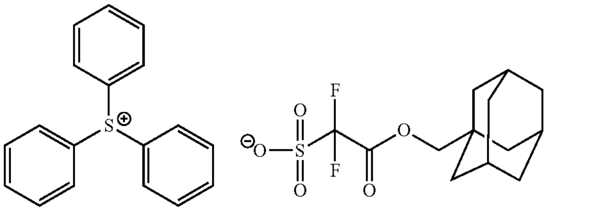
(Y-6)
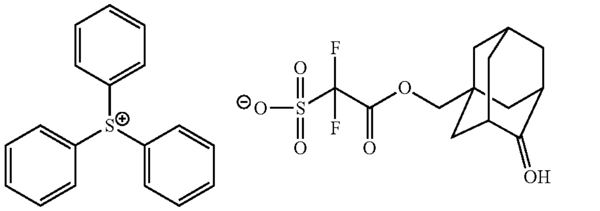
[Chem. 39-19]
(Y-24)
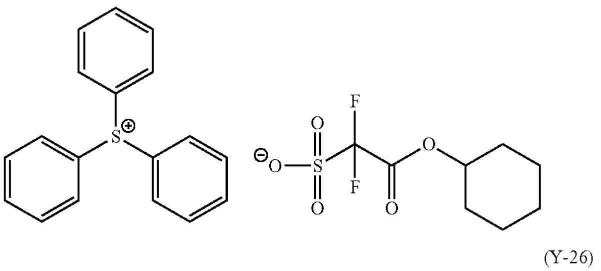
(Y-25)
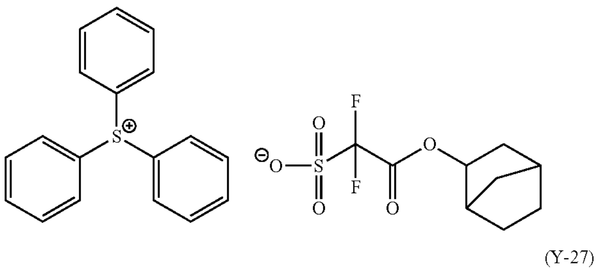
(Y-26)
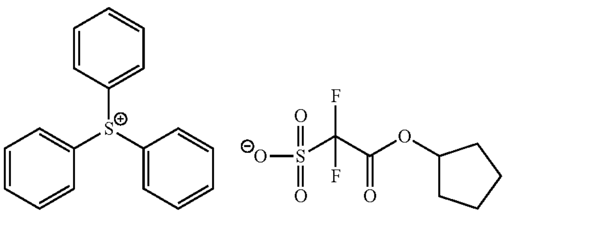
(Y-27)
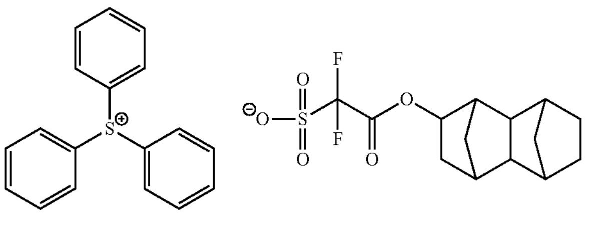
(Y-28)
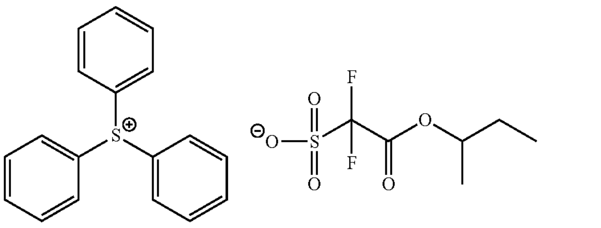
(Y-29)
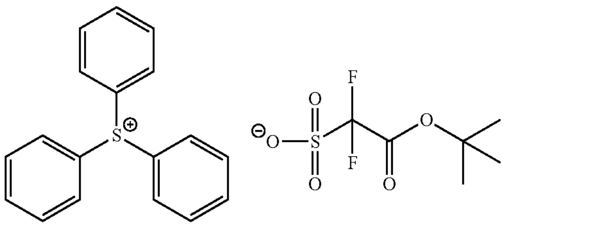

-continued
(Y-30)
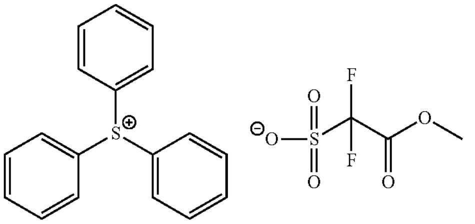
(Y-31)
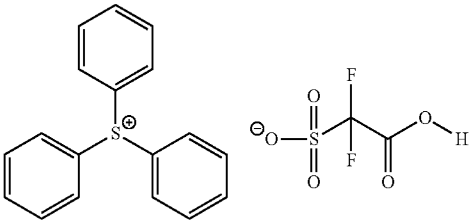
(Y-32)
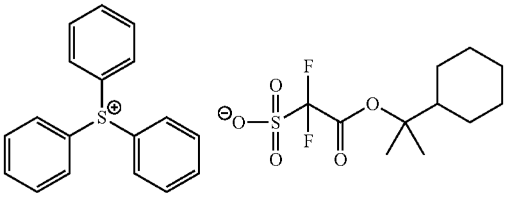
(Y-33)
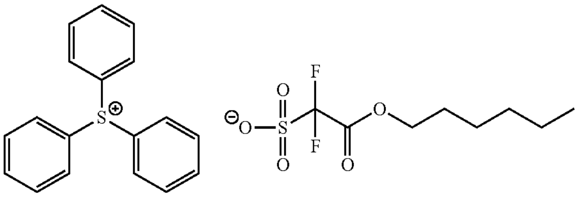
(Y-34)
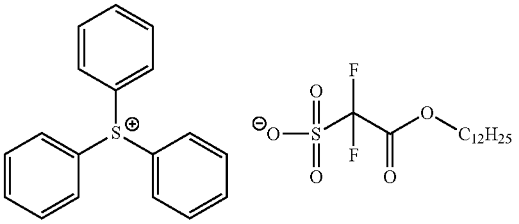
(Y-35)
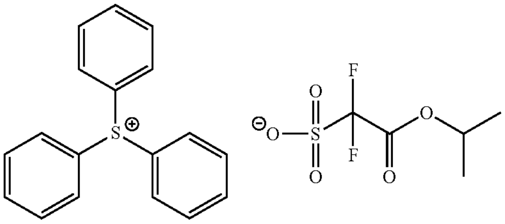
[Chem. 39-20]
(Y-61)
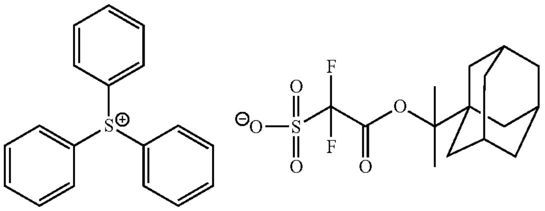
(Y-70)
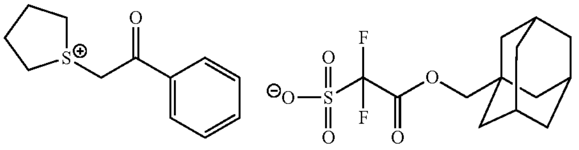
(Y-71)
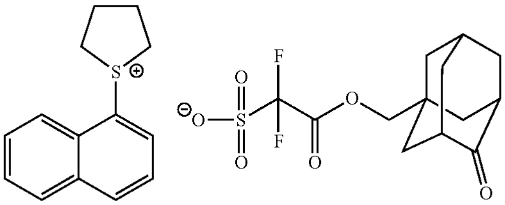
(Y-72)
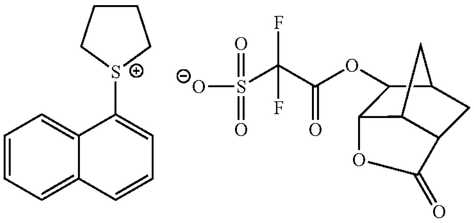
(Y-73)
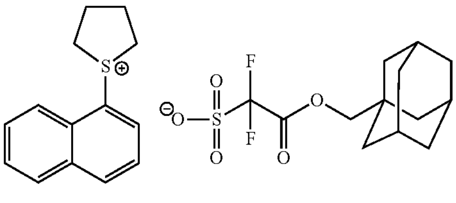
(Y-74)
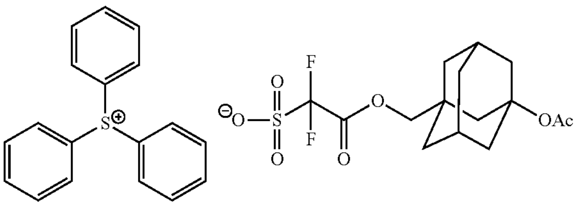

-continued (Y-75)

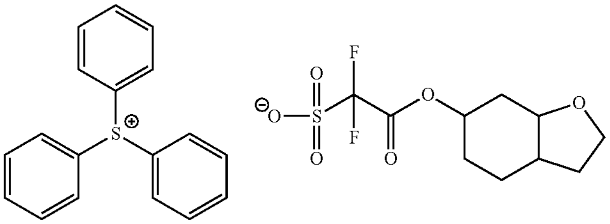

Furthermore, the photo-acid generator may be used alone or in combination of two or more kinds thereof. In the latter case, compounds capable of generating two kinds of organic acids differing in the number of all atoms excluding hydrogen atom by 2 or more are preferably combined.

Furthermore, the content of the photo-acid generator is preferably from 0.1 to 50% by mass, more preferably from 0.5 to 40% by mass, and still more preferably from 1 to 30% by mass, based on the total solid contents of the composition.

[4] Resin (Aa)

The composition according to the present invention may further contain a resin (Aa) containing at least either one of a fluorine atom and a silicon atom.

In the resin (Aa), at least either one of a fluorine atom and a silicon atom may be contained in the main chain or the side chain of the resin.

In the case where the resin (Aa) contains fluorine atoms, the resin preferably contains, as the fluorine atom-containing partial structure, a fluorine atom-containing alkyl group, a fluorine atom-containing cycloalkyl group or a fluorine atom-containing aryl group.

The fluorine atom-containing alkyl group, preferably having 1 to 10 carbon atoms, and more preferably 1 to 4 carbon atoms, is a linear or branched alkyl group with at least one hydrogen atom substituted with a fluorine atom, and may further have another substituent.

The fluorine atom-containing cycloalkyl group is a monocyclic or polycyclic cycloalkyl group with at least one hydrogen atom being substituted by a fluorine atom. This fluorine atom-containing cycloalkyl group may further have another substituent.

Examples of the fluorine atom-containing aryl group include an aryl group in which at least one hydrogen atom in an aryl group such as a phenyl group or naphthyl group is substituted with a fluorine atom and a fluorine atom-containing aryl group may further have other substituents.

Examples of the fluorine atom-containing alkyl group, the fluorine atom-containing cycloalkyl group, and the fluorine atom-containing aryl group include a group represented by any one of the following general formulae (F2) to (F4), but the present invention is not limited thereto.

[Chem. 40]

(F2)

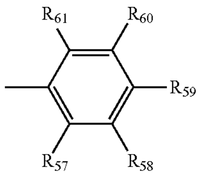

-continued (F3)

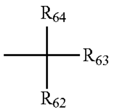

(F4)

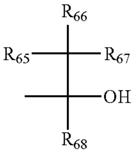

In the general formulae (F2) to (F4), $R_{57}$ to $R_{68}$ each independently represent a hydrogen atom, a fluorine atom, or an (linear or branched) alkyl group, provided that at least one of $R_{57}$ to $R_{61}$, at least one of $R_{62}$ to $R_{64}$, and at least one of $R_{65}$ to $R_{68}$ represent a fluorine atom or an alkyl group (preferably 1 to 4 carbon atoms) with at least one hydrogen atom substituted with a fluorine atom.

It is preferable that all of $R_{57}$ to $R_{61}$ and $R_{65}$ to $R_{67}$ be fluorine atoms. $R_{62}$, $R_{63}$, and $R_{68}$ are each preferably a fluoroalkyl group (preferably having 1 to 4 carbon atoms), and more preferably a perfluoroalkyl group having 1 to 4 carbon atoms. When $R_{62}$ and $R_{63}$ are each a perfluoroalkyl group, $R_{64}$ is preferably a hydrogen atom. $R_{62}$ and $R_{63}$ may be connected to each other to form a ring.

Specific examples of the group represented by the general formula (F2) include a p-fluorophenyl group, a pentafluorophenyl group, and a 3,5-di(trifluoromethyl)phenyl group.

Specific examples of the group represented by the general formula (F3) include a trifluoromethyl group, a pentafluoropropyl group, a pentafluoroethyl group, a heptafluorobutyl group, a hexafluoroisopropyl group, a heptafluoroisopropyl group, a hexafluoro(2-methyl)isopropyl group, a nonafluorobutyl group, an octafluoroisobutyl group, a nonafluorohexyl group, a nonafluoro-t-butyl group, a perfluoroisopentyl group, a perfluorooctyl group, a perfluoro(trimethyl)hexyl group, a 2,2,3,3-tetrafluorocyclobutyl group, and a perfluorocyclohexyl group. A hexafluoroisopropyl group, a heptafluoroisopropyl group, a hexafluoro(2-methyl)isopropyl group, an octafluoroisobutyl group, a nonafluoro-t-butyl group, and a perfluoroisopentyl group are preferred, and a hexafluoroisopropyl group and a heptafluoroisopropyl group are more preferred.

Specific examples of the group represented by the general formula (F4) include $—C(CF_3)_2OH$, $—C(C_2F_5)_2OH$, $—C(CF_3)(CH_3)OH$, and $—CH(CF_3)OH$, and among these, $—C(CF_3)_2OH$ is preferred.

The fluorine atom-containing partial structure may be bonded directly to the main chain or may be bonded to the main chain through a group selected from the group consisting of an alkylene group, a phenylene group, an ether bond, a thioether bond, a carbonyl group, an ester bond, an amide bond, a urethane bond, and a ureylene bond, or a group formed by a combination of two or more thereof.

Preferred examples of the repeating units having a fluorine atom are those shown below.

[Chem. 41]

(C-Ia)

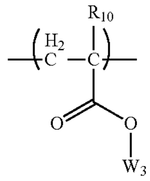

(C-Ib)

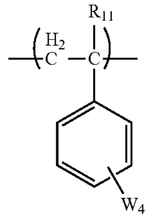

(C-Ic)

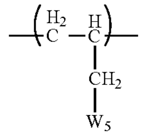

(C-Id)

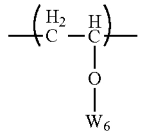

In the formulae, R10 and R11 each independently represent a hydrogen atom, a fluorine atom, or an alkyl group. The alkyl group is preferably a linear or branched alkyl group having 1 to 4 carbon atoms and may have a substituent, and the alkyl group having a substituent may include, in particular, a fluorinated alkyl group.

$W_3$ to $W_6$ each independently represent an organic group having at least one or more fluorine atoms. Specific examples thereof include the atomic groups of (F2) to (F4) above.

Furthermore, other than these, the resin (Aa) may contain a unit as shown below as the repeating units having a fluorine atom.

[Chem. 42]

(C-II)

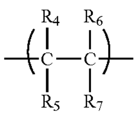

(C-III)

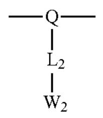

In the formulae, $R_4$ to $R_7$ each independently represent a hydrogen atom, a fluorine atom or an alkyl group. The alkyl group is preferably a linear or branched alkyl group having 1 to 4 carbon atoms and may have a substituent, and the alkyl group having a substituent may include, in particular, a fluorinated alkyl group.

However, at least one of $R_4$ to $R_7$ represents a fluorine atom. $R_4$ and $R_5$, or $R_6$ and $R_7$ may form a ring.

$W_2$ represents an organic group having at least one fluorine atom. Specific examples thereof include the atomic groups of (F2) to (F4) above.

$L_2$ represents a single bond or a divalent connecting group. The divalent connecting group is a substituted or unsubstituted arylene group, a substituted or unsubstituted alkylene group, a substituted or unsubstituted cycloalkylene group, —O—, —$SO_2$—, —CO—, —N(R)— (wherein R represents a hydrogen atom or an alkyl group), —$NHSO_2$—, or a divalent connecting group formed by a combination of a plurality of these groups.

Q represents an alicyclic structure. The alicyclic structure may have a substituent and may be monocyclic type or polycyclic type, and in the case of a polycyclic structure, the structure may be a crosslinked structure. The monocyclic type is preferably a cycloalkyl group having 3 to 8 carbon atoms, and examples thereof include a cyclopentyl group, a cyclohexyl group, a cyclobutyl group, and a cyclooctyl group. The polycyclic type includes a group having a bicyclo structure, a tricyclo structure, a tetracyclo structure, and the like and having 5 or more carbon atoms, and a cycloalkyl group having 6 to 20 carbon atoms is preferable and, for example, includes an adamantyl group, a norbornyl group, a dicyclopentyl group, a tricyclodecanyl group, a tetracyclododecyl group, or the like. Incidentally, parts of carbon atoms in the cycloalkyl group may be substituted with heteroatoms such as an oxygen atom. Particularly preferred examples of Q include a norbornyl group, a tricyclodecanyl group, a tetracyclododecyl group, or the like.

The resin (Aa) may contain a silicon atom.

An alkylsilyl structure (preferably a trialkylsilyl group) or a cyclosiloxane structure is preferred as a partial structure having a silicon atom.

Specific examples of the alkylsilyl structure or the cyclosiloxane structure include groups represented by the following formulae (CS-1) to (CS-3).

[Chem. 43]

(CS-1)

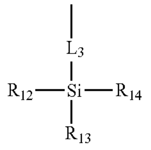

(CS-2)

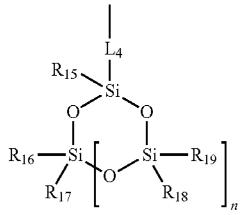

-continued (CS-3)

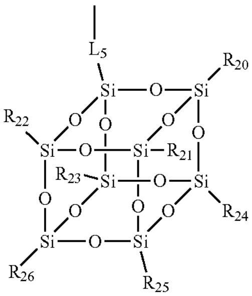

In the general formulae (CS-1) to (CS-3), $R_{12}$ to $R_{26}$ each independently represent a linear or branched alkyl group (preferably having 1 to 20 carbon atoms) or a cycloalkyl group (preferably having 3 to 20 carbon atoms).

$L_3$ to $L_5$ each represent a single bond or a divalent connecting group. The divalent connecting group is a single group or a combination of two or more groups selected from the group consisting of an alkylene group, a phenylene group, an ether bond, a thioether bond, a carbonyl group, an ester bond, an amide bond, a urethane bond, and an ureylene bond.

n represents an integer of 1 to 5. n is preferably an integer of 2 to 4.

The repeating units having at least either fluorine atoms or silicon atoms are preferably (meth)acrylate-based repeating units.

Specific examples of the repeating units having at least either fluorine atoms or silicon atoms are shown below, but the present invention is not limited thereto. In the specific examples, $X_1$ represents a hydrogen atom, —$CH_3$, —F, or —$CF_3$, and $X_2$ represents —F or —$CF_3$.

[Chem. 44-1]

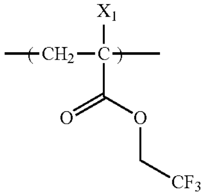

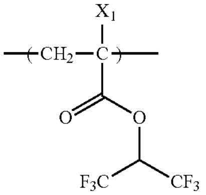

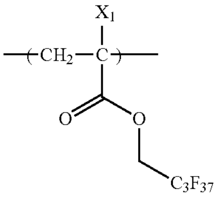

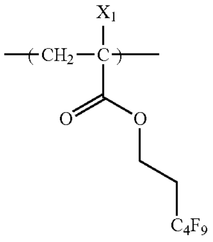

-continued

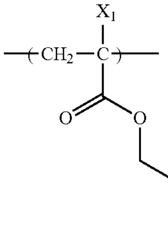

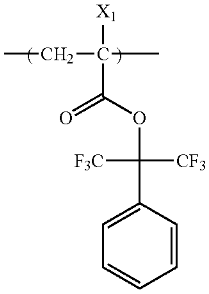

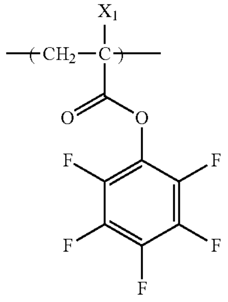

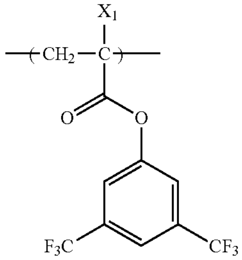

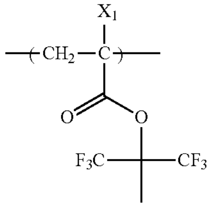

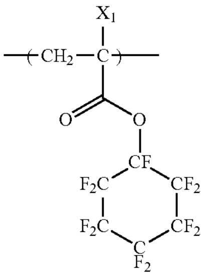

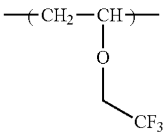

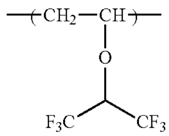

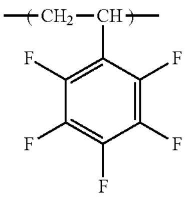

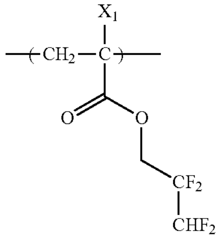

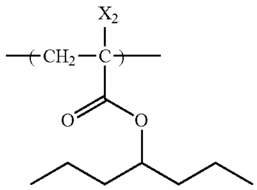

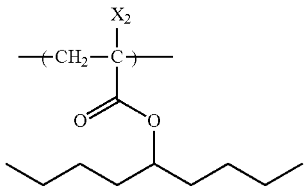

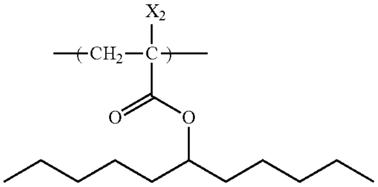

-continued
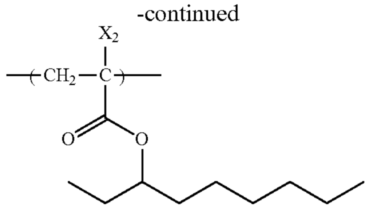
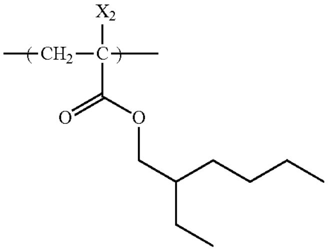
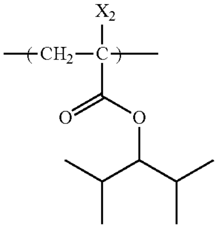
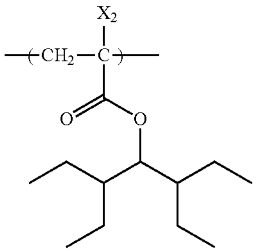
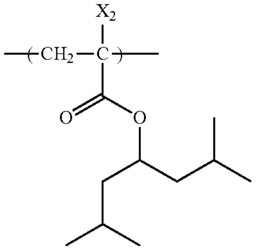
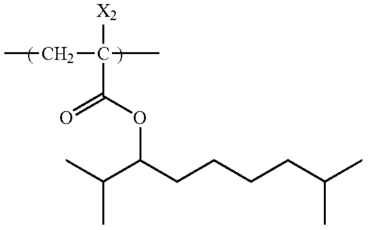
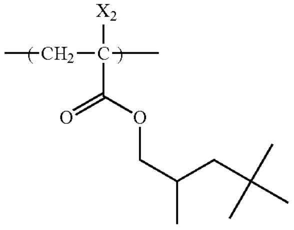
[Chem. 44-2]
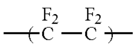
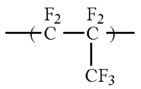
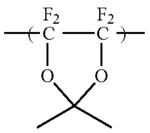
-continued
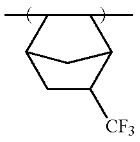
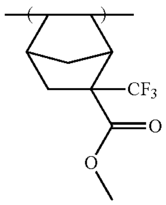
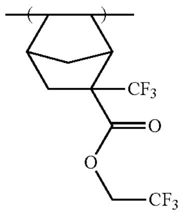
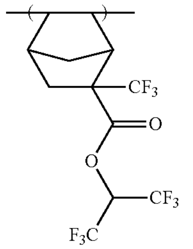
[Chem. 44-3]
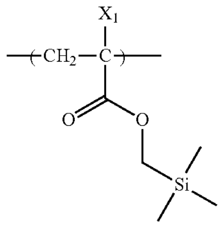
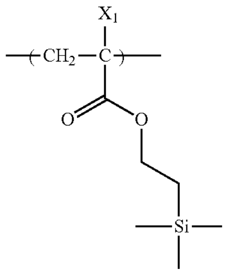
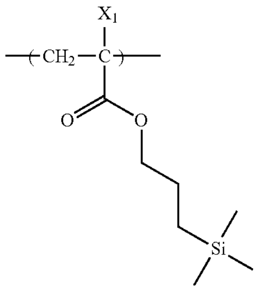
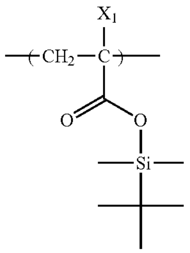
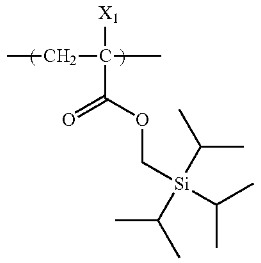
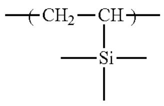

-continued

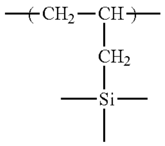
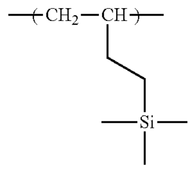
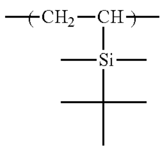

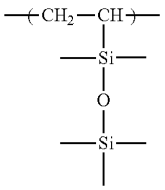
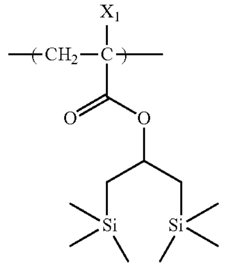

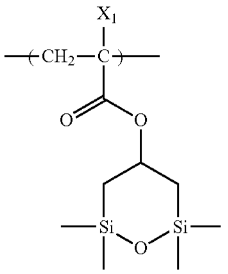
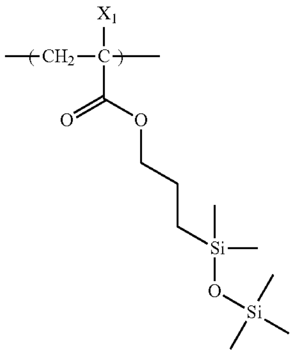

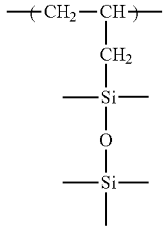
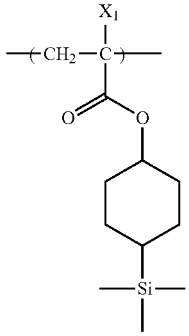
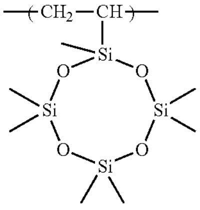

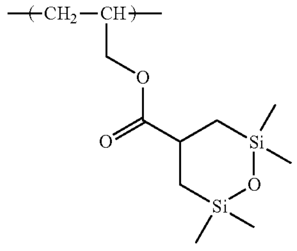

-continued

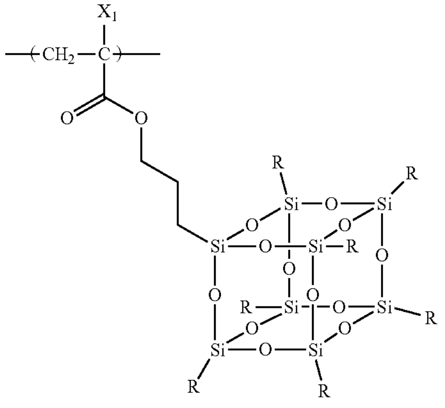

R = $CH_3$, $C_2H_5$, $C_3H_7$, $C_4H_9$

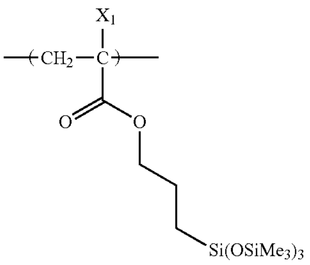

The resin (Aa) preferably has a repeating unit (b) having at least one group selected from the group consisting of the following (x) to (z).

(x) an alkali-soluble group (y) a group capable of decomposing by the action of an alkali developer to increase the degree of solubility with respect to an alkali developer (z) a group capable of decomposing by the action of an acid which generates by irradiation with actinic rays or radiation to increase the degree of solubility with respect to an alkali developer Specific examples of the repeating unit (bx) having an alkali-soluble group (x) are shown below, but the present invention in not limited thereto. Further, in specific examples, $X_1$ represents a hydrogen atom, —$CH_3$, —F, or —$CF_3$.

[Chem. 45-1]

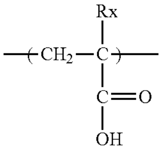
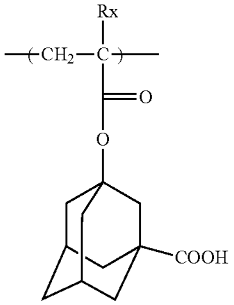

-continued
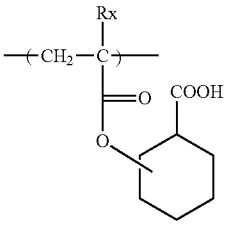
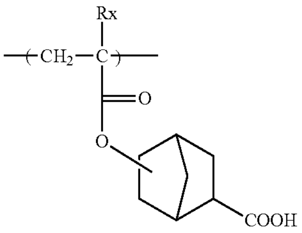
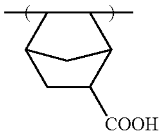
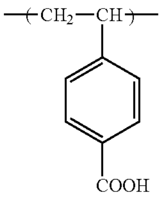
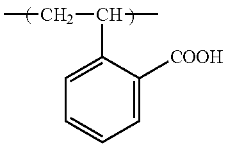
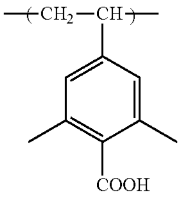
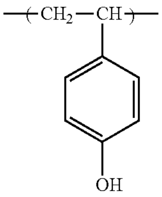
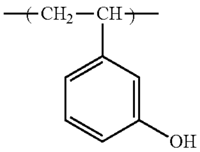
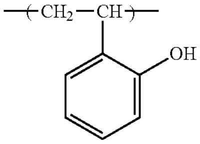
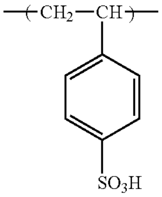
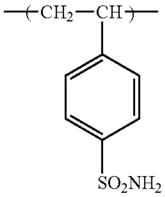
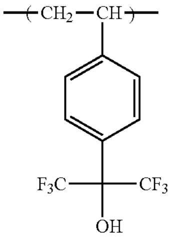
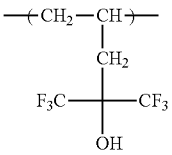
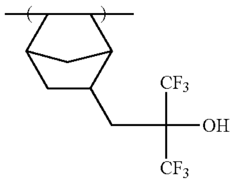
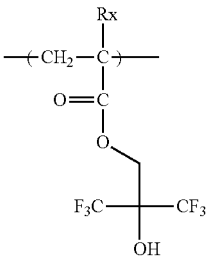
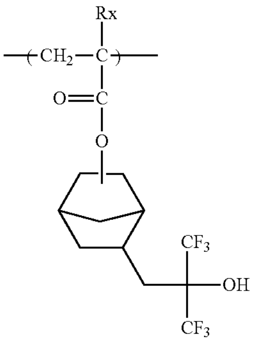
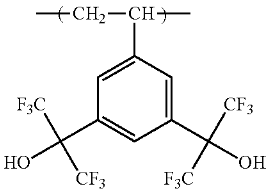
-continued
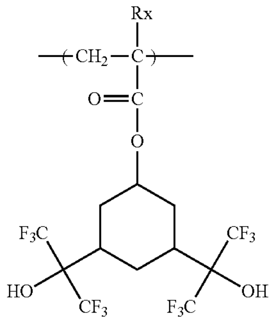
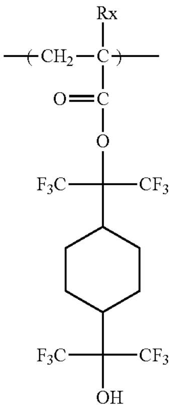
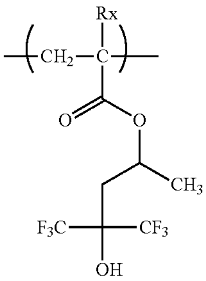
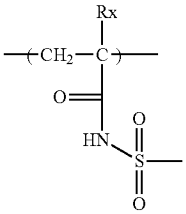
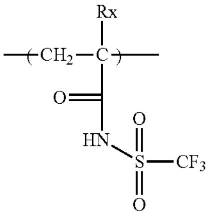
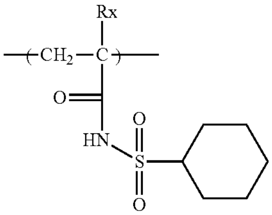
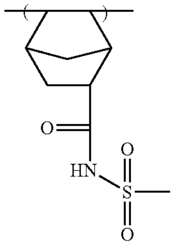
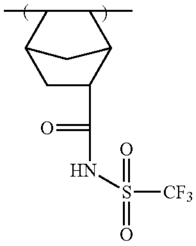
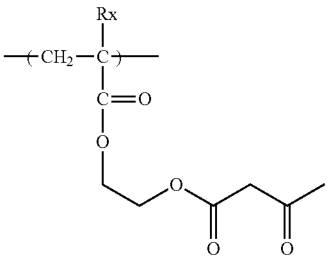
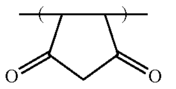
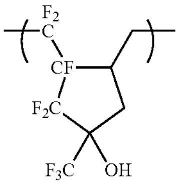

-continued

[Chem. 45-2]

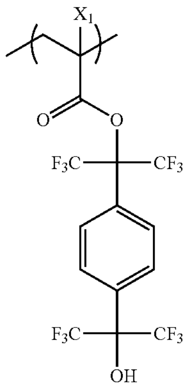

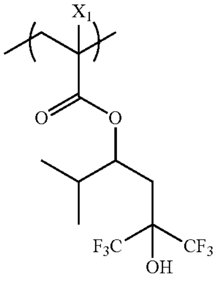

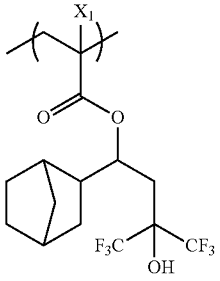

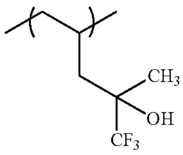

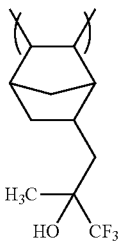

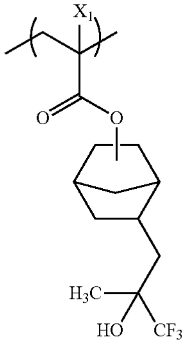

In formulae, Rx represents H, $CH_3$, $CF_3$ and $CH_2OH$.

Examples of the group (y) of which the degree of solubility increases in an alkali developer include a lactone group, a carboxylic ester group (—COO—), an anhydride group (—C(O)OC(O)—), an acid imide group (—NHCONH—), a carboxylic thioester group (—COS—), a carbonic ester group (—OC(O)O—), a sulfuric ester group (—$OSO_2O$—), a sulfonic ester group (—$SO_2O$—), or the like, and a lactone group is preferable.

Specific examples of the repeating unit (by) having a group capable of increasing the solubility in an alkali developer are illustrated below, but the present invention is not limited thereto. In addition, specific examples of the repeating unit (A3) of the resin (Ab) can be also included as specific examples of the repeating unit (by).

Ra represents a hydrogen atom, a fluorine atom, a methyl group, or a trifluoromethyl group.

[Chem. 46-1]

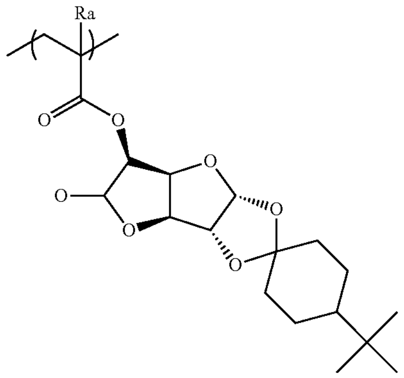

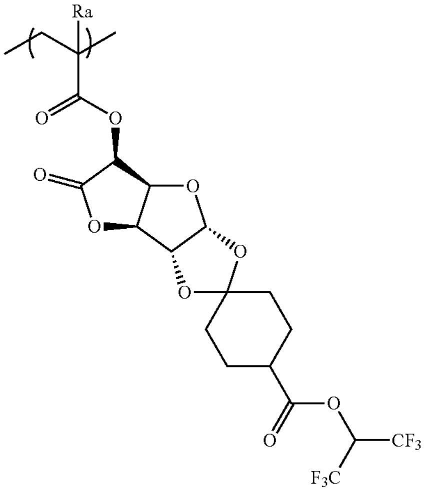

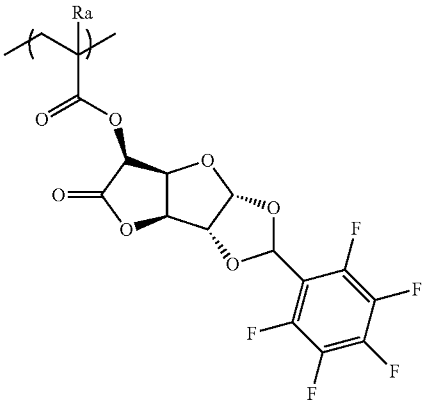

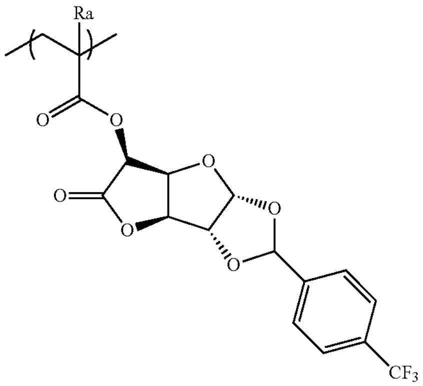

-continued
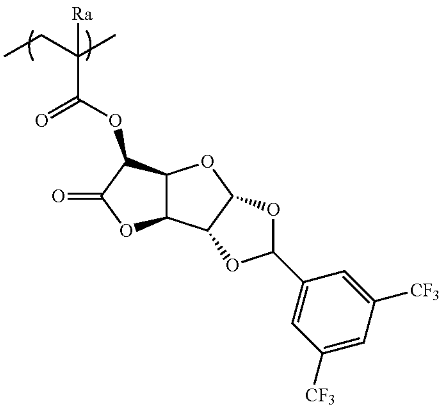
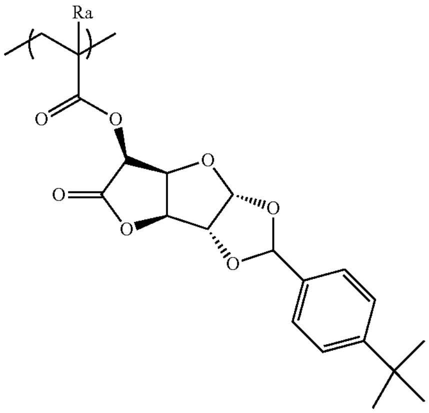
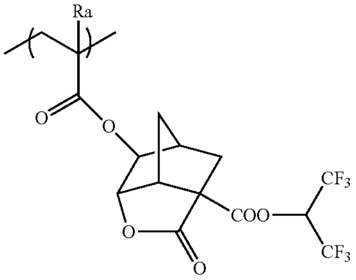
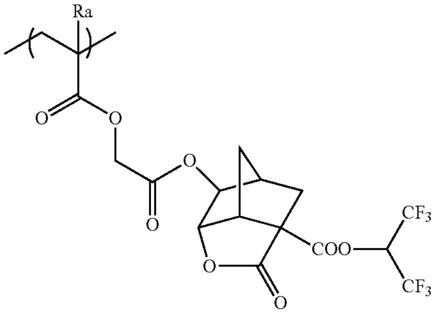
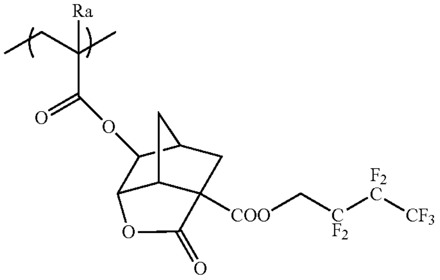
-continued
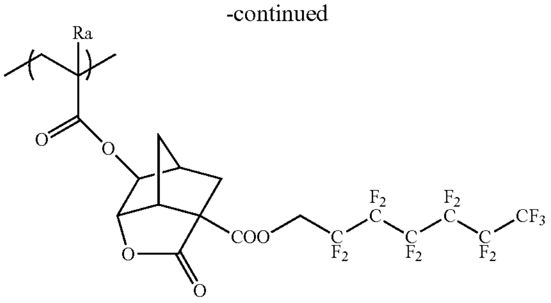
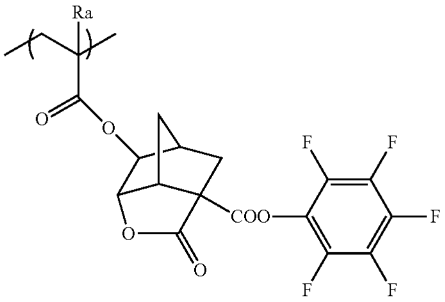
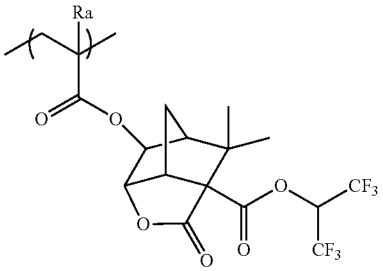
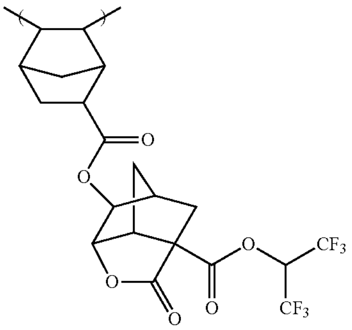
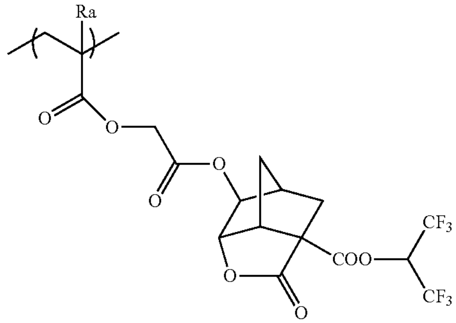

-continued
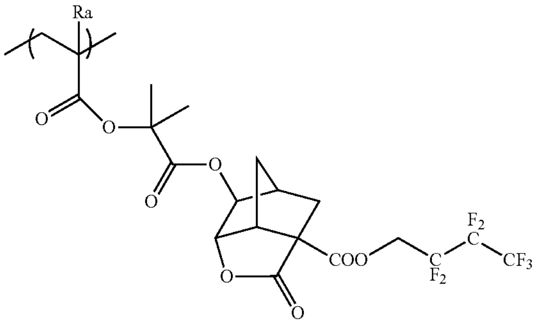
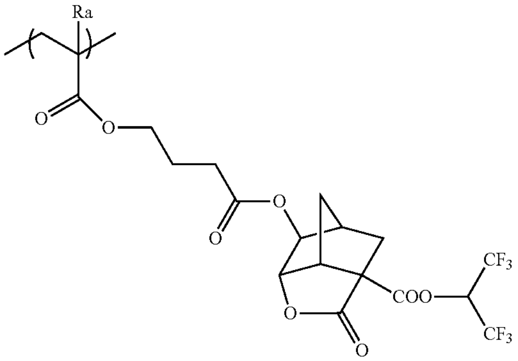
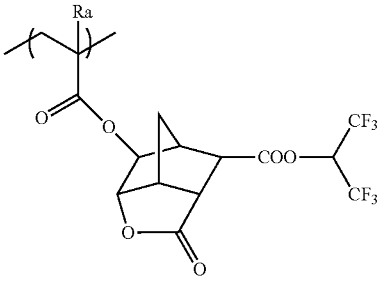
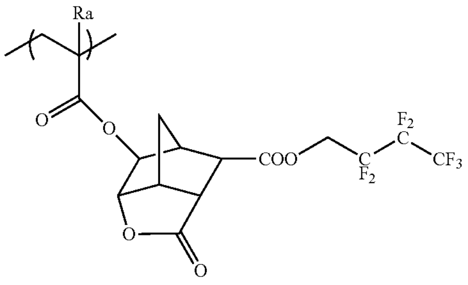
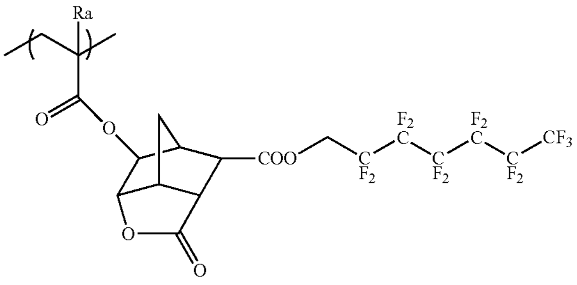
-continued
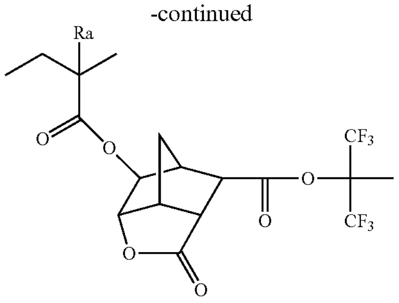
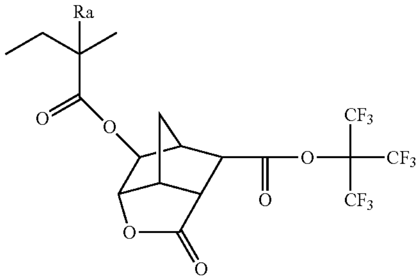
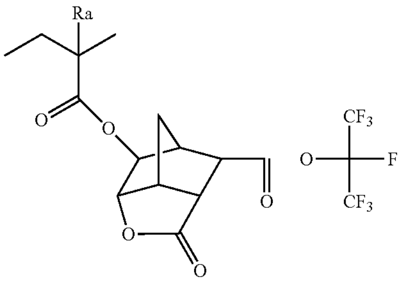
[Chem. 46-2]
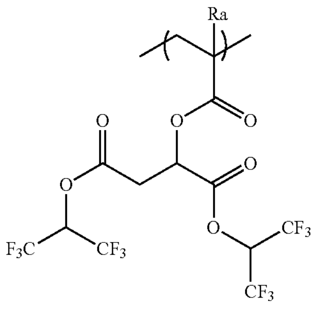
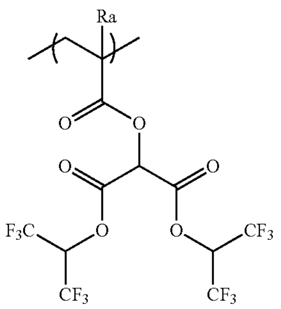

-continued

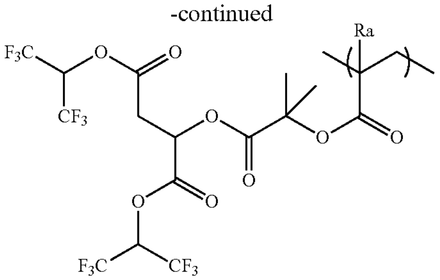

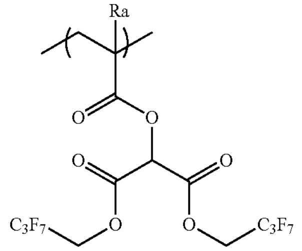

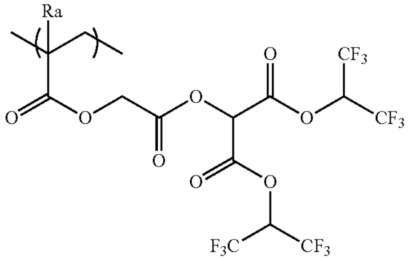

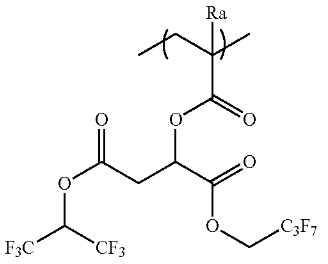

In a resin (Aa), a repeating unit (bz) having a group (z) capable of decomposing by the action of an acid which generates by irradiation with actinic rays or radiation to increase the degree of solubility with respect to an alkali developer, includes the same as a repeating unit having an acid-decomposable group included in the resin (Ab).

The resin (Aa) may further contain a repeating unit represented by the following general formula (III).

[Chem. 47]

(III)

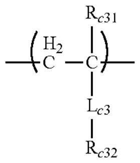

In the general formula (III), $Rc_{31}$ represents an alkyl group, a cyano group or —$CH_2$—O-$Rac_2$ group which may be substituted with a hydrogen atom, an alkyl group or a fluorine atom. In the formula, $Rac_2$ represents a hydrogen atom, an alkyl group or an acyl group. $Rc_{31}$ is preferably a hydrogen atom, a methyl group, a hydroxymethyl group or a trifluoromethyl group, and more preferably a hydrogen atom or a methyl group.

$Rc_{32}$ represents a group containing an alkyl group, a cycloalkyl group, an alkenyl group, a cycloalkenyl group or an aryl group. These groups may be substituted with a group having a fluorine atom or a silicon atom, or the like.

$Lc_3$ represents a single bond or a divalent connecting group.

It is also preferable that the resin (Aa) further contain a repeating unit represented by the following general formula (BII-AB).

[Chem. 48]

(BII-AB)

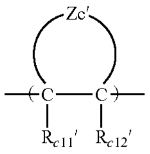

In the formula (BII-AB), $R_{C11}$' and $R_{C12}$' each independently represent a hydrogen atom, a cyano group, a halogen atom or an alkyl group.

$Z_C$' includes two bonded carbon atoms (C—C) and represents an atomic group for forming an alicyclic structure.

In the case where each group in the repeating units represented by the general formulae (III) and (BII-AB) is substituted with a fluorine atom- or silicon atom-containing group, the repeating unit corresponds also to the repeating units having at least either fluorine atoms or silicon atoms.

Specific examples of the repeating units represented by the general formulae (III) and (BII-AB) are shown below, but the present invention is not limited thereto. In the formulae, Ra represents H, $CH_3$, $CH_2OH$, $CF_3$, or CN. Incidentally, the repeating unit where Ra is $CF_3$ corresponds also to the repeating units having at least either fluorine atoms or silicon atoms.

[Chem. 49]

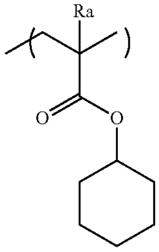

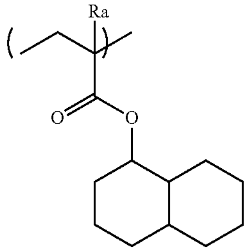

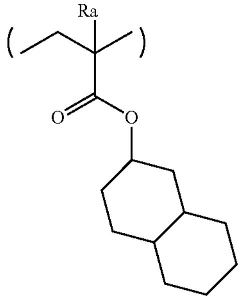

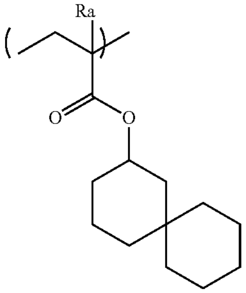

-continued
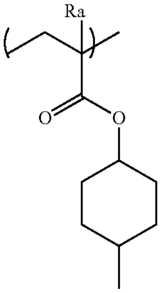
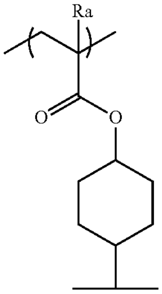
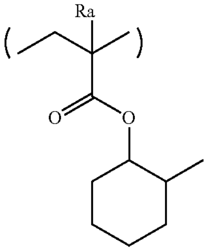
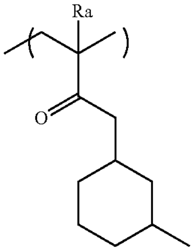
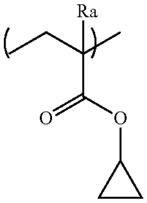
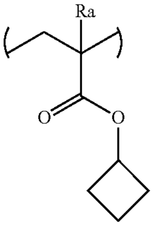
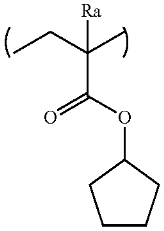
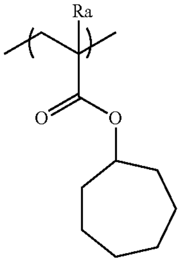
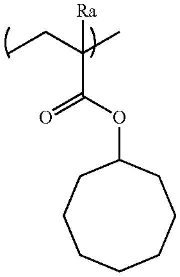
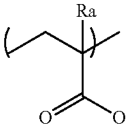
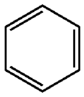
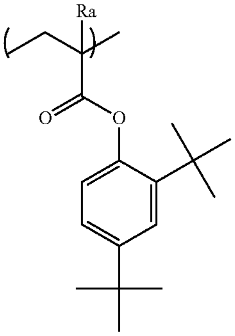
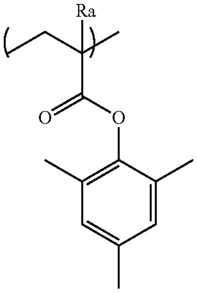
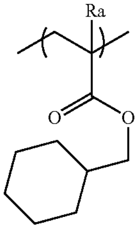
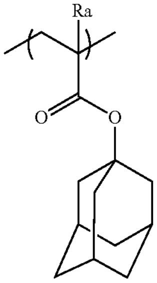
-continued
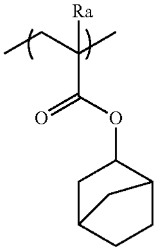
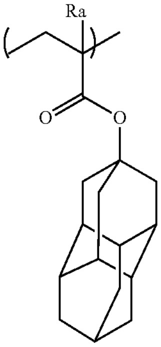
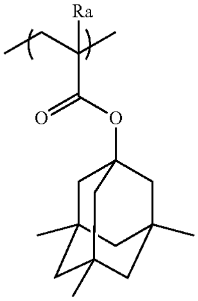
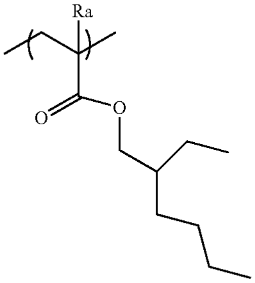
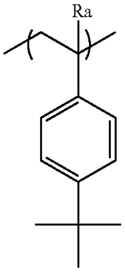
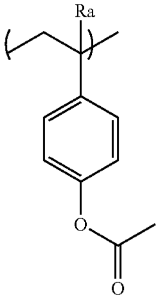
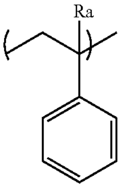
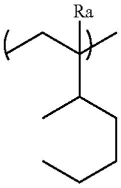
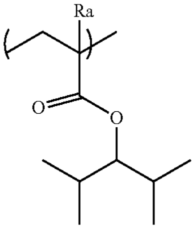
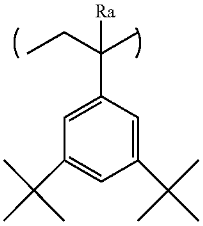
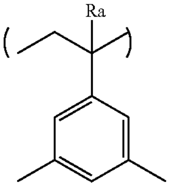
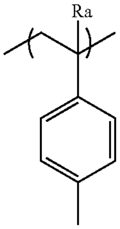
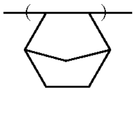
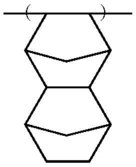
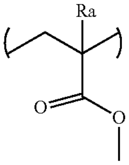
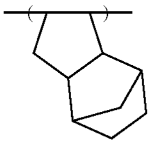

It is natural that the resin (Aa) contains a small amount of impurities such as metals, similarly to the resin (Ab), and the amount of residual monomers and oligomer components is preferably from 0 to 10% by mass, more preferably from 0 to 5% by mass and further preferably from 0 to 1% by mass. When these conditions are satisfied, a resist composition free from time course change of foreign substances in a liquid or sensitivity or the like can be obtained. Furthermore, in view of the resolution, the resist shape, the side wall of a resist pattern, the roughness, or the like, the molecular weight distribution (Mw/Mn, also referred to as "dispersity") is preferably in a range of 1 to 3, more preferably 1 to 2, still more preferably 1 to 1.8, and most preferably 1 to 1.5.

As for the resin (Aa), various commercially available products may be also used, or the resin may be synthesized by an ordinary method (for example, radical polymerization). Examples of the general synthesis method include a batch polymerization method of dissolving monomer species and an initiator in a solvent and heating the solution, thereby effecting the polymerization, and a dropping polymerization method of adding dropwise a solution containing monomer species and an initiator to a heated solvent over 1 to 10 hours. A dropping polymerization method is preferable.

A reaction solvent, a polymerization initiator, a condition of reaction (temperature, concentration or the like) and a purification method after reaction are the same as those described in the resin (Ab).

Specific examples of the resin (Aa) are shown below. In addition, the molar ratio of the repeating units (corresponding to the respective repeating units from left in order), the weight average molecular weight and the degree of dispersion of the respective resins are shown in the following Table 1.

[Chem. 50-1]

(Aa-1)

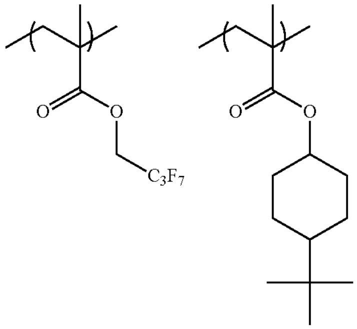

(Aa-2)

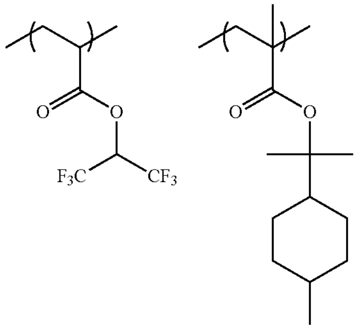

-continued (Aa-3)

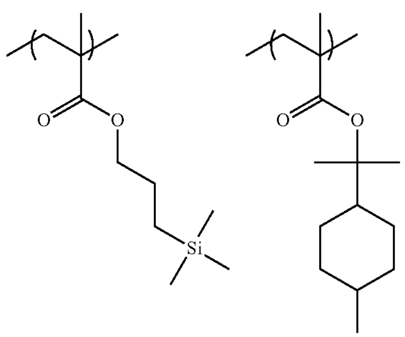

(Aa-4)

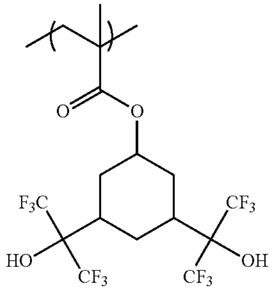

(Aa-5)

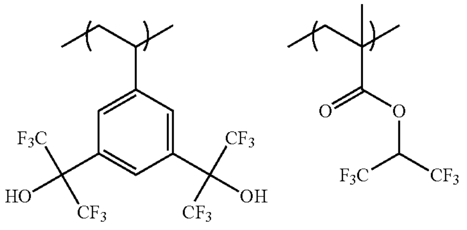

(Aa-6)

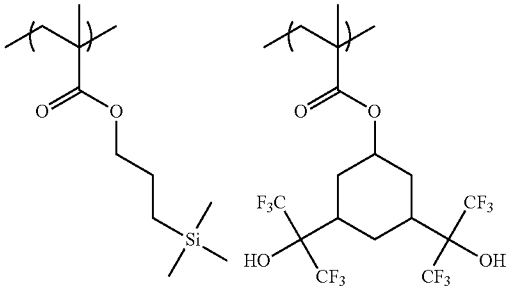

(Aa-7)

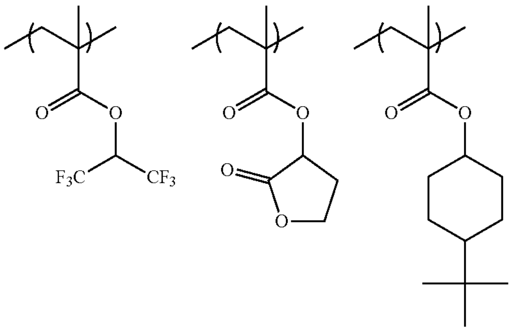

-continued
(Aa-8)
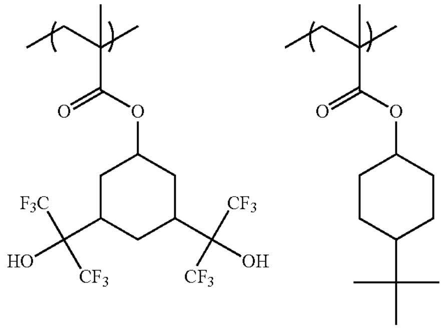
(Aa-9)
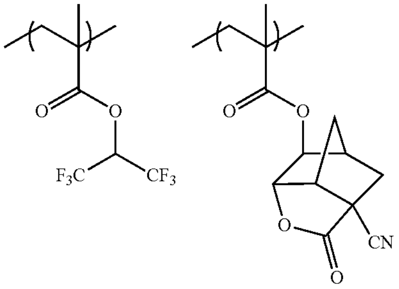
(Aa-10)
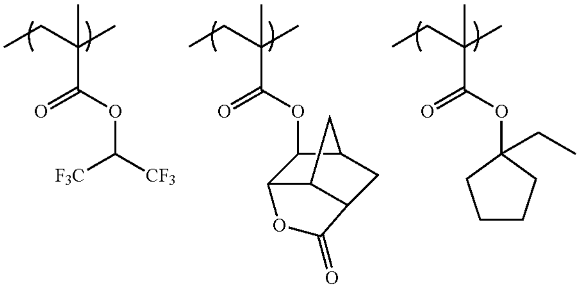
(Aa-11)
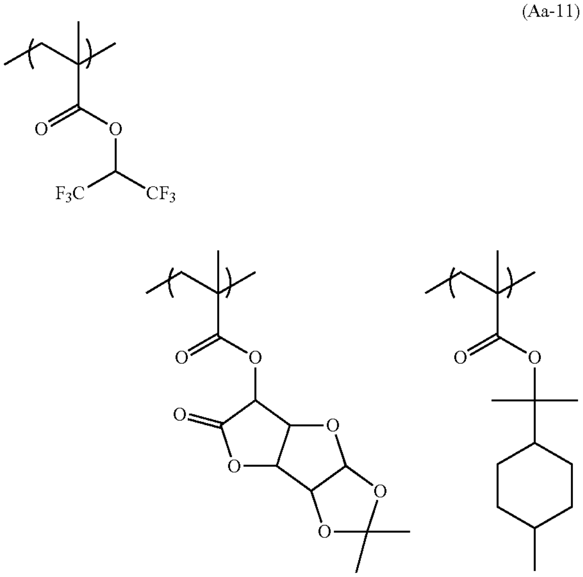
-continued
(Aa-12)
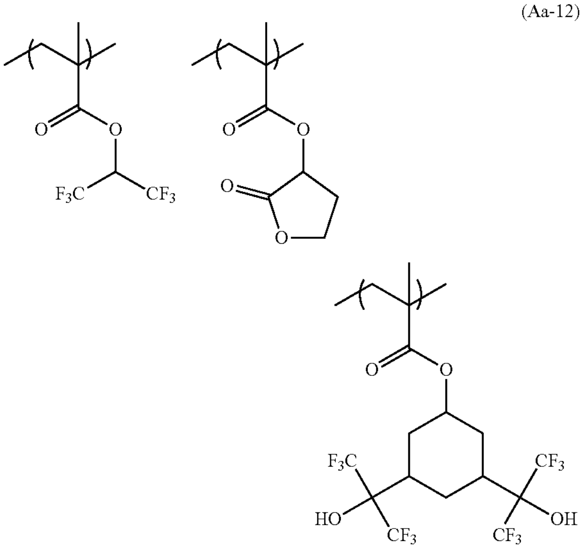
(Aa-13)
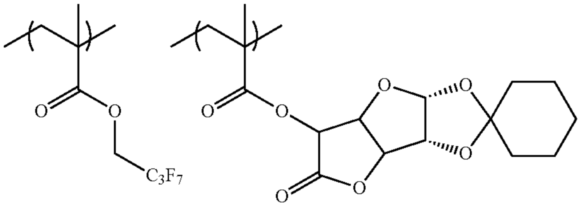
(Aa-14)
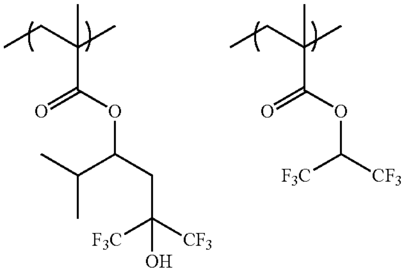
(Aa-15)
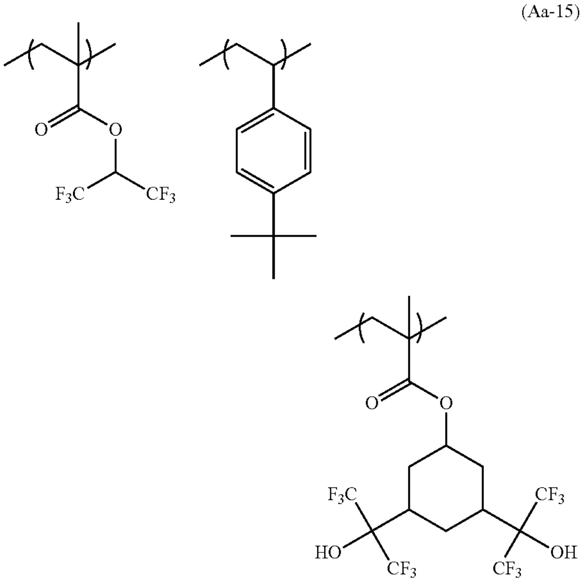

-continued
(Aa-16)
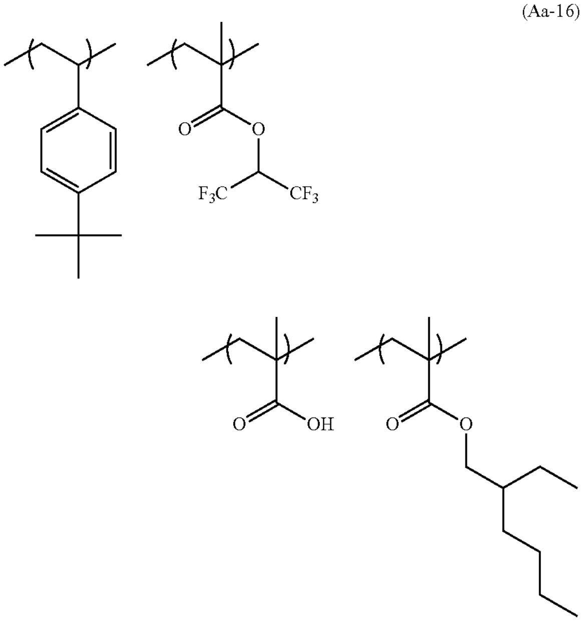
(Aa-17)
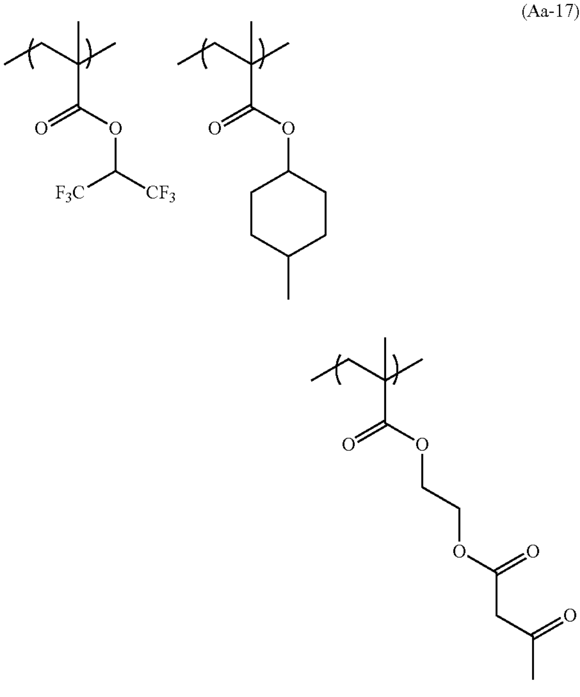
(Aa-18)
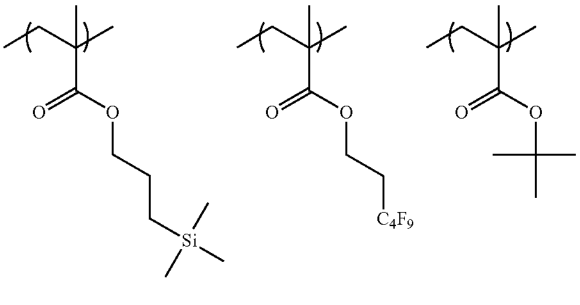
-continued
(Aa-19)
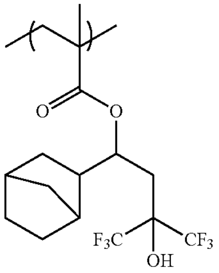
(Aa-20)
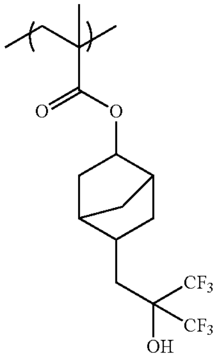
(Aa-21)
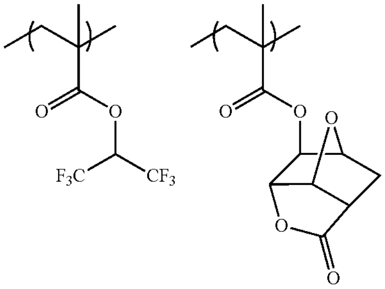
(Aa-22)
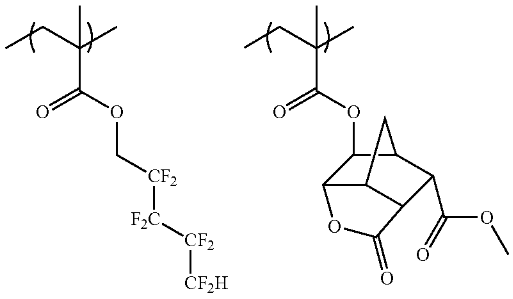

-continued
[Chem. 50-2]
(Aa-23)
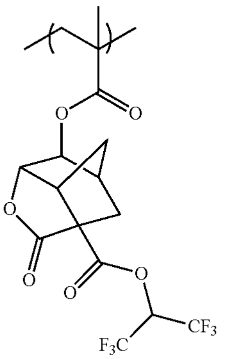
(Aa-24)
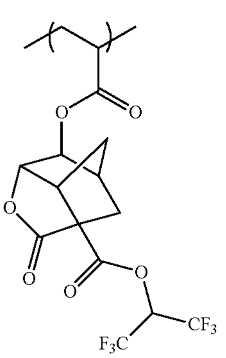
(Aa-25)
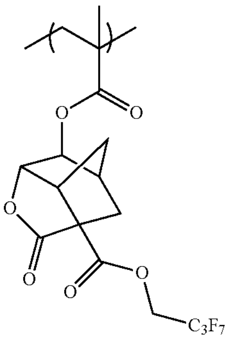
(Aa-26)
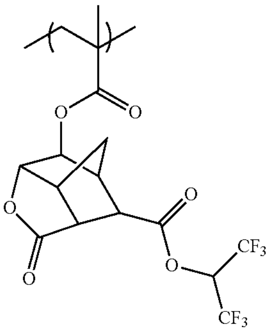
-continued
(Aa-27)
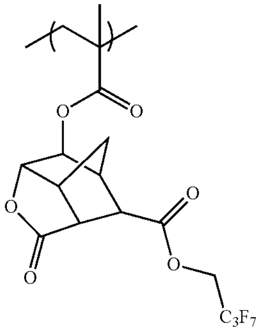
(Aa-28)
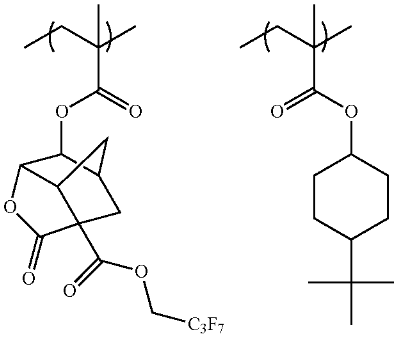
(Aa-29)
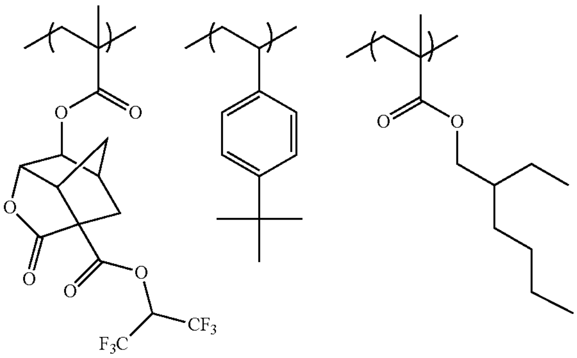
(Aa-30)
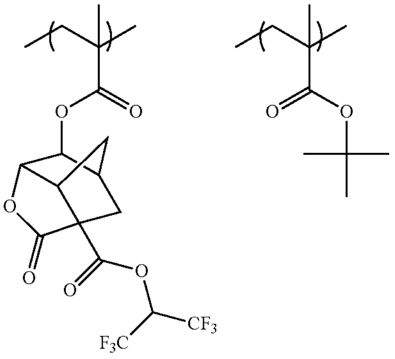

-continued
(Aa-31)
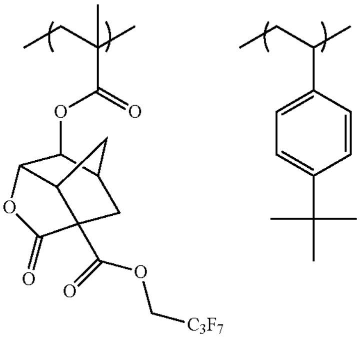
(Aa-32)
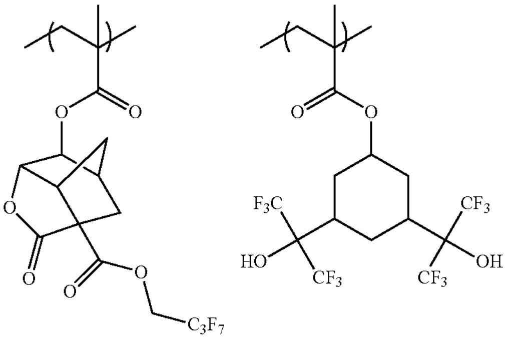
(Aa-33)
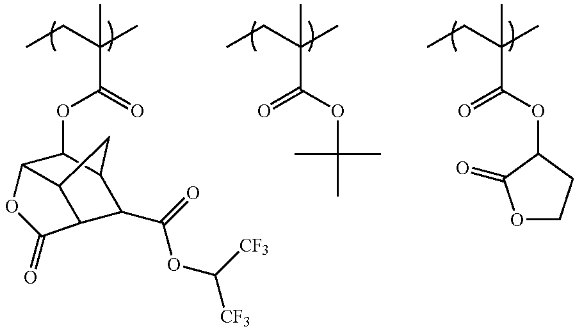
(Aa-34)
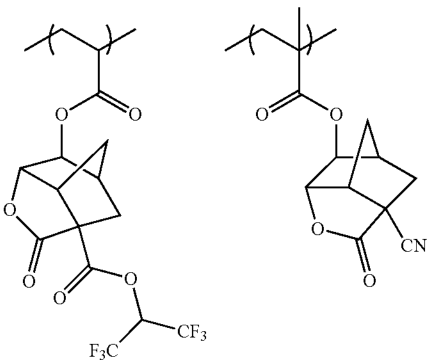
-continued
(Aa-35)
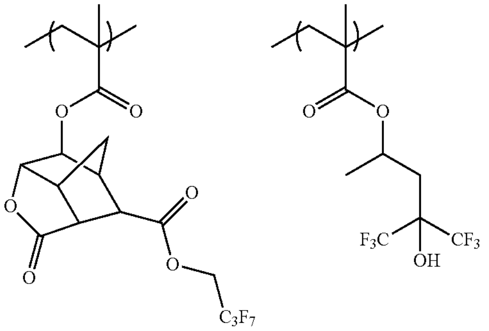
(Aa-36)
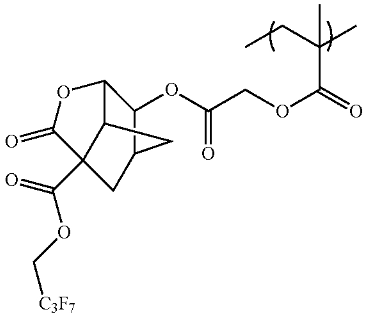
(Aa-37)
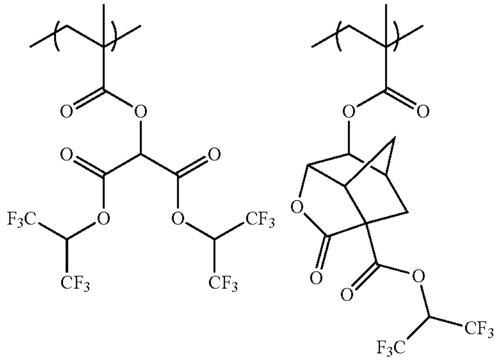
(Aa-38)
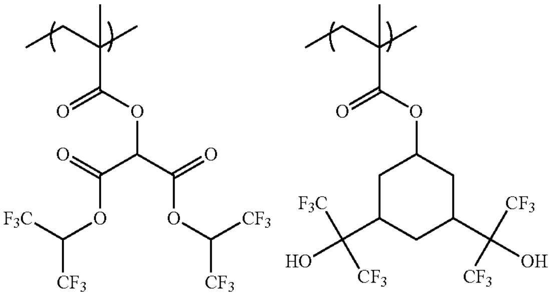

-continued
(Aa-39)
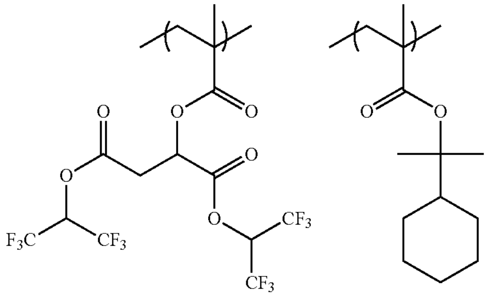
(Aa-40)
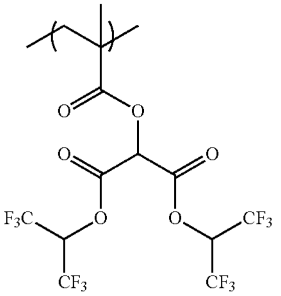
(Aa-41)
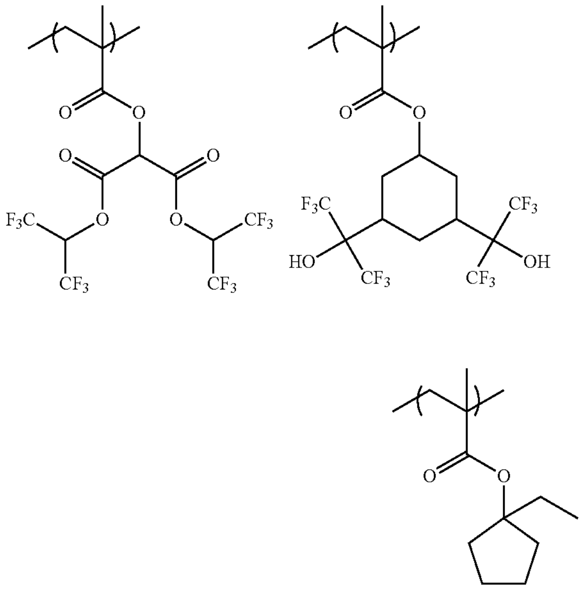
(Aa-42)
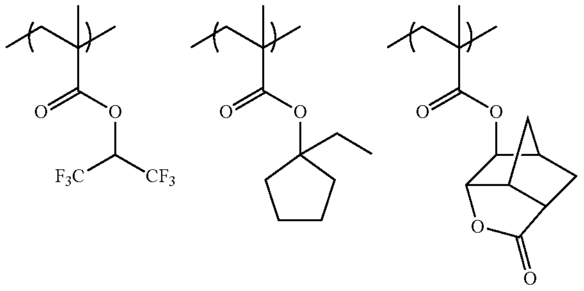
-continued
[Chem. 50-3]
(Aa-43)
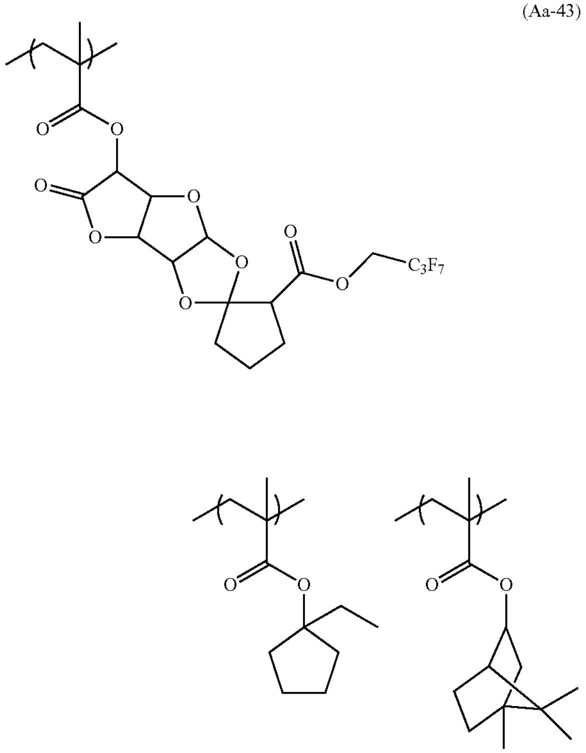
(Aa-44)
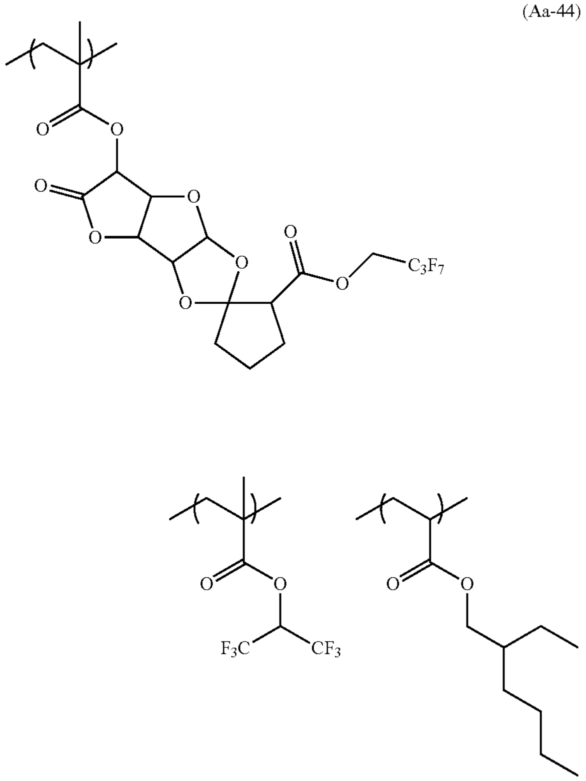

-continued
(Aa-45)
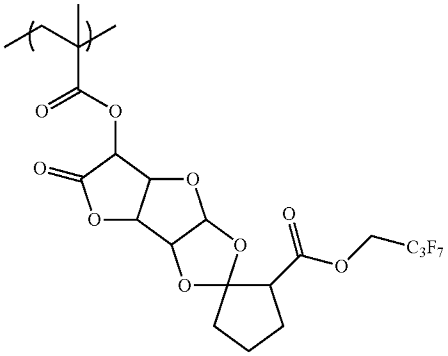
(Aa-46)
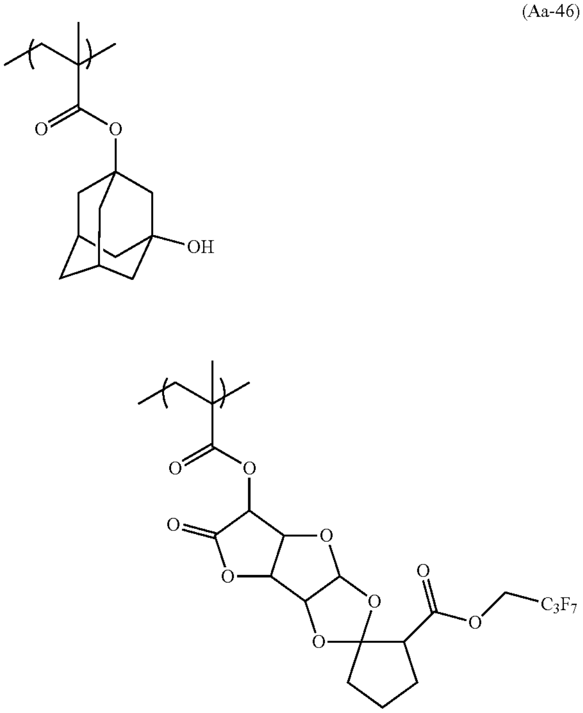
(Aa-47)
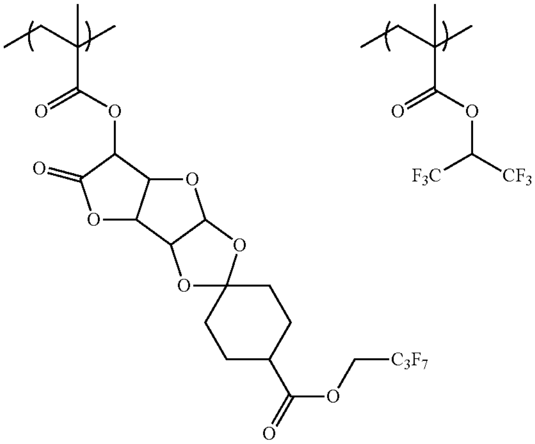
-continued
(Aa-48)
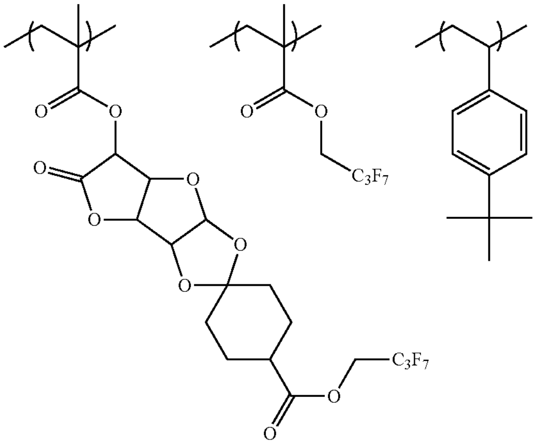
(Aa-49)
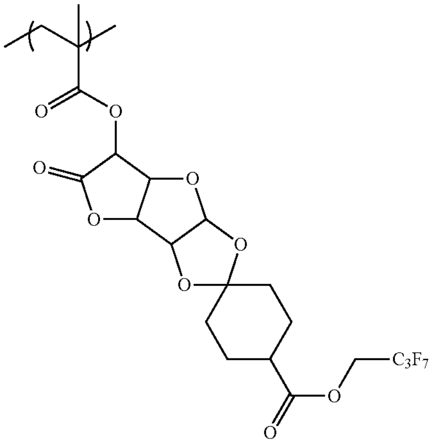
(Aa-50)
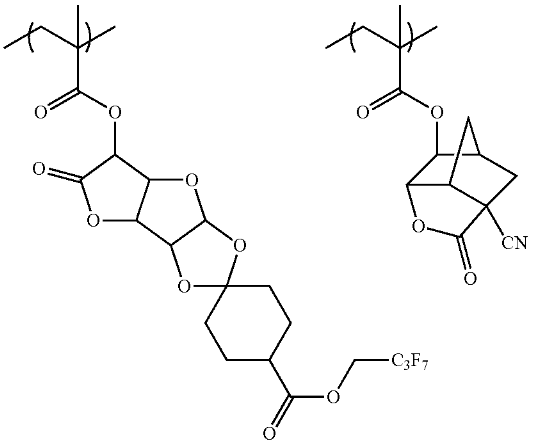

-continued
(Aa-51)
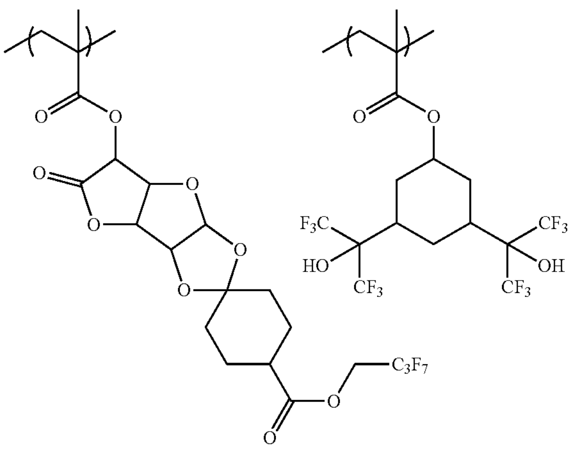
(Aa-52)
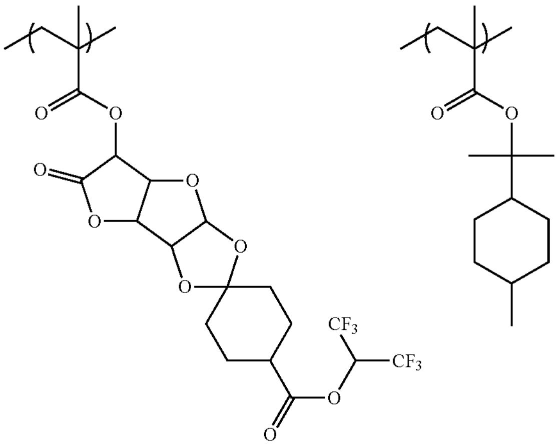
(Aa-53)
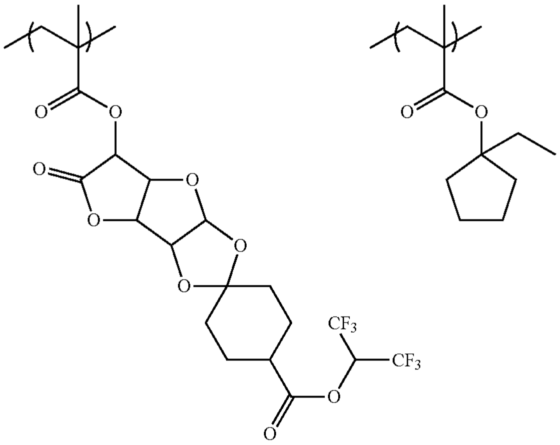
-continued
(Aa-54)
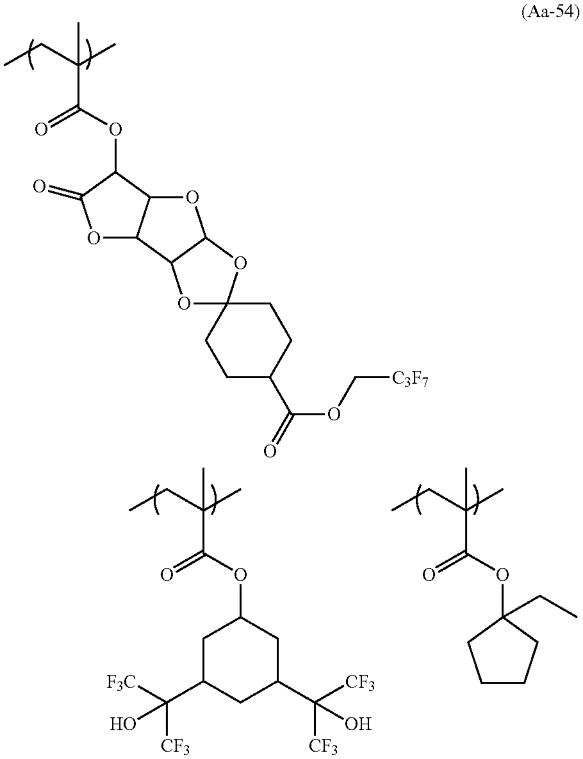
(Aa-55)
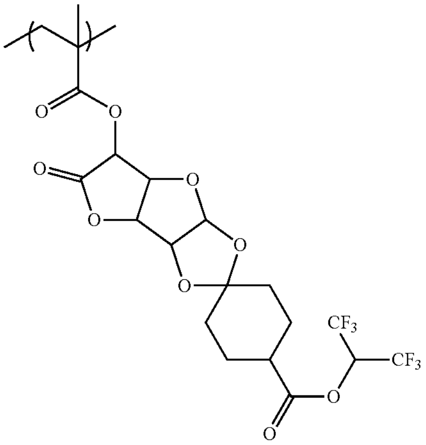
TABLE 1
| Polymer | Compositional ratio (mol %) | Mw | Mw/ Mn |
|---|---|---|---|
| Aa-1 | 50/50 | 6000 | 1.5 |
| Aa-2 | 30/70 | 6500 | 1.4 |
| Aa-3 | 45/55 | 8000 | 1.4 |
| Aa-4 | 100 | 15000 | 1.7 |
| Aa-5 | 60/40 | 6000 | 1.4 |
| Aa-6 | 40/60 | 8000 | 1.4 |
| Aa-7 | 30/40/30 | 8000 | 1.4 |
| Aa-8 | 60/40 | 8000 | 1.3 |
| Aa-9 | 50/50 | 6000 | 1.4 |
| Aa-10 | 40/40/20 | 7000 | 1.4 |
| Aa-11 | 40/30/30 | 9000 | 1.6 |
| Aa-12 | 30/30/40 | 6000 | 1.4 |
| Aa-13 | 60/40 | 9500 | 1.4 |
| Aa-14 | 60/40 | 8000 | 1.4 |

TABLE 1-continued

| Polymer | Compositional ratio (mol %) | Mw | Mw/ Mn |
|---|---|---|---|
| Aa-15 | 35/35/30 | 7000 | 1.4 |
| Aa-16 | 50/40/5/5 | 6800 | 1.3 |
| Aa-17 | 20/30/50 | 8000 | 1.4 |
| Aa-18 | 25/25/50 | 6000 | 1.4 |
| Aa-19 | 100 | 9500 | 1.5 |
| Aa-20 | 100 | 7000 | 1.5 |
| Aa-21 | 50/50 | 6000 | 1.6 |
| Aa-22 | 40/60 | 9600 | 1.3 |
| Aa-23 | 100 | 20000 | 1.7 |
| Aa-24 | 100 | 25000 | 1.4 |
| Aa-25 | 100 | 15000 | 1.7 |
| Aa-26 | 100 | 12000 | 1.8 |
| Aa-27 | 100 | 18000 | 1.3 |
| Aa-28 | 70/30 | 15000 | 2.0 |
| Aa-29 | 80/15/5 | 18000 | 1.8 |
| Aa-30 | 60/40 | 25000 | 1.8 |
| Aa-31 | 90/10 | 19000 | 1.6 |
| Aa-32 | 60/40 | 20000 | 1.8 |
| Aa-33 | 50/30/20 | 11000 | 1.6 |
| Aa-34 | 60/40 | 12000 | 1.8 |
| Aa-35 | 60/40 | 15000 | 1.6 |
| Aa-36 | 100 | 22000 | 1.8 |
| Aa-37 | 20/80 | 35000 | 1.6 |
| Aa-38 | 30/70 | 12000 | 1.7 |
| Aa-39 | 30/70 | 9000 | 1.5 |
| Aa-40 | 100 | 9000 | 1.5 |
| Aa-41 | 40/15/45 | 12000 | 1.9 |
| Aa-42 | 30/30/40 | 13000 | 2.0 |
| Aa-43 | 40/40/20 | 23000 | 2.1 |
| Aa-44 | 65/30/5 | 25000 | 1.6 |
| Aa-45 | 100 | 15000 | 1.7 |
| Aa-46 | 20/80 | 9000 | 1.7 |
| Aa-47 | 70/30 | 18000 | 1.5 |
| Aa-48 | 60/20/20 | 18000 | 1.8 |
| Aa-49 | 100 | 12000 | 1.4 |
| Aa-50 | 60/40 | 20000 | 1.6 |
| Aa-51 | 70/30 | 33000 | 2.0 |
| Aa-52 | 60/40 | 19000 | 1.8 |
| Aa-53 | 50/50 | 15000 | 1.5 |
| Aa-54 | 40/20/40 | 35000 | 1.9 |
| Aa-55 | 100 | 16000 | 1.4 |

Since the hydrophobic resin (Aa) containing at least either fluorine atoms or silicon atoms is included in the actinic ray-sensitive or radiation-sensitive resin composition of the present invention, the resin (Aa) is unevenly distributed at a surface layer of the film formed of the actinic ray-sensitive or radiation-sensitive resin composition and when the liquid immersion medium is water, the receding contact angle of the film surface with water can be increased, thereby enhancing the followability of the liquid for liquid immersion.

The receding contact angle of the film including the actinic ray-sensitive or radiation-sensitive resin composition of the present invention that has been baked but is not yet exposed, as measured at the exposure temperature, generally room temperature of 23±3° C. and a humidity of 45±5%, is preferably in the range of 60° to 90°, more preferably 65° or more, still more preferably 70° or more and most preferably 75° or more.

The resin (Aa) is, as described above, unevenly distributed at the interface but unlike a surfactant, need not necessarily have a hydrophilic group in the molecule and may not contribute to uniform mixing of polar/nonpolar substances.

In the liquid immersion exposure step, the liquid for liquid immersion needs to move on a wafer following the movement of an exposure head that is scanning the wafer at a high speed and forming an exposure pattern. Therefore, the contact angle of the liquid for liquid immersion with the resist film in a dynamic state is important, and the resist is required to have a performance of allowing liquid droplets to follow the high-speed scanning of an exposure head without leaving any liquid droplets.

A development residue (scum) and a BLOB defect are easily deteriorated after an alkali development due to the resin (Aa) being hydrophobicity, however, since the alkaline solution rate increases compared to a liner type resin by having 3 or more polymer chains through at least one furcation part, the performance of a development residue (scum) and a BLOB defect are improved.

When the resin (Aa) contains fluorine atoms, the content of the fluorine atoms is preferably from 5 to 80% by mass, and more preferably from 10 to 80% by mass, based on the molecular weight of the resin (Aa). The proportion of the repeating units containing a fluorine atom is preferably from 10 to 100% by mass, and more preferably 30 to 100% by mass, based on all repeating units in the resin (Aa).

When the resin (Aa) contains silicon atoms, the content of the silicon atoms is preferably from 2 to 50% by mass, and more preferably from 2 to 30% by mass, based on the molecular weight of the resin (Aa). In addition, the proportion of the repeating units containing a silicon atom is preferably from 10 to 90% by mass, and more preferably 20 to 80% by mass, based on all the repeating units of the resin (Aa).

The weight average molecular weight of the resin (Aa) is preferably 1,000 to 100,000, more preferably 2,000 to 50,000, and still more preferably 3,000 to 30,000. Here, the weight average molecular weight of the resin shows a polystyrene equivalent molecular weight that is measured by GPC (carrier: tetrahydrofuran (THF)). Specifically, the weight average molecular weight (Mw) and the number average molecular weight (Mn) of the resin (Aa) may be obtained by using, for example, an HLC-8120 (manufactured by Tosoh Corporation) using a TSK gel Multipore HXL-M column (manufactured by Tosoh Corporation, 7.8 mm ID×30.0 cm) as a column and THF (tetrahydrofuran) as an eluent.

The content of the resin (Aa) in the actinic ray-sensitive or radiation-sensitive resin composition may be adjusted appropriately to use so that the receding contact angle of the film formed of the actinic ray-sensitive or radiation-sensitive resin composition falls within the above-specified range. The content of the resin (Aa) is preferably 0.01 to 20% by mass, more preferably 0.1 to 15% by mass, still more preferably 0.1 to 10% by mass, and particularly preferably 0.5 to 8% by mass, based on the total solid contents of the actinic ray-sensitive or radiation-sensitive resin composition.

The resins (Aa) may be used alone or in combination of two or more thereof.

[5] Basic Compound

The composition according to the present invention may further contain a basic compound (except the nitrogen-containing compound (N)). The basic compound is preferably a compound having higher basicity than phenol. Further, this basic compound is preferably an organic basic compound, and more preferably a nitrogen-containing basic compound.

The usable nitrogen-containing basic compound is not particularly limited, but, for example, the compounds classified into (1) to (7) below can be used.

(1) Compound Represented by the General Formula (BS-1)

[Chem. 51]

(BS-1)

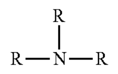

In the general formula (BS-1),

R's each independently represent any a hydrogen atom or an organic group, provided that at least one of three R's is an organic group. This organic group is a linear or branched alkyl group, a monocyclic or polycyclic cycloalkyl group, an aryl group, or an aralkyl group.

The number of carbon atoms of the alkyl group as R is not particularly limited, but, it is usually 1 to 20, and preferably 1 to 12.

The number of carbon atoms of the cycloalkyl group as R is not particularly limited, but it is usually 3 to 20, and preferably 5 to 15.

The number of carbon atoms of the aryl group as R is not particularly limited, but it is usually 6 to 20, and preferably 6 to 10. In particular, examples of the aryl group include a phenyl group and a naphthyl group.

The number of carbon atoms of the aralkyl group as R is not particularly limited, but it is usually 7 to 20, and preferably 7 to 11. In particular, examples of the aralkyl group include a benzyl group.

In the alkyl group, the cycloalkyl group, the aryl group, and the aralkyl group as R, a hydrogen atom may be substituted with a substituent. Examples of the substituent include an alkyl group, a cycloalkyl group, an aryl group, an aralkyl group, a hydroxyl group, a carboxyl group, an alkoxy group, an aryloxy group, an alkylcarbonyloxy group, and an alkyloxycarbonyl group.

Moreover, in the compounds represented by the general formula (BS-1), it is preferable that at least two members out of R's be an organic group.

Specific examples of the compound represented by the general formula (BS-1) include tri-n-butylamine, tri-n-pentylamine, tri-n-octylamine, tri-n-decylamine, triisodecylamine, dicyclohexylmethylamine, tetradecylamine, pentadecylamine, hexadecylamine, octadecylamine, didecylamine, methyloctadecylamine, dimethylundecylamine, N,N-dimethyldodecylamine, methyldioctadecylamine, N,N-dibutylaniline, N,N-dihexylaniline, 2,6-diisopropylaniline, and 2,4,6-tri(t-butyl) aniline.

Furthermore, preferred examples of the basic compound represented by the general formula (BS-1) include those in which at least one of the R's is an alkyl group substituted with a hydroxyl group can be mentioned. Specific examples of the compound include triethanolamine and N,N-dihydroxyethylaniline.

Moreover, an alkyl group as R may have an oxygen atom or a sulfur atom in an alkyl chain. That is, an oxyalkylene chain or the like may be formed. The oxyalkylene chain is preferably —$CH_2CH_2O$—. Specific examples thereof include tris (methoxyethoxyethyl)amine, and the compounds exemplified in column 3 line 60 et seq. of U.S. Pat. No. 6,040,112A.

Examples of the basic compound represented by the general formula (BS-1) include the following.

[Chem. 52-1]

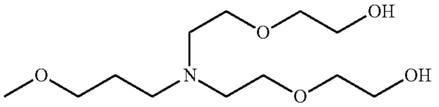

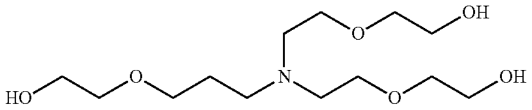

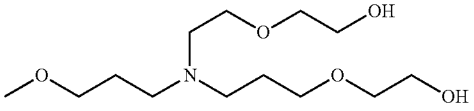

-continued

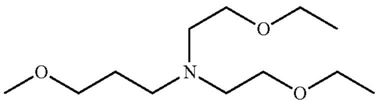

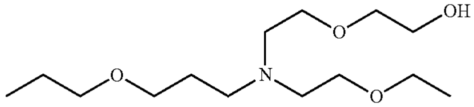

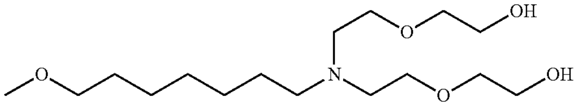

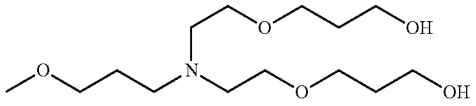

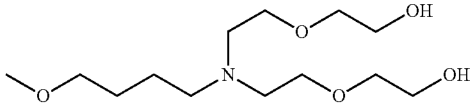

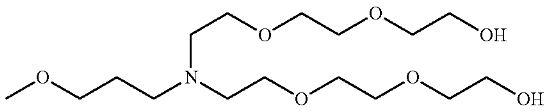

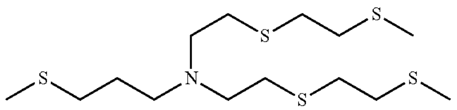

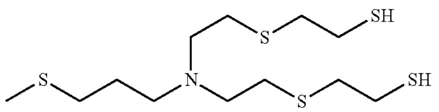

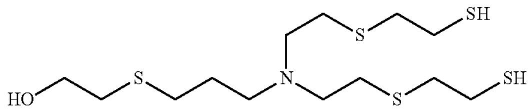

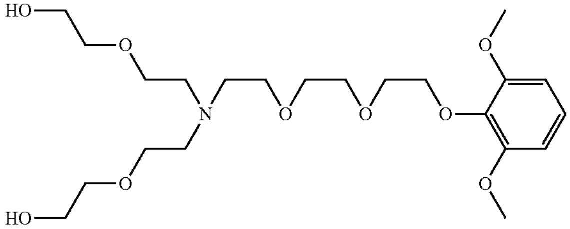

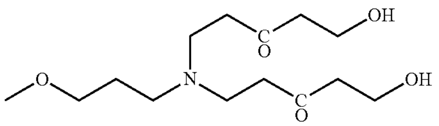

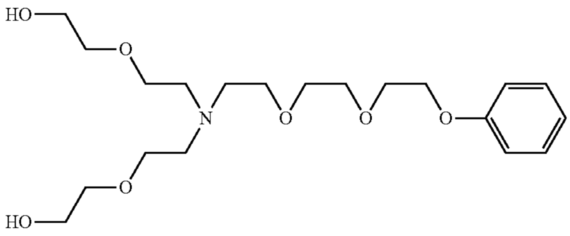

[Chem. 52-2]

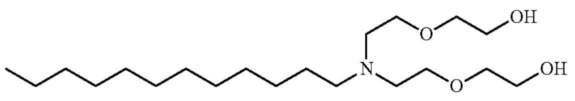

-continued

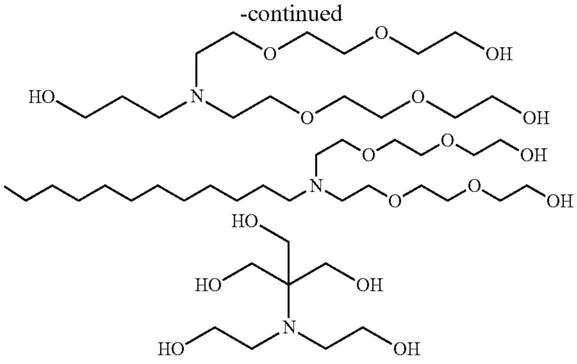

(2) Compound Having a Nitrogen-Containing Heterocycle Structure

A nitrogen-containing heterocycle may have aromatic properties or may not have aromatic properties. Further, it may have a plurality of nitrogen atoms. Also it may have a heteroatom other than nitrogen. Specifically, examples thereof include compounds having an imidazole structure (2-phenylbenzoimidazole, 2,4,5-triphenylimidazole, and the like), compounds having a piperidine structure (N-hydroxyethylpiperidine, bis(1,2,2,6,6-pentamethyl-4-piperidyl) sebacate, and the like), compounds having a pyridine structure (4-dimethylaminopyridine and the like), and compounds having an antipyrine structure (antipyrine, hydroxyantipyrine, and the like).

In addition, compounds with two or more ring structures can be appropriately used. Specific examples thereof include 1,5-diazabicyclo[4.3.0]non-5-ene and 1,8-diazabicyclo [5.4.0]-undec-7-ene.

(3) Amine Compound Having a Phenoxy Group

The amine compounds containing a phenoxy group are those having a phenoxy group at the end opposite to the nitrogen atom of the alkyl group included in the amine compounds. The phenoxy group may have a substituent, such as an alkyl group, an alkoxy group, a halogen atom, a cyano group, a nitro group, a carboxyl group, a carboxylic ester group, a sulfonic ester group, an aryl group, an aralkyl group, an acyloxy group, and an aryloxy group.

This compound having at least one oxyalkylene chain between the phenoxy group and the nitrogen atom are more preferred. The number of oxyalkylene chains in one molecule is preferably in the range of 3 to 9, and more preferably 4 to 6. Among the oxyalkylene chains, —$CH_2CH_2O$— is particularly preferable.

Specific examples thereof include 2-[2-{2-(2,2-dimethoxy-phenoxyethoxy)ethyl}-bis-(2-methoxyethyl)]-amine, compounds (C1-1) to (C3-3) exemplified in the paragraph 0066 of US2007/0224539A1, and the like.

The amine compound having a phenoxy group can be obtained by, for example, first heating a primary or secondary amine having a phenoxy group and a haloalkyl ether so as to effect a reaction therebetween, subsequently adding an aqueous solution of a strong base such as sodium hydroxide, potassium hydroxide, and tetraalkylammonium, and thereafter carrying out an extraction with an organic solvent such as ethyl acetate and chloroform. Alternatively, the amine compound having a phenoxy group can be obtained by first heating a primary or secondary amine and a haloalkyl ether having a phenoxy group at its end so as to effect a reaction therebetween, subsequently adding an aqueous solution of a strong base such as sodium hydroxide, potassium hydroxide, and a tetraalkylammonium, and thereafter carrying out an extraction with an organic solvent such as ethyl acetate and chloroform.

(4) Ammonium Salt

As the basic compound, an ammonium salt may also be suitably used. Examples of the anion of the ammonium salt include halide, sulfonate, borate, and phosphate. Among these, halide and sulfonate are particularly preferred.

The halide is particularly preferably chloride, bromide or iodide.

The sulfonate is particularly preferably organic sulfonate having 1 to 20 carbon atoms. Examples of the organic sulfonate include an alkyl sulfonate and an aryl sulfonate each having 1 to 20 carbon atoms.

The alkyl group contained in the alkyl sulfonate may have a substituent. Examples of the substituent include a fluorine atom, a chlorine atom, a bromine atom, an alkoxy group, an acyl group, and an aryl group. Specific examples of the alkyl sulfonate include methane sulfonate, ethane sulfonate, butane sulfonate, hexane sulfonate, octane sulfonate, benzyl sulfonate, trifluoromethane sulfonate, pentafluoroethane sulfonate and nonafluorobutane sulfonate.

Examples of the aryl group contained in aryl sulfonate include a phenyl group, a naphthyl group and an anthryl group. These aryl groups may have a substituent. Preferred examples of the substituent include a linear or branched alkyl group having 1 to 6 carbon atoms and a cycloalkyl group having 3 to 6 carbon atoms. Specific preferred examples thereof include a methyl group, an ethyl group, an n-propyl group, an isopropyl group, an n-butyl group, an i-butyl group, a t-butyl group, an n-hexyl group, and a cyclohexyl group. Examples of the other substituent include an alkoxy group having 1 to 6 carbon atoms, a halogen atom, a cyano group, a nitro group, an acyl group and an acyloxy group.

The ammonium salt may be hydroxide or carboxylate. In this case, the ammonium salt is particularly preferably tetraalkylammonium hydroxide having 1 to 8 carbon atoms, such as tetramethylammonium hydroxide, tetraethylammonium hydroxide and tetra-(n-butyl)ammonium hydroxide.

Preferred examples of the basic compound include guanidine, aminopyridine, aminoalkylpyridine, aminopyrrolidine, indazole, imidazole, pyrazole, pyrazine, pyrimidine, purine, imidazoline, pyrazoline, piperazine, aminomorpholine, and aminoalkylmorpholine. They may further have a substituent.

Preferred examples of the substituent include an amino group, an aminoalkyl group, an alkylamino group, an aminoaryl group, an arylamino group, an alkyl group, an alkoxy group, an acyl group, an acyloxy group, an aryl group, an aryloxy group, a nitro group, a hydroxyl group, and a cyano group.

Particularly preferred examples of the basic compound include guanidine, 1,1-dimethyl guanidine, 1,1,3,3-tetramethyl guanidine, imidazole, 2-methylimidazole, 4-methylimidazole, N-methylimidazole, 2-phenylimidazole, 4,5-diphenylimidazole, 2,4,5-triphenylimidazole, 2-aminopyridine, 3-aminopyridine, 4-aminopyridine, 2-dimethylaminopyridine, 4-dimethylaminopyridine, 2-diethylaminopyridine, 2-(aminomethyl)pyridine, 2-amino-3-methylpyridine, 2-amino-4-methylpyridine, 2-amino-5-methylpyridine, 2-amino-6-methylpyridine, 3-aminoethylpyridine, 4-aminoethylpyridine, 3-aminopyrrolidine, piperazine, N-(2-aminoethyl)piperazine, N-(2-aminoethyl)piperidine, 4-amino-2,2,6,6-tetramethylpiperidine, 4-piperidinopiperidine, 2-iminopiperidine, 1-(2-aminoethyl) pyrrolidine, pyrazole, 3-amino-5-methylpyrazole, 5-amino-3-methyl-1-p-tolylpyrazole, pyrazine, 2-(aminomethyl)-5-methylpyrazine, pyrimidine, 2,4-diaminopyrimidine, 4,6- dihydroxypyrimidine, 2-pyrazoline, 3-pyrazoline, N-aminomorpholine and N-(2-aminoethyl) morpholine.

(5) Compound containing a functional group with proton acceptor properties, and which is decomposed by the irradiation of actinic rays or radiation to produce a compound exhibiting lower proton acceptor properties, or no proton acceptor properties, or exhibiting acid properties derived from the proton acceptor properties (PA)

The composition according to the present invention may further contain, as a basic compound, a compound containing a functional group with proton acceptor properties, and which is decomposed by the irradiation of actinic rays or radiation to produce a compound exhibiting lower proton acceptor properties lower, or no proton acceptor properties, or exhibiting acid properties derived from the proton acceptor properties (hereinafter also referred to as a compound (PA)).

The functional group with proton acceptor properties refers to a functional group is a group, or an electron, capable of electrostatic interaction with a proton, and, for example, means a functional group with a macrocyclic structure, such as a cyclopolyether, or a functional group containing a nitrogen atom with an unshared electron pair not contributing to π-conjugation. The nitrogen atom with an unshared electron pair not contributing to π-conjugation is, for example, a nitrogen atom with any of the partial structures of the following general formula.

[Chem. 53]

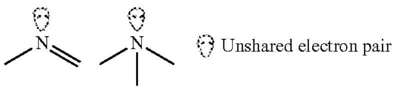

Examples of the partial structures of the functional groups with proton acceptor properties include crown ether, azacrown ether, primary to tertiary amine, pyridine, imidazole and pyrazine structures.

The compound (PA) produces a compound which is decomposed by the irradiation of actinic rays or radiation to exhibit lower proton acceptor properties, or no proton acceptor properties, or exhibit acid properties derived from the proton acceptor properties. Here, exhibiting lower proton acceptor properties, or no proton acceptor properties, or exhibiting acid properties derived from the proton acceptor properties means the change of proton acceptor properties due to the proton being added to the functional groups with proton acceptor properties, specifically, the decrease of the equilibrium constant at chemical equilibrium when the proton adducts are generated from the compound (PA) having the functional groups with proton acceptor properties and the proton.

The proton acceptor properties can be ascertained by performing pH measurement. In the present invention, it is preferable for the acid dissociation constant pKa of the compound produced by the decomposition of the compound (PA) by irradiation of actinic rays or radiation to satisfy the relationship $pKa<-1$, satisfying the relationship $-13<pKa<-1$ is more preferred, and satisfying the relationship $-13<pKa<-3$ is further more preferred.

In the present invention, the acid dissociation constant pKa refers to the acid dissociation constant pKa in an aqueous solution, for example, any of those listed in Chemical Handbook (II) (Revised 4th Edition, 1993, edited by The Chemical Society of Japan, published by Maruzen Co., Ltd.) and the lower the value of acid dissociation constant is, the greater the acid strength is. The acid dissociation constant pKa in an aqueous solution, specifically, can be actually surveyed by measuring the acid dissociation constant at 25° C. using an infinitely dilute aqueous solution, and can be also obtained by calculating values based on Hammett substituent constants and database of well-known literature value using the following software package 1.

Software package 1: Advanced Chemistry Development (ACD/Labs) SoftwareV8.14 for Solaris (1994-2007ADC/Labs)

Specific examples of the compound (PA) are illustrated below, but the present invention is not limited thereto.)

[Chem. 54-1]

(PA-1)

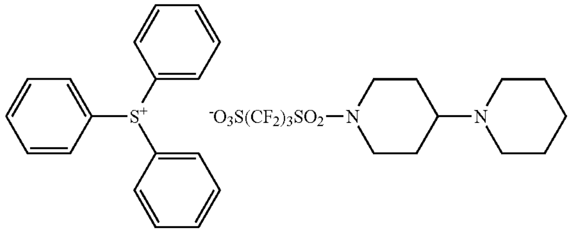

(PA-2)

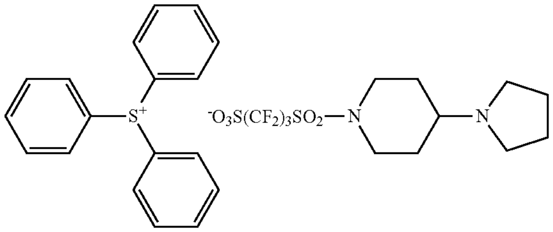

(PA-5)

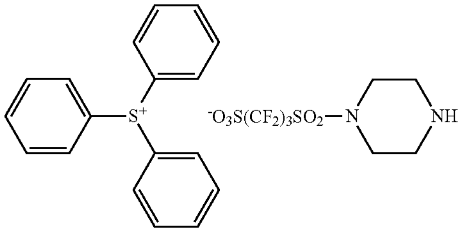

(PA-6)

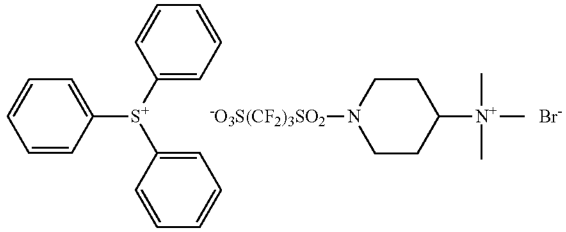

(PA-8)

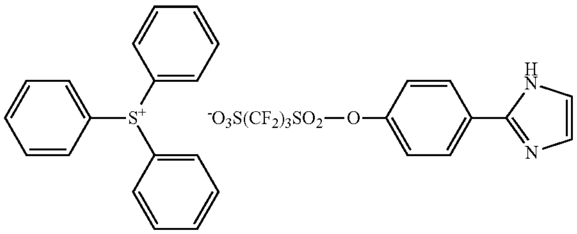

-continued
(PA-11)
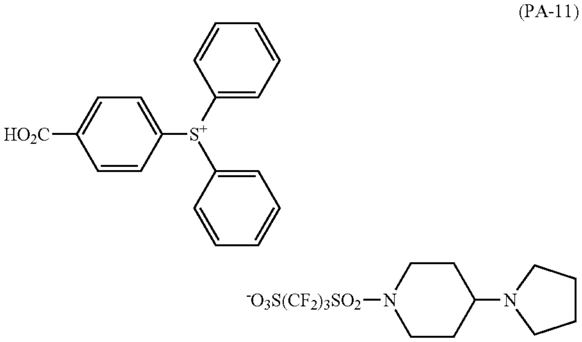
(PA-14)
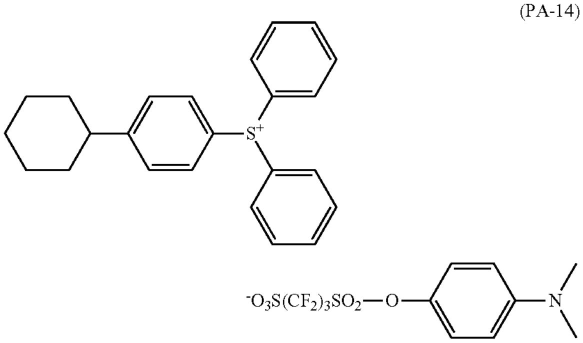
[Chem. 54-2]
(PA-18)
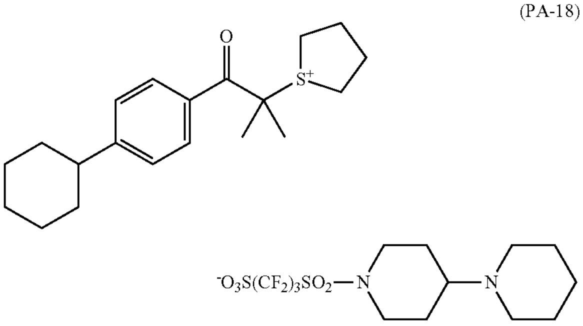
(PA-20)
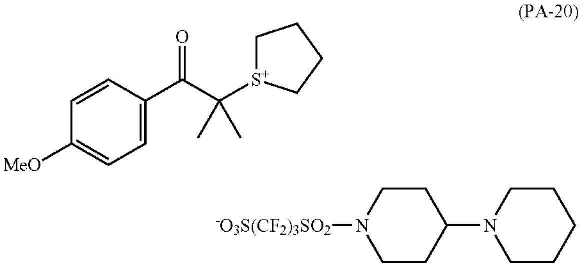
(PA-21)
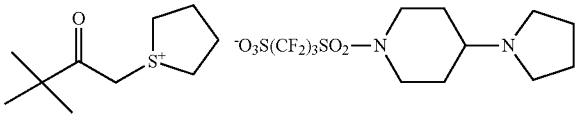
(PA-22)
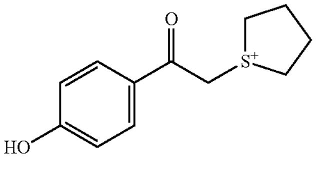
-continued
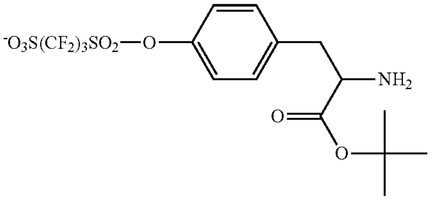
(PA-23)
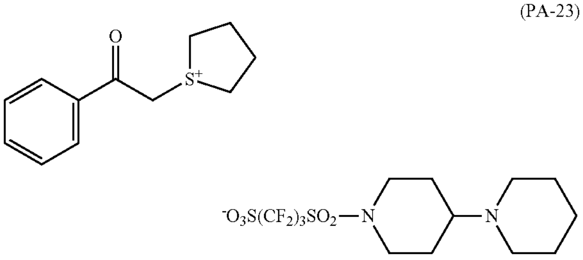
(PA-26)
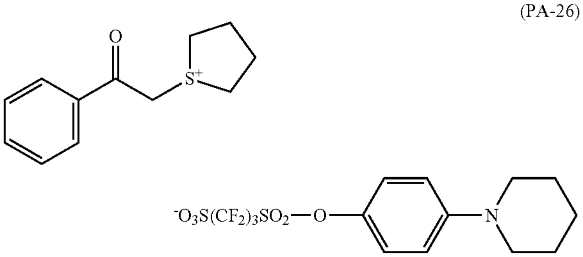
(PA-27)
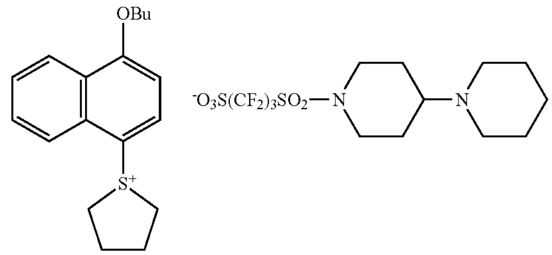
(PA-29)
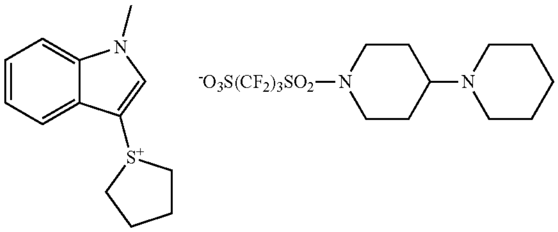
[Chem. 54-3]
(PA-33)
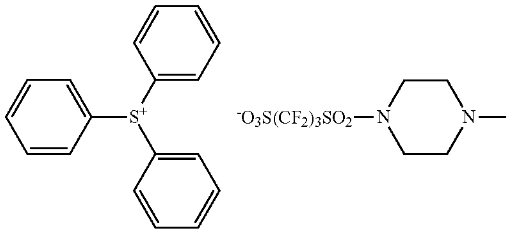

-continued
(PA-35)
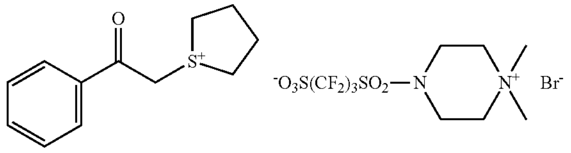
(PA-38)
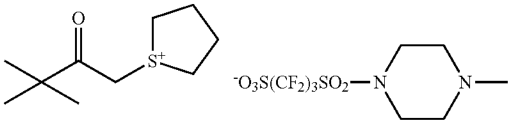
(PA-39)
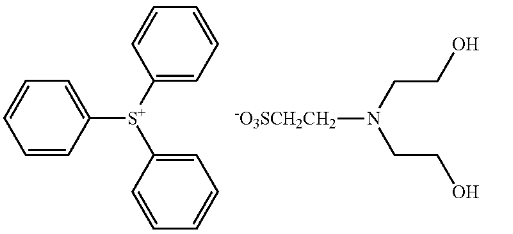
(PA-42)
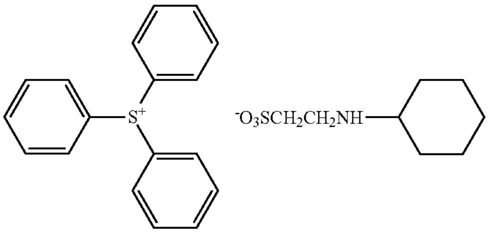
(PA-44)
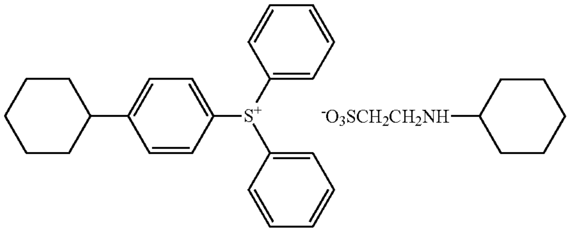
(PA-47)
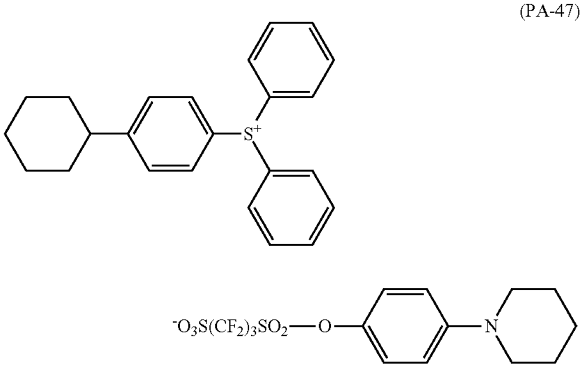
-continued
[Chem. 54-4]
(PA-50)
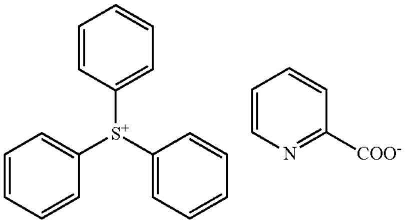
(PA-51)
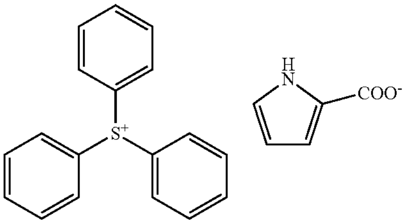
(PA-52)
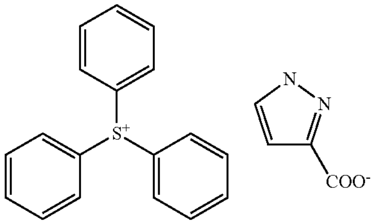
(PA-55)
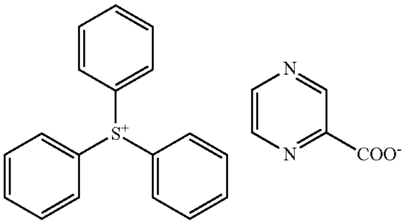
[Chem. 54-5]
(PA-60)
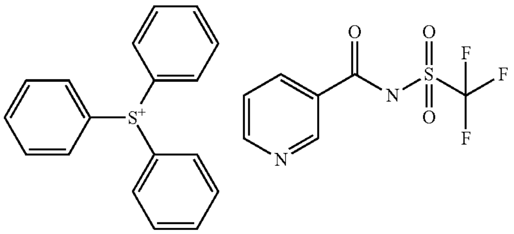
(PA-61)
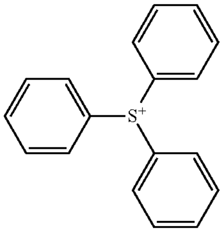

-continued
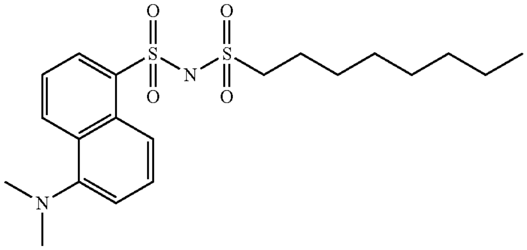
(PA-64)
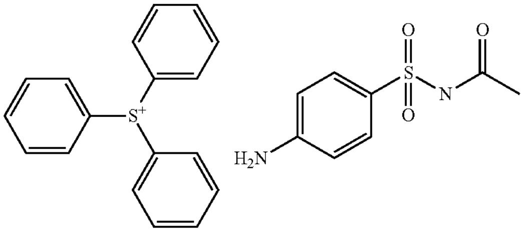
[Chem. 54-6]
(PA-72)
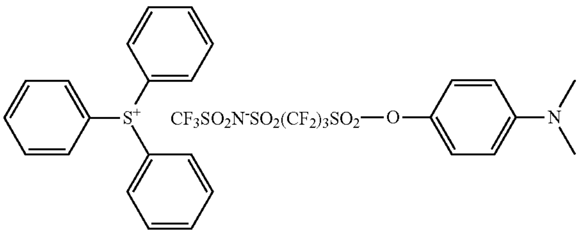
(PA-73)
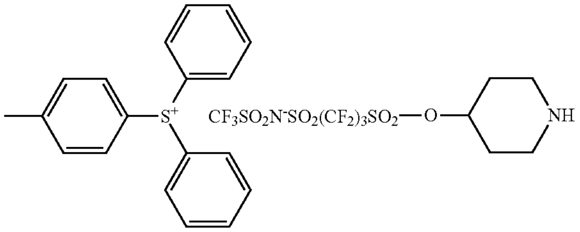
(PA-74)
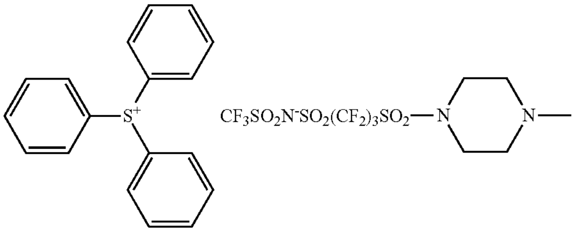
[Chem. 54-7]
(PA-76)
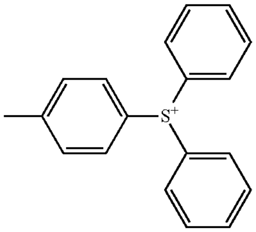
-continued
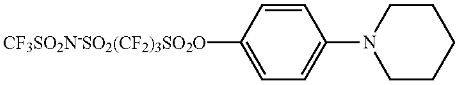
(PA-86)
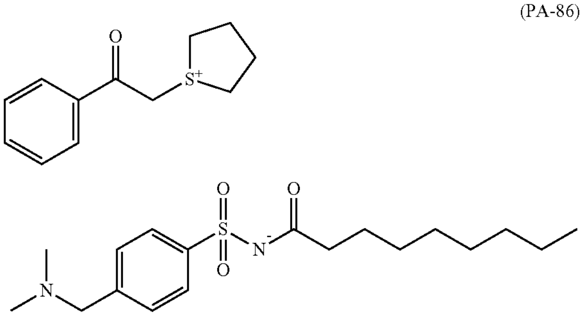
[Chem. 54-8]
(PA-91)
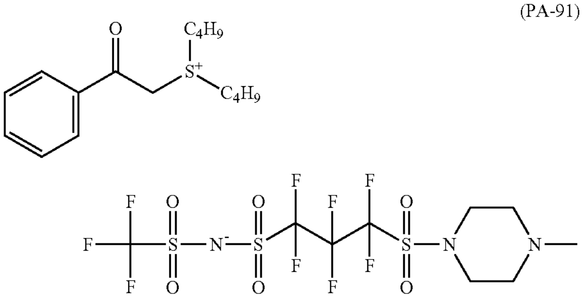
(PA-94)
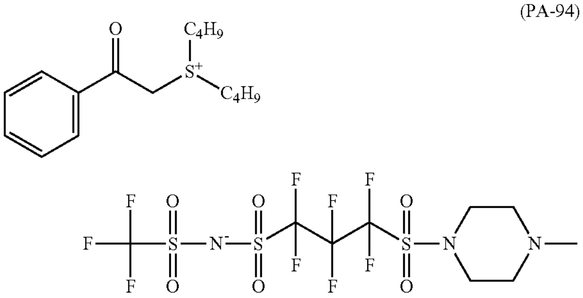
(PA-97)
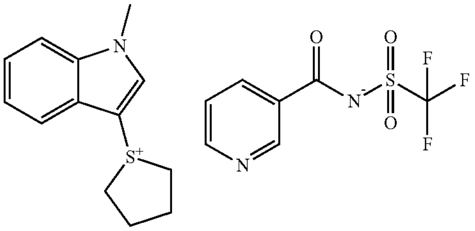
(PA-98)
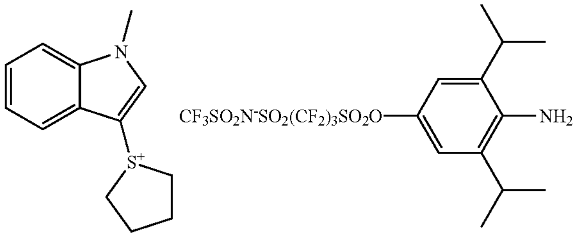

-continued (PA-99)

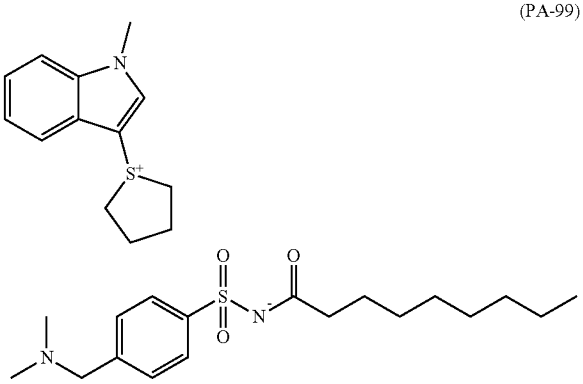

(PA-101)

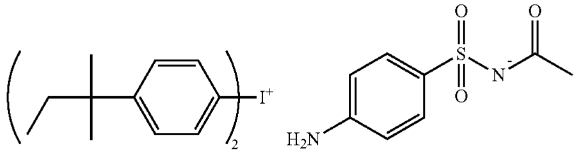

In the composition of the present invention, the content of the compound (PA) in the entire composition is preferably in the range of 0.1 to 10% by mass, and more preferably 1 to 8% by mass, based on the total solid contents.

(6) Guanidine Compound

The composition of the present invention may further contain a guanidine compound having a structure represented by the following formula.

[Chem. 55]

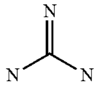

The guanidine compound exhibits strong basicity because dispersion of positive electric charges of a conjugate acid is stabilized by three nitrogen atoms.

As for the basicity of the guanidine compound (A) of the present invention, the pKa of the conjugate acid is preferably 6.0 or more, and more preferably from 7.0 to 20.0 in view of high neutralization reactivity with an acid and excellent roughness performance, and still more preferably from 8.0 to 16.0.

Due to such strong basicity, the compound can suppress the diffusion of an acid and contribute to the formation of an excellent pattern shape.

In the present invention, the log P is a logarithmic value of the n-octanol/water partition coefficient (P) and is an effective parameter capable of characterizing the hydrophilicity/hydrophobicity for compounds over a wide range. The partition coefficient is usually determined by computation but not from experiments and in the present invention, a value computed using CS ChemDraw Ultra Ver. 8.0 software package (Crippen's fragmentation method) is employed.

Furthermore, the log P of the guanidine compound (A) is preferably 10 or less. When the log P is the value described above or less, the compound can be uniformly contained in the resist film.

The log P of the guanidine compound (A) in the present invention is preferably in a range of 2 to 10, more preferably in a range of 3 to 8, and still more preferably in a range of 4 to 8.

Furthermore, the guanidine compound (A) in the present invention preferably contains no nitrogen atoms except for in the guanidine structure.

Specific examples of the guanidine compound are shown below, but the present invention is not limited thereto.

[Chem. 56-1]

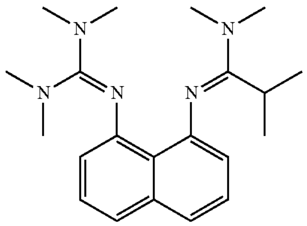

Log P: 4.29

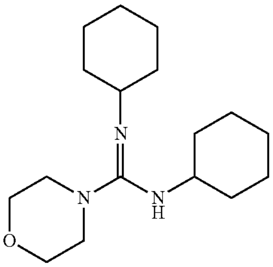

Log P: 3.32

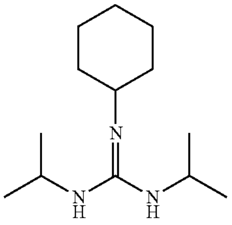

Log P: 3.1

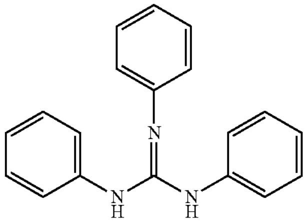

Log P: 5.24

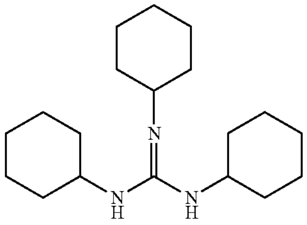

Log P: 4.89

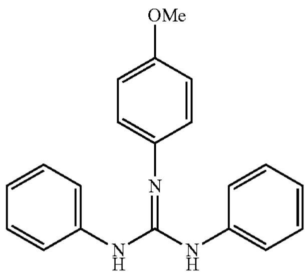

Log P: 5.11

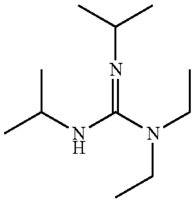

Log P: 2.61

-continued

[Chem. 56-2]

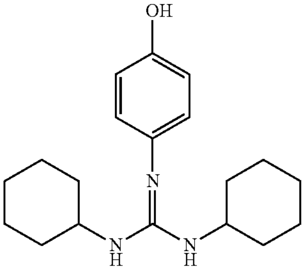

Log P: 4.61

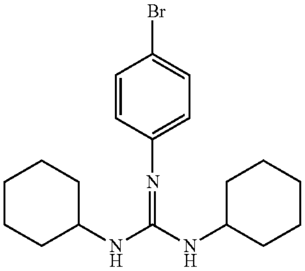

Log P: 5.83

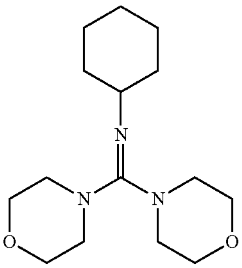

Log P: 1.75

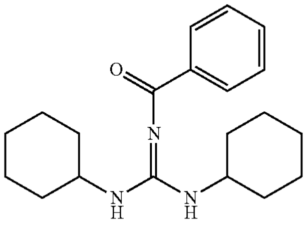

Log P: 4.95

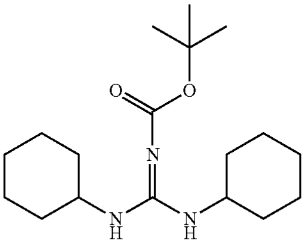

Log P: 4.51

[Chem. 56-3]

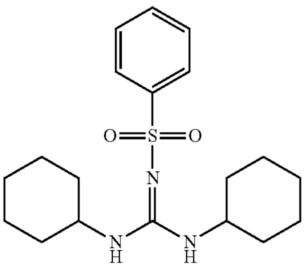

Log P: 4.55

-continued

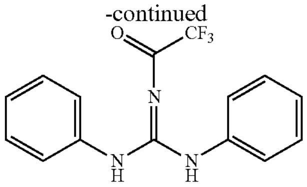

Log P: 4.43

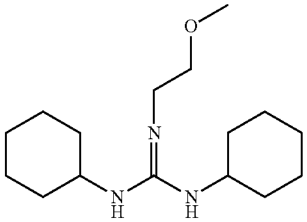

Log P: 3.18

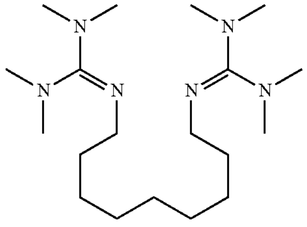

Log P: 4.4

(7) Low Molecular Compound Having a Nitrogen Atom and Having a Group Leaving by the Action of an Acid The composition in the present invention may contain a low molecular compound (hereinafter, also referred to as a "low molecular compound (D)" or a "compound (D)") having a nitrogen atom and having a group leaving by the action of an acid other than the nitrogen-containing compound (N) above. The low molecular compound (D) preferably has basicity after the group leaving by the action of an acid leaves.

The group leaving by the action of an acid is not particularly limited, but an acetal group, a carbonate group, a carbamate group, a tertiary ester group, a tertiary hydroxyl group, and a hemiaminal ether group are preferred, and a carbamate group and a hemiaminal ether group are particularly preferred.

The molecular weight of the low molecular compound (D) containing a group leaving by the action of an acid is preferably from 100 to 1,000, more preferably from 100 to 700, and particularly preferably from 100 to 500.

As the compound (D), an amine derivative containing group leaving by the action of an acid on a nitrogen atom is preferred.

The compound (D) may contain a carbamate group having a protecting group on a nitrogen atom. The protecting group constituting the carbamate group can be represented by the following general formula (d-1).

[Chem. 57]

(d-1)

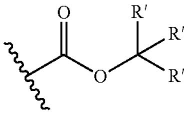

In the general formula (d-1), each R' independently represents a hydrogen atom, a linear or branched alkyl group, a cycloalkyl group, an aryl group, an aralkyl group, or an alkoxyalkyl group. R's may be bonded to each other to form a ring.
R' is preferably a linear or branched alkyl group, cycloalkyl group, or aryl group. R' is more preferably a linear or branched alkyl group or a cycloalkyl group.
Specific structures of these groups are shown below.
[Chem. 58]
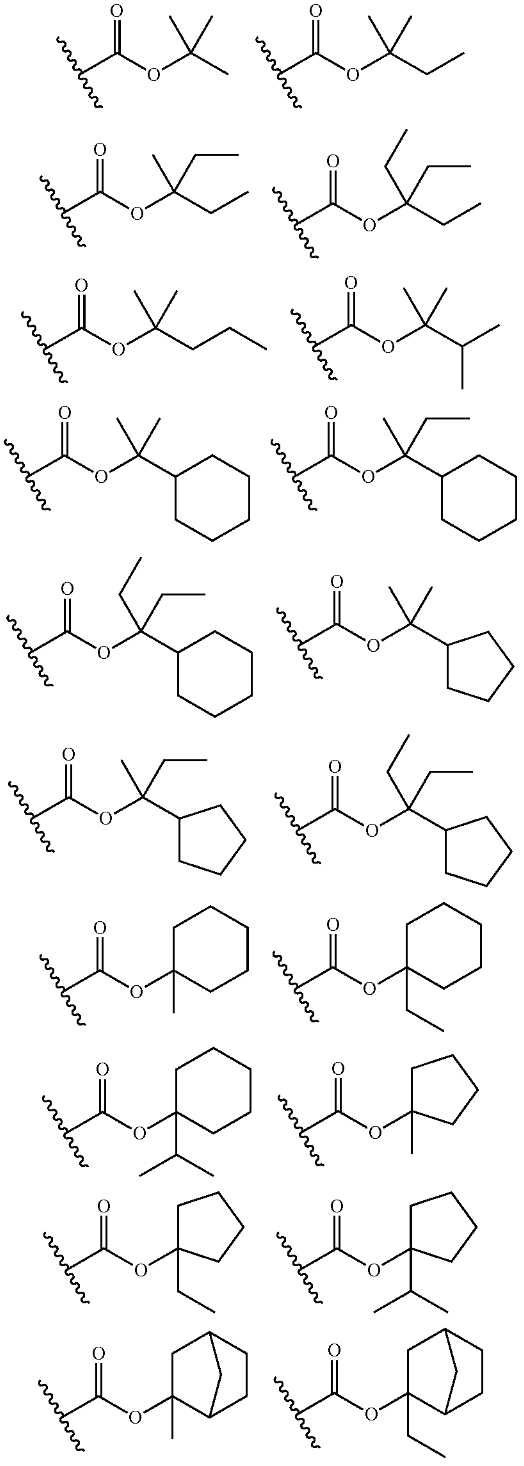
-continued
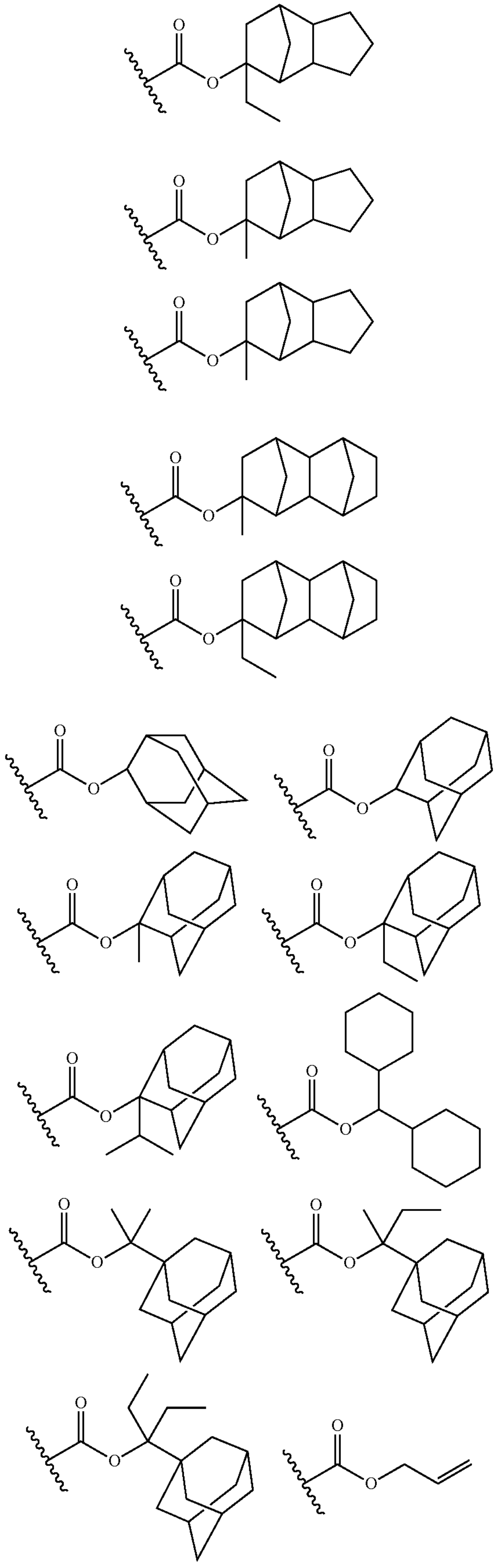

-continued

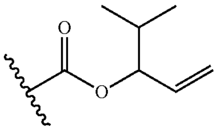
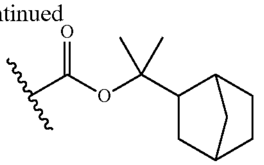
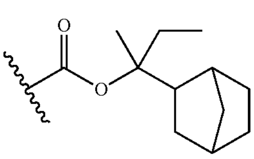
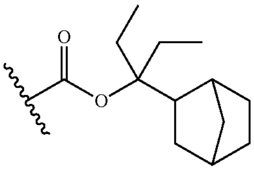
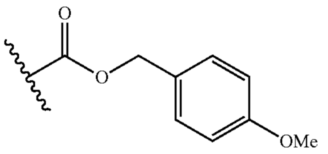
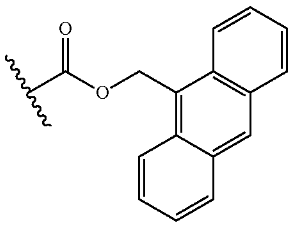
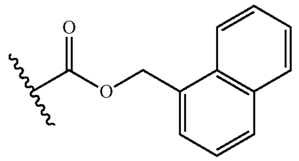
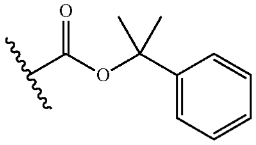
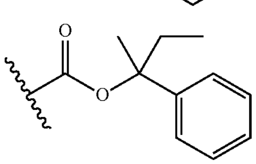
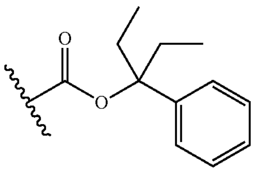
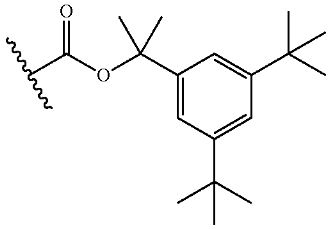

The compound (D) can be also formed by any combination of the basic compound as described later and a structure represented by the general formula (d-1).

The compound (D) is particularly preferably one having a structure represented by the following general formula (A).

Furthermore, the compound (D) may correspond to the basic compound as long as it is a low molecular compound containing a group leaving by the action of an acid.

[Chem. 59]

(A)

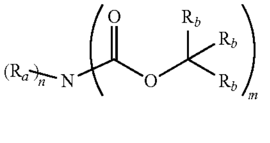

In the general formula (A), Ra represents a hydrogen atom, an alkyl group, a cycloalkyl group, an aryl group, or an aralkyl group. Further, with n=2, two Ra's may be the same as or different from each other, or the two Ra's may be bonded to each other to form a divalent heterocyclic hydrocarbon group (preferably having 20 or less carbon atoms) or a derivative thereof.

Rb's each independently represent a hydrogen atom, an alkyl group, a cycloalkyl group, an aryl group, an aralkyl group, or an alkoxyalkyl group. However, when 1 or more Rb's are hydrogen atoms in —C(Rb)(Rb)(Rb), at least one of other Rb's is a cycloalkyl group, a 1-alkoxyalkyl group or an aryl group.

At least two Rb's may be bonded to form an alicyclic hydrocarbon group, an aromatic hydrocarbon group, a heterocyclic hydrocarbon group, or a derivative thereof.

n represents an integer of 0 to 2 and m represents an integer of 1 to 3, with n+m=3.

In the general formula (A), each of the alkyl group, the cycloalkyl group, the aryl group, and the aralkyl group represented by Ra and Rb may be substituted with a functional group such as a hydroxyl group, a cyano group, an amino group, a pyrrolidino group, a piperidino group, a morpholino group, and an oxo group, an alkoxy group, or a halogen atom. The alkoxyalkyl group represented by Rb is also the same.

Examples of the alkyl group, cycloalkyl group, aryl group and aralkyl group (each of the alkyl group, the cycloalkyl group, the aryl group, and the aralkyl group may be substituted with the above-described functional group, an alkoxy group, or a halogen atom) of Ra and/or Rb include:

a group derived from a linear or branched alkane such as methane, ethane, propane, butane, pentane, hexane, heptane, octane, nonane, decane, undecane, and dodecane, or a group where the group derived from an alkane is substituted with one or more kinds of or one or more groups of cycloalkyl groups such as a cyclobutyl group, a cyclopentyl group, and a cyclohexyl group;

a group derived from a cycloalkane such as cyclobutane, cyclopentane, cyclohexane, cycloheptane, cyclooctane, norbornane, adamantane, and noradamantane, or a group where the group derived from a cycloalkane is substituted with one or more kinds of or one or more groups of linear or branched alkyl groups such as a methyl group, an ethyl group, an n-propyl group, an i-propyl group, an n-butyl group, a 2-methylpropyl group, a 1-methylpropyl group, and a t-butyl group;

a group derived from an aromatic compound such as benzene, naphthalene or anthracene, or a group where the group derived from an aromatic compound is substituted with one or more kinds of or one or more groups of linear or branched alkyl groups such as a methyl group, an ethyl group, an n-propyl group, an i-propyl group, an n-butyl group, a 2-methylpropyl group, a 1-methylpropyl group, and a t-butyl group;

a group derived from a heterocyclic compound such as pyrrolidine, piperidine, morpholine, tetrahydrofuran, tetrahydropyran, indole, indoline, quinoline, perhydroquinoline, indazole, benzimidazole, or a group where the group derived from a heterocyclic compound is substituted with one or more kinds of or one or more groups of liner or branched alkyl groups or groups derived from a aromatic compound;

a group where the group derived from a linear or branched alkane or the group derived from a cycloalkane is substituted with one or more kinds of or one or more groups of aromatic compound-derived groups such as a phenyl group, a naphthyl group and an anthracenyl group; and a group where the substituent above is substituted with a functional group such as a hydroxyl group, a cyano group, an amino group, a pyrrolidino group, a piperidino group, a morpholino group, and an oxo group.

In addition, examples of the divalent heterocyclic hydrocarbon group (preferably 1 to 20 carbon atoms) in which the Ra's are bonded to each other to form or the derivative thereof include a group where a group derived from a heterocyclic compound such as pyrrolidine, piperidine, morpholine, 1,4,5,6-tetrahydropyrimidine, 1,2,3,4-tetrahydroquinoline, 1,2,3,6-tetrahydropyridine, homopiperazine, 4-azabenzimidazole, benzotriazole, 5-azabenzotriazole, 1H-1,2,3-triazole, 1,4,7-triazacyclononane, tetrazole, 7-azaindole, indazole, benzimidazole, imidazo[1,2-a]pyridine, (1S,4S)-(+)-2,5-diazabicyclo[2.2.1]heptane, 1,5,7-triazabicyclo[4.4.0]deck-5-en, indole, indoline, 1,2,3,4-tetrahydroquinoxaline, perhydroquinoline, 1,5,9-triazacyclododecane, or a group where the group is derived from a heterocyclic compound is substituted with one or more kinds of or one or more groups of a group derived from a linear or branched alkane, a group derived from a cycloalkane, a group derived from a aromatic compound, a group derived from a heterocyclic compound, and a functional group such as a hydroxyl group, a cyano group, an amino group, a pyrrolidino group, a piperidino group, a morpholino group, an oxo group.

Specific examples of the particularly preferable compound (D) in the present invention are shown below, but the present invention is not limited thereto.

[Chem. 60-1]

(D-1)

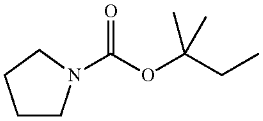

(D-2)

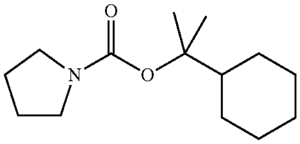

(D-3)

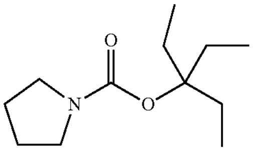

(D-4)

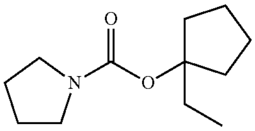

(D-5)

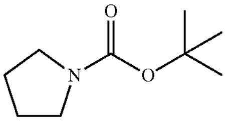

-continued (D-6)

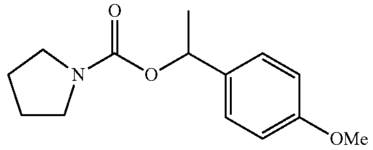

(D-7)

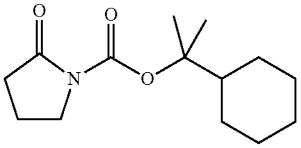

(D-8)

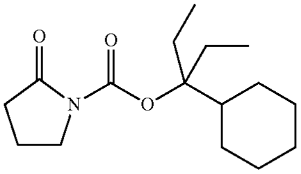

(D-9)

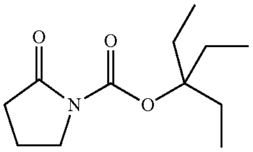

(D-10)

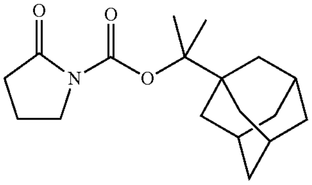

(D-11)

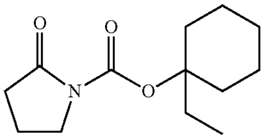

(D-12)

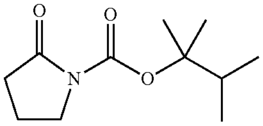

(D-13)

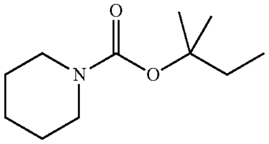

(D-14)

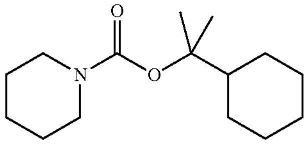

-continued
(D-15)
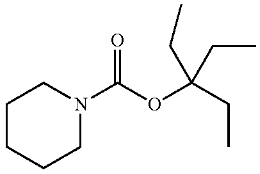
(D-16)
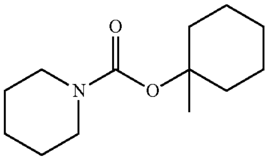
(D-17)
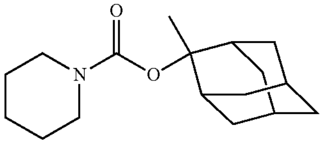
(D-18)
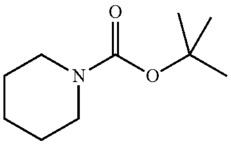
(D-19)
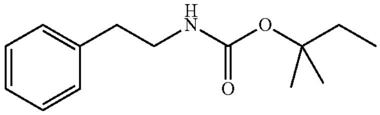
(D-20)
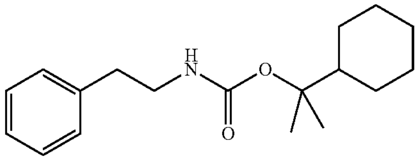
(D-21)
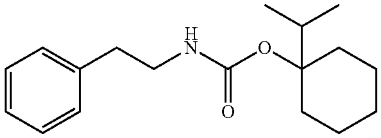
(D-22)
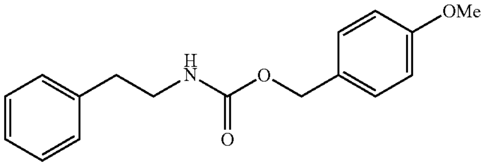
(D-23)
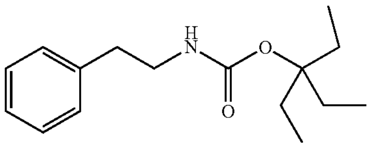
-continued
(D-24)
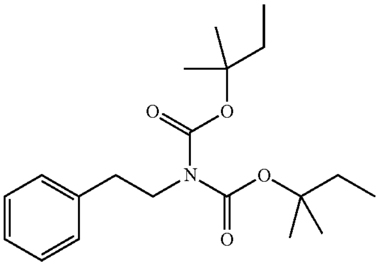
(D-25)
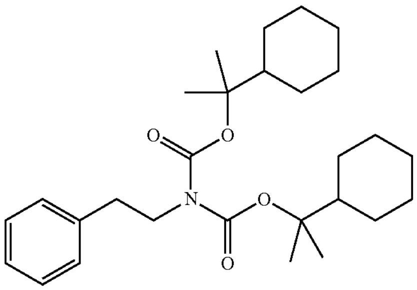
(D-26)
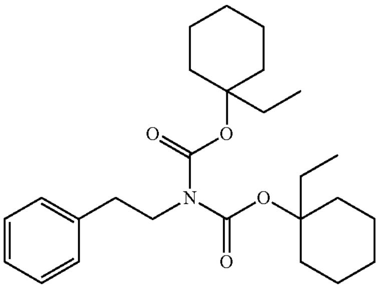
(D-27)
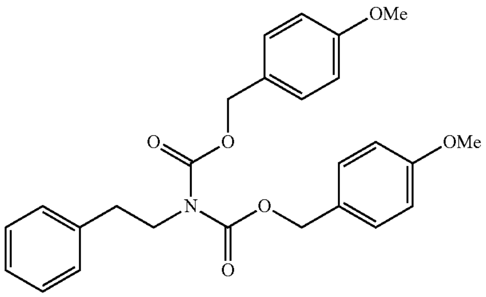
(D-28)
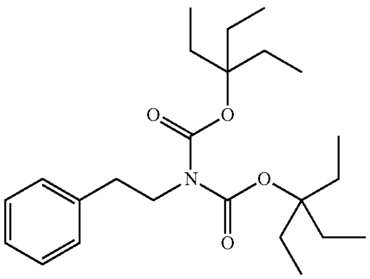

-continued
(D-29)
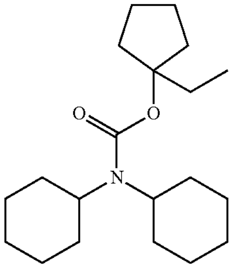
(D-30)
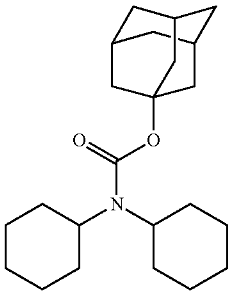
(D-31)
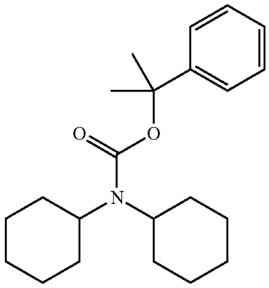
(D-32)
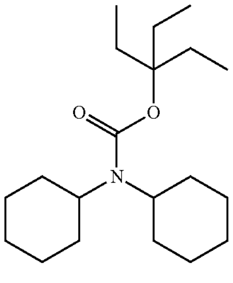
(D-33)
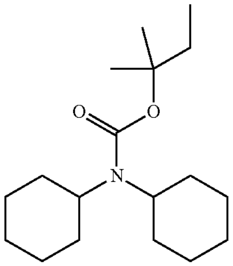
-continued
[Chem. 60-2]
(D-34)
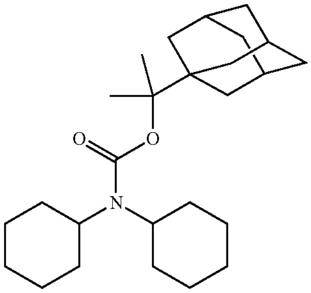
(D-35)
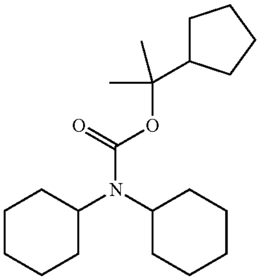
(D-36)
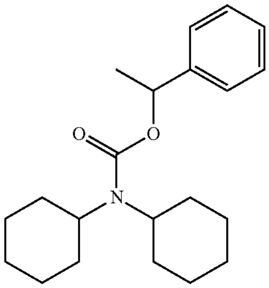
(D-37)
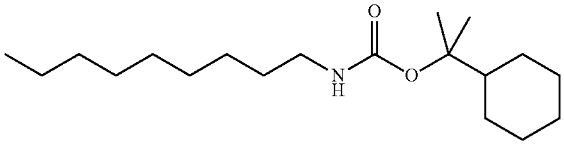
(D-38)
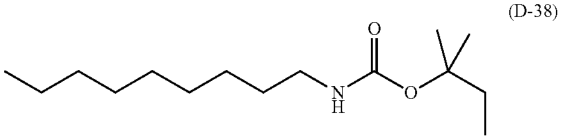
(D-39)
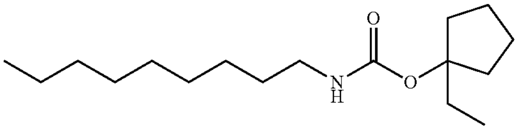
(D-40)
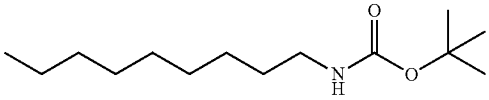

-continued
(D-41)
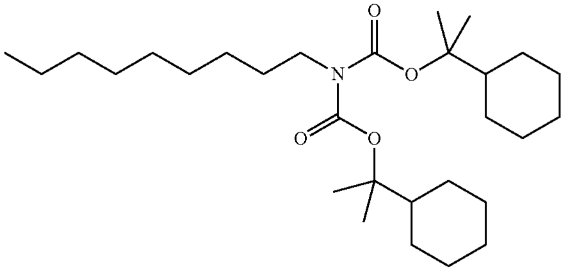
(D-42)
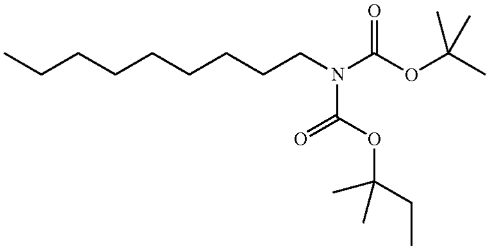
(D-43)
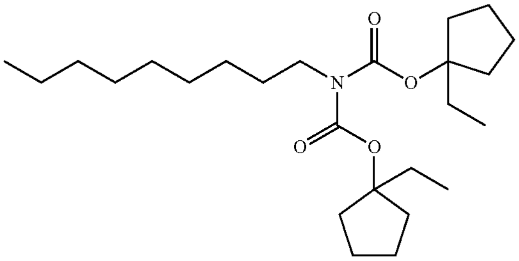
(D-44)
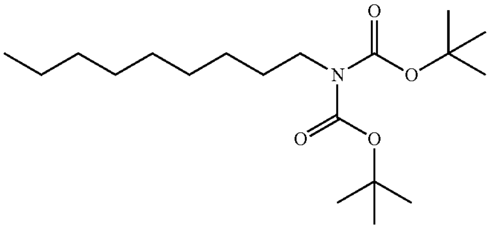
(D-45)
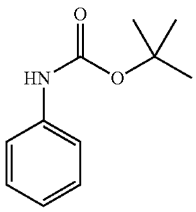
(D-46)
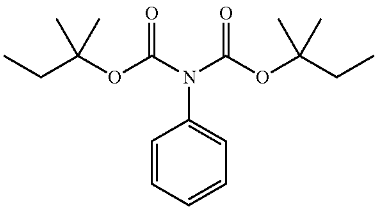
-continued
(D-47)
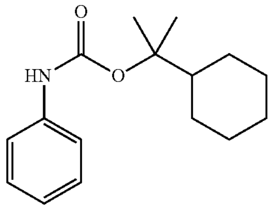
(D-48)
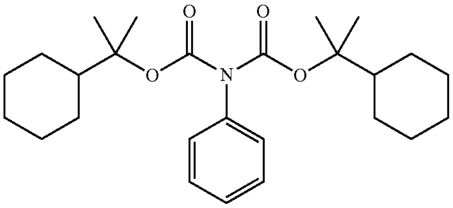
(D-49)
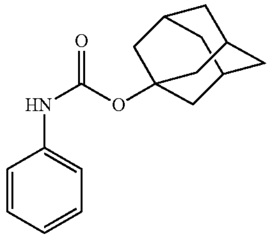
(D-50)
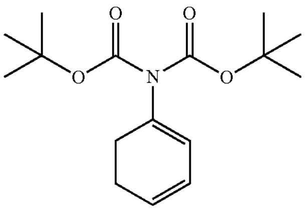
(D-51)
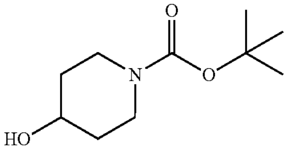
(D-52)
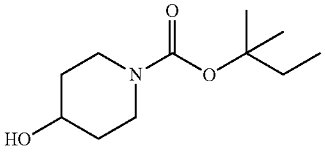
(D-53)
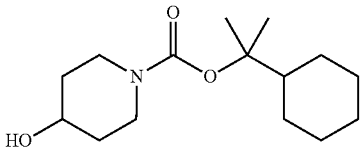
(D-54)
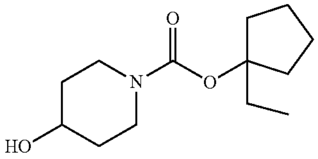

-continued (D-55)

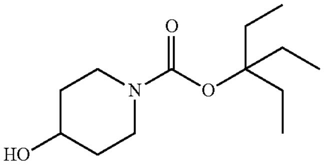

[Chem. 60-3]

(D-56)

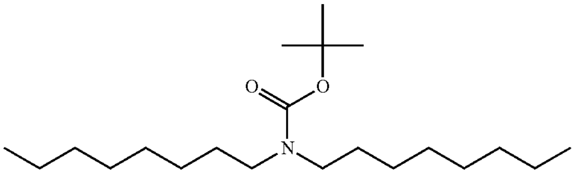

(D-57)

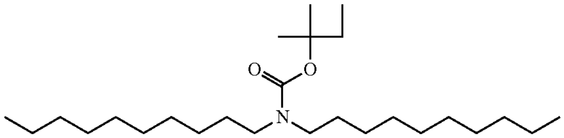

(D-58)

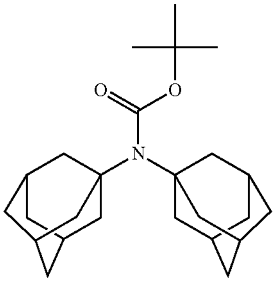

(D-59)

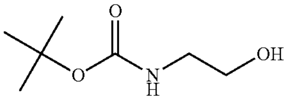

(D-60)

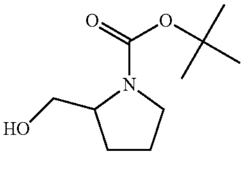

(D-61)

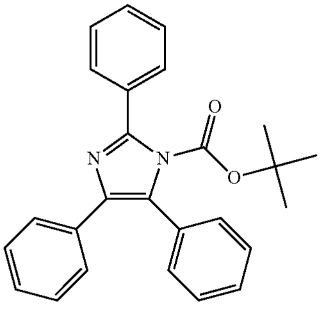

-continued (D-62)

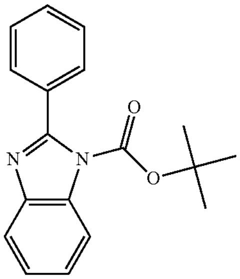

(D-63)

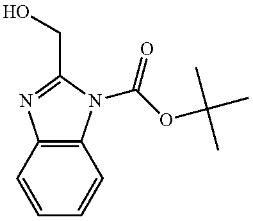

(D-64)

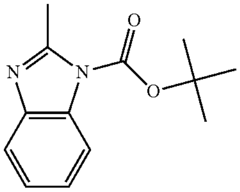

(D-65)

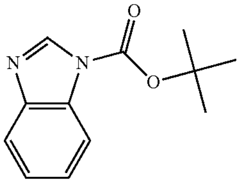

The compound represented by the general formula (A) can be synthesized, based on JP2007-298569A and JP2009-199021A, and the like.

In the present invention, the low molecular compound (D) may be used alone or in mixture of two or more kinds thereof.

The composition of the present invention may or may not contain the low molecular compound (D), but in the case where it contains the low molecular compound (D), the content of the compound (D) is usually from 0.001 to 20% by mass, preferably from 0.001 to 10% by mass, more preferably from 0.01 to 5% by mass, based on the total solid contents of the composition combined with the basic compound.

Other examples of the compounds usable in the composition according to the present invention include the compounds synthesized in Examples of JP2002-363146A, and the compounds described in paragraph 0108 of JP2007-298569A.

Photosensitive basic compounds may be used as the basic compound. As photosensitive basic compounds, use can be made of, for example, the compounds described in JP2003-524799A, J. Photopolym. Sci & Tech. Vol. 8, p. 543-553 (1995), etc.

The molecular weight of the basic compound is usually from 100 to 1,500, preferably from 150 to 1,300, and more preferably from 200 to 1,000.

This basic compound may be used alone or in combination of two or more kinds thereof.

In the case where the composition according to the present invention contains a basic compound, the content of the basic compound is preferably 0.01 to 8.0% by mass, more preferably 0.1 to 5.0% by mass, and particularly preferably 0.2 to 4.0% by mass, based on the total solid contents of the composition.

The molar ratio of the basic compound to the photo-acid generator is preferably from 0.01 to 10, more preferably from 0.05 to 5, and still more preferably from 0.1 to 3. When this molar ratio is excessively high, the sensitivity and/or resolution may decrease in some cases. When this molar ratio is excessively small, there is a possibility that tapering in the pattern occurs between the exposure and the heating (post-bake). The molar ratio is more preferably from 0.05 to 5, and still more preferably from 0.1 to 3. The photo-acid generator as used in the molar ratio is based on the total amount of the repeating unit (B) of the resin and the photo-acid generator which the resin may further contain.

Preferred examples of the basic compound include guanidine, aminopyridine, aminoalkylpyridine, aminopyrrolidine, indazole, imidazole, pyrazole, pyrazine, pyrimidine, purine, imidazoline, pyrazoline, piperazine, aminomorpholine, and aminoalkylmorpholine. These may further have a substituent.

Preferred examples of the substituent include an amino group, an aminoalkyl group, an alkylamino group, an aminoaryl group, an arylamino group, an alkyl group, an alkoxy group, an acyl group, an acyloxy group, an aryl group, an aryloxy group, a nitro group, a hydroxyl group, and a cyano group.

Particularly preferred examples of the basic compound include guanidine, 1,1-dimethyl guanidine, 1,1,3,3-tetramethyl guanidine, imidazole, 2-methylimidazole, 4-methylimidazole, N-methylimidazole, 2-phenylimidazole, 4,5-diphenylimidazole, 2,4,5-triphenylimidazole, 2-aminopyridine, 3-aminopyridine, 4-aminopyridine, 2-dimethylaminopyridine, 4-dimethylaminopyridine, 2-diethylaminopyridine, 2-(aminomethyl)pyridine, 2-amino-3-methylpyridine, 2-amino-4-methylpyridine, 2-amino-5-methylpyridine, 2-amino-6-methylpyridine, 3-aminoethylpyridine, 4-aminoethylpyridine, 3-aminopyrrolidine, piperazine, N-(2-aminoethyl)piperazine, N-(2-aminoethyl)piperidine, 4-amino-2,2,6,6-tetramethylpiperidine, 4-piperidinopiperidine, 2-iminopiperidine, 1-(2-aminoethyl) pyrrolidine, pyrazole, 3-amino-5-methylpyrazole, 5-amino-3-methyl-1-p-tolylpyrazole, pyrazine, 2-(aminomethyl)-5-methylpyrazine, pyrimidine, 2,4-diaminopyrimidine, 4,6-dihydroxypyrimidine, 2-pyrazoline, 3-pyrazoline, N-aminomorpholine and N-(2-aminoethyl) morpholine.

[6] Surfactant

The composition of the present invention may further contain a surfactant. The surfactant is particularly preferably a fluorine-based and/or silicon-based surfactant.

Examples of the fluorine-based and/or silicone-based surfactant include Megaface F176 or Megaface R08 manufactured by DIC Corporation, PF656 and PF6320 manufactured by OMNOVA SOLUTIONS, INC., Troy Sol S-366 manufactured by Troy Chemical Co., Ltd., Fluorad FC430 manufactured by Sumitomo 3M Ltd., and polysiloxane polymer KP-341 manufactured by Shin-Etsu Chemical Co., Ltd.

Surfactants other than these fluorine-based and/or silicone-based surfactants may also be used. Examples of such other surfactants include nonionic surfactants such as polyoxyethylene alkyl ethers and polyoxyethylene alkylaryl ethers.

Moreover, other generally known surfactants may also be appropriately used. Examples of the useful surfactants include those described in 0273 et seq. of US 2008/0248425 A1.

These surfactants may be used alone or in combination of two or more kinds thereof.

In the case where the composition according to the present invention further contains a surfactant, the amount of surfactant used is preferably in the range of 0.0001 to 2% by mass, and more preferably 0.001 to 1% by mass, based on the total solid contents of the composition.

[7] Dye

The composition according to the present invention may further include a dye. Examples of suitable dyes include oil dyes and basic dyes. Specific examples thereof include Oil Yellow #101, Oil Yellow #103, Oil Pink #312, Oil Green BG, Oil Blue BOS, Oil Blue #603, Oil Black BY, Oil Black BS and Oil Black T-505 (all manufactured by Orient Chemical Industries, Ltd.), Crystal Violet (CI42555), Methyl Violet (CI42535), Rhodamine B (CI45170B), Malachite Green (CI42000), and Methylene Blue (CI52015).

[8] Photo-Base Generator

The composition according to the present invention may further contain a photo-base generator. When a photo-base generator is contained, a more excellent pattern can be formed.

Examples of the photo-base generator include compounds described in JP1992-151156A (JP-H04-151156A), JP1992-162040A (JP-H04-162040A), JP1993-197148A (JP-H05-197148A), JP1993-5995A (JP-H05-5995), JP1994-194834A (JP-H06-194834), JP1996-146608A (JP-H08-146608A), and JP1998-83079 (JP-H10-83079A), and EP622,682B.

Specific preferred examples of the photo-base generator include 2-nitrobenzylcarbamate, 2,5-dinitrobenzylcyclohexylcarbamate, N-cyclohexyl-4-methylphenylsulfonamide, and 1,1-dimethyl-2-phenylethyl-N-isopropylcarbamate.

[9] Antioxidant

The composition according to the present invention may further contain an antioxidant. When an antioxidant is contained, the organic material can be prevented from oxidation in the presence of oxygen.

Examples of the antioxidant include a phenol-based antioxidant, an antioxidant composed of an organic acid derivative, a sulfur-containing antioxidant, a phosphorus-based antioxidant, an amine-based antioxidant, an antioxidant composed of an amine-aldehyde condensate, and an antioxidant composed of an amine-ketone condensate. Among these antioxidants, a phenol-based antioxidant or an antioxidant composed of an organic acid derivative is particularly preferably used. When such an antioxidant is used, the function as an antioxidant can be brought out without deteriorating the performance of the composition.

As the phenol-based antioxidant, for example, substituted phenols, and bis-, tris-, and poly-phenols may be used.

Examples of the substituted phenols include 1-oxy-3-methyl-4-isopropylbenzene, 2,6-di-tert-butylphenol, 2,6-di-tert-butyl-4-ethylphenol, 2,6-di-tert-butyl-4-methylphenol, 4-hydroxymethyl-2,6-di-tert-butylphenol, butylhydroxyanisole, 2-(1-methylcyclohexyl)-4,6-dimethylphenol, 2,4-dimethyl6-tert-butylphenol, 2-methyl-4,6-dinonylphenol, 2,6-di-tert-butyl-dimethylamino-p-cresol, 6-(4-hydroxy-3,5-di-tert-butylanilino)2,4-bis-octyl-thio-1,3,5 triazine, n-octadecyl-3-(4'-hydroxy-3',5'-di-tert-butylphenyl)propionate, octylated phenol, aralkyl-substituted phenols, alkylated-p-cresol, and hindered phenol.

Examples of the bis, tris or polyphenols include 4,4'-dihydroxydiphenly, methylenebis(dimethyl-4,6-phenol), 2,2'-methylene-bis-(4-methyl-6-tert-butylphenol), 2,2'-methylene-bis-(4-methyl-6-cyclohexylphenol), 2,2'-methylene-bis-(4-ethyl-6-tert-butylphenol), 4,4'-methylene-bis-(2,6-di-tert-butylphenol), 2,2'-methylene-bis-(6-α-methyl-benzyl-p-cresol), methylene-bridged polyalkyl phenol, 4,4'- butylidenebis-(3-methyl-6-tert-butylphenol), 1,1-bis-(4-hydroxyphenyl)-cyclohexane, 2,2'-dihydroxy-3,3"-di-(α-methylcyclohexyl)-5,5'-dimethyl diphenyl methane, alkylated bisphenol, hindered bisphenol, 1,3,5-trimethyl-2,4,6-tris(3,5-di-tert-butyl-4-hydroxybenzyl)benzene, tris-(2-methyl-4-hydroxy-5-tert-butylphenyl)butane, and tetrakis-[methylene-3-(3',5'-di-tert-butyl-4'-hydroxyphenyl)propionate]methane.

Preferred examples of the antioxidants include 2,6-di-t-butyl-4-methylphenol, 4-hydroxymethyl-2,6-di-t-butylphenol, 2,2'-methylene bis(4-methyl-6-t-butylphenol), butylhydroxyanisole, t-butylhydroquinone, 2,4,5-trihydroxybutyrophenone, nordihydroguaiaretic acid, propyl gallate, octyl gallate, lauryl gallate, and isopropyl citrate. Among these, 2,6-di-t-butyl-4-methylphenol, 4-hydroxymethyl-2,6-di-t-butylphenol, butylhydroxyanisole and t-butylhydroquinone are preferred, and 2,6-di-t-butyl-4-methylphenol and 4-hydroxymethyl-2,6-di-t-butylphenol are more preferred.

These antioxidants may be used alone or in combination of two or more kinds thereof.

In the case where the composition according to the present invention contains an antioxidant, the addition amount of antioxidant is preferably 1 ppm or more, more preferably 5 ppm or more, still more preferably 10 ppm or more, even still more preferably 50 ppm or more, particularly preferably 100 ppm or more, and most preferably 100 to 1,000 ppm.

[10] Solvent

The composition according to the present invention may further contain a solvent. As the solvent, an organic solvent is typically used. Examples of the organic solvent include alkylene glycol monoalkyl ether carboxylate, alkylene glycol monoalkyl ether, alkyl lactate, alkyl alkoxypropionate, cyclic lactone (preferably having 4 to 10 carbon atoms), a monoketone compound (preferably having 4 to 10 carbon atoms) which may contain a ring, alkylene carbonate, alkyl alkoxyacetate, and alkyl pyruvate.

Preferred examples of the alkylene glycol monoalkyl ether carboxylate include propylene glycol monomethyl ether acetate (PGMEA; also called 1-methoxy-2-acetoxypropane), propylene glycol monoethyl ether acetate, propylene glycol monopropyl ether acetate, propylene glycol monobutyl ether acetate, propylene glycol monomethyl ether propionate, propylene glycol monoethyl ether propionate, ethylene glycol monomethyl ether acetate, and ethylene glycol monoethyl ether acetate.

Examples of the alkylene glycol monoalkyl ether include propylene glycol monomethyl ether (PGME; also called 1-methoxy-2-propanol), propylene glycol monoethyl ether, propylene glycol monopropyl ether, propylene glycol monobutyl ether, ethylene glycol monomethyl ether, and ethylene glycol monoethyl ether.

Examples of the alkyl lactate include methyl lactate, ethyl lactate, propyl lactate, and butyl lactate.

Examples of the alkyl alkoxypropionate include ethyl 3-ethoxypropionate, methyl 3-methoxypropionate, methyl 3-ethoxypropionate, and ethyl 3-methoxypropionate.

Examples of the cyclic lactone include β-propiolactone, β-butyrolactone, γ-butyrolactone, α-methyl-γ-butyrolactone, β-methyl-γ-butyrolactone, γ-valerolactone, γ-caprolactone, γ-octanoic lactone, and α-hydroxy-γ-butyrolactone.

Examples of the monoketone compound which may contain a ring include 2-butanon, 3-methylbutanon, pinacolone, 2-pentanone, 3-pentanone, 3-methly-2-pentanone, 4-methly-2-pentanone, 2-methly-3-pentanone, 4,4-dimethly-2-pentanone, 2,4-dimethly-3-pentanone, 2,2,4,4-tetramethly-3-pentanone, 2-hexanone, 3-hexanone, 5-methly-3-hexanone, 2-heptanone, 3-heptanone, 4-heptanone, 2-methly-3-heptanone, 5-methly-3-heptanone, 2,6-dimethly-4-heptanone, 2-octanone, 3-octanone, 2-nonanone, 3-nonanone, 5-nonanone, 2-decanone, 3-decanone, 4-decanone, 5-hexen-2-one, 3-penten-2-one, cyclopentanone, 2-methlycyclopentanone, 3-methlycyclopentanone, 2,2-dimethlycyclopentanone, 2,4,4-trimethlycyclopentanone, cyclohexanone, 3-methlycyclohexanone, 4-methlycyclohexanone, 4-ethlycyclohexanone, 2,2-dimethlycyclohexanone, 2,6-dimethlycyclohexanone, 2,2,6-trimethlycyclohexanone, cycloheptanone, 2-methlycycloheptanone, and 3-methlycycloheptanone.

Examples of the alkylene carbonate include propylene carbonate, vinylene carbonate, ethylene carbonate, and butylene carbonate.

Examples of the alkyl alkoxyacetate include 2-methoxyethyl acetate, 2-ethoxyethyl acetate, 2-(2-ethoxyethoxy)ethyl acetate, 3-methoxy-3-methylbutyl acetate, and 1-methoxy-2-propyl acetate.

Examples of the alkyl pyruvate include methyl pyruvate, ethyl pyruvate, and propyl pyruvate.

As the solvent, a solvent having a boiling point of 130° C. or higher at ordinary temperature under atmospheric pressure is preferably used. Specific examples thereof include cyclopentanone, γ-butyrolactone, cyclohexanone, ethyl lactate, ethylene glycol monoethyl ether acetate, PGMEA, ethyl 3-ethoxypropionate, ethyl pyruvate, 2-ethoxyethyl acetate, 2-(2-ethoxyethoxy)ethyl acetate, and propylene carbonate.

These solvents may be used alone or in a mixture of two or more kinds thereof. In the latter case, a mixed solvent of a solvent containing a hydroxyl group and a solvent not containing a hydroxyl group are preferably used.

Examples of the solvent containing a hydroxyl group include ethylene glycol, ethylene glycol monomethyl ether, ethylene glycol monoethyl ether, propylene glycol, PGME, propylene glycol monoethyl ether, and ethyl lactate. Among these, PGME and ethyl lactate are particularly preferred.

Examples of the solvent not containing a hydroxyl group include PGMEA, ethyl ethoxypropionate, 2-heptanone, γ-butyrolactone, cyclohexanone, butyl acetate, N-methylpyrrolidone, N,N-dimethylacetamide and dimethylsulfoxide. Among these, propylene glycol monomethyl ether acetate, ethyl ethoxypropionate, 2-heptanone, γ-butyrolactone, cyclohexanone and butyl acetate are preferred. Among these, PGMEA, ethyl ethoxypropionate and 2-heptanone are particularly preferred.

In the case of using a mixed solvent of a solvent containing a hydroxyl group and a solvent not containing a hydroxyl group, the mass ratio therebetween is preferably from 1/99 to 99/1, more preferably from 10/90 to 90/10, and still more preferably from 20/80 to 60/40.

Incidentally, when a mixed solvent containing 50% by mass or more of a hydroxyl group-free solvent is used, particularly excellent coating uniformity can be achieved. Incidentally, the solvent is particularly preferably a mixed solvent of PGMEA and one or more kinds of other solvents.

The content of the solvent in the composition of the present invention may be appropriately adjusted according to the desired film thickness or the like, but the composition is usually prepared such that the entire solid content concentration of the composition becomes from 0.5 to 30% by mass, preferably from 1.0 to 20% by mass, and more preferably from 1.5 to 10% by mass.

<Pattern Forming Method>

The present invention relates to an actinic ray-sensitive or radiation-sensitive film formed using the above-described composition of the present invention. In addition, a pattern forming method in the present invention, containing (a) forming a film including a composition, (b) irradiating the film with actinic rays or radiation (that is, exposing), and (c) developing the irradiated film with actinic rays or radiation.

The composition according to the present invention is typically used as follows. That is, the composition according to the present invention is typically coated on a support such as substrate to form a film. The thickness of the film is preferably from 0.02 to 0.1 μm. The method for coating the composition on a substrate is preferably spin coating, and the revolution speed is preferably from 1,000 to 3,000 rpm.

For example, the composition is coated on such a substrate (for example, a silicon/silicon dioxide-coated substrate, and a silicon nitride and chromium-deposited quartz substrate) as used in the production of a precision integrated circuit device, an imprint mold or the like, by using a spinner, a coater, or the like. Thereafter, the coating is dried to obtain actinic ray-sensitive or radiation-sensitive film (hereinafter also referred to as a resist film). Incidentally, a known antireflection film may also be previously provided by coating.

Next, the actinic ray-sensitive or radiation-sensitive film described above is irradiated with actinic rays or radiation and is developed preferably after baking is performed (normally at 80 to 150° C. and more preferably at 90 to 130° C.). By performing baking, a more excellent pattern can be obtained.

Examples of the actinic ray or radiation include infrared light, visible light, ultraviolet light, far ultraviolet light, X ray and electron beam. An actinic ray or radiation having, for example, a wavelength of 250 nm or less, particularly 220 nm or less, is preferred. Examples of such actinic rays or radiation include KrF excimer laser (248 nm), ArF excimer laser (193 nm), F2 excimer laser (157 nm), X ray, and electron beam. Preferred examples of the actinic ray or radiation include KrF excimer laser, electron beam, X ray, and EUV light. Electron beam, X ray, and EUV light are more preferable.

That is, the present invention also relates to actinic ray-sensitive or radiation-sensitive resin composition for KrF excimer laser, electron beam, X ray or EUV light (preferably electron beam, X ray, or EUV light).

A developer used in the developing may be a developer containing an organic solvent as a main component (hereinafter, also referred to as an "organic-based developer") or may be an alkali developer. In a case where the composition in the present invention is used for a formation of the negative-tone pattern to develop using an organic-based developer, for example, the process disclosed in JP2010-217884A can be used.

In a case where the pattern forming method of the present invention includes developing using an alkali developer, as the alkali developer, for example, an aqueous alkaline solution including inorganic alkalis such as sodium hydroxide, potassium hydroxide, sodium carbonate, sodium silicate, sodium metasilicate, and aqueous ammonia; primary amines such as ethylamine and n-propylamine; secondary amines such as diethylamine and di-n-butylamine; tertiary amines such as triethylamine and methyl diethylamine; alcoholamines such as dimethylethanolamine and triethanolamine; quaternary ammonium salts such as tetramethyl ammonium hydroxide and tetraethyl ammonium hydroxide; and cyclic amines such as pyrrole and piperidine may be included.

Furthermore, an appropriate amount of alcohols and/or a surfactant may be added to the alkali developer.

The concentration of the alkali developer is usually from 0.1 to 20% by mass. pH of the alkali developer is generally 10.0 to 14.0.

As a rinsing liquid used in rinsing treatment performed after alkali development, pure water is used, and a surfactant may be added thereto in an appropriate amount for use.

In addition, after the development treatment or rinsing treatment, treatment for removing the developer or rinsing liquid attached onto the pattern by using supercritical fluid can be performed.

In a case where a pattern forming method in the present invention includes developing using a developer containing an organic solvent, as an organic-based developer, a polar solvent such as an ester-based solvent (butyl acetate, ethyl acetate, or the like), a ketone-based solvent (2-heptanone, cyclohexanone, or the like), an alcohol-based solvent, an amide-based solvent, or an ether-based solvent and a hydrocarbon-based solvent may be used. A plurality of the solvents above may be mixed or a mixture of the solvent and a solvent other than the solvents above or water may be used. However, the moisture content in the whole organic-based developer is preferably less than 10% by mass, and it is more preferable that the developer substantially do not contain moisture.

A surfactant can be optionally added to the organic-based developer in an appropriate amount. The amount of the surfactant used is generally 0.001 to 5% by mass, preferably 0.005 to 2% by mass, and even more preferably 0.01 to 0.5% by mass, based on the total amount of the developer.

After the developing using a developer containing an organic solvent, washing with a rinsing liquid may be included, however, in view of throughput (productivity), the amount of a rinsing liquid used, or the like, washing is not preferably included using a rinsing liquid.

The rinsing liquid used in rinsing which is performed after the developing using a developer which contains an organic solvent is not particularly limited as long as the rinsing liquid does not dissolve the resist pattern, and a solution containing a general organic solvent can be used as the rinsing liquid. As the rinsing liquid, it is preferable to use a rinsing liquid containing at least one kind of organic solvent selected from a group consisting of a hydrocarbon-based solvent, a ketone-based solvent, an ester-based solvent, an alcohol-based solvent, an amide-based solvent and an ether-based solvent. The rinsing liquid to which a surfactant has been added in an appropriate amount can also be used.

The present invention also relates to a semiconductor device produced by process including the pattern forming method of the present invention as described above. The semiconductor device of the present invention may be suitably mounted on an electric/electronic device (domestic appliances, OA•media-related devices, optical devices, communication devices and the like).

Here, for the details of a case where an imprint mold structure is manufactured by using the composition according to the present invention, for example, reference may be made to JP4109085B, JP2008-162101A, "Science and New Technology in Nanoimprint", edited by Yoshihiko Hirai, Frontier Publishing,

EXAMPLES

Below, the present invention will be described in further detail with reference to Examples, but the contents of the present invention are not limited thereto.

<Nitrogen-Containing Compound (N)>

Benzimidazole can be obtained from Tokyo Chemical Industry Co., Ltd., Aldrich, Wako Pure Chemical Industries Ltd., or the like. In addition, the desired benzimidazole as a starting material is easily synthesized using a method disclosed in Bioorganic and Medicinal Chemistry Letters, 2008, vol. 18, #5, p 1573-1576, Journal of Organic Chemistry, 2008, vol. 73, #10, p 3848-3853, or the like.

Synthesis Example 1

Synthesis of Compound (AM-24)

A compound (AM-24) was synthesized in accordance with to the following scheme.

[Chem. 61]

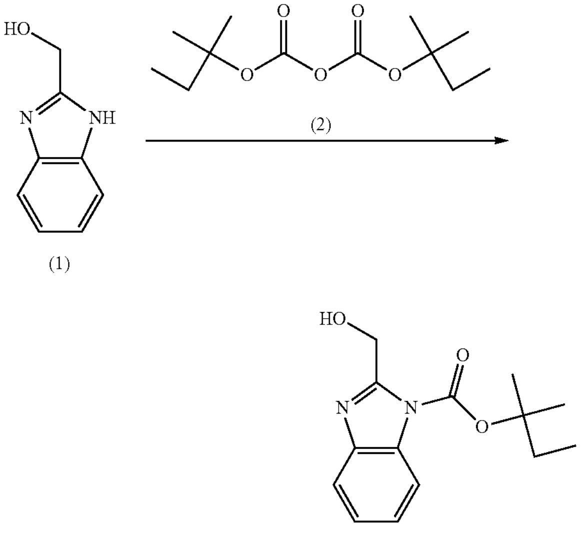

(1) (2) (AM-xx)

After dissolving 5.00 g of a compound (1) in 20.00 g of tetrahydrofuran, the mixture was cooled to 0° C. 8.73 g of a compound (2) was added dropwise thereto and the mixture was stirred at room temperature for 10 hours. After 300 g of ethyl acetate was added to the obtained reaction solution and an organic layer was washed for 3 times with 100 g of an aqueous solution of saturated ammonium chloride, the organic layer was further washed with 100 g of ion-exchange water for three times. Thereafter, the organic layer was dried with anhydrous magnesium sulfate and next, a solvent was distillated. The obtained residue was isolated and purified using a column chromatography and 7.81 g of a compound (AM-24) was obtained.

$^1$H-NMR (ppm, $CDCl_3$): 1.03 (3H, t), 1.70 (6H, s), 2.10 (2H, q), 4.23 (1H, t), 4.99 (2H, d), 7.32-7.39 (2H, m), 7.65-7.67 (1H, m), 7.97-7.99 (1H, m).

[Other Nitrogen-Containing Compound]

As a nitrogen-containing compound (N) other than the above-described compound (AM-24), from among nitrogen-containing compounds (AM-1) to (AM-54) described before, the compounds represented in Tables 3 to 6 were synthesized in the same method of the synthesis example 1 as above to use.

Resin (Ab)

Synthesis Example 2

Synthesis of Resin (Ab-14)

A resin (Ab-14) was synthesized in the same method as the synthesis method of a polymer (B-2) disclosed in a paragraph 0153 of JP2007-052193A.

Synthesis Example 3

Synthesis of Resin (Ab-97)

A resin (Ab-97) was synthesized in the same method of a polymer (A-1) disclosed in a paragraph 0357 of JP2009-86358A.

Synthesis Example 4

Synthesis of Resin (Ab-245)

The resin (Ab-245) was synthesized in accordance with the following scheme.

[Chem. 62]

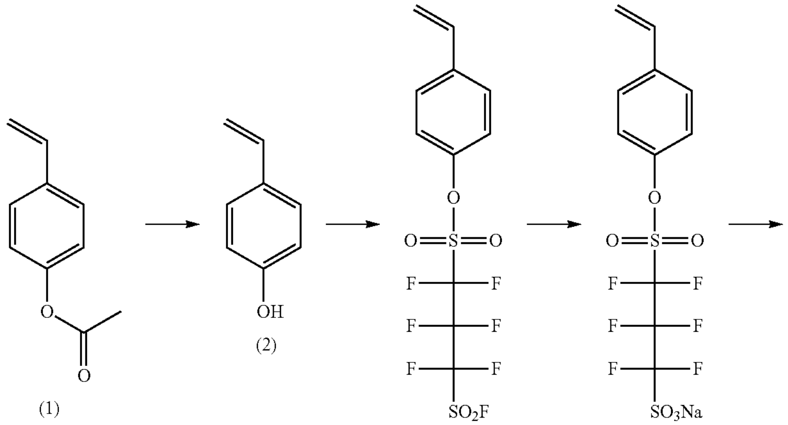

(1) (2) (3) (4)

-continued

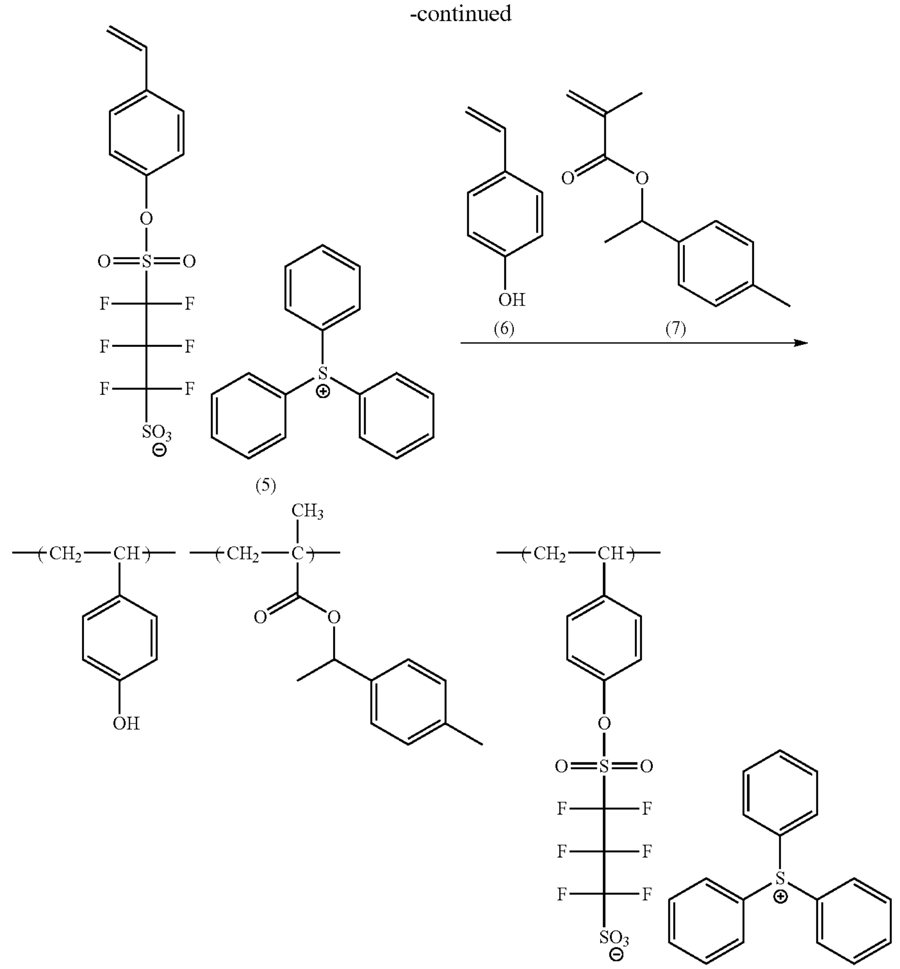

(5)

(6)

(7)

P-42

(Synthesis of Compound (5))

100.00 g of the compound (1) was dissolved in 400 g of ethyl acetate. The obtained solution was cooled to 0° C., and 47.60 g of sodium methoxide (28% by-mass methanol solution) was added dropwise thereto over 30 minutes. Thereafter, the mixture was stirred at room temperature over 5 hours. After ethyl acetate was added to the obtained reaction solution and an organic layer was washed for 3 times with distilled water, the organic layer was dried with anhydrous sodium sulfate and next, a solvent was distillated. In this way, 131.70 g of a compound (2) (54% by mass ethyl acetate solution) was obtained.

56.00 g of ethyl acetate was added to 18.52 g of the compound (2) (54% by mass ethyl acetate solution). 31.58 g of 1,1,2,2,3,3-hexafluoropropane-1,3-disulfonyl difluoride was added thereto, followed by cooling to 0° C. A solution in which 12.63 g of triethylamine was dissolved in 25.00 g of ethyl acetate, was added dropwise to obtained reaction solution over 30 minutes and the mixture was stirred over 4 hours with a solution temperature being maintained at 0° C. After ethyl acetate was added thereto and an organic layer was washed for three times with saturated saline solution, the organic layer was dried with anhydrous sodium sulfate and next, a solvent was distillated. In this way, 32.90 g of a compound (3) was obtained.

245 g of 1N sodium hydroxide aqueous solution was added to a reaction solution which is obtained by 35.00 g of a compound (3) being dissolved in 315 g of methanol and being cooled to 0° C. and the mixture was stirred for 2 hours at room temperature. After a solvent was distillated from the obtained reaction solution, ethyl acetate was added thereto, and after an organic layer was washed with saturated saline solution for three times, the organic layer was dried with anhydrous sodium sulfate and next a solvent was distillated. In this way, 34.46 g of a compound (4) was obtained.

28.25 g of the compound (4) was dissolved in 254.25 g of methanol, 23.34 g of triphenylsulfonium bromide was added thereto and the mixture was stirred at room temperature for 3 hours. After a solvent was distillated from the obtained reaction solution, distilled water was added and an object was extracted from a water layer using chloroform for three times. The obtained organic layer was washed with distilled water for three times, and then the solvent was removed by distillation. In this way, 42.07 g of a compound (5) was obtained.

(Synthesis of Resin (Ab-245))

8.15 g of a compound (6) (53.1% by mass propylene glycol monomethyl ether solution), 6.14 g of a compound (7), 7.31 g of the compound (5) and 2.07 g of a polymerization initiator V-601 (manufactured by Wako Pure Chemical Industries, Ltd.) were dissolved in 30.13 g of propylene glycol monomethyl ether (PGME) to prepare a solution. 7.53 g of PGME was put into a reaction vessel under a nitrogen gas atmosphere and the above-described solution was added dropwise over 2 hours into in a system at 85° C. After the obtained reaction solution was heated and stirred over 4 hours, the mixture left to be cooled to room temperature.

The reaction solution was diluted by the addition of 30 g of acetone. The diluted solution was added dropwise to 1,000 g of hexane/ethyl acetate=8/2, and the polymer was precipitated and filtered. 250 g of hexane/ethyl acetate=8/2 was used and poured into the filtered solid for washing. The obtained solid was dissolved in 70 g of acetone, and the solution was added dropwise to 700 g of methanol/distilled water=1/9 to precipitate a polymer, followed by filtration. 150 g of methanol/distilled water=1/9 was used and poured into the filtered solid for washing. Thereafter, the washed solid was provided to be dried under reduced pressure to obtain 13.87 g of a resin Ab-245.

[Other Resin (Ab)]

As a resin (Ab) other than the above-described resins (Ab-14), (Ab-97) and (Ab-245), from among resins (Ab-1) to (Ab-311) described before, each resin represented in Table 2 was synthesized in the same method as a method described in synthesis examples 2 to 4.

With respect to the resins (Ab) synthesized above, the weight average molecular weight and the dispersity were measured using GPC (manufactured by Tosoh Corp., HLC-8120; Tsk gel Multipore HXL-M). The results with the compositional ratio are shown in the following Table 2. Further, in this GPC measurement, THF was used as the solvent. A positional relation of each repeating unit in each resin shown in specific examples corresponds to a positional relation of the number of the compositional ratio in Table 2.

TABLE 2

| | Weight average molecular weight | Compositional ratio | | | | | Dispersity |
|---|---|---|---|---|---|---|---|
| Ab-14 | 3,000 | 70 | 30 | — | — | — | 1.10 |
| Ab-17 | 12,000 | 10 | 65 | 25 | — | — | 1.12 |
| Ab-97 | 18,000 | 50 | 40 | 10 | — | — | 1.61 |
| Ab-120 | 7,000 | 60 | 40 | — | — | — | 1.45 |
| Ab-143 | 8,500 | 40 | 15 | 20 | 25 | — | 1.69 |
| Ab-167 | 3,500 | 55 | 45 | — | — | — | 1.12 |
| Ab-173 | 4,000 | 60 | 40 | — | — | — | 1.15 |
| Ab-178 | 24,000 | 50 | 35 | 15 | — | — | 1.65 |
| Ab-232 | 10,000 | 45 | 10 | 35 | 10 | — | 1.55 |
| Ab-233 | 11,000 | 10 | 35 | 10 | 35 | 10 | 1.53 |
| Ab-234 | 10,000 | 10 | 35 | 10 | 35 | 10 | 1.56 |
| Ab-238 | 5,000 | 45 | 25 | 5 | 25 | — | 1.73 |
| Ab-240 | 20,000 | 55 | 40 | 5 | — | — | 1.50 |
| Ab-245 | 9,000 | 40 | 48 | 12 | — | — | 1.38 |
| Ab-269 | 3,500 | 65 | 35 | — | — | — | 1.13 |
| Ab-275 | 5,000 | 70 | 30 | — | — | — | 1.14 |
| Ab-277 | 4,000 | 75 | 25 | — | — | — | 1.11 |
| Ab-281 | 12,000 | 30 | 10 | 60 | — | — | 1.55 |
| Ab-282 | 15,000 | 45 | 55 | — | — | — | 1.58 |
| Ab-283 | 9,000 | 20 | 5 | 75 | — | — | 1.60 |
| Ab-284 | 3,000 | 60 | 40 | — | — | — | 1.15 |
| Ab-289 | 11,000 | 55 | 45 | — | — | — | 1.58 |
| Ab-291 | 10,000 | 55 | 45 | — | — | — | 1.55 |
| Ab-292 | 7,000 | 60 | 40 | — | — | — | 1.52 |

<Resin (Aa)>

As a resin (Aa), from among resins (Aa-1) to (Aa-55) described before, (Aa-1), (Aa-16), (Aa-29) and (Aa-52) represented in Table 3 to Table 6 were used.

<Photo-Acid Generator>

As a photo-acid generator, from among compounds (B-1) to (B-183), (Y-1) to (Y-75) and (z128) to (z139) described before, the compounds represented in Table 3 to Table 6 were used.

<Basic Compound>

As basic compounds other than a nitrogen-containing compound (N) in the present invention, any of the following (N-1) to (N-6) were used.

[Chem. 63]

(N-1)

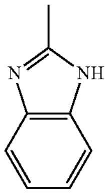

(N-2)

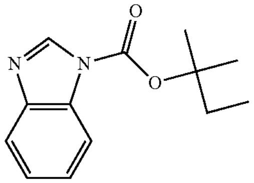

(N-3)

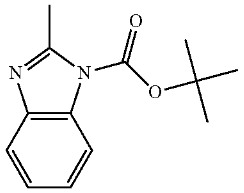

(N-4)

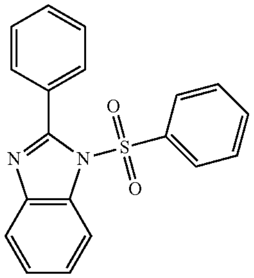

(N-5)

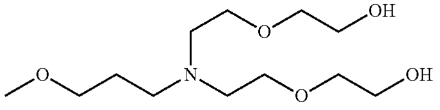

(N-6)

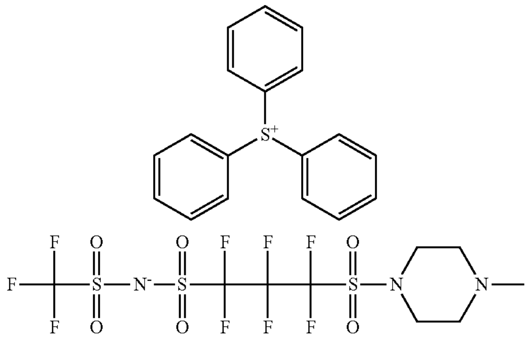

<Surfactant>

As a surfactant, any of the following W-1 to W-4 were used.

W-1: Megaface R08 (manufactured by DIC CORPORATION; fluorine and silicon-based)

W-2: polysiloxane polymer KP-341 (manufactured by Shin-Etsu Chemical Co., Ltd; silicon-based)

W-3: Troysol S-366 (manufactured by Troy Chemical; fluorine-based)

W-4: PF6320 (manufactured by OMNOVA solution Inc.; fluorine-based)

<Solvent>

As solvents, any of the following S-1 to S-4 were appropriately mixed to use.

S-1: PGMEA (b.p.=146° C.).

S-2: PGME (b.p.=120° C.).

S-3: methyl lactate (b.p.=145° C.).

S-4: cyclohexanone (b.p.=157° C.).

<Developer>

G-1: butyl acetate

G-2: methyl amyl ketone (2-heptanone)

G-3: anisole

<Rinsing Liquid>

G-4: 4-methyl-2-pentanol

G-5: 1-hexanol

G-6: decane

<Resist Evaluation: EB Exposure/Alkali Development/Positive-Tone>

The respective components shown in Table 3 below were dissolved in the solvent shown in the same Tables to prepare a solution having a solid content concentration of 3.0% by mass. The solution was filtrated using a polytetrafluoroethylene filter having pore size of 0.1 μm to obtain a positive-tone resist solution.

The numerical value of "% by mass" shown in Table 3 is a value based on the entire solid content excluding the surfactant of the composition. Incidentally, the content of the surfactant is 0.01% by mass with respect to the entire solid content excluding the surfactant of the composition.

The positive-tone resist solution was applied on a silicon substrate where a hexamethyldisilazane treatment has been carried out, using a spin coater. The applied film was heated on a hotplate for 90 seconds at 110° C. to obtain a resist film with an average film thickness of 100 nm.

This resist film was irradiated with electron beam using an electron beam irradiation apparatus (HL750, manufactured by Hitachi, Ltd., accelerating voltage: 50 keV). Immediately after irradiation, the resist film was heated on a hotplate for 90 seconds at 130° C. After this, this resist film was developed for 60 seconds at 23° C. using a concentration of 2.38% by mass of an aqueous solution of tetramethylammonium hydroxide and was dried after being rinsed using pure water for 30 seconds. In this way, a line-and-space pattern (line: space=1:1) was formed.

<Resist Evaluation: EB Exposure/Organic Solvent Development/Negative-Tone>

The respective components shown in Table 4 below were dissolved in the solvent shown in the same Tables to prepare a solution having a solid content concentration of 3.0% by mass. This solution was finely filtered through a membrane filter having a pore size of 0.1 μm to obtain a resist solution.

The numerical value of "% by mass" shown in Table 4 is a value based on the entire solid content excluding the surfactant of the composition. Incidentally, the content of the surfactant is 0.01% by mass with respect to the entire solid content excluding the surfactant of the composition.

A pattern formation was carried out in the same manner as for the alkali development/positive pattern except that the development was carried out by means of an organic-based developer instead of the alkali developer while irradiating the inverted drawing area with an electron beam, the development was carried out for 30 seconds instead of 60 seconds, and an organic rinsing liquid was used instead of pure water as the rinsing liquid.

The sensitivity, the pattern shape and the resolution of the obtained a positive-tone pattern and a negative-tone pattern were evaluated using the evaluation method explained later.

[Sensitivity]

Firstly, the cross-sectional shape of a line and space pattern which has been obtained was observed by using a scanning electron microscope (S-4800 manufactured by Hitachi Ltd.). Then, the minimum irradiation energy when resolving a line with a line width of 100 nm was obtained and the value was set as "the sensitivity ($\mu C/cm^2$)".

[Pattern Shape]

The cross-sectional shape of the 100-nm line pattern (line: space=1:1) at the irradiation dose giving the sensitivity above was observed by using a scanning electron microscope (S-4800, manufactured by Hitachi, Ltd.). Then, the shape thereof was evaluated by "rectangular", "reverse taper" or "taper".

[Resolution]

In the sensitivity obtained above, a minimum nm at which resolution could be made with line:space=1:1 was observed by using a scanning electron microscope.

The evaluation results were shown in Table 3 and Table 4.

TABLE 3

(EB Exposure/Alkali Development/Positive-tone)

| | Resist composition | | | | | | Evaluation result | | |
|---|---|---|---|---|---|---|---|---|---|
| | Resin (Aa) | Resin (Ab) (63% by mass) | Solvent (mass ratio) | Photo-acid generator (35% by mass) | Basic compound (2% by mass) | Surfactant (0.01% by mass) | Sensitivity ($\mu C/cm^2$) | Pattern shape | Resolution (nm) |
| Example 1 | — | Ab-17 | S-4/S-3 (80/20) | B-110 | AM-49/N-5 (80/20) | W-3 | 15 | rectangular | 37.5 |
| *4Example 2 | — | Ab-178 | S-2 | B-122 | AM-32 | W-3 | 21 | rectangular | 50.0 |
| *4Example 3 | — | Ab-178 | S-2 | B-122 | AM-34 | W-3 | 24 | rectangular | 62.5 |
| *4Example 4 | — | Ab-178 | S-2 | B-122 | AM-40 | W-3 | 27 | rectangular | 75.0 |
| *3Example 5 | Aa-16 | Ab-240 | S-2/S-3 (80/20) | — | AM-4 | W-4 | 22 | rectangular | 62.5 |
| *3Example 6 | Aa-16 | Ab-240 | S-2/S-3 (80/20) | — | AM-5 | W-4 | 21 | rectangular | 62.5 |
| *3Example 7 | Aa-16 | Ab-240 | S-2/S-3 (80/20) | — | AM-6 | W-4 | 22 | rectangular | 62.5 |
| *3Example 8 | Aa-16 | Ab-240 | S-2/S-3 (80/20) | — | AM-7 | W-4 | 23 | rectangular | 62.5 |

TABLE 3-continued

| (EB Exposure/Alkali Development/Positive-tone) | | | | | | | | | |
|---|---|---|---|---|---|---|---|---|---|
| | Resist composition | | | | | | Evaluation result | | |
| | Resin (Aa) | Resin (Ab) (63% by mass) | Solvent (mass ratio) | Photo-acid generator (35% by mass) | Basic compound (2% by mass) | Surfactant (0.01% by mass) | Sensitivity ($\mu C/cm^2$) | Pattern shape | Resolution (nm) |
| *3Example 9 | Aa-16 | Ab-240 | S-2/S-3 (80/20) | — | AM-8 | W-4 | 23 | rectangular | 62.5 |
| *3Example 10 | Aa-16 | Ab-240 | S-2/S-3 (80/20) | — | AM-3 | W-4 | 28 | rectangular | 75.0 |
| *3Example 11 | Aa-16 | Ab-240 | S-2/S-3 (80/20) | — | AM-1 | W-4 | 32 | rectangular | 87.5 |
| *3Example 12 | Aa-16 | Ab-240 | S-2/S-3 (80/20) | — | AM-53 | W-4 | 35 | rectangular | 100.0 |
| *1Example 13 | Aa-29 | Ab-173 | S-1/S-2 (70/30) | B-123 | AM-23 | W-4 | 10 | rectangular | 25.0 |
| *1Example 14 | Aa-29 | Ab-173 | S-1/S-2 (70/30) | B-123 | AM-26 | W-4 | 13 | rectangular | 37.5 |
| Example 15 | — | Ab-14 | S-1/S-2 (80/20) | B-119 | AM-24 | W-4 | 11 | rectangular | 25.0 |
| Example 16 | — | Ab-14 | S-1/S-2 (80/20) | B-119 | AM-30 | W-4 | 16 | rectangular | 37.5 |
| Example 17 | — | Ab-14 | S-1/S-2 (80/20) | B-119 | AM-38 | W-4 | 20 | rectangular | 50.0 |
| *2Example 18 | — | Ab-232 | S-2/S-4 (70/30) | — | AM-42 | W-2 | 21 | rectangular | 62.5 |
| *2Example 19 | — | Ab-233 | S-2/S-4 (70/30) | — | AM-42 | W-2 | 18 | rectangular | 50.0 |
| *2Example 20 | — | Ab-234 | S-2/S-4 (70/30) | — | AM-42 | W-2 | 14 | rectangular | 37.5 |
| *2Example 21 | — | Ab-245 | S-2/S-1 (90/10) | — | AM-43 | W-1 | 15 | rectangular | 37.5 |
| *2Example 22 | — | Ab-245 | S-2/S-1 (90/10) | — | AM-48 | W-1 | 20 | rectangular | 50.0 |
| *2Example 23 | — | Ab-245 | S-2/S-1 (90/10) | — | AM-50 | W-1 | 24 | rectangular | 62.5 |
| *2Example 24 | — | Ab-245 | S-2/S-1 (90/10) | — | AM-29 | W-1 | 24 | rectangular | 75.0 |
| Example 25 | — | Ab-143 | S-4/S-1 (90/10) | B-118 | AM-28 | W-3 | 17 | rectangular | 50.0 |
| Example 26 | — | Ab-143 | S-4/S-1 (90/10) | B-118 | AM-33 | W-3 | 28 | rectangular | 75.0 |
| Example 27 | — | Ab-143 | S-4/S-1 (90/10) | B-118 | AM-44 | W-3 | 33 | rectangular | 87.5 |
| Example 28 | — | Ab-143 | S-4/S-1 (90/10) | B-118 | AM-54 | W-3 | 35 | rectangular | 100.0 |
| *1Example 29 | Aa-52 | Ab-120 | S-3/S-2 (90/10) | Y-70 | AM-25 | W-2 | 12 | rectangular | 25.0 |
| Example 30 | — | Ab-97 | S-1/S-2 (90/10) | B-149 | AM-36 | W-4 | 13 | rectangular | 25.0 |
| Example 31 | — | Ab-167 | S-1/S-4 (80/20) | Y-61 | AM-22 | W-3 | 22 | rectangular | 50.0 |
| Example 32 | — | Ab-167 | S-1/S-4 (80/20) | Y-61 | AM-27 | W-3 | 26 | rectangular | 62.5 |
| *2Example 33 | — | Ab-238 | S-3/S-4 (80/20) | — | AM-39/N-6 (50/50) | W-3 | 12 | rectangular | 25.0 |
| Example 34 | — | Ab-269 (78) | S-1/S-2 (90/10) | B-182 (20) | AM-24 | W-2 | 17 | rectangular | 37.5 |
| Example 35 | — | Ab-284 (58) | S-1/S-2 (70/30) | B-182 (40) | AM-43 | W-1 | 15 | rectangular | 37.5 |
| Example 36 | — | Ab-275 (68) | S-1/S-2 (70/30) | B-182 (30) | AM-36 | W-4 | 20 | rectangular | 37.5 |
| Example 37 | — | Ab-277 (73) | S-1/S-2 (60/40) | B-182 (25) | AM-27 | W-3 | 22 | rectangular | 50.0 |
| Example 38 | — | Ab-289 (88) | S-1/S-2 (80/20) | z132 (10) | AM-48 | W-4 | 21 | rectangular | 50.0 |
| Example 39 | — | Ab-291 (78) | S-1/S-2 (90/10) | z128 (20) | AM-22 | W-4 | 25 | rectangular | 62.5 |
| Example 40 | — | Ab-292 (68) | S-1/S-2 (50/50) | z130 (30) | AM-24 | W-3 | 27 | rectangular | 75.0 |
| Example 41 | — | Ab-281 (83) | S-1/S-2 (80/20) | B-121 (15) | AM-43 | W-4 | 24 | rectangular | 50.0 |
| Example 42 | — | Ab-282 (63) | S-1/S-2 (50/50) | B-181 (35) | AM-25 | W-3 | 18 | rectangular | 62.5 |
| Example 43 | — | Ab-283 (78) | S-1/S-2 (60/40) | B-180 (20) | AM-50 | W-4 | 21 | rectangular | 50.0 |

TABLE 3-continued (EB Exposure/Alkali Development/Positive-tone)

| | Resist composition | | | | | | Evaluation result | | |
|---|---|---|---|---|---|---|---|---|---|
| | Resin (Aa) | Resin (Ab) (63% by mass) | Solvent (mass ratio) | Photo-acid generator (35% by mass) | Basic compound (2% by mass) | Surfactant (0.01% by mass) | Sensitivity (μC/cm²) | Pattern shape | Resolution (nm) |
| Comparative Example 1 | — | Ab-97 | S-1/S-2 (90/10) | B-149 | N-2 | W-4 | 40 | reverse taper | 125.0 |
| *[3]Comparative Example 2 | Aa-16 | Ab-240 | S-2/S-3 (80/20) | — | N-1 | W-4 | 38 | reverse taper | 125.0 |
| Comparative Example 3 | — | Ab-17 | S-4/S-3 (80/20) | B-110 | N-5 | W-3 | 41 | reverse taper | 125.0 |
| *[1]Comparative Example 4 | Aa-52 | Ab-120 | S-3/S-2 (90/10) | Y-70 | N-3 | W-2 | 39 | reverse taper | 125.0 |
| Comparative Example 5 | — | Ab-167 | S-1/S-4 (80/20) | Y-61 | N-4 | W-3 | 40 | reverse taper | 125.0 |

*[1]In Examples 13, 14 and 29 and a comparative example 4, the resist compositions were prepared by containing 5% by mass of a resin (Aa) and 58% by mass of a resin (Ab).
*[2]In Examples 18 to 24 and 33, the resist compositions were prepared by containing 98% by mass of a resin (Ab).
*[3]In Examples 5 to 12 and a comparative example 2, the resist compositions were prepared by containing 5% by mass of a resin (Aa) and 93% by mass of a resin (Ab).
*[4]In Examples 2 to 4, the resist compositions were prepared by containing 88% by mass of a resin (Ab) and 10% by mass of a photo-acid generator.

TABLE 4

(EB Exposure/Organic Solvent Development/Negative-tone)

| | Resist composition | | | | | | | | Evaluation result | | |
|---|---|---|---|---|---|---|---|---|---|---|---|
| | Resin (Aa) (% by mass) | Resin (Ab) (63% by mass) | Solvent (mass ratio) | Photo-acid generator (% by mass) | Basic compound (2% by mass) | Surfactant (0.01% by mass) | Developer | Rinsing liquid | Sensitivity (μC/cm²) | Pattern shape | Resolution (nm) |
| Example 44 | — | Ab-178 (88) | S-2 | B-122 (10) | AM-24 | W-3 | G-1 | G-6 | 15 | rectangular | 62.5 |
| Example 45 | — | Ab-245 (98) | S-2/S-1 (90/10) | — | AM-36 | W-1 | G-1 | — | 20 | rectangular | 75.0 |
| Example 46 | — | Ab-143 (63) | S-4/S-1 (90/10) | B-118 (35) | AM-48 | W-3 | G-1 | G-5 | 19 | rectangular | 62.5 |
| Example 47 | — | Ab-97 (63) | S-1/S-2 (90/10) | z130 (35) | AM-27 | W-4 | G-3 | — | 27 | rectangular | 87.5 |
| Example 48 | — | Ab-281 (83) | S-1/S-2 (80/20) | B-121 (15) | AM-43 | W-4 | G-1 | — | 25 | rectangular | 62.5 |
| Example 49 | — | Ab-282 (63) | S-1/S-2 (50/50) | B-181 (35) | AM-25 | W-3 | G-1 | G-4 | 19 | rectangular | 62.5 |
| Example 50 | Aa-1 (10) | Ab-283 (68) | S-1/S-2 (60/40) | B-180 (20) | AM-50 | W-4 | G-2 | — | 23 | rectangular | 62.5 |
| Comparative Example 6 | — | Ab-97 (63) | S-1/S-2 (90/10) | z130 (35) | N-4 | W-4 | G-3 | — | 36 | taper | 125.0 |
| Comparative Example 7 | — | Ab-245 (98) | S-2/S-1 (90/10) | — | N-2 | W-1 | G-1 | — | 34 | taper | 125.0 |

<Resist Evaluation: EUV Exposure/Alkali Development/Positive-Tone>

The respective components shown in Table 5 below were dissolved in the solvent shown in the same Tables to prepare a solution having a solid content concentration of 1.5% by mass. The solution was filtrated using a polytetrafluoroethylene filter having pore size of 0.1 μm to obtain a positive-tone resist solution.

The numerical value of "% by mass" shown in Table 5 is a value based on the entire solid content excluding the surfactant of the composition. Incidentally, the content of the surfactant is 0.01% by mass with respect to the entire solid content excluding the surfactant of the composition.

The positive-tone resist solution was applied on a silicon substrate where a hexamethyldisilazane treatment has been carried out, using a spin coater. The applied film was heated and dried on a hotplate for 90 seconds at 120° C. to obtain a resist film with an average film thickness of 50 nm.

This resist film was irradiated with EUV light using an EUV exposure apparatus. Immediately after irradiation, the resist film was heated on a hotplate for 90 seconds at 130° C. After this, this resist film was developed for 60 seconds at 23° C. using a concentration of 2.38% by mass of an aqueous solution of tetramethylammonium hydroxide and was dried after being rinsed using pure water for 30 seconds. In this way, a line-and-space pattern (line:space=1:1) was formed.

<Resist Evaluation: EUV Exposure/Organic Solvent Development/Negative-Tone>

The respective components shown in Table 6 below were dissolved in the solvent shown in the same Tables to prepare a solution having a solid content concentration of 1.5% by mass. This solution was finely filtered through a membrane filter having a pore size of 0.05 μm to obtain a resist solution.

The numerical value of "% by mass" shown in Table 6 is a value based on the entire solid content excluding the surfactant of the composition. Incidentally, the content of the surfactant is 0.01% by mass with respect with the entire solid content excluding the surfactant of the composition.

A pattern formation was carried out in the same manner as for the alkali development/positive pattern except that the development was carried out by means of an organic developer instead of the alkali developer using an exposing mask that inverted the pattern of the exposed mask, the development was carried out for 30 seconds instead of 60 seconds, and an organic rinsing liquid was used instead of pure water as the rinsing liquid.

For each of the obtained positive-tone pattern and the negative-tone pattern, the sensitivity, the pattern shape, the resolution, and DOF were evaluated by the evaluation methods described below.

[Sensitivity]

Firstly the cross-sectional shape of a line and space pattern which has been obtained was observed by using a scanning electron microscope (S-4800 manufactured by Hitachi Ltd.). Then, the minimum irradiation energy when resolving a line with a line width of 50 nm was obtained and the value was set as "the sensitivity ($mJ/cm^2$)".

[Pattern Shape]

The cross-sectional shape of the 100 nm line pattern (line: space=1:1) at the irradiation dose giving the sensitivity above was observed by using a scanning electron microscope (S-4800, manufactured by Hitachi, Ltd.). Then, the shape thereof was evaluated in two stages of "rectangular" and "taper".

[Resolution]

In the sensitivity obtained above, a minimum nm at which resolution could be made with line:space=1:1 was observed by using a scanning electron microscope.

[Defocus Latitude (DOF)]

For a 50 nm line pattern (line:space=1:1), a 50 nm isolated line (line:space=1:10), and a 50 nm isolated trench pattern, an acceptable range of focus variation was determined and a common focus variation width (μm) acceptable in all was determined.

The evaluation results were shown in Table 5 and Table 6.

TABLE 5

(EUV Exposure/Alkali Development/Positive-tone)

| | Resist composition | | | | | | Evaluation result | | | |
|---|---|---|---|---|---|---|---|---|---|---|
| | Resin (Aa) | Resin (Ab) (% by mass) | Solvent (mass ratio) | Photo-acid generator (35% by mass) | Basic compound (2% by mass) | Surfactant (0.01% by mass) | Sensitivity ($mJ/cm^2$) | Pattern shape | Resolution (nm) | DOF (μm) |
| Example 1 | — | Ab-17 | S-4/S-3 (80/20) | B-110 | AM-49/N-5 (80/20) | W-3 | 14 | rectangular | 28.0 | 0.25 |
| *[4]Example 2 | — | Ab-178 | S-2 | B-122 | AM-32 | W-3 | 19 | rectangular | 32.0 | 0.25 |
| *[4]Example 3 | — | Ab-178 | S-2 | B-122 | AM-34 | W-3 | 23 | rectangular | 34.0 | 0.20 |
| *[4]Example 4 | — | Ab-178 | S-2 | B-122 | AM-40 | W-3 | 26 | rectangular | 36.0 | 0.15 |
| *[3]Example 5 | Aa-16 | Ab-240 | S-2/S-3 (80/20) | — | AM-4 | W-4 | 22 | rectangular | 34.0 | 0.25 |
| *[3]Example 6 | Aa-16 | Ab-240 | S-2/S-3 (80/20) | — | AM-5 | W-4 | 21 | rectangular | 34.0 | 0.25 |
| *[3]Example 7 | Aa-16 | Ab-240 | S-2/S-3 (80/20) | — | AM-6 | W-4 | 22 | rectangular | 34.0 | 0.25 |
| *[3]Example 8 | Aa-16 | Ab-240 | S-2/S-3 (80/20) | — | AM-7 | W-4 | 23 | rectangular | 34.0 | 0.25 |
| *[3]Example 9 | Aa-16 | Ab-240 | S-2/S-3 (80/20) | — | AM-8 | W-4 | 23 | rectangular | 34.0 | 0.25 |
| *[3]Example 10 | Aa-16 | Ab-240 | S-2/S-3 (80/20) | — | AM-3 | W-4 | 27 | rectangular | 36.0 | 0.20 |
| *[3]Example 11 | Aa-16 | Ab-240 | S-2/S-3 (80/20) | — | AM-1 | W-4 | 30 | rectangular | 38.0 | 0.15 |
| *[3]Example 12 | Aa-16 | Ab-240 | S-2/S-3 (80/20) | — | AM-53 | W-4 | 30 | rectangular | 40.0 | 0.10 |
| *[1]Example 13 | Aa-29 | Ab-173 | S-1/S-2 (70/30) | B-123 | AM-23 | W-4 | 8 | rectangular | 24.0 | 0.30 |
| *[1]Example 14 | Aa-29 | Ab-173 | S-1/S-2 (70/30) | B-123 | AM-26 | W-4 | 12 | rectangular | 26.0 | 0.25 |
| Example 15 | — | Ab-14 | S-1/S-2 (80/20) | B-119 | AM-24 | W-4 | 9 | rectangular | 26.0 | 0.30 |
| Example 16 | — | Ab-14 | S-1/S-2 (80/20) | B-119 | AM-30 | W-4 | 14 | rectangular | 28.0 | 0.25 |
| Example 17 | — | Ab-14 | S-1/S-2 (80/20) | B-119 | AM-38 | W-4 | 18 | rectangular | 30.0 | 0.20 |
| *[2]Example 18 | — | Ab-232 | S-2/S-4 (70/30) | — | AM-42 | W-2 | 20 | rectangular | 32.0 | 0.15 |
| *[2]Example 19 | — | Ab-233 | S-2/S-4 (70/30) | — | AM-42 | W-2 | 16 | rectangular | 30.0 | 0.20 |
| *[2]Example 20 | — | Ab-234 | S-2/S-4 (70/30) | — | AM-42 | W-2 | 13 | rectangular | 28.0 | 0.25 |
| *[2]Example 21 | — | Ab-245 | S-2/S-1 (90/10) | — | AM-43 | W-1 | 14 | rectangular | 28.0 | 0.30 |
| *[2]Example 22 | — | Ab-245 | S-2/S-1 (90/10) | — | AM-48 | W-1 | 18 | rectangular | 30.0 | 0.25 |
| *[2]Example 23 | — | Ab-245 | S-2/S-1 (90/10) | — | AM-50 | W-1 | 22 | rectangular | 34.0 | 0.20 |
| *[2]Example 24 | — | Ab-245 | S-2/S-1 (90/10) | — | AM-28 | W-1 | 26 | rectangular | 36.0 | 0.15 |

TABLE 5-continued (EUV Exposure/Alkali Development/Positive-tone)

| | Resist composition | | | | | | Evaluation result | | | |
|---|---|---|---|---|---|---|---|---|---|---|
| | Resin (Aa) | Resin (Ab) (% by mass) | Solvent (mass ratio) | Photo-acid generator (35% by mass) | Basic compound (2% by mass) | Surfactant (0.01% by mass) | Sensitivity (mJ/cm²) | Pattern shape | Resolution (nm) | DOF (μm) |
| Example 25 | — | Ab-143 | S-4/S-1 (90/10) | B-118 | AM-28 | W-3 | 17 | rectangular | 30.0 | 0.25 |
| Example 26 | — | Ab-143 | S-4/S-1 (90/10) | B-118 | AM-33 | W-3 | 30 | rectangular | 36.0 | 0.20 |
| Example 27 | — | Ab-143 | S-4/S-1 (90/10) | B-118 | AM-44 | W-3 | 26 | rectangular | 38.0 | 0.15 |
| Example 28 | — | Ab-143 | S-4/S-1 (90/10) | B-118 | AM-54 | W-3 | 26 | rectangular | 40.0 | 0.10 |
| *1 Example 29 | Aa-52 | Ab-120 | S-3/S-2 (90/10) | Y-70 | AM-25 | W-2 | 11 | rectangular | 26.0 | 0.30 |
| Example 30 | — | Ab-97 | S-1/S-2 (90/10) | B-149 | AM-36 | W-4 | 10 | rectangular | 26.0 | 0.30 |
| Example 31 | — | Ab-167 (63) | S-1/S-4 (80/20) | Y-61 | AM-22 | W-3 | 22 | rectangular | 34.0 | 0.20 |
| Example 32 | — | Ab-167 (63) | S-1/S-4 (80/20) | Y-61 | AM-27 | W-3 | 25 | rectangular | 36.0 | 0.15 |
| *2 Example 33 | — | Ab-238 (63) | S-3/S-4 (80/20) | — | AM-39/N-6 (50/50) | W-3 | 10 | rectangular | 26.0 | 0.30 |
| Example 34 | — | Ab-269 (78) | S-1/S-2 (90/10) | B-182 (20) | AM-24 | W-2 | 16 | rectangular | 24.0 | 0.30 |
| Example 35 | — | Ab-284 (58) | S-1/S-2 (70/30) | B-182 (40) | AM-43 | W-1 | 14 | rectangular | 26.0 | 0.30 |
| Example 36 | — | Ab-275 (68) | S-1/S-2 (70/30) | B-182 (30) | AM-36 | W-4 | 20 | rectangular | 30.0 | 0.20 |
| Example 37 | — | Ab-277 (73) | S-1/S-2 (60/40) | B-182 (25) | AM-27 | W-3 | 21 | rectangular | 28.0 | 0.25 |
| Example 38 | — | Ab-289 (88) | S-1/S-2 (80/20) | z132 (10) | AM-48 | W-4 | 19 | rectangular | 32.0 | 0.15 |
| Example 39 | — | Ab-291 (78) | S-1/S-2 (90/10) | z128 (20) | AM-22 | W-4 | 24 | rectangular | 28.0 | 0.20 |
| Example 40 | — | Ab-292 (68) | S-1/S-2 (50/50) | z130 (30) | AM-24 | W-3 | 26 | rectangular | 30.0 | 0.25 |
| Example 41 | — | Ab-281 (83) | S-1/S-2 (80/20) | B-121 (15) | AM-43 | W-4 | 23 | rectangular | 34.0 | 0.15 |
| Example 42 | — | Ab-282 (63) | S-1/S-2 (50/50) | B-181 (35) | AM-25 | W-3 | 18 | rectangular | 28.0 | 0.20 |
| Example 43 | — | Ab-283 (78) | S-1/S-2 (60/40) | B-180 (20) | AM-50 | W-4 | 20 | rectangular | 30.0 | 0.25 |
| Comparative Example 1 | — | Ab-97 | S-1/S-2 (90/10) | B-149 | N-2 | W-4 | 38 | taper | 50.0 | 0.05 |
| *3 Comparative Example 2 | Aa-16 | Ab-240 | S-2/S-3 (80/20) | — | N-1 | W-4 | 39 | taper | 50.0 | 0.05 |
| Comparative Example 3 | — | Ab-17 | S-4/S-3 (80/20) | B-110 | N-5 | W-3 | 38 | taper | 50.0 | 0.05 |
| *1 Comparative Example 4 | Aa-52 | Ab-120 | S-3/S-2 (90/10) | Y-70 | N-3 | W-2 | 40 | taper | 50.0 | 0.05 |
| Comparative Example 5 | — | Ab-167 | S-1/S-4 (80/20) | Y-61 | N-4 | W-3 | 39 | taper | 50.0 | 0.05 |

*1 In Examples 13, 14 and 29 and a comparative example 4, the resist compositions were prepared by containing 5% by mass of a resin (Aa) and 58% by mass of a resin (Ab).
*2 In Examples 18 to 24 and 33, the resist compositions were prepared by containing 98% by mass of a resin (Ab).
*3 In Examples 5 to 12 and a comparative example 2, the resist compositions were prepared by containing 5% by mass of a resin (Aa) and 93% by mass of a resin (Ab).
*4 In Examples 2 to 4, the resist compositions were prepared by containing 88% by mass of a resin (Ab) and 10% by mass of a photo-acid generator.

TABLE 6

(EUV Exposure/Organic Solvent Development/Negative-tone)

| | Resist composition | | | | | | | | Evaluation result | | | |
|---|---|---|---|---|---|---|---|---|---|---|---|---|
| | Resin (Aa) (% by mass) | Resin (Ab) (% by mass) | Solvent (mass ratio) | Photo-acid generator (% by mass) | Basic compound (2% by mass) | Surfactant (0.01% by mass) | Developer | Rinsing liquid | Sensitivity (mJ/cm²) | Pattern shape | Resolution (nm) | DOF (μm) |
| Example 44 | — | Ab-178 (88) | S-2 | B-122 (10) | AM-24 | W-3 | G-1 | G-6 | 16 | rectangular | 34.0 | 0.15 |

TABLE 6-continued (EUV Exposure/Organic Solvent Development/Negative-tone)

| | Resist composition | | | | | | | | Evaluation result | | | |
|---|---|---|---|---|---|---|---|---|---|---|---|---|
| | Resin (Aa) (% by mass) | Resin (Ab) (% by mass) | Solvent (mass ratio) | Photo-acid generator (% by mass) | Basic compound (2% by mass) | Surfactant (0.01% by mass) | Developer | Rinsing liquid | Sensitivity ($mJ/cm^2$) | Pattern shape | Resolution (nm) | DOF (μm) |
| Example 45 | — | Ab-245 (98) | S-2/S-1 (90/10) | — | AM-36 | W-1 | G-1 | — | 20 | rectangular | 36.0 | 0.15 |
| Example 46 | — | Ab-143 (63) | S-41S-1 (90/10) | B-118 (35) | AM-48 | W-3 | G-1 | G-5 | 22 | rectangular | 36.0 | 0.20 |
| Example 47 | — | Ab-97 (63) | S-1/S-2 (90/10) | z130 (35) | AM-27 | W-4 | G-3 | — | 24 | rectangular | 34.0 | 0.20 |
| Example 48 | — | Ab-281 (83) | S-1/S-2 (80/20) | B-121 (15) | AM-43 | W-4 | G-1 | — | 25 | rectangular | 34.0 | 0.15 |
| Example 49 | — | Ab-282 (63) | S-1/S-2 (50/50) | B-181 (35) | AM-25 | W-3 | G-1 | G-4 | 20 | rectangular | 30.0 | 0.20 |
| Example 50 | Aa-1 (10) | Ab-283 (68) | S-1/S-2 (60/40) | B-180 (20) | AM-50 | W-4 | G-2 | — | 21 | rectangular | 30.0 | 0.25 |
| Comparative Example 6 | — | Ab-97 (63) | S-1/S-2 (90/10) | z130 (35) | N-4 | W-4 | G-3 | — | 35 | taper | 52.0 | 0.05 |
| Comparative Example 7 | — | Ab-245 (98) | S-2/S-1 (90/10) | — | N-2 | W-1 | G-1 | — | 36 | taper | 50.0 | 0.05 |

According to the results described above, it is understood that the composition of the present invention can be suitably used in lithography process of manufacturing electronic devices such as various kinds of semiconductor elements or a recording medium.

What is claimed is:

1. An actinic ray-sensitive or radiation-sensitive resin composition comprising a nitrogen-containing compound (N) which is represented by the following general formula (N1), and at least one of a resin (Ab) of which the polarity changes by the action of an acid, containing a repeating unit (B) having a structural site which generates an acid by irradiation with actinic rays or radiation and a compound which generates an acid by irradiation with actinic rays or radiation:

(N1)

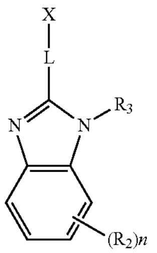

wherein, in the general formula (N1),

X represents a group including a hetero atom;

L represents a single bond or an alkylene group;

$R_2$ represents a substituent, and in the case where a plurality of $R_2$'s are present, they may be the same as or different from each other and a plurality of $R_2$'s may be bonded to each other to form a ring;

$R_3$ represents —$COOR_4$ and a carbon atom in $R_4$ which is bonded to the —COO group in —$COOR_4$ is a tertiary carbon atom; and n represents an integer of 0 to 4.

2. The actinic ray-sensitive or radiation-sensitive resin composition according to claim 1, wherein $R_4$ in —$COOR_4$ is a tertiary alkyl group having 5 or more carbon atoms.

3. The actinic ray-sensitive or radiation-sensitive resin composition according to claim 1, wherein X is a hydroxyl group or a cyano group.

4. The actinic ray-sensitive or radiation-sensitive resin composition according to claim 1, wherein the nitrogen-containing compound (N) which is represented by the general formula (N1) is represented by any of the following general formulae:

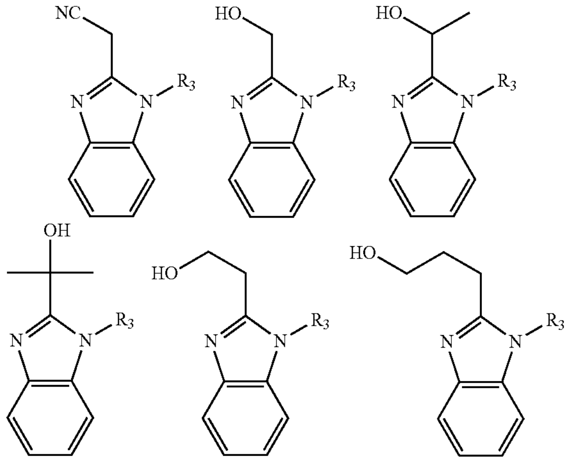

wherein, in the general formulae, $R_3$ represents —$COOR_4$ and a carbon atom in $R_4$ which is bonded to the —COO group in —$COOR_4$ is a tertiary carbon atom.

5. The actinic ray-sensitive or radiation-sensitive resin composition according to claim 4, wherein $R_4$ in —$COOR_4$ is t-amyl.

6. The actinic ray-sensitive or radiation-sensitive resin composition according to claim 1, wherein the resin (Ab) contains at least one kind of repeating unit (A) which is represented by the following general formula (A):

(A)

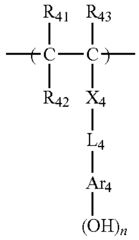

(A)

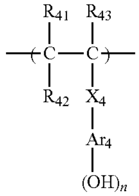

wherein, in the general formula (A), $R_{41}$, $R_{42}$ and $R_{43}$ each independently represents an hydrogen atom, an alkyl group, a cycloalkyl group, a halogen atom, a cyano group or an alkoxycarbonyl group, and, $R_{42}$ may be bonded to $Ar_4$ to form a ring and in this case, $R_{42}$ represents a single bond or an alkylene group;

$X_4$ represents a single bond, —COO— or —$CONR_{64}$, and, $R_{64}$ represents a hydrogen atom or an alkyl group;

$L_4$ represents a single bond or an alkylene group;

$Ar_4$ represents a (n+1)-valent aromatic ring group and in a case of being bonded to $R_{42}$ to form a ring, represents a (n+2)-valent aromatic ring group; and n represents an integer of 1 to 4.

7. An actinic ray-sensitive or radiation-sensitive film comprising the actinic ray-sensitive or radiation-sensitive resin composition according to claim 1.

8. A pattern forming method comprising: forming a film including a composition according to claim 1, irradiating the film with actinic rays or radiation, and developing the irradiated film with actinic rays or radiation.

9. The pattern forming method according to claim 8, wherein the actinic rays or radiation is EUV light.

10. An actinic ray-sensitive or radiation-sensitive resin composition comprising a nitrogen-containing compound (N) which is represented by any of the following general formulas, and, at least one of a resin (Ab) of which the polarity changes by the action of an acid, containing a repeating unit (B) having a structural site which generates an acid by irradiation with actinic rays or radiation and a compound which generates an acid by irradiation with actinic rays or radiation:

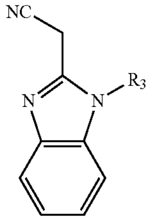

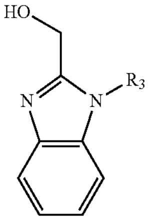

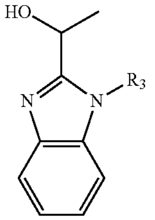

-continued

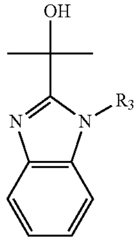

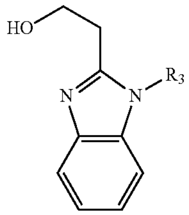

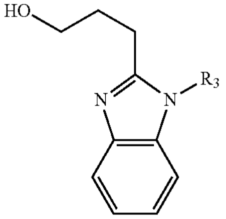

wherein, in the general formulas, $R_3$ represents a hydrogen atom or —$COOR_4$ and $R_4$ represents an alkyl group, an aryl group, an aralkyl group, an alkenyl group or a cycloalkyl group.

11. The actinic ray-sensitive or radiation-sensitive resin composition according to claim 10, wherein $R_3$ is a hydrogen atom or —$COOR_4$ and a carbon atom in $R_4$ which is bonded to the —COO group in —$COOR_4$ is a tertiary carbon atom.

12. The actinic ray-sensitive or radiation-sensitive resin composition according to claim 10, wherein $R_3$ is a hydrogen atom or —$COOR_4$ and $R_4$ is a tertiary alkyl group having 5 or more carbon atoms.

13. The actinic ray-sensitive or radiation-sensitive resin composition according to claim 10, wherein $R_3$ is —$COOR_4$ and $R_4$ is t-amyl.

14. The actinic ray-sensitive or radiation-sensitive resin composition according to claim 10, wherein the resin (Ab) contains at least one kind of repeating unit (A) which is represented by the following general formula (A):

(A)

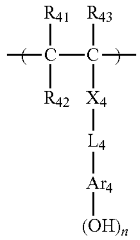

wherein, in the general formula (A), $R_{41}$, $R_{42}$ and $R_{43}$ each independently represents a hydrogen atom, an alkyl group, a cycloalkyl group, a halogen atom, a cyano group or an alkoxycarbonyl group, and, $R_{42}$ may be bonded to $Ar_4$ to form a ring and in this case, $R_{42}$ represents a single bond or an alkylene group;

$X_4$ represents a single bond, —COO— or —$CONR_{64}$, and, $R_{64}$ represents a hydrogen atom or an alkyl group;

$L_4$ represents a single bond or an alkylene group;

$Ar_4$ represents a (n+1)-valent aromatic ring group and in a case of being bonded to $R_{42}$ to form a ring, represents a (n+2)-valent aromatic ring group; and n represents an integer of 1 to 4.

15. An actinic ray-sensitive or radiation-sensitive film comprising the actinic ray-sensitive or radiation-sensitive resin composition according to claim 10.

16. A pattern forming method comprising: forming a film including a composition according to claim 10, irradiating the film with actinic rays or radiation, and developing the irradiated film with actinic rays or radiation.

17. The pattern forming method according to claim 16, wherein the actinic rays or radiation is EUV light.

* * * * *